(12) United States Patent
Kore et al.

(10) Patent No.: US 12,385,039 B2
(45) Date of Patent: Aug. 12, 2025

(54) TRINUCLEOTIDE CAP ANALOGS, PREPARATION AND USES THEREOF

(71) Applicant: LIFE TECHNOLOGIES CORPORATION, Carlsbad, CA (US)

(72) Inventors: Anilkumar Kore, Austin, TX (US); Senthilvelan Annamalai, Austin, TX (US); Shanmugasundaram Muthian, Austin, TX (US); Robert Potter, San Marcos, CA (US); Tyson Vonderfecht, Carlsbad, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 616 days.

(21) Appl. No.: 17/364,956

(22) Filed: Jul. 1, 2021

(65) Prior Publication Data

US 2022/0002716 A1 Jan. 6, 2022

Related U.S. Application Data

(60) Provisional application No. 63/197,607, filed on Jun. 7, 2021, provisional application No. 63/047,465, filed on Jul. 2, 2020.

(51) Int. Cl.
| | | |
|---|---|---|
| C12N 15/00 | (2006.01) | |
| A61K 31/7088 | (2006.01) | |
| A61K 38/45 | (2006.01) | |
| A61K 47/54 | (2017.01) | |
| C07H 21/00 | (2006.01) | |
| C12N 9/12 | (2006.01) | |
| C12N 15/11 | (2006.01) | |

(52) U.S. Cl.
CPC .......... *C12N 15/11* (2013.01); *A61K 31/7088* (2013.01); *A61K 38/45* (2013.01); *A61K 47/549* (2017.08); *C07H 21/00* (2013.01); *C12N 9/1247* (2013.01); *C12Y 207/07006* (2013.01); *C12N 2310/3231* (2013.01); *C12N 2310/3519* (2013.01); *C12N 2320/32* (2013.01)

(58) Field of Classification Search
CPC .... A61K 47/26; A61K 47/549; A61K 9/1271; A61K 47/555; C07K 14/7051; C07K 2319/036; C12N 2310/20; C12N 2310/321
USPC ...................................................... 424/94.5
See application file for complete search history.

(56) References Cited

U.S. PATENT DOCUMENTS

2019/0211368 A1   7/2019 Butora et al.

FOREIGN PATENT DOCUMENTS

| WO | WO-2017053297 A1 | 3/2017 |
|---|---|---|
| WO | WO-2018078053 A1 | 5/2018 |
| WO | WO-2021162567 A1 | 8/2021 |

OTHER PUBLICATIONS

Kisselev L., (Structure, 2002, vol. 10: 8-9.*
Kwiatkowski et al., (Biochemistry 38:11643-11650, 1999.*
Wristlock et al., (Quarterly Reviews of Biophysics 2003, vol. 36 (3): 307-340.*
Davos et al., (Proteins: Structure, Function and Genetics, 2000, vol. 41: 98-107.*
Holstein J.M., et al., "Dual 5' Cap Labeling Based on Regioselective RNA Methyltransferases and Bioorthogonal Reactions," Chemistry—A European Journal, May 2, 2017, vol. 23, No. 25, XP055860503, pp. 6165-6173.
Muttach F., et al., "Synthetic mRNA Capping," Beilstein Journal of Organic Chemistry, Dec. 20, 2017, vol. 13, XP055605691, pp. 2819-2832.
PCT/US2021/040037, International Search Report and Written Opinion, Jan. 31, 2022, 21 pages.
Senthilvelan A., et al., "Trinucleotide Cap Analogue Bearing a Locked Nucleic Acid Moiety: Synthesis, mRNA Modification, and Translation for Therapeutic Applications," Organic Letters, Jun. 4, 2021, vol. 23, No. 11, XP055858877, pp. 4133-4136, Retrieved from the Internet URL: https://pubs.acs.org/doi/pdf/10.1021/acs.orglett.1c01037.
Sikorski P.J., et al., "The Identity and Methylation Status of the First Transcribed Nucleotide in Eukaryotic mRNA 5' Cap Modulates Protein Expression in Living Cells," Nucleic Acids Research, Jan. 27, 2020, vol. 48, No. 4, XP055747723, pp. 1607-1626.
Warminski M., et al., "Amino-Functionalized 5' Cap Analogs as Tools for Site-Specific Sequence-Independent Labeling of mRNA," Bioconjugate Chemistry, Jul. 19, 2017, vol. 28, No. 7, XP055860480, pp. 1978-1992, Retrieved from the internet URL: https://pubs.acs.org/doi/pdf/10.1021/acs.bioconjchem.7b00291.
Warminski M., et al., "mRNA Cap Modification through Carbamate Chemistry: Synthesis of Amino- and Carboxy-Functionalised Cap Analogues Suitable for Labelling and Bioconjugation : Amino-and Carboxy-Functionalised mRNA Cap Analogues," European Journal of Organic Chemistry, Oct. 1, 2015, vol. 2015, No. 28, XP055860514, pp. 6153-6169.
Worch R., et al., "Translocation of 5'mRNA Cap Analogue-Peptide Conjugates Across the Membranes of Giant Unilamellar Vesicles," BBA-Biomembranes Acta, Feb. 1, 2016, vol. 1858, No. 2, XP055325446, pp. 311-317.
Senthilvelan A., et al., "Click-iT Trinucleotide Cap Analog: Synthesis, mRNA Translation, and Detection," Bioorganic & Medicinal Chemistry, 2023, vol. 77, 7 pages.

* cited by examiner

*Primary Examiner* — Robert B Mondesi
*Assistant Examiner* — Mohammad Y Meah

(57) ABSTRACT

This specification generally relates to trinucleotide RNA cap analogs, methods of use thereof, and kits comprising same. In particular, the trinucleotide cap analogs provided herein permit ready detection and/or isolation of capped RNA transcripts in vitro and translation of capped mRNAs in vivo.

16 Claims, 21 Drawing Sheets

Specification includes a Sequence Listing.

SEQUENCE LISTING

<160> NUMBER OF SEQ ID NOS: 597

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Tyr Ser Thr Pro Pro Lys Lys Arg Lys Val Glu Asp Pro
1               5                   10                  15

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Tyr Ser Thr Pro Pro Lys Thr Arg Arg Arg Pro
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Tyr Ser Thr Pro Gly Arg Lys Lys Arg
1               5                   10

<210> SEQ ID NO 4
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Tyr Ser Thr Pro Arg Arg Asn Arg Arg Arg Trp
1               5                   10

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Pro Asp Glu Val Lys Arg Lys Lys Lys Pro Pro Thr Ser Tyr Gly
1               5                   10                  15

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 6

Pro Arg Arg Thr Lys Pro Pro Thr Ser Tyr Gly
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Lys Lys Arg Gly Pro Thr Ser Tyr Gly
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Trp Arg Arg Arg Asn Arg Arg Pro Thr Ser Tyr Gly
1               5                   10

<210> SEQ ID NO 9
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Tyr Gly Pro Pro Lys Lys Lys Arg Lys Val Glu Ala Pro Tyr Lys
1               5                   10                  15

Ala

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Pro Ala Ala Lys Arg Val Lys Leu Asp
1               5

<210> SEQ ID NO 11
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Arg Gln Arg Arg Asn Glu Leu Lys Arg Ser Pro
1               5                   10

```
<210> SEQ ID NO 12
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Lys Arg Pro Ala Ala Thr Lys Lys Ala Gly Gln Ala Lys Lys Lys Lys
1               5                   10                  15

<210> SEQ ID NO 13
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Val Arg Lys Lys Arg Lys Thr Glu Glu Glu Ser Pro Leu Lys Asp Lys
1               5                   10                  15

Asp Ala Lys Lys Ser Lys Gln Glu
            20

<210> SEQ ID NO 14
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Arg Leu Arg Arg Asp Ala Gly Gly Arg Gly Gly Val Tyr Glu His Leu
1               5                   10                  15

Gly Gly Ala Pro Arg Arg Arg Lys
            20

<210> SEQ ID NO 15
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Lys Arg Lys Gly Asp Glu Val Asp Gly Val Asp Glu Cys Ala Lys Lys
1               5                   10                  15

Ser Lys Lys

<210> SEQ ID NO 16
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Asn Gln Ser Ser Asn Phe Gly Pro Met Lys Gly Gly Asn Phe Gly Gly
1               5                   10                  15

Arg Ser Ser Gly Pro Tyr Gly Gly Gly Gly Gln Tyr Phe Ala Lys Pro
```

20                  25                  30

Arg Asn Gln Gly Gly Tyr
         35

<210> SEQ ID NO 17
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Gly Lys Arg Thr Ala Asp Gly Ser Glu Phe Glu Ser Pro Lys Lys
1               5                   10                  15

Ala Arg Lys Val Glu Ala Tyr Pro Lys Ala Trp
            20                  25

<210> SEQ ID NO 18
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Gly Lys Arg Thr Ala Asp Gly Ser Glu Phe Glu Ser Pro Lys Lys
1               5                   10                  15

Lys Arg Ala Val Glu Ala Tyr Pro Lys Ala Trp
            20                  25

<210> SEQ ID NO 19
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Gly Lys Arg Thr Ala Asp Gly Ser Glu Phe Glu Ser Pro Lys Lys
1               5                   10                  15

Lys Ala Lys Val Glu Ala Tyr Pro Lys Ala Trp
            20                  25

<210> SEQ ID NO 20
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Gly Lys Arg Thr Ala Asp Gly Ser Glu Phe Glu Ser Pro Lys Lys
1               5                   10                  15

Lys Arg Lys Val Glu Ala Pro Tyr Lys Ala Trp Lys
            20                  25

<210> SEQ ID NO 21
<211> LENGTH: 26
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 21

Gly Gly Lys Arg Thr Ala Asp Gly Ser Glu Phe Glu Ser Pro Lys Lys
1               5                   10                  15

Lys Arg Lys Val Glu Tyr Lys Ala Trp Lys
            20                  25

<210> SEQ ID NO 22
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Tyr Gly Pro Ala Ala Lys Arg Val Lys Leu Asp Glu Ala Tyr Pro
1               5                   10                  15

Lys Ala Trp Lys
            20

<210> SEQ ID NO 23
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Gly Lys Arg Thr Ala Asp Gly Ser Glu Phe Glu Pro Ala Ala Lys
1               5                   10                  15

Arg Val Lys Leu Asp Glu Ala Tyr Pro Lys Ala Trp Lys
            20                  25

<210> SEQ ID NO 24
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gly Thr Gly Pro Lys Lys Lys Arg Lys Val Gly Gly Gly Gly Tyr Gly
1               5                   10                  15

Pro Lys Lys Lys Arg Leu Val Gly
            20

<210> SEQ ID NO 25
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Lys Arg Pro Ala Ala Thr Lys Lys Ala Gly Gln Ala Lys Lys Lys Lys
1               5                   10                  15

Leu Glu Ala Tyr Pro Lys Ala Trp Lys
            20                  25

<210> SEQ ID NO 26
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ala Thr Lys Gly Thr Lys Arg Ser Tyr Glu Gln Met Glu Thr Gly Glu
1               5                   10                  15

<210> SEQ ID NO 27
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gly Lys Trp Glu Arg Lys Pro Ile Arg Cys Ala Ser
1               5                   10

<210> SEQ ID NO 28
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gly Tyr Gly Lys Arg Thr Ala Asp Ser Gln His Ser Thr Pro Pro Lys
1               5                   10                  15

Lys Lys Arg Lys Val Glu Ala Pro Tyr Lys Ala Trp Lys
                20                  25

<210> SEQ ID NO 29
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Lys Arg Thr Ala Asp Ser Gln His Ser Thr Pro Pro Lys Lys Lys Arg
1               5                   10                  15

Lys Val Glu Ala Pro Tyr Lys Ala Trp Lys
                20                  25

<210> SEQ ID NO 30
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Gly Tyr Gly Pro Pro Lys Lys Arg Lys Val Glu Ala Pro Tyr Lys
1               5                   10                  15

Ala Trp Lys Trp Ala Lys Tyr Pro Ala Met Arg Arg Ala His His Arg
                20                  25                  30

```
Arg Arg Arg Ala Ser His Arg Arg Thr Thr Thr Gly Thr
        35                  40                  45

<210> SEQ ID NO 31
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Gly Tyr Gly Pro Pro Lys Lys Lys Arg Lys Val Glu Ala Pro Tyr Lys
1               5                   10                  15

Ala Trp Lys Arg Gly Ala Arg Arg Tyr Ser Lys Met Lys Arg Arg Arg
            20                  25                  30

Arg Arg Val Ala Arg Arg His Arg Arg Pro
        35                  40

<210> SEQ ID NO 32
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Phe Trp Gly Tyr Gly Tyr Gly Pro Pro Lys Lys Lys Arg Lys Val Glu
1               5                   10                  15

Ala Pro Tyr Lys Ala Trp Lys
            20

<210> SEQ ID NO 33
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gly Lys Pro Ser Ser Asp Asp Glu Ala Thr Ala Asp Ser Gln His Ser
1               5                   10                  15

Thr Pro Pro Lys Lys Lys Glu Arg Lys Val Glu Asp
            20                  25

<210> SEQ ID NO 34
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gly Lys Pro Thr Ala Asp Asp Gln His Ser Thr Pro Pro Lys Lys Lys
1               5                   10                  15

Arg Lys Val Glu Asp
            20

<210> SEQ ID NO 35
<211> LENGTH: 27
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 35

Gly Gly Lys Arg Thr Ala Asp Gly Ser Glu Phe Glu Ser Pro Lys Lys
1               5                   10                  15

Ala Arg Lys Val Glu Ala Tyr Pro Lys Ala Lys
            20                  25

<210> SEQ ID NO 36
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Glu Lys Ile Arg Leu Arg Pro Gly Arg Lys Lys Arg Tyr Arg Leu Lys
1               5                   10                  15

His Leu

<210> SEQ ID NO 37
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Pro Glu Gly Thr Arg Gln Ala Arg Arg Asn Arg Arg Arg Arg Trp Arg
1               5                   10                  15

Lys Arg

<210> SEQ ID NO 38
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Pro Glu Gly Thr Arg Gln Pro Arg Asn Arg Arg Arg Arg Trp Arg
1               5                   10                  15

Lys Arg

<210> SEQ ID NO 39
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gly Val Lys Arg Ser Tyr Gly Ala Ala Arg Gly Asp Asp Arg Arg Arg
1               5                   10                  15

Pro Asn Val Val Ala Pro Tyr Lys Ala Trp
            20                  25

<210> SEQ ID NO 40
```

```
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Lys Ser Val Pro Asn Arg Thr Arg Thr Tyr Ile Lys Leu Lys Arg Leu
1               5                   10                  15

Arg Phe Lys Gly Ala Pro Tyr Lys Ala Trp
            20                  25

<210> SEQ ID NO 41
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Glu Met Arg Arg Arg Arg Glu Glu Glu Gly Leu Gln Leu Arg Lys Gln
1               5                   10                  15

Lys Arg Glu Glu Gln Leu Phe Lys Arg Arg Asn
            20                  25

<210> SEQ ID NO 42
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Phe Glu Ala Ala Leu Ala Glu Ala Leu Ala Glu Ala Leu Ala
1               5                   10

<210> SEQ ID NO 43
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Leu Ala Arg Leu Leu Pro Arg Leu Leu Ala Arg Leu
1               5                   10

<210> SEQ ID NO 44
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gly Leu Leu Glu Glu Leu Leu Glu Leu Leu Glu Glu Leu Trp Glu Glu
1               5                   10                  15

Leu Leu Glu Gly
            20

<210> SEQ ID NO 45
```

```
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gly Trp Glu Gly Leu Ile Glu Gly Ile Glu Gly Gly Trp Glu Gly Leu
1               5                   10                  15

Ile Glu Gly

<210> SEQ ID NO 46
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gly Leu Phe Glu Ala Leu Ala Glu Phe Ile Glu Gly Gly Trp Glu Gly
1               5                   10                  15

Leu Ile Glu Gly
            20

<210> SEQ ID NO 47
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gly Leu Phe Glu Ala Leu Leu Glu Leu Leu Glu Ser Leu Trp Glu Leu
1               5                   10                  15

Leu Leu Glu Ala
            20

<210> SEQ ID NO 48
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gly Gly Tyr Cys Leu Glu Lys Trp Met Ile Val Ala Ser Glu Leu Lys
1               5                   10                  15

Cys Phe Gly Asn Thr Ala
            20

<210> SEQ ID NO 49
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gly Gly Tyr Cys Leu Thr Arg Trp Met Leu Ile Glu Ala Glu Leu Lys
1               5                   10                  15
```

```
Cys Phe Gly Asn Thr Ala Val
            20
```

<210> SEQ ID NO 50
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

```
Trp Glu Ala Ala Leu Ala Glu Ala Leu Ala Glu Ala Leu Ala Glu His
1               5                   10                  15

Leu Ala Glu Ala Leu Ala Glu Ala Leu Glu Ala Leu Ala Ala
            20                  25                  30
```

<210> SEQ ID NO 51
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

```
Gly Leu Phe Gly Ala Ile Ala Gly Phe Ile Glu Asn Gly Trp Glu Gly
1               5                   10                  15

Met Ile Asp Gly Trp Tyr Gly
            20
```

<210> SEQ ID NO 52
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

```
Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25
```

<210> SEQ ID NO 53
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

```
Gly Arg Lys Lys Arg Arg Gln Arg Arg Arg Pro Pro Gln
1               5                   10
```

<210> SEQ ID NO 54
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Arg Gln Ile Lys Ile Trp Phe Gln Asn Arg Arg Met Lys Trp Lys Lys
1               5                   10                  15

<210> SEQ ID NO 55
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 56
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Trp Glu Ala Lys Leu Ala Lys Ala Leu Ala Lys Ala Leu Ala Lys His
1               5                   10                  15

Leu Ala Lys Ala Leu Ala Lys Ala Leu Lys Ala Cys Glu Ala
            20                  25                  30

<210> SEQ ID NO 57
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gly Leu Phe Lys Ala Leu Leu Lys Leu Leu Lys Ser Leu Trp Lys Leu
1               5                   10                  15

Leu Leu Lys Ala
            20

<210> SEQ ID NO 58
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gly Leu Phe Arg Ala Leu Leu Arg Leu Leu Arg Ser Leu Trp Arg Leu
1               5                   10                  15

Leu Leu Arg Ala
            20

<210> SEQ ID NO 59
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Gly Leu Phe Glu Ala Leu Leu Glu Leu Leu Glu Ser Leu Tyr Glu Leu
1               5                   10                  15
Leu Leu Glu Ala
            20

<210> SEQ ID NO 60
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Gly Leu Phe Glu Ala Leu Glu Glu Leu Trp Glu Ala
1               5                   10

<210> SEQ ID NO 61
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gly Leu Phe Leu Leu Glu Glu Trp Leu Glu
1               5                   10

<210> SEQ ID NO 62
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gly Leu Phe Leu Leu Glu Glu Trp Leu Glu Lys
1               5                   10

<210> SEQ ID NO 63
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gly Leu Phe Glu Ala Leu Leu Glu Leu Leu Glu Ser Leu Trp Glu Leu
1               5                   10                  15
Leu Leu Glu Ala Lys
            20

<210> SEQ ID NO 64
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

```
Gly Leu Phe Lys Leu Leu Glu Glu Trp Leu Glu
1               5                   10
```

<210> SEQ ID NO 65
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

```
Gly Leu Phe Lys Leu Leu Glu Glu Trp Leu Glu Lys
1               5                   10
```

<210> SEQ ID NO 66
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

```
Gly Leu Phe Glu Ala Ile Ala Glu Phe Ile Glu Gly Gly Trp Glu Gly
1               5                   10                  15

Leu Ile Glu Gly
            20
```

<210> SEQ ID NO 67
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

```
Gly Leu Phe Lys Ala Ile Ala Lys Phe Ile Lys Gly Gly Trp Lys Gly
1               5                   10                  15

Leu Ile Lys Gly
            20
```

<210> SEQ ID NO 68
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

```
Ile Arg Phe Lys Lys Thr Lys Leu Ile Ala Ser Ile Ala Met Ala Leu
1               5                   10                  15

Cys
```

<210> SEQ ID NO 69
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

```
Ala Leu Ala Gly Thr Ile Ile Ala Gly Ala Ser Leu Thr Phe Gln Val
```

```
1               5                  10                  15
Leu Asp Lys Val Leu Glu Glu Leu Gly Lys Val Ser Arg Lys
         20                  25                  30
```

<210> SEQ ID NO 70
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

```
Gly Leu Phe Glu Ala Ile Glu Gly Phe Ile Glu Asn Gly Trp Glu Gly
1               5                  10                  15
Met Ile Asp Gly Trp Tyr Gly
            20
```

<210> SEQ ID NO 71
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

```
Gly Tyr Ile Cys Arg Arg Ala Arg Gly Asp Asn Pro Asp Asp Arg Cys
1               5                  10                  15
Thr
```

<210> SEQ ID NO 72
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

```
Gly Leu Phe Glu Ala Ile Ala Glu Phe Ile Glu Gly Gly Trp Glu Gly
1               5                  10                  15
Leu Ile Glu Gly Cys Ala
            20
```

<210> SEQ ID NO 73
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

```
Gly Leu Phe His Ala Ile Ala His Phe Ile His Gly Gly Trp His Gly
1               5                  10                  15
Leu Ile His Gly Trp Trp Tyr Gly
            20
```

<210> SEQ ID NO 74
<211> LENGTH: 30
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 74

Arg Arg Arg Gln Arg Arg Lys Lys Arg Gly Asp Ile Met Gly Glu
1               5                   10                  15

Trp Gly Asn Glu Ile Phe Gly Ala Ile Ala Gly Phe Leu Gly
            20                  25                  30

<210> SEQ ID NO 75
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Gly Leu Phe Glu Ala Ile Ala Asp Phe Ile Glu Asn Gly Trp Glu Gly
1               5                   10                  15

Met Ile Asp Gly Gly Gly
            20

<210> SEQ ID NO 76
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Ala Leu Ala Gly Thr Ile Ile Ala Gly Ala Ser Leu Thr Phe Gln Val
1               5                   10                  15

Leu Asp Lys Val Leu Glu Glu Leu Gly Lys Val Ser Arg Lys Lys
            20                  25                  30

<210> SEQ ID NO 77
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Ile Arg Phe Lys Lys Thr Lys Leu Ile Ala Ser Ile Ala Met Ala
1               5                   10                  15

<210> SEQ ID NO 78
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gly Leu Trp His Leu Leu His Leu Trp Arg Arg Leu Leu Arg Leu
1               5                   10                  15

Leu Arg

<210> SEQ ID NO 79
<211> LENGTH: 21
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 79

Lys Lys Ile Met Leu Leu Leu Met Thr Leu Leu Leu Val Ser Leu Pro
1               5                   10                  15

Leu Ala Gln Glu Gln
            20

<210> SEQ ID NO 80
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Gly Leu Phe Glu Ala Leu Leu Glu Leu Leu Glu Ser Leu Trp Glu Leu
1               5                   10                  15

Leu Leu Glu Ala Trp Tyr Gly
            20

<210> SEQ ID NO 81
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Arg Leu Leu Arg Leu Leu Leu Arg Leu Trp Arg Arg Leu Leu Arg Leu
1               5                   10                  15

Leu Arg

<210> SEQ ID NO 82
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Leu Leu Glu Leu Glu Leu Leu Glu Leu Leu Leu Glu Leu Glu
1               5                   10                  15

Leu Leu Glu Leu Glu Leu Leu Leu Glu Leu
            20                  25

<210> SEQ ID NO 83
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Gly Leu Phe Glu Ala Leu Leu Glu Leu Leu Glu Ser Leu Trp Glu Leu
1               5                   10                  15

Leu Leu Glu Ala Arg Arg Arg Arg Arg Arg Arg Arg
            20                  25
```

<210> SEQ ID NO 84
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Gly Leu Phe Glu Ala Leu Leu Glu Leu Leu Glu Ser Leu Trp Glu Leu
1               5                   10                  15

Leu Leu Glu Ala Arg Arg Arg Arg Arg Arg
            20                  25

<210> SEQ ID NO 85
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Gly Leu Phe Glu Ala Leu Leu Glu Leu Leu Glu Ser Leu Trp Glu Leu
1               5                   10                  15

Leu Leu Glu Ala Lys Lys Lys Lys Lys Lys Lys Lys
            20                  25

<210> SEQ ID NO 86
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Gly Leu Phe Glu Ala Leu Leu Glu Leu Leu Glu Ser Leu Trp Glu Leu
1               5                   10                  15

Leu Leu Glu Ala Lys Lys Lys Lys Lys Lys
            20                  25

<210> SEQ ID NO 87
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Gly Leu Phe Glu Ala Leu Leu Glu Leu Leu Glu Ser Leu Trp Glu Leu
1               5                   10                  15

Leu Leu Glu Ala Lys Lys
            20

<210> SEQ ID NO 88
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Gly Leu Phe Glu Ala Leu Leu Glu Leu Leu Glu Ser Leu Trp Glu Leu
1               5                   10                  15

Leu Leu Glu Ala Lys Lys Lys Lys
            20

<210> SEQ ID NO 89
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Gly Leu Phe Glu Ala Leu Leu Glu Leu Leu Glu Ser Leu Trp Glu Leu
1               5                   10                  15

Leu Leu Glu Ala Glu Glu
            20

<210> SEQ ID NO 90
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Gly Leu Phe Glu Ala Leu Leu Glu Leu Leu Glu Ser Leu Trp Glu Leu
1               5                   10                  15

Leu Leu Glu Ala Glu Glu Glu Glu
            20

<210> SEQ ID NO 91
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Gly Leu Phe Glu Ala Leu Leu Glu Leu Leu Glu Ser Leu Trp Glu Leu
1               5                   10                  15

Leu Leu Glu Ala Glu Glu Glu Glu Glu Glu
            20                  25

<210> SEQ ID NO 92
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gly Leu Phe Glu Ala Leu Leu Glu Leu Leu Glu Ser Leu Trp Glu Leu
1               5                   10                  15

Leu Leu

<210> SEQ ID NO 93
<211> LENGTH: 36
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 93

Pro Leu Ser Ser Ile Phe Ser Arg Ile Gly Asp Pro Arg Gly Ala Arg
1               5                   10                  15

Arg Tyr Ala Lys Met Lys Arg Arg Arg Arg Val Ala Arg Arg His
            20                  25                  30

Arg Arg Arg Pro
        35

<210> SEQ ID NO 94
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Gly Pro Phe His Tyr Phe Gln Phe Leu Phe Pro Pro Val
1               5                   10

<210> SEQ ID NO 95
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Gly Ser Ser Ser Trp Trp Gln Arg Trp Trp Pro Pro Trp
1               5                   10

<210> SEQ ID NO 96
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Arg Arg Arg Gln Arg Arg Lys Lys Arg
1               5

<210> SEQ ID NO 97
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Lys Lys Lys Lys
1

<210> SEQ ID NO 98
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 98

Lys Lys Lys Lys Lys Lys
1               5

<210> SEQ ID NO 99
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Lys Lys Lys Lys Lys Lys Lys Lys
1               5

<210> SEQ ID NO 100
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Lys Lys Lys Lys Lys Lys Lys Lys Lys Lys
1               5                   10

<210> SEQ ID NO 101
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Lys Lys Lys Lys Lys Lys Lys Lys Lys Lys Lys Lys
1               5                   10

<210> SEQ ID NO 102
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Lys Lys Lys Lys Lys Lys Lys Lys Lys Lys Lys Lys Lys Lys Lys Lys
1               5                   10                  15

<210> SEQ ID NO 103
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Lys Lys Lys Lys Lys Lys Lys Lys Lys Lys Lys Lys Lys Lys Lys Lys
1               5                   10                  15

Lys Lys Lys Lys
            20
```

```
<210> SEQ ID NO 104
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Lys Lys Lys Lys Lys Lys Lys Lys Lys Lys Lys Lys Lys Lys Lys Lys
1               5                   10                  15

Lys Lys Lys Lys Lys Lys Lys Lys
            20

<210> SEQ ID NO 105
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Arg Arg Arg Arg
1

<210> SEQ ID NO 106
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Arg Arg Arg Arg Arg Arg
1               5

<210> SEQ ID NO 107
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Arg Arg Arg Arg Arg Arg Arg Arg
1               5

<210> SEQ ID NO 108
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Arg Arg Arg Arg Arg Arg Arg Arg Arg Arg
1               5                   10

<210> SEQ ID NO 109
<211> LENGTH: 12
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 109

Arg Arg Arg Arg Arg Arg Arg Arg Arg Arg
1               5                   10

<210> SEQ ID NO 110
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Arg Arg Arg Arg Arg Arg Arg Arg Arg Arg Arg Arg Arg Arg Arg Arg
1               5                   10                  15

<210> SEQ ID NO 111
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Arg Arg Arg Arg Arg Arg Arg Arg Arg Arg Arg Arg Arg Arg Arg Arg
1               5                   10                  15

Arg Arg Arg Arg
            20

<210> SEQ ID NO 112
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Arg Arg Arg Arg Arg Arg Arg Arg Arg Arg Arg Arg Arg Arg Arg Arg
1               5                   10                  15

Arg Arg Arg Arg Arg Arg Arg Arg
            20

<210> SEQ ID NO 113
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Tyr Lys Ala
1

<210> SEQ ID NO 114
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

```
Lys Lys Lys Lys Lys Lys Lys Lys Trp Lys Gly Gly Gly Ala Cys
1               5                   10                  15

Tyr Gly Leu Pro His Leu Phe Cys Gly
            20                  25
```

<210> SEQ ID NO 115
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

```
Tyr Lys Ala Lys Lys Lys Lys Lys Lys Lys Trp Lys
1               5                   10
```

<210> SEQ ID NO 116
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

```
Lys Thr Pro Lys Lys Ala Lys Lys Pro Lys Thr Pro Lys Lys Ala Lys
1               5                   10                  15

Lys Pro
```

<210> SEQ ID NO 117
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

```
Lys Lys Ala Lys Lys Pro Ala Ala Thr Arg Lys Ser Ser Lys Asn Pro
1               5                   10                  15

Lys Lys Pro Lys Thr Val Lys Pro Lys Lys Val Ala Lys
            20                  25
```

<210> SEQ ID NO 118
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

```
Arg Gly Ala Arg Arg Tyr Ser Lys Met Lys Arg Arg Arg Arg Arg Val
1               5                   10                  15

Ala Arg Arg His Arg Arg Arg Pro
            20
```

<210> SEQ ID NO 119
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 119

Thr Arg Gln Ala Arg Arg Asn Arg Arg Arg Trp Arg Glu Arg Gln
1               5                   10                  15

Arg Gly Ser Gly Ser Gly
            20

<210> SEQ ID NO 120
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Lys Arg Pro Arg Gly Arg Pro Lys Gly Ser Lys Asn Trp Arg Arg
1               5                   10                  15

Arg Lys Arg Arg Ala Ser Arg Arg Ser Pro Arg Arg Arg
            20                  25

<210> SEQ ID NO 121
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Lys Arg Gly Arg Gly Arg Pro Arg Lys Gln Pro Pro Lys Glu Pro Ser
1               5                   10                  15

Glu Val Pro Thr Pro Lys Arg Pro Arg Gly Arg Pro Lys Gly Ser Lys
            20                  25                  30

Asn Lys

<210> SEQ ID NO 122
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Lys Glu Lys Tyr Glu Lys Asp Ile Ala Ala Tyr Arg Ala Lys Gly Lys
1               5                   10                  15

Pro Ala Ala Lys Lys Gly Val Val Lys Ala Glu Lys Ser Lys Lys Lys
            20                  25                  30

Lys

<210> SEQ ID NO 123
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Tyr Lys Ala Lys Lys Lys Lys Lys Lys Lys Lys Lys Trp Lys
1               5                   10                  15
```

```
<210> SEQ ID NO 124
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Lys Lys Lys Lys Lys Lys Lys Gly Gly Cys
1               5                   10

<210> SEQ ID NO 125
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Tyr Arg Ala Arg Arg Arg Arg Arg Arg Arg Arg Trp Arg
1               5                   10

<210> SEQ ID NO 126
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Tyr Arg Ala Arg Arg Arg Arg Arg Arg Arg Arg Arg Arg Trp Arg
1               5                   10                  15

<210> SEQ ID NO 127
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Lys Gly Asp Pro Lys Lys Pro Arg Gly Lys Met Ser Ser Tyr Ala Phe
1               5                   10                  15

Phe Val Gln Thr Cys Arg Glu Glu His Lys Lys Lys His Pro Asp Ala
            20                  25                  30

Ser Val Asn Phe Ser Glu Phe Ser Lys Lys
        35                  40

<210> SEQ ID NO 128
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Lys Lys Gln Leu Lys Lys Gln Leu Lys Lys Gln Leu Lys Gln Trp Lys
1               5                   10                  15

<210> SEQ ID NO 129
<211> LENGTH: 16
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 129

Lys Lys Ser Pro Lys Lys Ser Pro Lys Lys Ser Pro Lys Lys Ser Lys
1               5                   10                  15

<210> SEQ ID NO 130
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Lys Leu Ser Lys Leu Glu Lys Lys Ser Lys Leu Glu Lys
1               5                   10

<210> SEQ ID NO 131
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Lys Leu Ser Lys Leu Glu Lys Lys Leu Ser Lys Leu Glu Lys Lys Ser
1               5                   10                  15

Lys Leu Glu Lys
            20

<210> SEQ ID NO 132
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Lys Ser Leu Lys Lys Ser Leu Lys Lys Ser Leu Lys Lys Ser Lys
1               5                   10                  15

<210> SEQ ID NO 133
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Lys Ile Arg Arg Arg Gly Lys Asn Lys Val Ala Ala Arg Thr Cys Arg
1               5                   10                  15

Gln Arg Arg Thr Asp Arg
            20

<210> SEQ ID NO 134
<211> LENGTH: 22
<212> TYPE: PRT
<213> ORGANISM: Artificial Sequence
<220> FEATURE:
<223> OTHER INFORMATION: Description of Artificial Sequence: Synthetic
```

```
                         peptide

<400> SEQUENCE: 134

Lys Ile Arg Arg Arg Gly Lys Asn Lys Val Ala Ala Gln Asn Cys Arg
1               5                   10                  15

Lys Arg Lys Leu Glu Thr
            20

<210> SEQ ID NO 135
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Lys Arg Arg Ile Arg Arg Glu Lys Asn Lys Met Ala Ala Ala Lys Cys
1               5                   10                  15

Arg Asn Arg Arg Arg Glu Leu Thr
            20

<210> SEQ ID NO 136
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Lys Asp Arg Ser Asn Leu Leu Glu Arg His Thr Arg
1               5                   10

<210> SEQ ID NO 137
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Lys Arg Pro Ala Ala Thr Lys Lys Ala Gly Gln Ala Lys Lys Lys Leu
1               5                   10                  15

<210> SEQ ID NO 138
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Arg Arg Arg Arg Arg Arg Glu Glu Glu Glu
1               5                   10

<210> SEQ ID NO 139
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139
```

```
Arg Arg Arg Arg Arg Arg Glu Glu Glu Glu Glu Glu
1               5                   10
```

<210> SEQ ID NO 140
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

```
Arg Arg Arg Arg Arg Arg Glu Glu Glu Glu Glu Glu Glu Glu
1               5                   10
```

<210> SEQ ID NO 141
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

```
Arg Arg Arg Arg Arg Arg Arg Arg Glu Glu Glu Glu
1               5                   10
```

<210> SEQ ID NO 142
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

```
Arg Arg Arg Arg Arg Arg Arg Arg Glu Glu Glu Glu Glu Glu
1               5                   10
```

<210> SEQ ID NO 143
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

```
Arg Arg Arg Arg Arg Arg Arg Arg Glu Glu Glu Glu Glu Glu Glu Glu
1               5                   10                  15
```

<210> SEQ ID NO 144
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

```
Arg Arg Arg Arg Arg Arg Arg Arg Arg Arg Arg Arg Glu Glu Glu Glu
1               5                   10                  15
```

<210> SEQ ID NO 145
<211> LENGTH: 18
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 145

Arg Arg Arg Arg Arg Arg Arg Arg Arg Arg Arg Glu Glu Glu Glu
1               5                   10                  15

Glu Glu

<210> SEQ ID NO 146
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Arg Arg Arg Arg Arg Arg Arg Arg Arg Arg Arg Arg Glu Glu Glu Glu
1               5                   10                  15

Glu Glu

<210> SEQ ID NO 147
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Lys Leu Ser Lys Leu Glu Lys Lys
1               5

<210> SEQ ID NO 148
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Ser Lys Leu Glu Lys
1               5

<210> SEQ ID NO 149
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Lys Leu Ser Lys Leu Glu Lys Lys Leu Ser Lys Leu Glu Lys Lys
1               5                   10                  15

<210> SEQ ID NO 150
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150
```

Pro Lys Lys Lys Arg Lys Val Gly Gly Gly Arg Gly Asp Ser Pro
1               5                   10                  15

<210> SEQ ID NO 151
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Leu Pro His Lys Ser Met Pro Cys Gly
1               5

<210> SEQ ID NO 152
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Gly Ala Cys Leu Gln His Lys Ser Met Pro Cys Gly
1               5                   10

<210> SEQ ID NO 153
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Tyr Gly Leu Pro His Leu Phe Cys Gly
1               5

<210> SEQ ID NO 154
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Ser Glu Arg Ser Met Asn Phe Cys Gly
1               5

<210> SEQ ID NO 155
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Asp His Tyr Ser Leu Tyr Glu Asp Leu Glu Arg Gly Thr Asp Lys
1               5                   10                  15

<210> SEQ ID NO 156
<211> LENGTH: 16
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 156

Ile Ser Leu Pro Arg Thr Ser Gly Ala Gln Arg Ala Ser Thr Thr Arg
1               5                   10                  15

<210> SEQ ID NO 157
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Glu Lys Leu Gln Thr Lys Tyr Gly Leu Pro His Lys Val Glu Phe Cys
1               5                   10                  15

Gly

<210> SEQ ID NO 158
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Thr Arg Ile Ser Glu Ser Gln Ala Lys Pro Gly Asp
1               5                   10

<210> SEQ ID NO 159
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Leu Val Phe Phe Asp Tyr
1               5

<210> SEQ ID NO 160
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Trp Gly Gly Asn Gly Pro Thr Thr Phe Asp Cys Ser Gly Tyr Thr Lys
1               5                   10                  15

Tyr Val Phe Ala Lys
            20

<210> SEQ ID NO 161
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 161

Ile Asn Ile Gly Thr Thr Gly Trp Gly Asp His Tyr Ser Leu Tyr
1               5                   10                  15

<210> SEQ ID NO 162
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Tyr Asp Asn Ile His Gly
1               5

<210> SEQ ID NO 163
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Ala Gly Trp Gly Lys Phe Leu Val Gly Phe Gly Arg Val
1               5                   10

<210> SEQ ID NO 164
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Ser Ile Gly Tyr Pro Leu Pro
1               5

<210> SEQ ID NO 165
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Thr Thr His Trp Gly Phe Thr Leu
1               5

<210> SEQ ID NO 166
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

His Leu Gln Ile Gln Pro Tyr Pro Gln Ile Ser Gly
1               5                   10

<210> SEQ ID NO 167
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 167

Lys Leu Asn Ile Val Ser Val Asn Gly
1               5

<210> SEQ ID NO 168
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Arg Gly His
1

<210> SEQ ID NO 169
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Asp Asn Arg Ile Arg Leu Gln Ala Lys Ala Ala
1               5                   10

<210> SEQ ID NO 170
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Lys Ile Lys Met Val Ile Ser Trp Lys Gly
1               5                   10

<210> SEQ ID NO 171
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Leu Pro Trp Tyr Ser Tyr Leu Tyr Ala Val Ser Ala
1               5                   10

<210> SEQ ID NO 172
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Trp Asn Leu Pro Trp Tyr Tyr Ser Val Ser Pro Thr
1               5                   10
```

```
<210> SEQ ID NO 173
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Trp Asn Leu
1

<210> SEQ ID NO 174
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Pro Trp Tyr Tyr Ser Val Ser Pro Thr
1               5

<210> SEQ ID NO 175
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Ser Ser Trp Glu Ser Tyr Lys Ser Gly Gly Gly Thr Arg Leu
1               5                   10

<210> SEQ ID NO 176
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Arg Asp Trp Ser Ser Gln His Pro Gly Arg Cys Asn Gly Glu Thr His
1               5                   10                  15

Leu Lys

<210> SEQ ID NO 177
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Ser Leu Pro Thr Leu Thr Leu
1               5

<210> SEQ ID NO 178
<211> LENGTH: 21
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 178

Val Ile Cys Thr Gly Gly Asp Tyr Ser Phe Ala Leu Pro Val Gly Gln
1               5                   10                  15

Trp Pro Val Met Thr
            20

<210> SEQ ID NO 179
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Asp Lys Pro Ser Tyr Gln Phe Gly Gly His Asn Ser Val Asp Phe Glu
1               5                   10                  15

Glu Asp Thr Leu Pro Lys Val
            20

<210> SEQ ID NO 180
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Arg Ala Arg Arg Lys Arg Ala Ser Ala Thr Gln Leu Tyr Gln Thr
1               5                   10                  15

Cys Lys Ala Ser Gly Thr Cys Pro Pro Asp
            20                  25

<210> SEQ ID NO 181
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Ser Gly Asp Tyr Ser Phe Ala Leu Pro Val Gly Gln Trp Pro Trp Met
1               5                   10                  15

Thr Gly

<210> SEQ ID NO 182
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Cys Thr Gly Gly Asp Tyr Ser Phe Ala Leu Pro Val Gly Gln Trp Pro
1               5                   10                  15

Trp

<210> SEQ ID NO 183
```

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Phe Tyr Tyr Asp Tyr Asp Phe Phe Phe Asp Tyr Trp Gly Gln Gly
1               5                   10                  15

<210> SEQ ID NO 184
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

His Leu Arg Arg Leu Arg Arg Arg Leu Leu Arg Glu Ala Glu Gly
1               5                   10                  15

<210> SEQ ID NO 185
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Asp Tyr Tyr Cys Ala Ala Trp Asp Asp Ser Leu Asn Gly Tyr Ser Val
1               5                   10                  15

Phe

<210> SEQ ID NO 186
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Tyr Tyr Cys Leu Gln Ser Met Glu Asp Pro Tyr Thr Phe Gly Gly
1               5                   10                  15

<210> SEQ ID NO 187
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Tyr Tyr Cys Ala Arg Ser Asp Gly Asn Tyr Gly Tyr Tyr Tyr Ala Leu
1               5                   10                  15

Asp Tyr Asp Tyr
            20

<210> SEQ ID NO 188
<211> LENGTH: 12
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 188

Ala Ala Arg Ser Pro Ser Tyr Tyr Arg Tyr Asp Tyr
1               5                   10

<210> SEQ ID NO 189
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Gly Pro Tyr Tyr Ala Met Asp Tyr Asp
1               5

<210> SEQ ID NO 190
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Tyr Tyr Cys Gln Gln Arg Ser Ser Tyr Pro Tyr Thr Glu Gly Gly Ala
1               5                   10                  15

Tyr Pro Lys Ala Trp Lys
            20

<210> SEQ ID NO 191
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Tyr Tyr Cys Gln Arg Tyr Asp Ser Asp Trp Ser Phe Gly Gln Gly Thr
1               5                   10                  15

Lys Leu

<210> SEQ ID NO 192
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Tyr Tyr Cys Ala Arg Ser Gly Tyr Tyr Ala Met Asp Tyr Trp Gly Gln
1               5                   10                  15

Gly Thr

<210> SEQ ID NO 193
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Arg Val Arg Arg Gly Ala Cys Arg Gly Asp Cys Leu Gly
1               5                   10

<210> SEQ ID NO 194
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Arg Val Arg Arg Gly Ala Cys Arg Tyr Asp Cys Leu Gly
1               5                   10

<210> SEQ ID NO 195
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Tyr Tyr Cys Ala Lys Gly Thr His Trp Gly Phe Trp Ser Gly Tyr Phe
1               5                   10                  15

Asp Tyr Trp Gly Gln Gly Thr
            20

<210> SEQ ID NO 196
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Gly Arg Glu Asn Tyr His Gly Cys Thr Thr His Trp Gly Phe Thr Leu
1               5                   10                  15

Cys

<210> SEQ ID NO 197
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Val Gln Ala Thr Gln Ser Asn Gln His Thr Pro Arg Gly Gly Gly Ser
1               5                   10                  15

Lys

<210> SEQ ID NO 198
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

```
Asp Pro Arg Ala Pro Gly Ser
1               5

<210> SEQ ID NO 199
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Tyr Tyr Cys Gln Gln Arg Ser Ser Tyr Pro Tyr Thr Phe Gly Gly
1               5                   10                  15

<210> SEQ ID NO 200
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Ala Ala Arg Ser Pro Ser Tyr Tyr Arg Tyr Asp Tyr Gly Pro Tyr Tyr
1               5                   10                  15

Ala Met Asp Tyr Asp
            20

<210> SEQ ID NO 201
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Gly Pro Lys Leu Thr Gly Ile Leu Ile Ser Ile Leu Ser Leu Phe Val
1               5                   10                  15

Glu Ser

<210> SEQ ID NO 202
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Lys Tyr Ile Leu Arg Trp Arg Pro Lys Asn Ser
1               5                   10

<210> SEQ ID NO 203
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Ile Lys Val Ala Val
1               5
```

```
<210> SEQ ID NO 204
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Trp Thr Pro Pro Arg Ala Gln Ile Thr Gly Tyr Arg Leu Thr Val Gly
1               5                   10                  15

Leu Thr Arg Arg
            20

<210> SEQ ID NO 205
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Ala Ala Ser Ile Lys Val Ala Val Ser Ala Asp Arg
1               5                   10

<210> SEQ ID NO 206
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Lys Leu Asp Ala Pro Thr
1               5

<210> SEQ ID NO 207
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Asn Arg Trp His Ser Ile Tyr Ile Thr Arg Phe Gly
1               5                   10

<210> SEQ ID NO 208
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Pro His Ser Arg Asn
1               5

<210> SEQ ID NO 209
<211> LENGTH: 12
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 209

Ser Ser Phe His Phe Asp Gly Ser Gly Tyr Ala Met
1               5                   10

<210> SEQ ID NO 210
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Arg Gly Asp Ser
1

<210> SEQ ID NO 211
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Ile Ala Phe Gln Arg Asn
1               5

<210> SEQ ID NO 212
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Gly Arg Gly Asp Ser Pro
1               5

<210> SEQ ID NO 213
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Thr Trp Tyr Lys Ile Ala Phe Gln Arg Arg Lys
1               5                   10

<210> SEQ ID NO 214
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Glu Asp Gly Ile His Glu Leu
1               5

```
<210> SEQ ID NO 215
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Ser Leu Val Arg Asn Arg Arg Val Ile Thr Ile Gln
1               5                   10

<210> SEQ ID NO 216
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Tyr Arg Val Arg Val Thr Pro Lys Glu Lys Thr Gly Pro Met Lys Glu
1               5                   10                  15

<210> SEQ ID NO 217
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Leu Gln Val Gln Leu Ser Arg
1               5

<210> SEQ ID NO 218
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Ser Pro Pro Arg Arg Ala Arg Val Thr
1               5

<210> SEQ ID NO 219
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Arg Lys Arg Leu Gln Val Gln Leu Ser Ile Arg Thr
1               5                   10

<210> SEQ ID NO 220
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220
```

```
Ala Thr Glu Thr Thr Ile Thr Ile Ser
1               5

<210> SEQ ID NO 221
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Asn Ala Pro Phe Pro Lys Leu Ser Trp Thr Ile Gln
1               5                   10

<210> SEQ ID NO 222
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 222

Val Ser Pro Pro Arg Arg Ala Arg Val Thr Asp Ala Thr Glu Thr Thr
1               5                   10                  15

Ile Thr Ile Ser Trp Arg Thr Lys Thr Glu Thr Ile Thr Gly Gly
            20                  25                  30

<210> SEQ ID NO 223
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Trp Thr Ile Gln Thr Thr Val Asp Arg Gly Leu Leu
1               5                   10

<210> SEQ ID NO 224
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Lys Pro Asp Val Arg Ser Tyr Thr Ile Thr Gly
1               5                   10

<210> SEQ ID NO 225
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Asp Thr Ile Asn Asn Gly Arg Asp His Met Ile Leu Ile
1               5                   10

<210> SEQ ID NO 226
```

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Ala Asn Gly Gln Thr Pro Ile Gln Arg Tyr Ile Lys
1               5                   10

<210> SEQ ID NO 227
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Met Ile Leu Ile Ser Ile Gly Lys Ser Gln Lys Arg Met
1               5                   10

<210> SEQ ID NO 228
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 228

Pro Arg Ala Arg Ile Thr Gly Tyr Ile Ile Lys Tyr Glu Lys Pro Gly
1               5                   10                  15

Ser Pro Pro Arg Glu Val Val Pro Arg Pro Arg Pro Gly Val
            20                  25                  30

<210> SEQ ID NO 229
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Pro Pro Phe Leu Met Leu Leu Lys Gly Ser Thr Arg
1               5                   10

<210> SEQ ID NO 230
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Trp Gln Pro Pro Arg Ala Arg Ile
1               5

<210> SEQ ID NO 231
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 231

Asn Gln Arg Leu Ala Ser Phe Ser Asn Ala Gln Gln Ser
1               5                   10

<210> SEQ ID NO 232
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Trp Gln Pro Pro Arg Ala Arg Ile Thr Gly Tyr Ile Ile Lys Tyr Glu
1               5                   10                  15

Lys Pro Gly

<210> SEQ ID NO 233
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Ile Ser Asn Val Phe Val Gln Arg Met Ser Gln Ser Pro Glu Val Leu
1               5                   10                  15

Asp

<210> SEQ ID NO 234
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Tyr Glu Lys Pro Gly Ser Pro Pro Arg Glu Val Val Pro Arg Pro Arg
1               5                   10                  15

Pro Gly Val

<210> SEQ ID NO 235
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Lys Ala Arg Ser Phe Asn Val Asn Gln Leu Leu Gln Asp
1               5                   10

<210> SEQ ID NO 236
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

```
Lys Asn Asn Gln Lys Ser Glu Pro Leu Ile Gly Arg Lys Lys Thr
1               5                   10                  15

<210> SEQ ID NO 237
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Lys Asn Ser Phe Met Ala Leu Tyr Leu Ser Lys Gly
1               5                   10

<210> SEQ ID NO 238
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Glu Ile Leu Asp Val Pro Ser Thr
1               5

<210> SEQ ID NO 239
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Lys Asn Ser Phe Met Ala Leu Tyr Leu Ser Lys Gly Arg Leu Val Phe
1               5                   10                  15

Ala Leu Gly

<210> SEQ ID NO 240
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Ile Asp Ala Pro Ser
1               5

<210> SEQ ID NO 241
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Arg Asp Ser Phe Val Ala Leu Tyr Leu Ser Glu Gly His Val Ile Phe
1               5                   10                  15

Ala Gly Leu Gly
            20
```

```
<210> SEQ ID NO 242
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Val Val Ile Asp Ala Ser Thr Ala Ile Asp Ala Pro Ser Asn Leu
1               5                   10                  15

<210> SEQ ID NO 243
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Lys Pro Arg Leu Gln Phe Ser Leu Asp Ile Gln Thr
1               5                   10

<210> SEQ ID NO 244
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Leu Asp Val Pro Ser
1               5

<210> SEQ ID NO 245
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Asp Gly Gln Trp His Ser Val Thr Val Ser Ile Lys
1               5                   10

<210> SEQ ID NO 246
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Arg Glu Asp Val
1

<210> SEQ ID NO 247
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247
```

```
Phe Val Leu Tyr Leu Gly Ser Lys Asn Ala Lys Lys
1               5                   10

<210> SEQ ID NO 248
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Pro His Ser Arg Asn Arg Gly Asp Ser Pro
1               5                   10

<210> SEQ ID NO 249
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Leu Ala Ile Lys Asn Asp Asn Leu Val Tyr Val Tyr
1               5                   10

<210> SEQ ID NO 250
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Leu Trp Val Thr Val Arg Ser Gln Gln Arg Gly Leu Phe
1               5                   10

<210> SEQ ID NO 251
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Ala Tyr Phe Ser Ile Val Lys Ile Glu Arg Val Gly
1               5                   10

<210> SEQ ID NO 252
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Gly Thr Asn Asn Trp Trp Gln Ser Pro Ser Ile Gln Asn
1               5                   10

<210> SEQ ID NO 253
<211> LENGTH: 12
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 253

Asp Val Ile Ser Leu Tyr Asn Phe Lys His Ile Tyr
1               5                   10

<210> SEQ ID NO 254
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Trp Val Thr Val Thr Leu Asp Leu Arg Gln Val Phe Gln
1               5                   10

<210> SEQ ID NO 255
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Phe Phe Asp Gly Ser Ser Tyr Ala Val Val Arg Asp
1               5                   10

<210> SEQ ID NO 256
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Arg Gln Val Phe Gln Val Ala Tyr Ile Ile Ile Lys Ala
1               5                   10

<210> SEQ ID NO 257
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Leu His Val Phe Tyr Asp Phe Gly Phe Gly Phe Ser Asn Gly
1               5                   10

<210> SEQ ID NO 258
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Leu Thr Arg Tyr Lys Ile Thr Pro Arg Arg Gly Pro Pro Thr
1               5                   10
```

```
<210> SEQ ID NO 259
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Leu Lys Lys Ala Gln Ile Asn Asp Ala Lys Tyr Arg Glu Ile Ser Ile
1               5                   10                  15

Ile Tyr His Asn
            20

<210> SEQ ID NO 260
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Leu Leu Glu Phe Thr Ser Ala Arg Tyr Ile Arg Leu
1               5                   10

<210> SEQ ID NO 261
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Arg Ala Tyr Phe Asn Gly Gln Ser Phe Ile Ala Ser
1               5                   10

<210> SEQ ID NO 262
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Tyr Ile Arg Leu Arg Leu Gln Arg Ile Arg Thr Leu
1               5                   10

<210> SEQ ID NO 263
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Ser Arg Leu Arg Gly Lys Asn Pro Thr Lys Gly Lys
1               5                   10

<210> SEQ ID NO 264
<211> LENGTH: 12
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 264

Arg Arg Tyr Tyr Tyr Ser Ile Lys Asp Ile Ser Val
1               5                   10

<210> SEQ ID NO 265
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Leu His Lys Lys Gly Lys Asn Ser Ser Lys Pro Lys
1               5                   10

<210> SEQ ID NO 266
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Ser Ile Asn Asn Thr Ala Val Asn Gln Arg Leu Thr
1               5                   10

<210> SEQ ID NO 267
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Arg Leu Lys Thr Arg Ser Ser His Gly Met Ile Phe
1               5                   10

<210> SEQ ID NO 268
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Gly Gly Phe Leu Lys Tyr Thr Val Ser Tyr Asp Ile
1               5                   10

<210> SEQ ID NO 269
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Gly Glu Lys Ser Gln Phe Ser Ile Arg Leu Lys Thr
1               5                   10
```

```
<210> SEQ ID NO 270
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Arg Asp Gln Leu Met Thr Val Leu Ala Asn Val Thr
1               5                   10

<210> SEQ ID NO 271
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Thr Leu Phe Leu Ala His Gly Arg Leu Val Phe Met
1               5                   10

<210> SEQ ID NO 272
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Ala Asn Val Thr His Leu Leu Ile Arg Ala Asn Tyr
1               5                   10

<210> SEQ ID NO 273
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

Leu Val Phe Met Phe Asn Val Gly His Lys Lys Leu
1               5                   10

<210> SEQ ID NO 274
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 274

Ala Gly Thr Phe Ala Leu Arg Gly Asp Asn Pro Gln Gly
1               5                   10

<210> SEQ ID NO 275
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 275
```

```
Thr Leu Phe Leu Ala His Gly Arg Leu Val Phe Met Phe Asn Val Gly
1               5                   10                  15

His Lys Lys Leu
            20

<210> SEQ ID NO 276
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

Val Leu Ile Lys Gly Gly Arg Ala Arg Lys His Val
1               5                   10

<210> SEQ ID NO 277
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 277

Asp Phe Met Thr Leu Phe Leu Ala His Gly Arg Leu Val Phe Met Gly
1               5                   10                  15

Asn Val Gly

<210> SEQ ID NO 278
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

Leu Ser Asn Ile Asp Tyr Leu Ile Lys Ala Ser
1               5                   10

<210> SEQ ID NO 279
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

His Lys Lys Leu Lys Ile Arg Ser Gln Glu Lys Tyr
1               5                   10

<210> SEQ ID NO 280
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

Leu Gln Gln Ser Arg Ile Ala Asn Ile Ser Met Glu
1               5                   10
```

```
<210> SEQ ID NO 281
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

Gly Ala Ala Trp Lys Ile Lys Gly Pro Ile Tyr Leu
1               5                   10

<210> SEQ ID NO 282
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282

Asn Leu Leu Leu Leu Leu Val Lys Ala Asn Leu Lys
1               5                   10

<210> SEQ ID NO 283
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283

Val Ile Arg Asp Ser Asn Val Val Gln Leu Asp Val
1               5                   10

<210> SEQ ID NO 284
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

His Arg Asp Glu Leu Leu Leu Trp Ala Arg Lys Ile
1               5                   10

<210> SEQ ID NO 285
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

Gly Leu Ile Tyr Tyr Val Ala His Gln Asn Gln Met
1               5                   10

<210> SEQ ID NO 286
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 286

Lys Arg Arg Ala Arg Asp Leu Val His Arg Ala Glu
1               5                   10

<210> SEQ ID NO 287
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 287

Asp Tyr Ala Thr Leu Gln Leu Gln Glu Gly Arg Leu His Phe Met Phe
1               5                   10                  15

Asp Leu Gly

<210> SEQ ID NO 288
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 288

Ser Gln Phe Gln Glu Ser Val Asp Asn Ile Thr Lys
1               5                   10

<210> SEQ ID NO 289
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 289

Lys Lys Gly Ser Tyr Asn Asn Ile Val Val His Val
1               5                   10

<210> SEQ ID NO 290
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 290

Pro Gly Gly Met Arg Glu Lys Gly Arg Lys Ala Arg
1               5                   10

<210> SEQ ID NO 291
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 291

Ala Asp Asn Leu Leu Phe Tyr Leu Gly Ser Ala Lys
1               5                   10

<210> SEQ ID NO 292
```

```
<210> SEQ ID NO 292
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

Met Glu Met Gln Ala Asn Leu Leu Leu Asp Arg Leu
1               5                   10

<210> SEQ ID NO 293
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 293

Gly Ser Ala Lys Phe Ile Asp Phe Leu Ala Ile Glu
1               5                   10

<210> SEQ ID NO 294
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 294

Leu Ser Glu Ile Lys Leu Leu Ile Ser Ala Arg
1               5                   10

<210> SEQ ID NO 295
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 295

Lys Val Ser Phe Leu Trp Trp Val Gly Ser Gly Val
1               5                   10

<210> SEQ ID NO 296
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 296

Arg Asp Phe Thr Lys Ala Thr Asn Ile Arg Leu Arg Phe Leu Arg
1               5                   10                  15

<210> SEQ ID NO 297
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 297
```

```
Ser Tyr Trp Tyr Arg Ile Glu Ala Ser Arg Thr Gly
1               5                   10
```

<210> SEQ ID NO 298
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 298

```
Ile Ser Thr Val Met Phe Lys Phe Arg Thr Phe Ser
1               5                   10
```

<210> SEQ ID NO 299
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 299

```
Tyr Phe Asp Gly Thr Gly Phe Ala Lys Ala Val Gly
1               5                   10
```

<210> SEQ ID NO 300
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 300

```
Lys Gln Ala Asn Ile Ser Ile Val Asp Ile Asp Ser Asn
1               5                   10
```

<210> SEQ ID NO 301
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 301

```
Asn Gly Gln Trp His Lys Val Thr Ala Lys Lys Ile
1               5                   10
```

<210> SEQ ID NO 302
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 302

```
Phe Ser Thr Arg Asn Glu Ser Gly Ile Ile Leu Leu
1               5                   10
```

<210> SEQ ID NO 303
<211> LENGTH: 12
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 303

Ala Lys Lys Ile Lys Asn Arg Leu Glu Leu Val Val
1               5                   10

<210> SEQ ID NO 304
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 304

Arg Arg Gln Thr Thr Gln Ala Tyr Tyr Ala Ile Phe
1               5                   10

<210> SEQ ID NO 305
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 305

Gly Phe Pro Gly Gly Leu Asn Gln Phe Gly Leu Thr Thr Asn
1               5                   10

<210> SEQ ID NO 306
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 306

Tyr Ala Ile Phe Leu Asn Lys Gly Arg Leu Glu Val
1               5                   10

<210> SEQ ID NO 307
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 307

Asn Gln Phe Gly Leu Thr Thr Asn Ile Arg Phe Arg Gly
1               5                   10

<210> SEQ ID NO 308
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 308

Lys Asn Arg Leu Thr Ile Glu Leu Glu Val Arg Thr
1               5                   10
```

```
<210> SEQ ID NO 309
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 309

Ile Arg Ser Leu Lys Leu Thr Lys Gly Thr Gly Lys Pro
1               5                   10

<210> SEQ ID NO 310
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 310

Gly Leu Leu Phe Tyr Met Ala Arg Ile Asn His Ala
1               5                   10

<210> SEQ ID NO 311
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 311

Ala Lys Ala Leu Glu Leu Arg Gly Val Gln Pro Val Ser
1               5                   10

<210> SEQ ID NO 312
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 312

Val Gln Leu Arg Asn Gly Phe Pro Tyr Phe Ser Tyr
1               5                   10

<210> SEQ ID NO 313
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 313

Gly Gln Leu Phe His Val Ala Tyr Ile Leu Ile Lys Phe
1               5                   10

<210> SEQ ID NO 314
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 314
```

```
His Lys Ile Lys Ile Val Arg Val Lys Gln Glu Gly
1               5                   10

<210> SEQ ID NO 315
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 315

Asn Val Leu Ser Leu Tyr Asn Phe Lys Thr Thr Phe
1               5                   10

<210> SEQ ID NO 316
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 316

Asp Phe Gly Thr Val Gln Leu Arg Asn Gly Phe Pro Phe Phe Ser Tyr
1               5                   10                  15

Asp Leu Gly

<210> SEQ ID NO 317
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 317

Ser Gln Arg Ile Tyr Gln Phe Ala Lys Leu Asn Tyr Thr
1               5                   10

<210> SEQ ID NO 318
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 318

Asn Ile Arg Leu Arg Phe Leu Arg Thr Asn Thr Leu
1               5                   10

<210> SEQ ID NO 319
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 319

Glu Val Asn Val Thr Leu Asp Leu Gly Gln Val Phe His
1               5                   10

<210> SEQ ID NO 320
<211> LENGTH: 12
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 320

Gly Lys Asn Thr Gly Asp His Phe Val Leu Tyr Met
1               5                   10

<210> SEQ ID NO 321
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 321

Gly Gln Val Phe His Val Ala Tyr Val Leu Ile Lys Phe
1               5                   10

<210> SEQ ID NO 322
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 322

Val Val Ser Leu Tyr Asn Phe Glu Gln Thr Phe Met Leu
1               5                   10

<210> SEQ ID NO 323
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 323

His Gln Gln Asp Leu Gly Thr Ala Gly Ser Cys Leu Arg Lys Phe Ser
1               5                   10                  15

Thr Met Phe Leu Phe
            20

<210> SEQ ID NO 324
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 324

Arg Phe Asp Gln Glu Leu Arg Leu Val Ser Tyr Asn
1               5                   10

<210> SEQ ID NO 325
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 325

His Gln Gln Asp Leu Gly Thr Ala Gly Ser Cys Leu Arg Lys Phe Ser
1               5                   10                  15

Thr Met Phe Leu Phe Cys Asn Ile
            20

<210> SEQ ID NO 326
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 326

Arg Leu Val Ser Tyr Ser Gly Val Leu Phe Phe Leu Lys
1               5                   10

<210> SEQ ID NO 327
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 327

Val Ala Glu Ile Asp Gly Ile Glu Leu
1               5

<210> SEQ ID NO 328
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 328

Asn Trp Arg His Ile Ser Tyr Ile Thr Arg Phe Gly
1               5                   10

<210> SEQ ID NO 329
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 329

Gly Ile Ile Phe Phe Leu
1               5

<210> SEQ ID NO 330
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 330

Lys Arg Leu Gln Val Gln Leu Arg Ser Ile Arg Thr
1               5                   10
```

```
<210> SEQ ID NO 331
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 331

Ala Ser Lys Ala Ile Gln Val Phe Leu Leu Gly Gly
1               5                   10

<210> SEQ ID NO 332
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 332

Thr Trp Tyr Lys Ile Ala Phe Gln Arg Asn Arg Lys
1               5                   10

<210> SEQ ID NO 333
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 333

Val Leu Val Arg Val Glu Arg Ala Thr Val Phe Ser
1               5                   10

<210> SEQ ID NO 334
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 334

Gln Val Phe Gln Val Ala Tyr Ile Ile Ile Lys Ala
1               5                   10

<210> SEQ ID NO 335
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 335

Thr Val Phe Ser Val Asp Gln Asp Asn Met Leu Glu
1               5                   10

<210> SEQ ID NO 336
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 336
```

```
Gly Glu Phe Tyr Phe Asp Leu Arg Leu Lys Gly Asp Lys
1               5                   10

<210> SEQ ID NO 337
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 337

Arg Leu Arg Gly Pro Gln Arg Val Phe Asp Leu His
1               5                   10

<210> SEQ ID NO 338
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 338

Gly Thr Pro Gly Pro Gln Gly Ile Ala
1               5

<210> SEQ ID NO 339
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 339

Phe Asp Leu His Gln Asn Met Gly Ser Val Asn
1               5                   10

<210> SEQ ID NO 340
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 340

Gly Gln Arg Asp Val Val
1               5

<210> SEQ ID NO 341
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 341

Leu Arg Ala His Ala Val Asp Val Asn Gly
1               5                   10

<210> SEQ ID NO 342
<211> LENGTH: 12
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 342

Thr Ala Gly Ser Cys Leu Arg Lys Phe Ser Thr Met
1               5                   10

<210> SEQ ID NO 343
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 343

Leu Phe Ser His Ala Val Ser Ser Asn Gly
1               5                   10

<210> SEQ ID NO 344
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 344

Lys Gly His Arg Gly Phe
1               5

<210> SEQ ID NO 345
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 345

Thr Ala Gly Ser Cys Leu Arg Lys Phe Ser Thr Met Phe Leu Phe
1               5                   10                  15

<210> SEQ ID NO 346
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 346

Thr Ala Gly Ser Cys Leu Arg Lys Phe Ser Thr Met Phe Leu Phe Cys
1               5                   10                  15

Asn Ile

<210> SEQ ID NO 347
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 347

Asp Leu Gly Thr Ala Gly Ser Cys Leu Arg Lys Phe Ser Thr Met
```

<210> SEQ ID NO 348
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 348

His Gln Gln Asp Leu Gly Thr Ala Gly Ser Cys Leu Arg Lys Phe Ser
1               5                   10                  15

Thr Met

<210> SEQ ID NO 349
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 349

Arg Asn Ile Ala Glu Ile Ile Lys Asp Ile
1               5                   10

<210> SEQ ID NO 350
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 350

Ser Ile Gly Phe Arg Gly Asp Gly Gln Thr Cys
1               5                   10

<210> SEQ ID NO 351
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 351

Leu Asn Arg Gln Glu Leu Phe Pro Phe Gly
1               5                   10

<210> SEQ ID NO 352
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 352

Arg Ile Gln Asn Leu Leu Lys Ile Thr Asn Leu Arg Ile Lys Phe Val
1               5                   10                  15

Lys

<210> SEQ ID NO 353
<211> LENGTH: 16

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 353

Lys Lys Gln Arg Phe Arg His Arg Asn Arg Lys Gly Tyr Arg Ser Gln
1               5                   10                  15

<210> SEQ ID NO 354
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 354

Ser Ile Asn Asn Thr Ala Val Met Gln Arg Leu Thr
1               5                   10

<210> SEQ ID NO 355
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 355

Phe Arg His Arg Asn Arg Lys Gly Tyr
1               5

<210> SEQ ID NO 356
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 356

Arg Tyr Arg Val Arg Val Thr Pro Lys Glu Lys Thr Gly Pro Met Lys
1               5                   10                  15

Glu

<210> SEQ ID NO 357
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 357

Ser Glu Thr Thr Val Lys Tyr Ile Phe Arg Leu His Glu
1               5                   10

<210> SEQ ID NO 358
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 358

```
Gly His Arg Gly Pro Thr Gly Arg Pro Gly Lys Arg Gly Lys Gln Gly
1               5                   10                  15

Gln Lys Gly Asp Ser
            20

<210> SEQ ID NO 359
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 359

Lys Ala Phe Asp Ile Thr Tyr Val Arg Leu Lys Phe
1               5                   10

<210> SEQ ID NO 360
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 360

Gly Asp Leu Gly Arg Pro Gly Arg Lys Gly Arg Pro Gly Pro Pro
1               5                   10                  15

<210> SEQ ID NO 361
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 361

Tyr Ile Gly Ser Arg
1               5

<210> SEQ ID NO 362
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 362

Arg Gly Glu Phe Tyr Phe Asp Leu Arg Leu Lys Gly Asp Lys
1               5                   10

<210> SEQ ID NO 363
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 363

Leu Ala Gly Ser Cys Leu Ala Arg Phe Ser Thr Met
1               5                   10

<210> SEQ ID NO 364
```

```
<210> SEQ ID NO 364
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 364

Leu Ala Leu Phe Leu Ser Asn Gly His Phe Val Ala
1               5                   10

<210> SEQ ID NO 365
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 365

Ile Ser Arg Cys Gln Val Cys Met Lys Lys Arg His
1               5                   10

<210> SEQ ID NO 366
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 366

Pro Gly Arg Trp His Lys Val Ser Val Arg Trp Glu
1               5                   10

<210> SEQ ID NO 367
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 367

Thr Asp Ile Pro Pro Cys Pro His Gly Trp Ile Ser Leu Trp Lys
1               5                   10                  15

<210> SEQ ID NO 368
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 368

Val Arg Trp Gly Met Gln Gln Ile Gln Leu Val Val
1               5                   10

<210> SEQ ID NO 369
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 369
```

```
Thr Ala Ile Pro Ser Cys Pro Glu Gly Thr Val Pro Leu Tyr Ser
1               5                   10                  15
```

<210> SEQ ID NO 370
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 370

```
Lys Met Pro Tyr Val Ser Leu Glu Leu Glu Met Arg
1               5                   10
```

<210> SEQ ID NO 371
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 371

```
Gly Pro Ala Gly Lys Asp Gly Glu Ala Gly Ala Gln Gly
1               5                   10
```

<210> SEQ ID NO 372
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 372

```
Val Leu Leu Gln Ala Asn Asp Gly Ala Gly Glu Phe
1               5                   10
```

<210> SEQ ID NO 373
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 373

```
Gly Leu Pro Gly Glu Arg
1               5
```

<210> SEQ ID NO 374
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 374

```
Asp Gly Arg Trp His Arg Val Ala Val Ile Met Gly
1               5                   10
```

<210> SEQ ID NO 375
<211> LENGTH: 12
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 375

Leu Ala Gly Ser Cys Leu Pro Val Phe Ser Thr Leu
1               5                   10

<210> SEQ ID NO 376
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 376

Ala Pro Val Asn Val Thr Ala Ser Val Gln Ile Gln
1               5                   10

<210> SEQ ID NO 377
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 377

Thr Ala Gly Ser Cys Leu Arg Arg Phe Ser Thr Met
1               5                   10

<210> SEQ ID NO 378
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 378

Lys Gln Gly Lys Ala Leu Thr Gln Arg His Ala Lys
1               5                   10

<210> SEQ ID NO 379
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 379

Thr Ala Gly Ser Cys Leu Arg Lys Phe
1               5

<210> SEQ ID NO 380
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 380

Arg Tyr Val Val Leu Pro Arg
1               5

```
<210> SEQ ID NO 381
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 381

Thr Ala Gly Ser Cys Leu
1               5

<210> SEQ ID NO 382
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 382

Ser Pro Tyr Thr Phe Ile Asp Ser Leu Val Leu Met Pro Tyr
1               5                   10

<210> SEQ ID NO 383
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 383

Thr Ala Gly
1

<210> SEQ ID NO 384
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 384

Pro Asp Ser Gly Arg
1               5

<210> SEQ ID NO 385
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 385

Gln Gln Asn Leu Gly Ser Val Asn Val Ser Thr Gly
1               5                   10

<210> SEQ ID NO 386
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 386
```

```
Ser Arg Ala Thr Ala Gln Lys Val Ser Arg Arg Ser
1               5                  10

<210> SEQ ID NO 387
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 387

Asp Pro Gly Tyr Ile Gly Ser Arg
1               5

<210> SEQ ID NO 388
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 388

Gly Ser Leu Ser Ser His Leu Glu Phe Val Gly Ile
1               5                  10

<210> SEQ ID NO 389
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 389

Val Ile Leu Gln Gln Ser Ala Ala Asp Ile Ala Arg
1               5                  10

<210> SEQ ID NO 390
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 390

Arg Asn Arg Leu His Leu Ser Met Leu Val Arg Pro
1               5                  10

<210> SEQ ID NO 391
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 391

Lys Asp Ile Ser Glu Lys Val Ala Val Tyr Ser Thr
1               5                  10

<210> SEQ ID NO 392
<211> LENGTH: 13
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 392

Ala Pro Met Ser Gly Arg Ser Pro Ser Leu Val Leu Lys
1               5                   10

<210> SEQ ID NO 393
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 393

Leu Gly Thr Ile Pro Gly
1               5

<210> SEQ ID NO 394
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 394

Ala Phe Gly Val Leu Ala Leu Trp Gly Thr Arg Val
1               5                   10

<210> SEQ ID NO 395
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 395

Thr Asp Ile Arg Val Thr Leu Asn Arg Leu Asn Thr Phe
1               5                   10

<210> SEQ ID NO 396
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 396

Ile Glu Asn Val Val Thr Thr Phe Ala Pro Asn Arg
1               5                   10

<210> SEQ ID NO 397
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 397

Ala Phe Ser Thr Leu Glu Gly Arg Pro Ser Ala Tyr
1               5                   10
```

<210> SEQ ID NO 398
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 398

Leu Glu Ala Glu Phe His Phe Thr His Leu Ile Met
1               5                   10

<210> SEQ ID NO 399
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 399

Thr Ser Ala Glu Ala Tyr Asn Leu Leu Leu Arg Thr
1               5                   10

<210> SEQ ID NO 400
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 400

His Leu Ile Met Thr Phe Lys Thr Phe Arg Pro Ala
1               5                   10

<210> SEQ ID NO 401
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 401

Leu Asn Arg Arg Tyr Glu Gln Ala Arg Asn Ile Ser
1               5                   10

<210> SEQ ID NO 402
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 402

Lys Thr Trp Gly Val Tyr Arg Tyr Phe Ala Tyr Asp
1               5                   10

<210> SEQ ID NO 403
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 403

Ser Leu Leu Ser Gln Leu Asn Asn Leu Leu Asp Gln
1               5                   10

<210> SEQ ID NO 404
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 404

Thr Asn Leu Arg Ile Lys Phe Val Lys Leu His Thr
1               5                   10

<210> SEQ ID NO 405
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 405

Arg Asp Ile Ala Glu Ile Ile Lys Asp Ile
1               5                   10

<210> SEQ ID NO 406
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 406

Lys Arg Leu Val Thr Gly Gln Arg
1               5

<210> SEQ ID NO 407
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 407

Ser His Ala Val Ser Ser
1               5

<210> SEQ ID NO 408
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 408

Gly Pro Gly Val Val Val Val Glu Arg Gln Tyr Ile
1               5                   10

<210> SEQ ID NO 409
<211> LENGTH: 6
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 409

Ala Asp Thr Pro Pro Val
1               5

<210> SEQ ID NO 410
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 410

Asn Glu Pro Lys Val Leu Lys Ser Tyr Tyr Tyr Ala Ile
1               5                   10

<210> SEQ ID NO 411
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 411

Leu Arg Ala His Ala Val Asp Ile Asn Gly
1               5                   10

<210> SEQ ID NO 412
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 412

Tyr Tyr Ala Ile Ser Asp Phe Ala Val Gly Gly Arg
1               5                   10

<210> SEQ ID NO 413
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 413

Asp Ser Ile Thr Lys Tyr Phe Gln Met Ser Leu Glu
1               5                   10

<210> SEQ ID NO 414
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 414

Leu Pro Phe Phe Asn Asp Arg Pro Trp Arg Arg Ala Thr
1               5                   10
```

<210> SEQ ID NO 415
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 415

Tyr Thr Ala Leu Ile Ile Ala Thr Asp Asn
1               5                   10

<210> SEQ ID NO 416
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 416

Phe Asp Pro Glu Leu Tyr Arg Ser Thr Gly His Gly Gly His
1               5                   10

<210> SEQ ID NO 417
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 417

Val Ile Thr Val Lys Asp Ile Asn Asp Asn
1               5                   10

<210> SEQ ID NO 418
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 418

Thr Asn Ala Val Gly Tyr Ser Val Tyr Asp Ile Ser
1               5                   10

<210> SEQ ID NO 419
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 419

Gly Leu Asp Arg Glu Ser Tyr Pro Tyr Tyr
1               5                   10

<210> SEQ ID NO 420
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 420

Ala Pro Val Lys Phe Leu Gly Asn Gln Val Leu Ser Tyr
1               5                   10

<210> SEQ ID NO 421
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 421

Met Lys Val Ser Ala Thr Asp Ala Asp Asp
1               5                   10

<210> SEQ ID NO 422
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 422

Ser Phe Ser Phe Arg Val Asp Arg Arg Asp Thr Arg
1               5                   10

<210> SEQ ID NO 423
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 423

Pro Gln Val Thr Arg Gly Asp Val Phe Thr Met Pro
1               5                   10

<210> SEQ ID NO 424
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 424

Thr Trp Ser Lys Val Gly Gly His Leu Arg Pro Gly Ile Val Gln Ser
1               5                   10                  15

Gly

<210> SEQ ID NO 425
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 425

Lys Glu Ala Glu Arg Glu Val Thr Asp Leu Leu Arg
1               5                   10

```
<210> SEQ ID NO 426
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 426

Arg Gly Asp Val
1

<210> SEQ ID NO 427
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 427

Ala Ala Glu Pro Leu Lys Asn Ile Gly Ile Leu Phe
1               5                   10

<210> SEQ ID NO 428
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 428

Phe Ala Leu Trp Asp Ala Ile Ile Gly Glu Leu
1               5                   10

<210> SEQ ID NO 429
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 429

Val Gly Val Ala Pro Gly
1               5

<210> SEQ ID NO 430
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 430

Leu Trp Pro Leu Leu Ala Val Leu Ala Ala Val Ala
1               5                   10

<210> SEQ ID NO 431
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 431
```

```
Pro Gly Val Gly Val
1               5

<210> SEQ ID NO 432
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 432

Val Phe Asp Asn Phe Val Leu Lys
1               5

<210> SEQ ID NO 433
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 433

Thr Ser Ile Lys Ile Arg Gly Thr Tyr Ser Glu Arg
1               5                   10

<210> SEQ ID NO 434
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 434

Thr Thr Ser Trp Ser Gln Cys Ser Lys Ser
1               5                   10

<210> SEQ ID NO 435
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 435

Asp Pro Glu Thr Gly Val
1               5

<210> SEQ ID NO 436
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 436

Lys Arg Ser Arg
1

<210> SEQ ID NO 437
<211> LENGTH: 10
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 437

Gln Gly Ala Asp Thr Pro Pro Val Gly Val
1               5                   10

<210> SEQ ID NO 438
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 438

Ser Val Val Tyr Gly Leu Arg
1               5

<210> SEQ ID NO 439
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 439

Pro Leu Asp Arg Glu Ala Ile Ala Lys Tyr
1               5                   10

<210> SEQ ID NO 440
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 440

Asp Gly Arg Gly Asp Ser Val Ala Tyr Gly
1               5                   10

<210> SEQ ID NO 441
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 441

His Ala Val Asp Ile
1               5

<210> SEQ ID NO 442
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 442

Leu Ala Leu Glu Arg Lys Asp His Ser Gly
1               5                   10
```

<210> SEQ ID NO 443
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 443

Asp Gln Asn Asp Asn
1               5

<210> SEQ ID NO 444
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 444

Tyr Ser Met Lys Lys Thr Thr Met Lys Ile Ile Pro Phe Asn Arg Leu
1               5                   10                  15

Thr Ile Gly

<210> SEQ ID NO 445
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 445

Gln Asp Pro Glu Leu Pro Asp Lys Asn Met
1               5                   10

<210> SEQ ID NO 446
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 446

Arg Gly Asp Phe
1

<210> SEQ ID NO 447
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 447

Leu Val Val Gln Ala Ala Asp Leu Gln Gly
1               5                   10

<210> SEQ ID NO 448
<211> LENGTH: 13
<212> TYPE: PRT
<213> ORGANISM: Artificial Sequence
<220> FEATURE:
<223> OTHER INFORMATION: Description of Artificial Sequence: Synthetic

```
                                peptide

<400> SEQUENCE: 448

Gly Val Tyr Tyr Gln Gly Gly Thr Tyr Ser Lys Ala Ser
1               5                   10

<210> SEQ ID NO 449
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 449

Asn Asp Asp Gly Gly Gln Phe Val Val Thr
1               5                   10

<210> SEQ ID NO 450
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 450

Thr Ala Gly Ser Cys Leu Arg Lys Phe Ser Cys Leu
1               5                   10

<210> SEQ ID NO 451
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 451

Tyr Ile Leu His Val Ala Val Thr Asn
1               5

<210> SEQ ID NO 452
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 452

Cys Asn Tyr Tyr Ser Asn Ser Tyr Ser Phe Trp Leu Ala Ser Leu Asn
1               5                   10                  15

Pro Glu Arg

<210> SEQ ID NO 453
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 453

Thr Tyr Arg Ile Trp Arg Asp Thr Ala Asn
1               5                   10
```

```
<210> SEQ ID NO 454
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 454

Thr Gly Leu Ser Cys Leu Gln Arg Phe Thr Thr Met
1               5                   10

<210> SEQ ID NO 455
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 455

Gly Phe Thr Cys Glu Cys Ser Ile Gly Phe Arg Gly Asp Gly Gln Thr
1               5                   10                  15

Cys Tyr Gly Ile Val Phe Trp Ser Glu Val
            20                  25

<210> SEQ ID NO 456
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 456

His His Leu Gly Gly Ala Lys Gln Ala Gly Asp Val
1               5                   10

<210> SEQ ID NO 457
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 457

Ser Cys Leu Pro Gly Phe Ser Gly Asp Gly Arg Ala Cys Arg Asp Val
1               5                   10                  15

Asp Glu Cys Gly His
            20

<210> SEQ ID NO 458
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 458

Met Ala Pro Arg Pro Ser Leu Ala Lys Lys Gln Arg Phe Arg His Arg
1               5                   10                  15

Asn Arg Lys Gly Tyr Arg Ser Gln Arg Gly His Ser Arg Gly
            20                  25                  30
```

<210> SEQ ID NO 459
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 459

Lys Lys Gln Lys Phe Arg His Arg Asn Arg Lys Gly Tyr Arg Ser Gln
1               5                   10                  15

<210> SEQ ID NO 460
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 460

Lys Lys Gln Lys Phe Lys His Arg Asn Arg Lys Gly Tyr Arg Ser
1               5                   10                  15

<210> SEQ ID NO 461
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 461

Lys Lys Gln Lys Phe Arg Arg Arg Asn Arg Lys Gly Tyr Arg Ser His
1               5                   10                  15

<210> SEQ ID NO 462
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 462

Thr Ala Ile Pro Pro Cys Pro His Gly Trp Ile Ser Leu Trp Lys
1               5                   10                  15

<210> SEQ ID NO 463
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 463

Lys Lys Gln Lys Ser Arg His Arg Ser Arg Lys Arg Tyr Arg Ser
1               5                   10                  15

<210> SEQ ID NO 464
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

```
-continued

<400> SEQUENCE: 464

Lys Lys Gln Lys Ser Arg Arg Arg Ser Arg Lys Gly Tyr Arg Ser
1               5                   10                  15

<210> SEQ ID NO 465
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 465

Ile Ser Arg Cys Thr Val Cys
1               5

<210> SEQ ID NO 466
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 466

Ile Ser Arg Cys Gln Val Cys Met Lys Arg Arg His
1               5                   10

<210> SEQ ID NO 467
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 467

Val Ser Arg Cys Thr Val Cys
1               5

<210> SEQ ID NO 468
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 468

Thr Asp Ile Pro Pro Cys Pro Gln Gly Trp Ile Ser Leu Trp Lys
1               5                   10                  15

<210> SEQ ID NO 469
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 469

Thr Val Lys Ala Gly Glu Leu Glu Lys Ile Ile Ser Arg Cys Gln Val
1               5                   10                  15

Met Lys Lys Arg His
            20
```

```
<210> SEQ ID NO 470
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 470

Thr Asp Ile Pro Ser Cys Pro His Gly Trp Ile Ser Leu Trp Lys
1               5                   10                  15

<210> SEQ ID NO 471
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 471

Thr Asp Ile Pro Pro Cys Pro Ala Gly Trp Ile Ser Leu Trp Lys
1               5                   10                  15

<210> SEQ ID NO 472
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 472

Thr Glu Ile Pro Pro Cys Pro Gln Gly Trp Ile Ser Leu Trp Lys
1               5                   10                  15

<210> SEQ ID NO 473
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 473

Thr Asp Val Pro Pro Cys Pro Gln Gly Trp Ile Ser Leu Trp Lys
1               5                   10                  15

<210> SEQ ID NO 474
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 474

Arg Leu Val Ser Tyr Asn Gly Ile Leu Phe Phe Leu Lys
1               5                   10

<210> SEQ ID NO 475
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 475
```

Arg Leu Val Ser Tyr Ser Gly Val Ile Phe Phe Leu Lys
1               5                   10

<210> SEQ ID NO 476
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 476

Arg Leu Val Ser Tyr Asn Gly Ile Leu Phe Phe Leu
1               5                   10

<210> SEQ ID NO 477
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 477

Arg Leu Val Ser Tyr Ser Gly Ile Ile Phe Phe Leu Lys
1               5                   10

<210> SEQ ID NO 478
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 478

Arg Phe Glu Gln Glu Leu Arg Leu Val Ser Tyr Ser Gly Val Leu Phe
1               5                   10                  15

Phe Leu Lys Gln
            20

<210> SEQ ID NO 479
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 479

Arg Leu Val Ser Tyr Asn Gly Ile Ile Phe Phe Leu Lys
1               5                   10

<210> SEQ ID NO 480
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 480

Asp Pro Ala Phe Lys Ile Glu Asp Pro Tyr Ser Pro Arg Ile Gln Asn
1               5                   10                  15

Leu Leu Lys Ile Thr Asn Leu Arg Ile Lys Phe Val Lys Leu
            20                  25                  30

<210> SEQ ID NO 481
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 481

Thr Lys Arg Phe Glu Gln Glu Leu Arg Leu Val Ser Tyr Ser Gly Val
1               5                   10                  15

Leu Phe Phe Leu
            20

<210> SEQ ID NO 482
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 482

Gly Gly Arg Leu Lys Tyr Ser Val Ala Phe
1               5                   10

<210> SEQ ID NO 483
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 483

Gly Gly Phe Leu Arg Tyr Thr Val Ser Tyr Asp Ile
1               5                   10

<210> SEQ ID NO 484
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 484

Gly Gly Phe Leu Lys Tyr Thr Val Ser Tyr Asp Val
1               5                   10

<210> SEQ ID NO 485
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 485

Leu Gly Asn Lys Leu Thr Ala Phe Gly Gly Phe Leu Lys Tyr Thr Val
1               5                   10                  15

Ser Tyr Asp Ile Pro Val
            20

<210> SEQ ID NO 486

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 486

Gly Gly Tyr Leu Lys Tyr Thr Val Ser Tyr Asp Ile
1               5                   10

<210> SEQ ID NO 487
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 487

Gly Glu Ile Phe Phe Asp Met Arg Leu Lys Gly Asp Lys
1               5                   10

<210> SEQ ID NO 488
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 488

Gly Glu Ile Tyr Phe Asp Leu Arg Leu Lys Gly Asp Lys
1               5                   10

<210> SEQ ID NO 489
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 489

Gly Glu Ile Tyr Leu Asp Met Arg Leu Lys Gly Asp Lys
1               5                   10

<210> SEQ ID NO 490
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 490

Ile Gly Gln Pro Gly Ala Lys Gly Glu Pro Gly Glu Phe Tyr Phe Asp
1               5                   10                  15

Leu Arg Leu Lys Gly Asp Lys Gly Asp Pro Gly Phe Pro Gly
                20                  25                  30

<210> SEQ ID NO 491
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 491

Gly Glu Val Phe Phe Asp Met Arg Leu Lys Gly Asp Lys
1               5                   10

<210> SEQ ID NO 492
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 492

Leu Ala Gly Ser Cys Leu Pro Ile Phe Ser Thr Leu
1               5                   10

<210> SEQ ID NO 493
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 493

Ala His Asn Gln Asp Leu Gly Leu Ala Gly Ser Cys Leu Ala Arg Phe
1               5                   10                  15

Ser Thr Met Pro Phe Leu Tyr Cys Asn Pro Gly Asp Ile Cys
            20                  25                  30

<210> SEQ ID NO 494
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 494

Gln Glu Lys Ala His Asn Gln Asp Leu Gly Leu Ala Gly Ser Cys Leu
1               5                   10                  15

Pro Val Phe Ser Thr Leu Pro Phe Ala Tyr Cys Asn Ile His
            20                  25                  30

<210> SEQ ID NO 495
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 495

Leu Ala Gly Ser Cys Leu Pro Val Phe Ser Thr Met
1               5                   10

<210> SEQ ID NO 496
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 496

```
Gly Asn Lys Arg Ala His Gly Gln Asp Leu Gly Thr Ala Gly Ser Cys
1               5                   10                  15

Leu Arg Arg Phe Ser Thr Met Pro Phe Met Phe Cys Asn Ile
            20                  25                  30

<210> SEQ ID NO 497
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 497

Arg Ala His Gly Gln Asp Leu Gly Thr Ala Gly Ser Cys Leu Arg Arg
1               5                   10                  15

Phe Ser Thr Met Pro
            20

<210> SEQ ID NO 498
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 498

Arg Lys Arg Leu Gln Val Gln Leu Asn Ile Arg Thr
1               5                   10

<210> SEQ ID NO 499
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 499

His Leu Val Leu Pro Leu Gln Gln Ser Asp Val Arg Lys Arg Leu Gln
1               5                   10                  15

Val Gln Leu Ser Ile Arg Thr Phe Ala Ser Ser Gly Leu Ile
            20                  25                  30

<210> SEQ ID NO 500
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 500

Arg Lys Arg Leu Ser Val Gln Leu Arg Ile Arg Thr
1               5                   10

<210> SEQ ID NO 501
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 501
```

```
Asp Leu Gly Thr Ala Gly Ser Cys Leu Arg Arg Phe Ser Thr Met
1               5                   10                  15
```

<210> SEQ ID NO 502
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 502

```
Arg Asn Ile Ala Glu Ile Ile Lys Asp Ile
1               5                   10
```

<210> SEQ ID NO 503
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 503

```
Thr Ala Gly Ser Cys Leu Arg Lys Phe Ser Thr Met Arg Arg Arg
1               5                   10                  15

Arg Arg Arg Arg Arg Arg Arg Arg
            20
```

<210> SEQ ID NO 504
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 504

```
Phe Thr Leu Thr Gly Leu Leu Gly Thr Leu Val Thr Met Gly Leu Leu
1               5                   10                  15

Thr
```

<210> SEQ ID NO 505
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 505

```
Ala Pro Tyr Lys Ala Trp Lys
1               5
```

<210> SEQ ID NO 506
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 506

```
Ser Thr Ser Lys Thr Asn Arg Gly Asp Ser Asn Trp Ser Lys Arg
1               5                   10                  15

Val Thr Asn Asn Lys Pro Ser
```

20

<210> SEQ ID NO 507
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 507

Ser Thr Ser Lys Arg Lys Arg Gly Asp Asp Ser Asn Trp Ser Lys Arg
1               5                   10                  15

Val Thr Lys Lys Lys Pro Ser
            20

<210> SEQ ID NO 508
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 508

Ser Thr Ser Lys Arg Lys Arg Gly Asp Asp Ser Asn Trp Ser Lys Arg
1               5                   10                  15

Val Ser Lys Lys Lys Pro Ser
            20

<210> SEQ ID NO 509
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 509

Ser Thr Ser Lys Arg Lys Arg Gly Asp Asp Ala Asn Trp Ser Lys Arg
1               5                   10                  15

Val Thr Lys Lys Lys Pro Ser
            20

<210> SEQ ID NO 510
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 510

Pro Leu Ala Gly Ser Lys Arg Lys Arg Ala Asp Glu Val Ala Trp Ser
1               5                   10                  15

Lys Arg Gly Thr Lys Lys Lys Pro Glu Arg
            20                  25

<210> SEQ ID NO 511
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 511

Pro Leu Ala Gly Ser Lys Arg Lys Arg Ala Asp Glu Val Ala Trp Ser
1               5                   10                  15

Lys Arg Gly Thr Lys Lys Lys Pro Glu Arg Thr Ser Ala Ala Arg Ala
                20                  25                  30

Gly Pro Ser Arg Arg Ile Arg
                35

<210> SEQ ID NO 512
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 512

Ser Thr Ser Lys Arg Lys Arg Gly Asp Asp Ala Asn Trp Ser Lys Arg
1               5                   10                  15

Thr Thr Lys Lys Lys Pro Ser Ser
                20

<210> SEQ ID NO 513
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 513

Ser Thr Ser Lys Arg Lys Arg Gly Asp Asp Ala Asn Trp Ser Lys Arg
1               5                   10                  15

Thr Thr Lys Lys Lys Pro Ser Ser Ala Gly Leu Lys Arg Ala Gly Ser
                20                  25                  30

Lys Ala Asp Arg Pro Ser Leu
                35

<210> SEQ ID NO 514
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 514

Pro Thr Thr Ala Gly Lys Arg Lys Arg Ser Asp Asp Ala Ala Trp Ser
1               5                   10                  15

Lys Arg Ala Arg Pro Lys Ala Gly Arg Thr
                20                  25

<210> SEQ ID NO 515
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 515

Pro Thr Thr Ala Gly Lys Arg Lys Arg Ser Asp Asp Ala Ala Trp Ser
1               5                   10                  15
```

```
Lys Arg Ala Arg Pro Lys Ala Gly Arg Thr Ser Ala Ala Pro Gly
            20                  25                  30

Thr Ser Val Arg Arg Ile Arg
        35
```

<210> SEQ ID NO 516
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 516

```
Ser Ser Ser Leu Gly Lys Arg Lys Arg Ser Asp Glu Gly Ala Trp Ser
1               5                   10                  15

Lys Gly Lys Ser Lys Lys Lys Ala Met Arg
            20                  25
```

<210> SEQ ID NO 517
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 517

```
Ser Ser Ser Leu Gly Lys Arg Lys Arg Ser Asp Glu Gly Ala Trp Ser
1               5                   10                  15

Lys Gly Lys Ser Lys Lys Lys Ala Met Arg Gly Ser Ser Arg Arg
            20                  25                  30

Pro Gly Pro Val Arg Gly Pro
        35
```

<210> SEQ ID NO 518
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 518

```
Pro Thr Thr Ala Gly Lys Arg Lys Arg Thr Asp Asp Ala Ala Trp Ser
1               5                   10                  15

Lys Arg Ala Arg Pro Lys Ala Gly Arg
            20                  25
```

<210> SEQ ID NO 519
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 519

```
Pro Thr Thr Ala Gly Lys Arg Lys Arg Thr Asp Asp Ala Ala Trp Ser
1               5                   10                  15

Lys Arg Ala Arg Pro Lys Ala Gly Arg Thr Ser Ala Ala Arg Pro Gly
            20                  25                  30

Thr Ala Val Arg Arg Val Arg
        35
```

<210> SEQ ID NO 520
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 520

Pro Ala Thr Ala Gly Lys Arg Lys Arg Ser Asp Asp Ala Ala Trp Ser
1               5                   10                  15

Lys Arg Ala Arg Pro Lys Ala Gly Arg Thr Ser Ala Ala Arg
            20                  25                  30

<210> SEQ ID NO 521
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 521

Pro Ala Thr Ala Gly Lys Arg Lys Arg Ser Asp Asp Ala Ala Trp Ser
1               5                   10                  15

Lys Arg Ala Arg Pro Lys Ala Gly Arg Thr Ser Ala Ala Arg Pro Gly
            20                  25                  30

Thr Ser Val Arg Arg Ile Arg
        35

<210> SEQ ID NO 522
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 522

Ser Ser Ser Leu Gly Lys Arg Lys Arg Ser Asn Gly Gly Asp Trp Ser
1               5                   10                  15

Lys Arg Ser Ala Lys Lys Lys Pro Ala
            20                  25

<210> SEQ ID NO 523
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 523

Ser Ser Ser Leu Gly Lys Arg Lys Arg Ser Asn Gly Gly Asp Trp Ser
1               5                   10                  15

Lys Arg Ser Ala Lys Lys Lys Pro Ala Gly Thr Pro Ser Arg Arg Ala
            20                  25                  30

Gly Pro Gly Arg Gly Pro Arg
        35

<210> SEQ ID NO 524
<211> LENGTH: 26
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 524

Ser Ser Ser Leu Gly Lys Arg Lys Arg Ser Asp Glu Gly Ala Trp Ser
1               5                   10                  15
Lys Gly Lys Ser Lys Lys Lys Ala Met Arg
            20                  25

<210> SEQ ID NO 525
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 525

Ser Ser Ser Leu Gly Lys Arg Lys Arg Ser Asp Glu Gly Ala Trp Ser
1               5                   10                  15
Lys Gly Lys Ser Lys Lys Lys Ala Met Arg Gly Ser Ser Ser Arg Arg
            20                  25                  30
Pro Gly Pro Val Arg Gly Pro
        35

<210> SEQ ID NO 526
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 526

Ser Thr Ser Lys Arg Lys Arg Gly Asp Asp Ala Asn Trp Asn Lys Arg
1               5                   10                  15
Pro Thr Lys Lys Lys Pro Ser Ser
            20

<210> SEQ ID NO 527
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 527

Ser Thr Ser Lys Arg Lys Arg Gly Asp Asp Ala Asn Trp Asn Lys Arg
1               5                   10                  15
Pro Thr Lys Lys Lys Pro Ser Ser Ala Gly Leu Lys Lys Ala Gly Ser
            20                  25                  30
Lys Ala Glu Arg Pro Ser Leu
        35

<210> SEQ ID NO 528
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 528

Ser Gly Ala Leu Lys Arg Lys Arg Ser Asp Glu Val Ala Trp Ser Arg
1               5                   10                  15

Arg Arg Pro Val Lys Lys Pro Val
            20

<210> SEQ ID NO 529
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 529

Ser Gly Ala Leu Lys Arg Lys Arg Ser Asp Glu Val Ala Trp Ser Arg
1               5                   10                  15

Arg Arg Pro Val Lys Lys Pro Val Arg Arg Ala Pro Pro Arg Ala
            20                  25                  30

Gly Pro Ser Val Arg Arg Gly
        35

<210> SEQ ID NO 530
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 530

Ser Gly Ala Leu Lys Arg Lys Arg Ser Asp Glu Val Ala Trp Ser Arg
1               5                   10                  15

Arg Lys Pro Ala Lys Lys Pro Ala Arg
            20                  25

<210> SEQ ID NO 531
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 531

Ser Gly Ala Leu Lys Arg Lys Arg Ser Asp Glu Val Ala Trp Ser Arg
1               5                   10                  15

Arg Lys Pro Ala Lys Lys Pro Ala Arg Gln Pro Pro Pro Arg Ala
            20                  25                  30

Gly Pro Ser Val Arg Arg Gly
        35

<210> SEQ ID NO 532
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 532

Ala Gly Ala Leu Lys Arg Lys Arg Ser Asp Glu Val Ala Trp Ser Arg
1               5                   10                  15
```

```
Arg Lys Pro Ala Lys Lys Pro Ala Arg
            20              25
```

<210> SEQ ID NO 533
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 533

```
Ala Gly Ala Leu Lys Arg Lys Arg Ser Asp Glu Val Ala Trp Ser Arg
1               5                   10                  15

Arg Lys Pro Ala Lys Lys Pro Ala Arg Ala Pro Pro Arg Ala Gly
            20                  25                  30

Pro Ser Val Arg Arg Gly Leu
            35
```

<210> SEQ ID NO 534
<211> LENGTH: 243
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 534

```
Ser Thr Ser Lys Arg Lys Arg Gly Asp Asp Ser Asn Trp Ser Lys Arg
1               5                   10                  15

Val Thr Lys Lys Lys Pro Ser Ser Ala Gly Leu Lys Arg Ala Gly Ser
            20                  25                  30

Lys Ala Asp Arg Pro Ser Leu Gln Ile Gln Thr Leu Gln His Ala Gly
            35                  40                  45

Thr Thr Met Ile Thr Val Pro Ser Gly Gly Val Cys Asp Leu Ile Asn
        50                  55                  60

Thr Tyr Ala Arg Gly Ser Asp Glu Gly Asn Arg His Thr Ser Glu Thr
65              70                  75                  80

Leu Thr Tyr Lys Ile Ala Ile Asp Tyr His Phe Val Ala Asp Ala Ala
                85                  90                  95

Ala Cys Arg Tyr Ser Asn Thr Gly Thr Gly Val Met Trp Leu Val Tyr
            100                 105                 110

Asp Thr Thr Pro Gly Gly Gln Ala Pro Thr Pro Gln Thr Ile Phe Ser
        115                 120                 125

Tyr Pro Asp Thr Leu Lys Ala Trp Pro Ala Thr Trp Lys Val Ser Arg
    130                 135                 140

Glu Leu Cys His Arg Phe Val Val Lys Arg Arg Trp Leu Phe Asn Met
145                 150                 155                 160

Glu Thr Asp Gly Arg Ile Gly Ser Asp Ile Pro Pro Ser Asn Ala Ser
                165                 170                 175

Trp Lys Pro Cys Lys Arg Asn Ile Tyr Phe His Lys Phe Thr Ser Gly
            180                 185                 190

Leu Gly Val Arg Thr Gln Trp Lys Asn Val Thr Asp Gly Gly Val Gly
        195                 200                 205

Ala Ile Gln Arg Gly Ala Leu Tyr Met Val Ile Ala Pro Gly Asn Gly
    210                 215                 220

Leu Thr Phe Thr Ala His Gly Gln Thr Arg Leu Tyr Phe Lys Ser Val
225                 230                 235                 240
```

Gly Asn Gln

<210> SEQ ID NO 535
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 535

Asp Pro Gln Asn Ala Leu Tyr Tyr Gln Pro Arg Val Pro Thr Ala Ala
1               5                   10                  15

Pro Thr Ser Gly Gly Val Pro Trp Ser Arg Val Gly Glu Val Ala Ile
            20                  25                  30

Leu Ser Phe Val Ala Leu Ile Cys Phe Tyr Leu Leu Tyr Leu Trp Val
        35                  40                  45

Leu Arg Asp Leu Ile Leu Val Leu Lys Ala Arg Gln Gly Arg Ser Thr
    50                  55                  60

Glu Glu Leu Ile Phe Gly Gly Gln Ala Val Asp Arg Ser Asn Pro Ile
65                  70                  75                  80

Pro Asn Ile Pro Ala Pro Pro Ser Gln Gly Asn Pro Gly Pro Phe Val
                85                  90                  95

Pro Gly Thr Gly
            100

<210> SEQ ID NO 536
<211> LENGTH: 292
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 536

Gly Ser Gln Leu Val Pro Pro Ser Ala Phe Asn Tyr Ile Glu Ser
1               5                   10                  15

Gln Arg Asp Glu Phe Gln Leu Ser His Asp Leu Thr Glu Ile Val Leu
            20                  25                  30

Gln Phe Pro Ser Thr Ala Ser Gln Ile Thr Ala Arg Leu Ser Arg Ser
        35                  40                  45

Cys Met Lys Ile Asp His Cys Val Ile Glu Tyr Arg Gln Gln Val Pro
    50                  55                  60

Ile Asn Ala Ser Gly Thr Val Ile Val Glu Ile His Asp Lys Arg Met
65                  70                  75                  80

Thr Asp Asn Glu Ser Leu Gln Ala Ser Trp Thr Phe Pro Ile Arg Cys
                85                  90                  95

Asn Ile Asp Leu His Tyr Phe Ser Ser Ser Phe Phe Ser Leu Lys Asp
                100                 105                 110

Pro Ile Pro Trp Lys Leu Tyr Tyr Arg Val Ser Asp Ser Asn Val His
            115                 120                 125

Gln Met Thr His Phe Ala Lys Phe Lys Gly Lys Leu Lys Leu Ser Ser
        130                 135                 140

Ala Lys His Ser Val Asp Ile Pro Phe Arg Ala Pro Thr Val Lys Ile
145                 150                 155                 160

Leu Ala Lys Gln Phe Ser Glu Lys Asp Ile Asp Phe Trp His Val Gly
                165                 170                 175

Tyr Gly Lys Trp Glu Arg Arg Leu Val Lys Ser Ala Ser Ser Ser Arg

```
            180                 185                 190
Phe Gly Leu Arg Gly Pro Ile Glu Ile Asn Pro Gly Glu Ser Trp Ala
        195                 200                 205

Thr Lys Ser Ala Ile Val Thr Pro Asn Arg Asn Ala Asp Leu Asp Ile
    210                 215                 220

Glu Glu Glu Leu Leu Pro Tyr Arg Glu Leu Asn Arg Leu Gly Thr Asn
225                 230                 235                 240

Ile Leu Asp Pro Gly Glu Ser Ala Ser Ile Val Gly Ile Gln Arg Ser
                245                 250                 255

Gln Ser Asn Ile Thr Met Ser Met Ser Gln Leu Asn Glu Leu Val Arg
            260                 265                 270

Ser Thr Val His Glu Cys Ile Lys Thr Ser Cys Ile Pro Ser Thr Pro
        275                 280                 285

Lys Ser Leu Ser
        290

<210> SEQ ID NO 537
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 537

Arg Thr Gly Val Lys Arg Ser Tyr Gly Ala Ala Arg Gly Asp Asp Arg
1               5                   10                  15

Arg Arg Pro Asn Val Val
            20

<210> SEQ ID NO 538
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 538

Ser Tyr Val Lys Thr Val Pro Asn Arg Thr Arg Thr Tyr Ile Lys Leu
1               5                   10                  15

Arg Val Arg

<210> SEQ ID NO 539
<211> LENGTH: 255
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 539

Met Tyr Ser Thr Ser Asn Arg Arg Gly Arg Ser Gln Thr Gln Arg Gly
1               5                   10                  15

Ser His Val Arg Arg Thr Gly Val Lys Arg Ser Tyr Gly Ala Ala Arg
            20                  25                  30

Gly Asp Asp Arg Arg Arg Pro Asn Val Val Ser Lys Thr Gln Val Glu
        35                  40                  45

Pro Arg Met Thr Ile Gln Arg Val Gln Glu Asn Gln Phe Gly Pro Glu
    50                  55                  60
```

-continued

```
Phe Val Leu Ser Gln Asn Ser Ala Leu Ser Thr Phe Val Thr Tyr Pro
 65                  70                  75                  80

Ser Tyr Val Lys Thr Val Pro Asn Arg Thr Arg Thr Tyr Ile Lys Leu
                 85                  90                  95

Lys Arg Val Arg Phe Lys Gly Thr Leu Lys Ile Glu Arg Gly Gln Gly
            100                 105                 110

Asp Thr Ile Met Asp Gly Pro Ser Asn Ile Glu Gly Val Phe Ser
        115                 120                 125

Met Val Ile Val Val Asp Arg Lys Pro His Val Ser Gln Ser Gly Arg
130                 135                 140

Leu His Thr Phe Asp Glu Leu Phe Gly Ala Arg Ile His Cys His Gly
145                 150                 155                 160

Asn Leu Ser Val Val Pro Ala Leu Lys Asp Arg Tyr Tyr Ile Arg His
                165                 170                 175

Val Thr Lys Arg Val Ser Leu Glu Lys Asp Thr Leu Leu Ile Asp
            180                 185                 190

Leu His Gly Thr Thr Gln Leu Ser Asn Lys Arg Tyr Asn Cys Trp Ala
        195                 200                 205

Ser Phe Ser Asp Leu Glu Arg Asp Cys Asn Gly Val Tyr Gly Asn Ile
210                 215                 220

Thr Lys Asn Ala Leu Leu Val Tyr Tyr Cys Trp Leu Ser Asp Ala Gln
225                 230                 235                 240

Ser Lys Ala Ser Thr Tyr Val Ser Phe Glu Leu Asp Tyr Leu Gly
                245                 250                 255
```

<210> SEQ ID NO 540
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 540

```
Arg Arg Arg Arg Arg Arg Arg Arg Arg Arg Arg Val Asp Tyr Gly
1               5                   10                  15

Lys Trp Glu Arg Lys Pro Ile Arg Cys Ala Ser Met Ser Arg
            20                  25                  30
```

<210> SEQ ID NO 541
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 541

```
Arg Arg Arg Arg Arg Arg Arg Arg Arg Arg Arg Gly Lys Trp Glu
1               5                   10                  15

Arg Lys Pro Ile Arg Cys Ala Ser
            20
```

<210> SEQ ID NO 542
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 542

Lys Lys Lys Lys Lys Lys Lys Lys Lys Lys Lys Lys Lys Lys Lys
1               5                   10                  15

Gly Lys Trp Glu Arg Lys Pro Ile Arg Cys Ala Ser
            20                  25

<210> SEQ ID NO 543
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 543

Arg Arg Arg Arg Arg Arg Arg Arg Arg Arg Arg Val Asp Phe Ser
1               5                   10                  15

His Val Asp Tyr Gly Lys Trp Glu Arg Lys Pro Ile Arg Cys Ala Ser
            20                  25                  30

Met Ser Arg Leu Gly Leu Arg Gly
        35                  40

<210> SEQ ID NO 544
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 544

Gly Val Lys Arg Ser Tyr Gly Ala Ala Arg Gly Asp Asp Arg Arg Arg
1               5                   10                  15

Pro Asn Val Val Ala Pro Tyr Lys Ala Trp Arg Arg Arg Arg Arg
            20                  25                  30

Arg Arg Arg Arg Arg Arg
        35

<210> SEQ ID NO 545
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 545

Lys Ser Val Pro Asn Arg Thr Arg Thr Tyr Ile Lys Leu Lys Arg Leu
1               5                   10                  15

Arg Phe Lys Gly Ala Pro Tyr Lys Ala Trp Arg Arg Arg Arg Arg
            20                  25                  30

Arg Arg Arg Arg Arg Arg
        35

<210> SEQ ID NO 546
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 546

```
Arg Thr Gly Val Lys Arg Ser Tyr Gly Ala Arg Gly Asp Asp Arg
1               5                   10                  15

Arg Arg Pro Asn Val Val Arg Arg Arg Arg Arg Arg Arg Arg Arg
            20                  25                  30

Arg Arg
```

<210> SEQ ID NO 547
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 547

```
Ser Tyr Val Lys Thr Val Pro Asn Arg Thr Arg Thr Tyr Ile Lys Gly
1               5                   10                  15

Gly Gly Gly Gly Arg Arg Arg Arg Arg Arg Arg Arg Arg Arg Arg Arg
            20                  25                  30
```

<210> SEQ ID NO 548
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 548

```
Val Asp Ile Pro Phe Arg Ala Pro Thr Ile Lys Ile Leu Ser Lys Gln
1               5                   10                  15

Phe Thr Glu Asp Asp Ile Asp Phe Trp His Val Gly Tyr Gly Lys Trp
            20                  25                  30

Glu Arg Lys Leu Val Arg Pro Ala Ser Leu Ser Gly Arg Arg Gly Leu
        35                  40                  45

Arg Arg
    50
```

<210> SEQ ID NO 549
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 549

```
Ile Asp Phe Trp His Val Gly Tyr Gly Lys Trp Glu Arg Lys Leu Val
1               5                   10                  15

Arg Pro Ala Ser Leu Ser Gly Arg Arg Gly Leu Arg Arg
            20                  25
```

<210> SEQ ID NO 550
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 550

```
Ile Asp Phe Trp Ser Val Glu Lys Gly Glu Thr Arg Arg Arg Leu Leu
1               5                   10                  15
```

```
Asn Pro Thr Pro His Ala His Ser Pro Arg Pro Ile Ala His Arg
            20                  25                  30

<210> SEQ ID NO 551
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 551

Ile Asp Phe Ser His Val Gly Tyr Gly Lys Trp Glu Arg Lys Met Ile
1               5                   10                  15

Arg Ser Ala Ser Ile Ser Arg Leu Gly Leu His Asn
            20                  25

<210> SEQ ID NO 552
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 552

Val Asp Phe Ser His Val Gly Tyr Gly Lys Trp Glu Arg Lys Leu Ile
1               5                   10                  15

Arg Ser Ala Ser Thr Val Lys Tyr Gly Leu Pro Ser
            20                  25

<210> SEQ ID NO 553
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 553

Ile Asp Phe Ser His Val Asp Tyr Gly Lys Val Glu Arg Lys Leu Val
1               5                   10                  15

Lys Cys Glu Ser Ser Ser Arg Leu Gly Leu His Ser
            20                  25

<210> SEQ ID NO 554
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 554

Ile Asp Phe Trp Ser Val Gly Arg Lys Ala Gln Gln Arg Lys Leu Val
1               5                   10                  15

Gln Gly Pro Ser Leu Ile Gly Ser Arg Ser Met Arg Tyr
            20                  25

<210> SEQ ID NO 555
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 555

Ile Asp Phe Trp Ser Val Gly Ser Lys Pro Gln Thr Arg Arg Leu Val
1               5                   10                  15

Asp Gly Ser Arg Leu Ile Gly His Ser Ser Arg Ser Leu Arg Val
            20                  25                  30

<210> SEQ ID NO 556
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 556

Ile Asp Phe Trp Ser Val Glu Arg Gly Glu Thr Arg Arg Arg Leu Leu
1               5                   10                  15

Asn Pro Thr Pro Ser Ala Gly Ser Asn Arg Ala Leu Ser Lys Arg
            20                  25                  30

<210> SEQ ID NO 557
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 557

Val Asp Phe Trp Ser Val Gly Lys Pro Lys Pro Ile Arg Arg Leu Ile
1               5                   10                  15

Gln Asn Asp Pro Gly Thr Asp Tyr Asp Thr Gly Pro Lys Tyr Arg
            20                  25                  30

<210> SEQ ID NO 558
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 558

Val Asp Phe Trp Ser Val Glu Lys Pro Lys Pro Ile Arg Arg Leu Leu
1               5                   10                  15

Asn Pro Gly Pro Asn Gln Gly Ser Tyr Pro Asn Thr Gly His Arg
            20                  25                  30

<210> SEQ ID NO 559
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 559

Val Asp Phe Ser His Val Asp Tyr Gly Lys Trp Glu Arg Lys Leu Ile
1               5                   10                  15

Arg Ser Ala Ser Thr Ser Arg Tyr Gly Leu Arg Ser
            20                  25

<210> SEQ ID NO 560
```

```
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 560

Val Asp Phe Ser His Val Asp Tyr Gly Lys Trp Glu Arg Lys Thr Leu
1               5                   10                  15

Arg Ser Arg Ser Leu Ser Arg Ile Gly Leu Thr Gly
            20                  25

<210> SEQ ID NO 561
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 561

Ile Asp Phe Trp His Val Gly Tyr Gly Lys Trp Glu Arg Arg Leu Val
1               5                   10                  15

Lys Ser Ala Ser Ser Arg Phe Gly Ile Arg Gly
            20                  25

<210> SEQ ID NO 562
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 562

Val Asp Phe Phe His Val Asp Tyr Gly Arg Trp Glu Arg Lys His Ile
1               5                   10                  15

Arg Cys Ala Ser Met Ser Arg Val Gly Leu Arg Gly
            20                  25

<210> SEQ ID NO 563
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 563

Gly Thr Phe Gln His Val Asp Tyr Gly Lys Trp Glu Arg Lys Pro Ile
1               5                   10                  15

Arg Cys Gln Ser Met Ser Arg Val Gly Tyr Arg Arg
            20                  25

<210> SEQ ID NO 564
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 564

Val Gly Tyr Gly Lys Trp Glu Arg Lys Leu Val Arg Pro Ala Ser Leu
1               5                   10                  15
```

Ser

<210> SEQ ID NO 565
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 565

Val Glu Lys Gly Glu Thr Arg Arg Arg Leu Leu Asn Pro Thr Pro His
1               5                   10                  15

Ala

<210> SEQ ID NO 566
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 566

Val Gly Tyr Gly Lys Trp Glu Arg Lys Leu Ile Arg Ser Ala Ser Thr
1               5                   10                  15

Val

<210> SEQ ID NO 567
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 567

Val Glu Lys Pro Lys Pro Ile Arg Arg Leu Leu Asn Pro Gly Pro Asn
1               5                   10                  15

Gln

<210> SEQ ID NO 568
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 568

Val Asp Tyr Gly Lys Trp Glu Arg Lys Leu Ile Arg Ser Ala Ser Thr
1               5                   10                  15

Ser

<210> SEQ ID NO 569
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 569

Val Asp Tyr Gly Lys Trp Glu Arg Lys Thr Leu Arg Ser Arg Ser Leu

```
                1               5                   10                  15
Ser

<210> SEQ ID NO 570
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 570

Val Gly Tyr Gly Lys Trp Glu Arg Arg Leu Val Lys Ser Ala Ser Ser
1               5                   10                  15

Ser

<210> SEQ ID NO 571
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 571

Val Asp Tyr Gly Arg Trp Glu Arg Lys His Ile Arg Cys Ala Ser Met
1               5                   10                  15

Ser

<210> SEQ ID NO 572
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 572

Val Glu Arg Pro Lys Pro Ile Arg Arg Leu Leu Thr Pro Thr Pro Gly
1               5                   10                  15

Cys

<210> SEQ ID NO 573
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 573

Pro Phe Arg Ala Pro Thr Ile Lys Ile Leu Ser Lys Gln Phe Thr Glu
1               5                   10                  15

Asp Asp Ile Asp Phe Trp His Val Gly Tyr Gly Lys Trp Glu Arg Lys
                20                  25                  30

Leu Val Arg Pro Ala Ser Leu Ser Gly Arg Arg Gly Leu Arg Arg
            35                  40                  45

<210> SEQ ID NO 574
<211> LENGTH: 44
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 574

Pro Phe Arg Ala Pro Thr Val Lys Ile Leu Ser Lys Gln Phe Thr Asp
1               5                   10                  15

Lys Asp Ile Asp Phe Ser His Val Gly Tyr Gly Lys Trp Glu Arg Lys
            20                  25                  30

Met Ile Arg Ser Ala Ser Ile Ser Arg Leu Gly Leu
        35                  40

<210> SEQ ID NO 575
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 575

Asp Ile Ala Phe Arg Ala Pro Thr Val Lys Ile Leu Ser Lys Gln Phe
1               5                   10                  15

Thr Asp Arg Asp Val Asp Phe Ser His Val Gly Tyr Gly Lys Trp Glu
            20                  25                  30

Arg Lys Leu Ile Arg Ser Ala Ser Thr Val Lys Tyr Gly Leu
        35                  40                  45

<210> SEQ ID NO 576
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 576

Asp Ile Arg Phe Lys Pro Pro Thr Ile Asn Ile Leu Ser Lys Asp Tyr
1               5                   10                  15

Thr Ala Asp Cys Val Asp Phe Trp Ser Val Glu Lys Pro Lys Pro Ile
            20                  25                  30

Arg Arg Leu Leu Asn Pro Gly Pro Asn Gln Gly Pro Tyr Pro Asn Thr
        35                  40                  45

Gly

<210> SEQ ID NO 577
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 577

Asp Ile Pro Phe Arg Ala Pro Thr Val Lys Ile His Ser Lys Gln Phe
1               5                   10                  15

Ser His Arg Asp Val Asp Phe Ser His Val Asp Tyr Gly Lys Trp Glu
            20                  25                  30

Arg Lys Thr Leu Arg Ser Arg Ser Leu Ser Arg Ile Gly Leu
        35                  40                  45

<210> SEQ ID NO 578
<211> LENGTH: 46
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 578

Asp Ile Pro Phe Arg Ala Pro Thr Val Lys Ile Leu Ala Lys Gln Phe
1               5                   10                  15

Ser Glu Lys Asp Ile Asp Phe Trp His Val Gly Tyr Gly Lys Trp Glu
            20                  25                  30

Arg Arg Leu Val Lys Ser Ala Ser Ser Arg Phe Gly Ile
        35                  40                  45

<210> SEQ ID NO 579
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 579

Asp Ile Pro Phe Arg Ala Pro Thr Val Lys Ile Leu Ser Lys Gln Phe
1               5                   10                  15

Thr Asp Lys Asp Val Asp Phe Phe His Val Asp Tyr Gly Arg Trp Glu
            20                  25                  30

Arg Lys His Ile Arg Cys Ala Ser Met Ser Arg Val Gly Leu
        35                  40                  45

<210> SEQ ID NO 580
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 580

Asp Ile Lys Tyr Lys Pro Pro Thr Ile Lys Ile Leu Ser Lys Asp Tyr
1               5                   10                  15

Thr Ala Asp Cys Val Asp Phe Trp Ser Val Glu Arg Pro Lys Pro Ile
            20                  25                  30

Arg Arg Leu Leu Thr Pro Thr Pro Gly Cys Gly
        35                  40

<210> SEQ ID NO 581
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 581

Ala Arg Thr Lys Gln Thr Ala Arg Lys Ser Thr Gly Gly Lys Ala Pro
1               5                   10                  15

Arg Lys Gln Leu Ala Thr Lys Ala Ala Arg Lys Ser Ala Pro Ala Thr
            20                  25                  30

Gly Gly Val Lys Lys Pro His Arg Tyr Arg Pro Gly Thr Val Ala
        35                  40                  45

<210> SEQ ID NO 582
<211> LENGTH: 34

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 582

Ser Gly Arg Gly Lys Gly Gly Lys Gly Leu Gly Lys Gly Gly Ala Lys
1               5                   10                  15

Arg His Arg Lys Val Leu Arg Asp Asn Ile Gln Gly Ile Thr Lys Pro
            20                  25                  30

Ala Ile

<210> SEQ ID NO 583
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 583

Gly Arg Lys Lys Arg Arg Gln Arg Arg Arg
1               5                   10

<210> SEQ ID NO 584
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 584
ttgaggttgc tagtgaaggc tagctacaac gaacagttgt gtcagaagc                49

<210> SEQ ID NO 585
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 585
agtaatacga ctcactatag ggagaacatt tgcttctgac acaac                    45

<210> SEQ ID NO 586
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 586
agtaatacga ctcactataa ggagaacatt tgcttctgac acaac                    45

<210> SEQ ID NO 587
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 587
```

```
agtaatacga ctcactatag tgagaacatt tgcttctgac acaac          45
```

<210> SEQ ID NO 588
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 588

```
agtaatacga ctcactatag cgagaacatt tgcttctgac acaac          45
```

<210> SEQ ID NO 589
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 589

```
agtaatacga ctcactatag agagaacatt tgcttctgac acaac          45
```

<210> SEQ ID NO 590
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 590

```
gccctctaga tcaaccactt tggccctct                            29
```

<210> SEQ ID NO 591
<211> LENGTH: 23
<212> TYPE: DNA
<213> ORGANISM: Unknown
<220> FEATURE:
<223> OTHER INFORMATION: Description of Unknown:
      T7 phage sequence

<400> SEQUENCE: 591

```
taatacgact cactataggg aga                                  23
```

<210> SEQ ID NO 592
<211> LENGTH: 23
<212> TYPE: DNA
<213> ORGANISM: Unknown
<220> FEATURE:
<223> OTHER INFORMATION: Description of Unknown:
      T3 phage sequence

<400> SEQUENCE: 592

```
aattaaccct cactaaaggg aga                                  23
```

<210> SEQ ID NO 593
<211> LENGTH: 23
<212> TYPE: DNA
<213> ORGANISM: Unknown
<220> FEATURE:
<223> OTHER INFORMATION: Description of Unknown:
    SP6 phage sequence
<220> FEATURE:
<221> NAME/KEY: modified_base
<222> LOCATION: (22)..(22)
<223> OTHER INFORMATION: a, c, t, g, unknown or other

<400> SEQUENCE: 593
atttaggtga cactatagaa gng                                         23

<210> SEQ ID NO 594
<211> LENGTH: 23
<212> TYPE: DNA
<213> ORGANISM: Unknown
<220> FEATURE:
<223> OTHER INFORMATION: Description of Unknown:
    K11 phage sequence

<400> SEQUENCE: 594
aattagggca cactataggg aac                                         23

<210> SEQ ID NO 595
<211> LENGTH: 10
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 595 natagggaga                                                        10

<210> SEQ ID NO 596
<211> LENGTH: 10
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 596
tataaggaga                                                        10

<210> SEQ ID NO 597
<211> LENGTH: 10
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 597
tatagtgaga                                                        10

TRINUCLEOTIDE CAP ANALOGS, PREPARATION AND USES THEREOF

FIELD

This specification generally relates to trinucleotide RNA cap analogs, methods of use thereof, and kits comprising same. In particular, the trinucleotide cap analogs provided herein permit ready detection and/or isolation of capped RNA transcripts in vitro and translation of capped mRNAs in vivo.

SEQUENCE LISTING

The instant application contains a Sequence Listing which has been submitted electronically in ASCII format and is hereby incorporated by reference in its entirety. Said ASCII copy, created on Jun. 24, 2021, is named LT01530_SL.txt and is 182,474 bytes in size.

BACKGROUND

Eukaryotic mRNAs bear a "cap" structure at their 5'-termini that is well known to play an important role in translation. Naturally occurring cap structures consist of a 7-methyl guanosine that is linked via a triphosphate bridge to the 5'-end of the first transcribed nucleotide, resulting in $m^7G(5')ppp(5')N$, where N is any nucleotide. The mRNA cap plays an important role in gene expression. It protects the mRNAs from degradation by exonucleases, enables transport of RNAs from the nucleus to the cytoplasm, and participates in assembly of the translation initiation complex. A dinucleotide in the form of $m^7G(5')ppp(5')G$ (mCAP) has been used as the primer in transcription with T7 or SP6 RNA polymerase in vitro to obtain RNAs having a cap structure at their 5'-termini. In vivo, the cap is added enzymatically. However, over the past 20 years or so, numerous studies have required the synthesis of proteins in an in vitro translation extract supplemented with in vitro synthesized mRNA. The prevailing method for the in vitro synthesis of capped mRNA employs mCAP as an initiator of transcription. A disadvantage of using mCAP, a pseudosymmetrical dinucleotide, has always been the propensity of the 3'-OH of either the G or $m^7G$ ($m^7Guo$) moiety to serve as the initiating nucleophile for transcriptional elongation resulting in ~50% of capped RNA that is translatable. This disadvantage was addressed by provision of modified cap analogs having the 3'-OH group of the $m^7G$ portion of the cap blocked to prevent transcription from that position (e.g., ARCA).

While caps may also be added to RNA molecules by the enzyme guanylyl transferase in the cell, caps are initially added to RNA during in vitro transcription where the cap is used as a primer for RNA polymerase. The 5' terminal nucleoside is normally a guanine, and is in the reverse orientation to all the other nucleotides, i.e., 5'GpppS'GpNpNp . . . and, in most instances, the cap contains two nucleotides, connected by a 5'-5' triphosphate linkage.

Transcription of RNA usually starts with a nucleoside triphosphate (usually a purine, A or G). When transcription occurs in vitro, it typically includes a phage RNA polymerase such as T7, T3 or SP6, a DNA template containing a phage polymerase promoter, nucleotides (ATP, GTP, CTP and UTP) and a buffer containing magnesium salt. The 5' cap structure enhances the translation of mRNA by helping to bind the eukaryotic ribosome and assuring recognition of the proper AUG initiator codon. This function may vary with the translation system and with the specific mRNA being synthesized.

During translation the cap is bound by translational initiation factor eIF4E and the cap-binding complex (CBC) recruits additional initiation factors. Decapping is catalyzed by proteins dcp1 and dcp2 which compete with eIF4E to bind to the cap. Translation results in amino acids as encoded by the mRNA to join together to form a peptide and occurs as three processes: initiation, elongation, and termination. Initiation in eukaryotes involves attachment of a ribosome which scans the mRNA for the first methionine codon. Elongation proceeds with the successive addition of amino acids until a stop codon is reached, terminating translation.

Capped RNA encoding specific genes can be transfected into eukaryotic cells or microinjected into cells or embryos to study the effect of translated product in the cell or embryo. If uncapped RNA is used, the RNA in these experiments is rapidly degraded and the yield of translated protein is much reduced.

Capped RNA can also be used to treat disease. Isolated dendritic cells from a patient can be transfected with capped RNA encoding immunogen. The dendritic cells translate the capped RNA into a protein that induces an immune response against this protein. In a small human study, immunotherapy with dendritic cells loaded with CEA capped RNA was shown to be safe and feasible for pancreatic patients (Morse et al., *Int. J. Gastrointest. Cancer,* 32, 1-6, (2002)). It was also noted that introducing a single capped RNA species into immature dendritic cells induced a specific T-cell response (Heiser et al., *J. Clin. Invest.,* 109, 409-417 (2002)).

However, capped RNA known in the art still has limitations with respect to their intracellular stability as well as their efficiency of in vitro transcription, for example with substrates such as T7-RNA-polymerase. Thus, there is still a need for mRNA cap analogs, such as locked capped RNA that can result in high levels of capping efficiency, improved translation efficiencies, and improved intracellular molecular stability of 5' capped mRNAs.

SUMMARY

The present disclosure relates to new modified trinucleotide cap analogs of Formula (I) as defined herein:

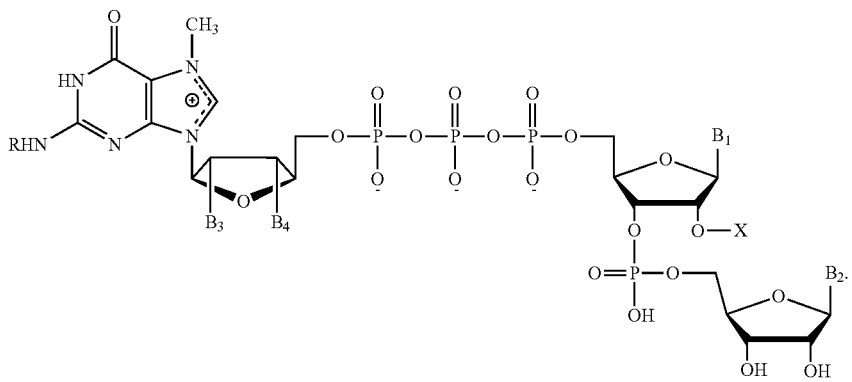

(I)

The trinucleotide cap analogs disclosed herein can result in high levels of capping efficiency and improved translation efficiencies. In at least one aspect, the trinucleotide cap analogs disclosed herein are improved substrates for T7-RNA polymerase and lead to a better transcription yield.

The trinucleotide cap analogs disclosed herein can result in improved intracellular molecular stability of 5' capped mRNAs. In at least one aspect, the trinucleotide cap analogs disclosed herein increase the intracellular stability of mRNA in vaccines.

In at least one aspect, the trinucleotide cap analogs disclosed herein can also serve as reporter moieties. In at least one aspect, the trinucleotide cap analogs disclosed herein improve transfection into specific cell lines.

The present disclosure also relates to compositions comprising the cap analogs, compositions comprising RNA having the cap analogs described herein covalently bonded thereto, methods for using mRNA species containing such analogs, as well as kits containing the novel cap analogs.

In a first aspect, this disclosure is directed to a trinucleotide cap analog of Formula (I):

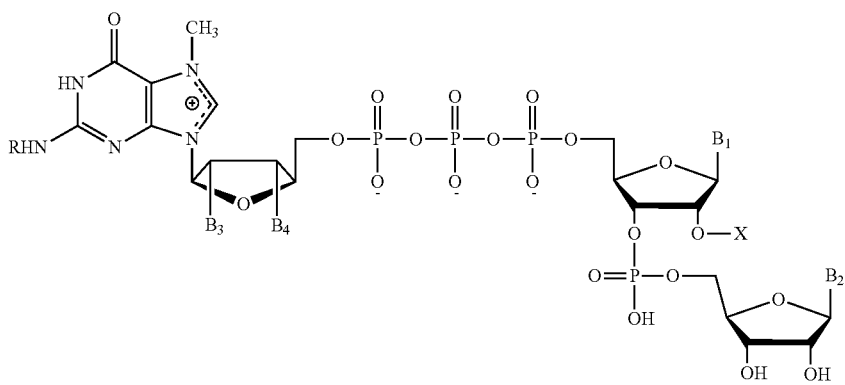

(I)

wherein
$B_3$ is chosen from —OH, halogen, dyes, —OR$^1$, wherein R$^1$ is chosen from propargyl, tert-butyldimethylsilyl, and a methylene bridge with the 4'C;
$B_4$ is chosen from —OH, dyes, and —OR$^2$, wherein R$^2$ is chosen from propargyl and tert-butyldimethylsilyl; or R$^1$ joins with R$^2$ such that $B_3$ and $B_4$ form-2',3'-O-isopropylidine;
on the condition that $B_3$ and $B_4$ cannot both be —OH X is chosen from —H and —CH$_3$;
$B_1$ and $B_2$ are each independently chosen from adenine, guanine, cytosine, and uracil;
R is chosen from H, a linker-bound cell-penetrating peptide, a linker-bound cell-penetrating peptide covalently linked to a dye, and a linker-bound dye.

In a second aspect, this disclosure is directed to a composition comprising a trinucleotide cap analog of Formula (I), or any of the embodiments thereof described herein.

In a third aspect, this disclosure is directed to a composition comprising RNA having a trinucleotide cap analog of Formula (I), or any of the embodiments thereof described herein.

In a fourth aspect, this disclosure is directed to a kit comprising a trinucleotide cap analog of Formula (I) or any of the embodiments thereof described herein; nucleotide triphosphate molecules; and an RNA polymerase.

In a fifth aspect, this disclosure is directed to a method of producing trinucleotide capped RNA comprising contacting a nucleic acid substrate with an RNA polymerase and a trinucleotide cap analog of Formula (I), or any of the embodiments thereof described herein, in the presence of nucleotide triphosphates under conditions and for a time sufficient to produce a trinucleotide capped RNA.

In a sixth aspect, this disclosure is directed to a method comprising contacting a cell with the trinucleotide cap analog of Formula (I), or any of the embodiments thereof described herein.

In a seventh aspect, this disclosure is directed to a method of increasing intracellular stability of an RNA, comprising incorporating a trinucleotide cap analog according to Formula (I), or any of the embodiments thereof described herein, into the RNA.

In an eighth aspect, this disclosure is directed to a method for introducing an RNA into a cell, comprising contacting the cell with a composition according to the present disclosure comprising a trinucleotide cap analog according to Formula (I), or any of the embodiments thereof described herein. In some examples, the cell is a dendritic cell, a tumor cell, a stem cell (iPSC, HSC, adult stem cell) or the like.

In a ninth aspect, this disclosure is directed to a method for RNA translation inhibition in a cell comprising contacting the cell with a composition according to the present disclosure comprising a trinucleotide cap analog according to Formula (I), or any of the embodiments thereof described herein.

Also provided herein are transcriptional initiation complexes comprising: (a) a nucleic acid molecule comprising a promoter region, the promoter region comprising a transcriptional initiation site, the transcriptional initiation site comprising a template strand, and (b) a capped primer comprising two or more (e.g., from about two to about twelve, from about two to about ten, from about two to about nine, from about two to about eight, from about two to about six, from about three to about eight, etc.) bases hybridized to the transcriptional initiation site comprising a template strand at least at positions −1 and +1, +1 and +2, or +2 and +3. In some instances, at least one (e.g., one, two, three, four, etc.) nucleotide at one or both adjacent positions (5' and/or 3') of the non-template strand of the initiation site is a transcriptional initiation blocking nucleotide. In some instances, the one or more transcriptional initiation blocking nucleotides are selected from the group consisting of (A) thymidine, (B) cytosine, (C) adenosine, and (D) a chemically modified nucleotide. Further, the initiation complex may comprise a template strand that is hybridized (e.g., partially hybridized) to a complementary non-template strand. Additionally, the template and/or non-template strand may contain a chemically modified nucleotide (e.g., deoxythymidine residue, 2'-deoxycytidine, etc.) at positions −1 and/or +1.

Positions −1, +1, and +2 of non-template strand of the transcriptional start site of promoters and transcriptional initiation complexes set out herein may comprise a nucleotide sequence selected from the group consisting of: A G T, A A T, A G C, A A C, A G A, A A A, G A T, G A C, G A A, G G T, G G C, G G A, A T T, A T C, and A T A.

Also provided herein are transcriptional initiation complexes comprising: (a) a nucleic acid molecule comprising a promoter region, the promoter region comprising a transcriptional initiation site, the transcriptional initiation site comprising a template strand, and (b) a non-naturally occurring capped primer comprising three or more bases hybridized to the DNA template at least at nucleotide positions −1 and +1, +1 and +2, or +2 and +3. Further, initiation complexes set out herein may comprise a non-naturally occurring capped primer is a capped primer set out herein.

Further provided herein are nucleic acid molecules comprising a promoter, wherein the promoter comprises the following non-template strand nucleotide sequence: TATY$_1$ Y$_2$Z, wherein Y$_1$ is at the −1 position, Y$_2$ is at the +1 position, and Z is at position +2, and wherein Z is a transcriptional initiation blocking nucleotide. Further, Z may be adenosine, cytosine, thymidine, or a chemically modified nucleotide. Such nucleic acid molecules may comprise a nucleotide sequence selected from the group consisting of (a) 5'-T A T A G T-3', (b) 5'-T A T A G C-3', and (c) 5'-T A T A A C-3'.

Also, provided herein are methods for producing mRNA molecules. Such methods may comprise contacting a DNA template with a capped primer and an RNA polymerase under condition that allow for the production of the mRNA molecules by a transcription reaction, wherein the DNA template comprises: (a) a nucleic acid molecule comprising a promoter region, the promoter region comprising a transcriptional initiation site, the transcriptional initiation site comprising a template strand, and (b) a capped primer comprising two or more bases hybridized to the transcriptional initiation site comprising a template strand at least at positions −1 and +1, +1 and +2, or +2 and +3, and wherein at least the nucleotide at the 5' adjacent position of the template strand of the initiation site is a transcriptional initiation blocking nucleotide. Further, RNA polymerases used in such methods include bacteriophage, bacterial, and eukaryotic (e.g., mammalian) RNA polymerases. In some instances, a bacteriophage RNA polymerase such as a T7 bacteriophage, a T3 bacteriophage, an SP6 bacteriophage, or a K11 bacteriophage RNA polymerase or variant thereof may be used in methods set out herein.

Further, mRNA molecules produced by methods set out herein may comprise a nucleotide sequence encoding one or more protein. Also, mRNA molecules produced by methods set out herein may be produced by in vitro or in vivo transcription reaction. Additionally, mRNA molecules produced by methods set out herein may be translated to produce proteins, for example by a coupled transcription/translation system.

In many instances, at least 70% (e.g., from about 70% to about 100%, from about 75% to about 100%, from about 80% to about 100%, from about 85% to about 100%, from about 90% to about 100%, from about 70% to about 98%, from about 80% to about 98%, etc.) of the mRNA molecules produced by methods set out herein will be capped.

In many instances, the yield of mRNA molecules (e.g., capped mRNA molecules) produced by methods set out herein will be greater than 3 mg/ml of reaction mixture.

BRIEF DESCRIPTION OF THE DRAWINGS

The skilled artisan will understand that the drawings, described below, are for illustration purposes only. The drawings are not intended to limit the scope of the present teachings in any way.

FIG. 17 discloses SEQ ID NO: 595.

FIG. 18 discloses SEQ ID NO: 596.

FIG. 19 discloses SEQ ID NO: 597.

DESCRIPTION OF THE SEQUENCES

Figure 1:
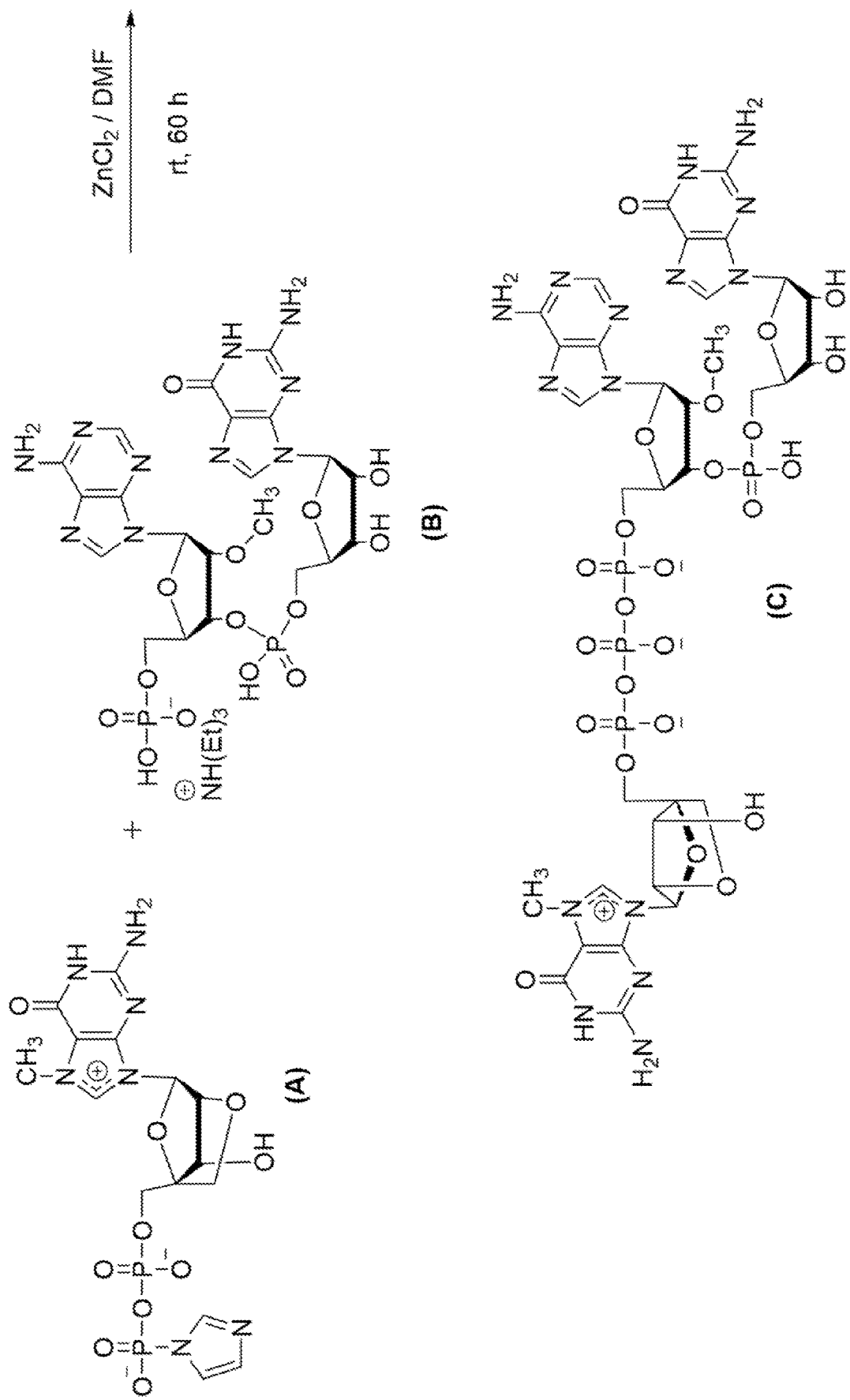
FIG. 1 illustrates an exemplary synthetic scheme for a trinucleotide cap analog described herein. In this illustration, the synthetic scheme combines imidazolide salt of 7 methyl (LNA) Guanosine 5' diphosphate (Imm7(LNA)GDP) (A) with (B) to form an exemplary trinucleotide analog of the present disclosure (C).
Figure 2:
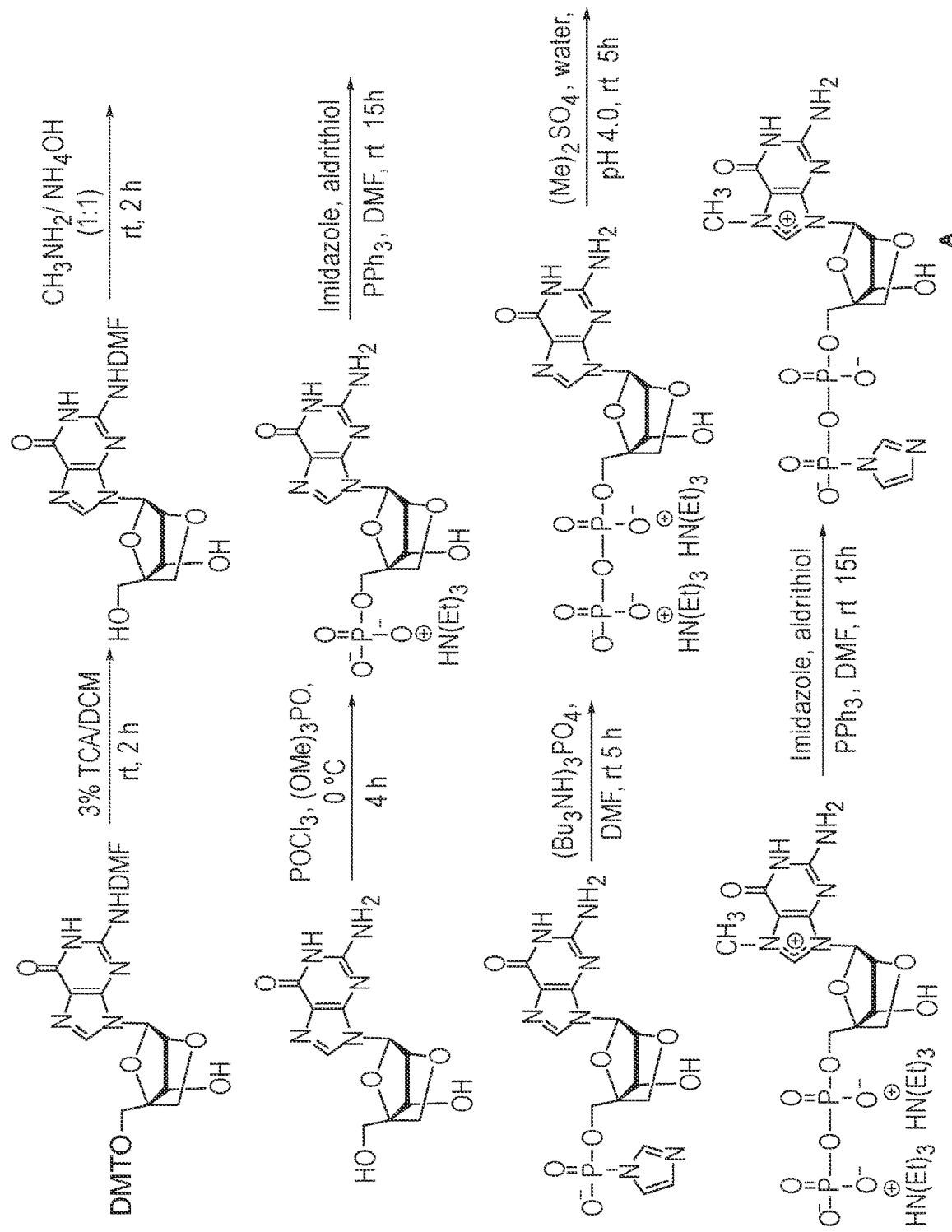
FIG. 2 illustrates an exemplary synthetic scheme to make imidazolide salt of 7 methyl (LNA) Guanosine 5' diphosphate (Imm7(LNA)GDP), which is part (A) of FIG. 1.
Figure 3:
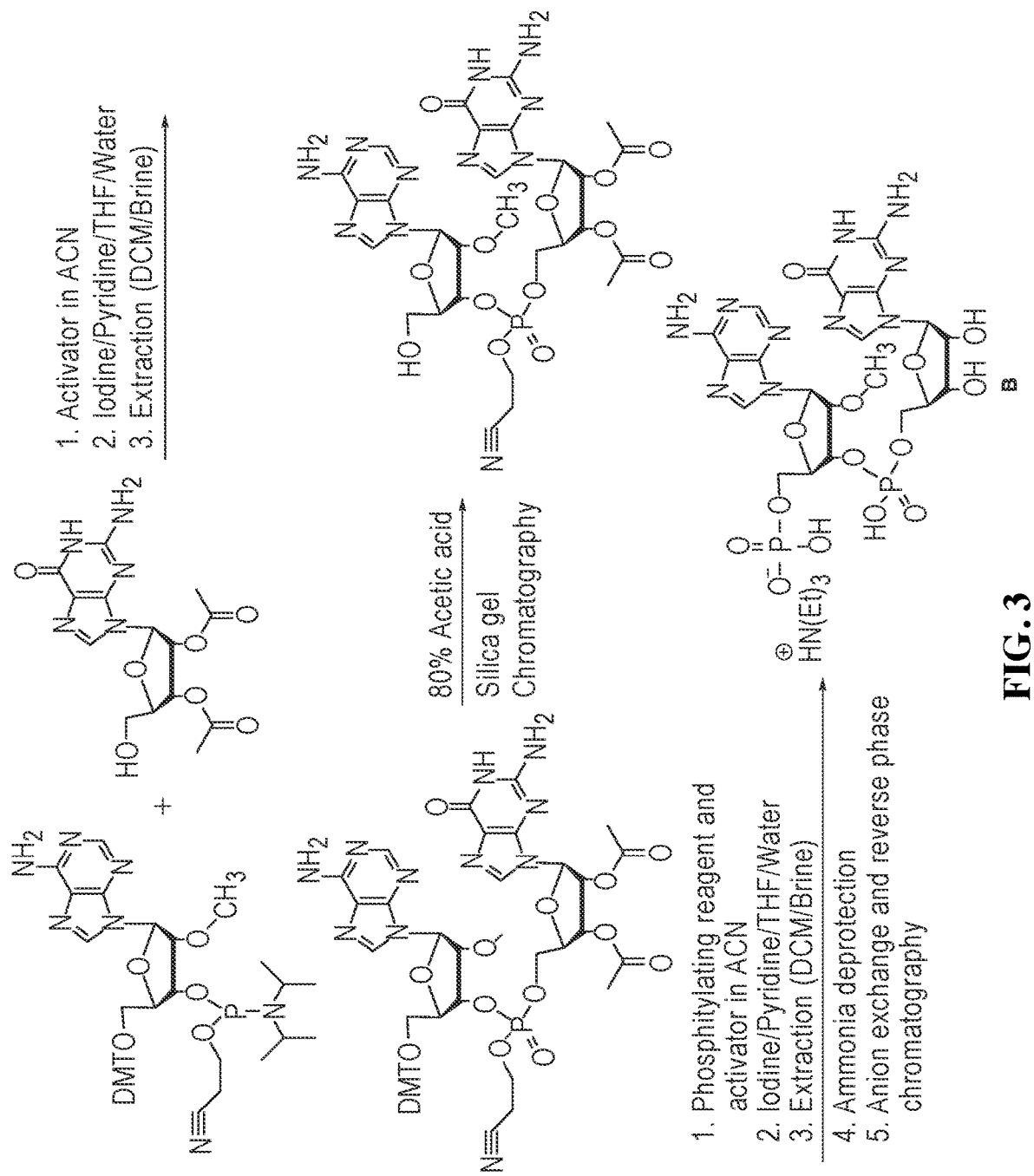
FIG. 3 illustrates an exemplary synthetic scheme to make the dinucleotide 5' phosphate dinucleotide such as pApG, which is part (B) of FIG. 1.
Figure 4:
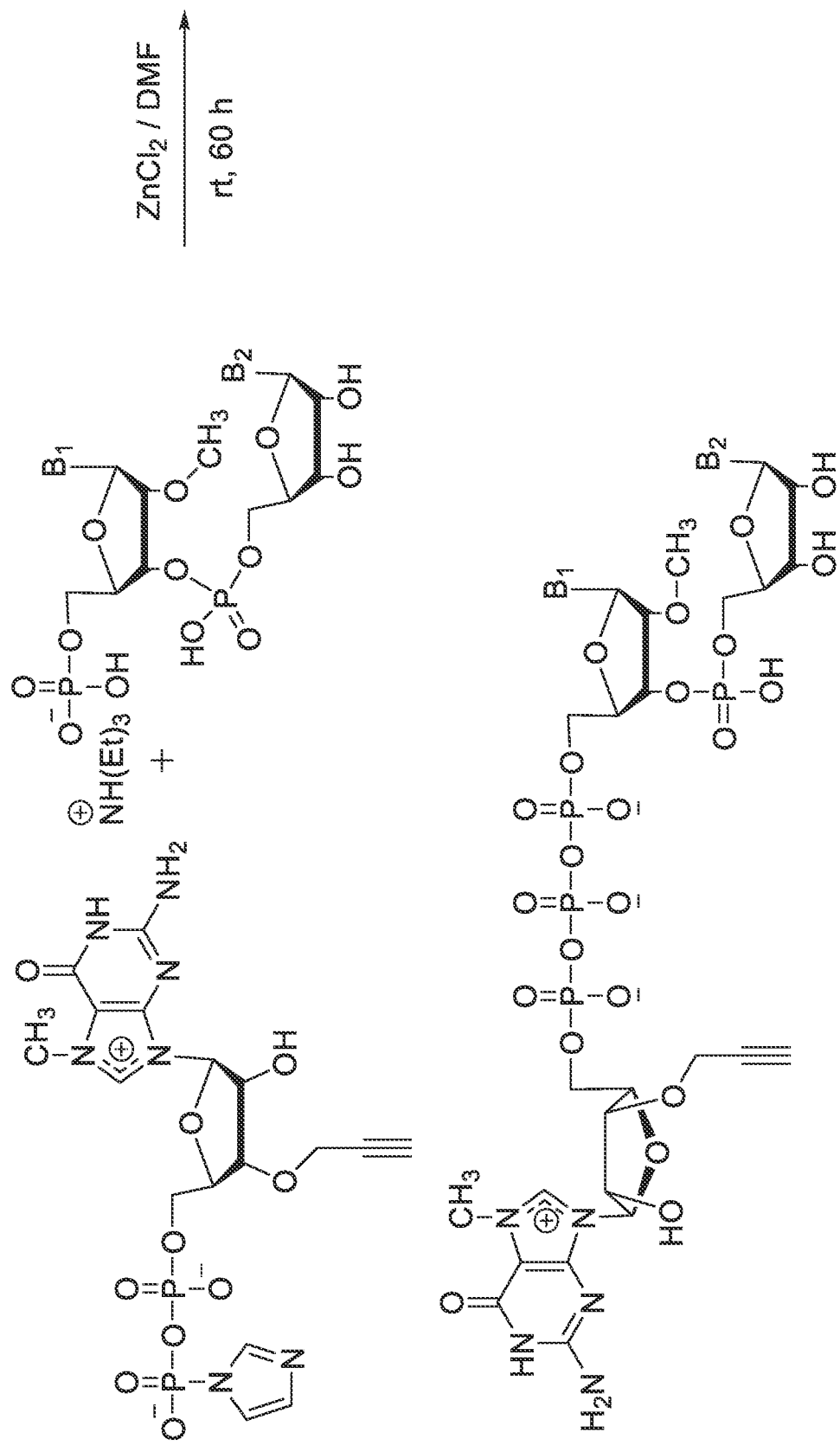
FIG. 4 illustrates an exemplary synthetic scheme for the trinucleotide cap analogs containing 3'-O-propargyl described herein. B$_1$=G, A, U, or C; B$_2$=G, A, U, or C
Figure 5:
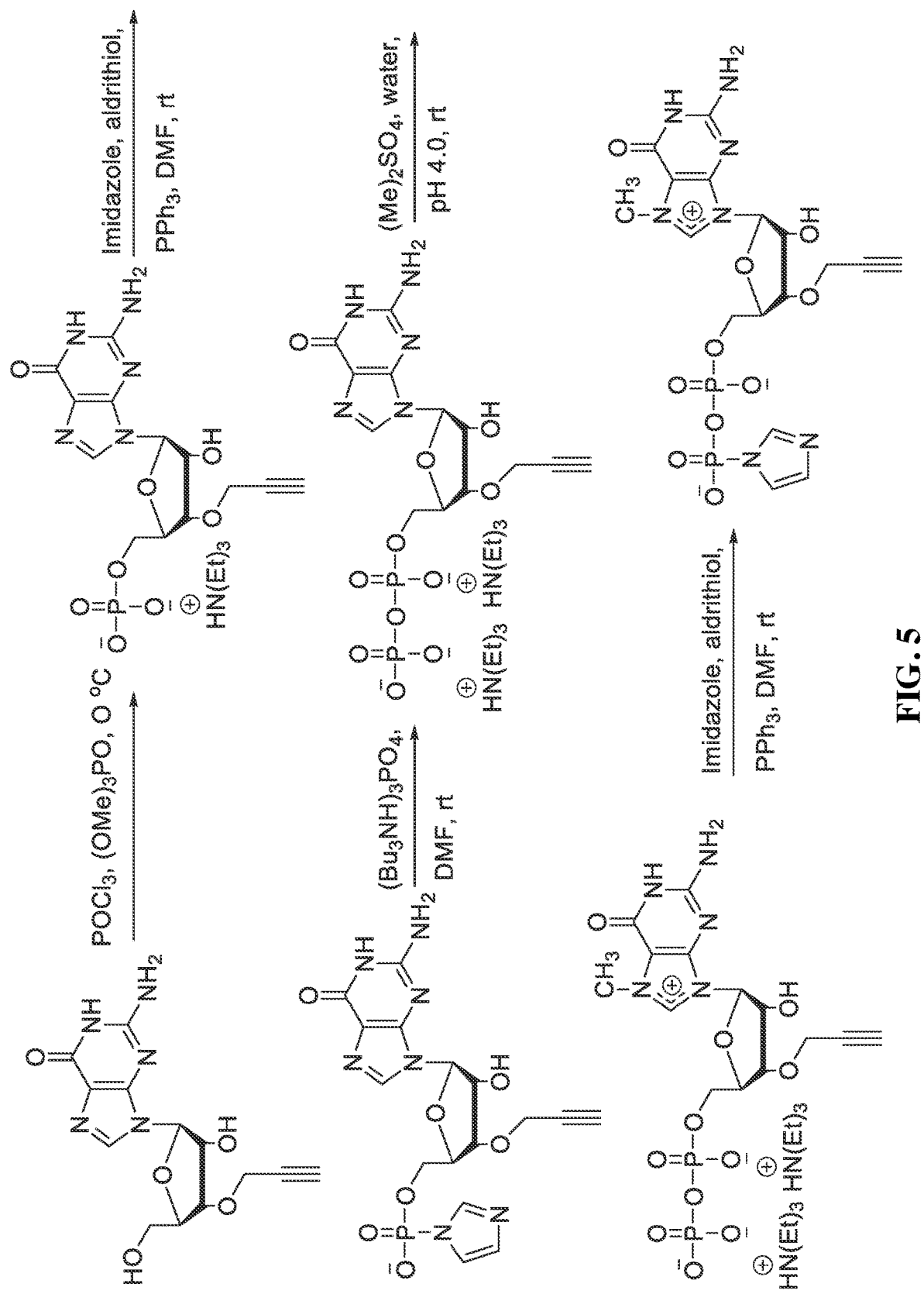
FIG. 5 illustrates an exemplary synthetic scheme to make imidazolide salt of 7 methyl 3'-O-propargyl Guanosine 5'-diphosphate (Imm$^{7,3'-O-propargyl}$ GDP), which is used in the synthetic scheme for the trinucleotide cap analogs containing 3'-O-propargyl of FIG. 4.
Figure 6:
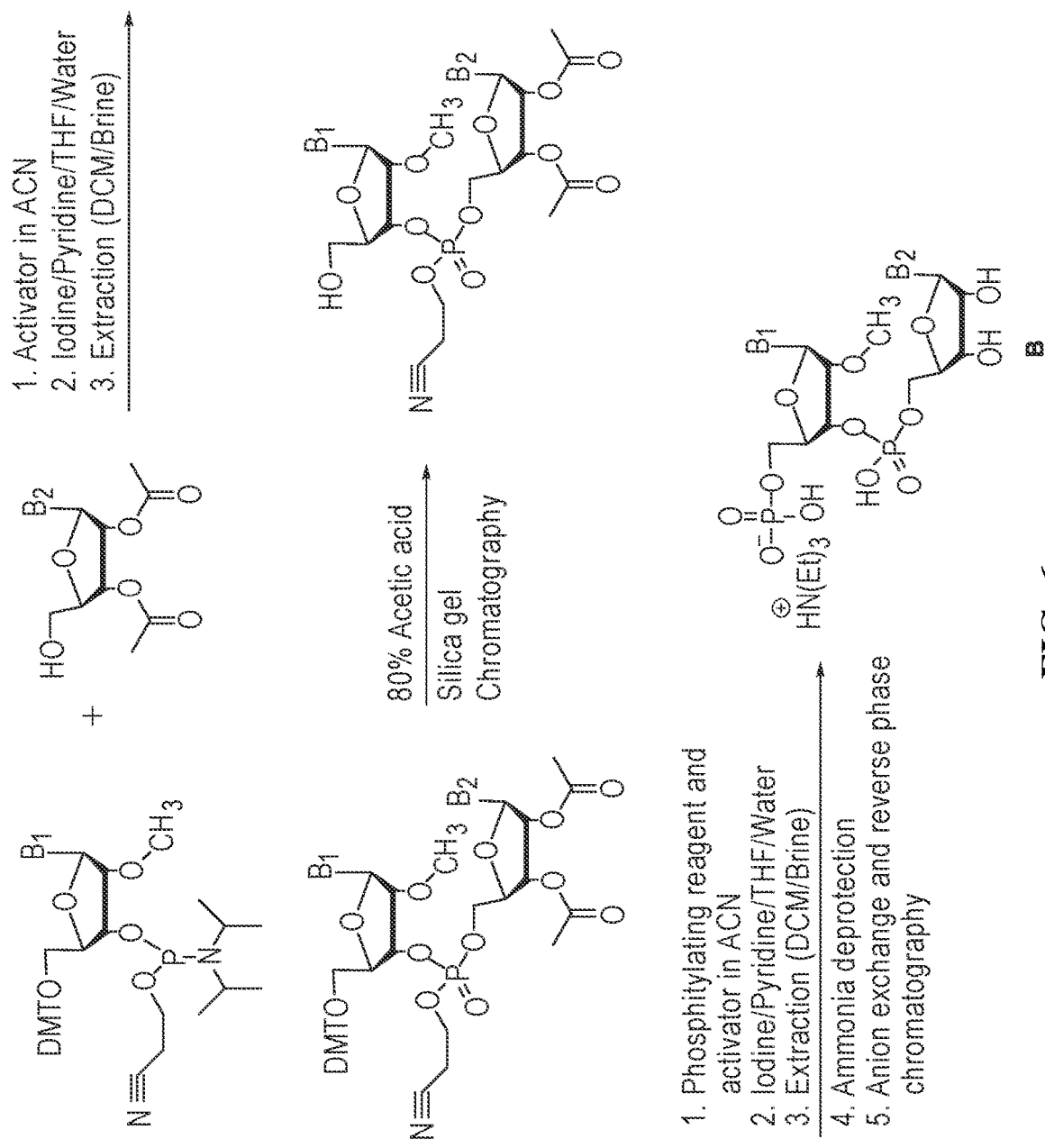
FIG. 6 illustrates an exemplary synthetic scheme to make dinucleotides to be used in synthesizing trinucleotide caps, including the trinucleotide cap analogs containing 3'-O-propargyl of FIG. 4. $B_1$=G, A, U, or C; $B_2$=G, A, U, or C
Figure 7:
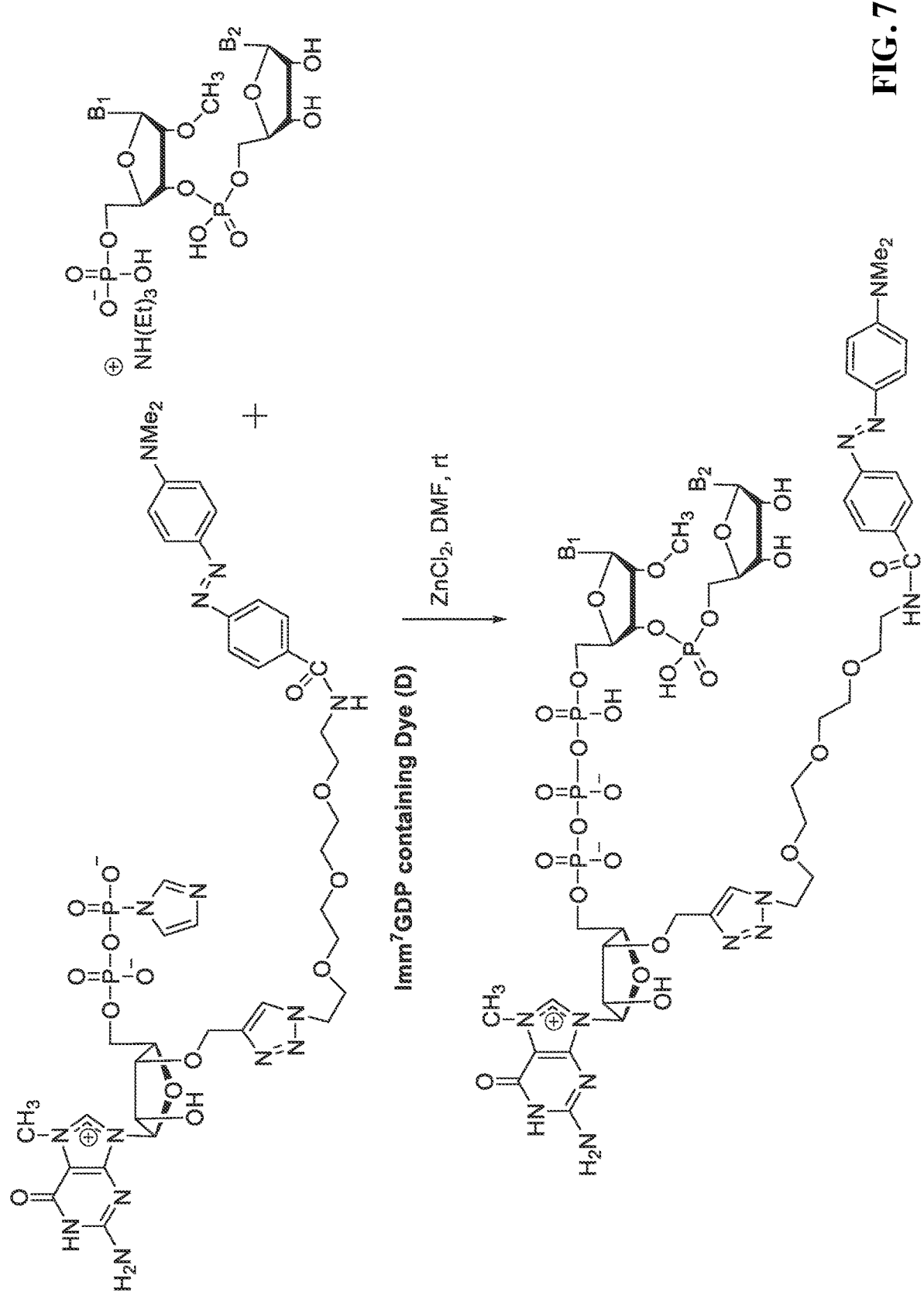
FIG. 7 illustrates an exemplary synthetic scheme to make trinucleotide cap analogs containing a dye as described herein. $B_1$=G, A, U, or C; $B_2$=G, A, U, or C
Figure 8A:
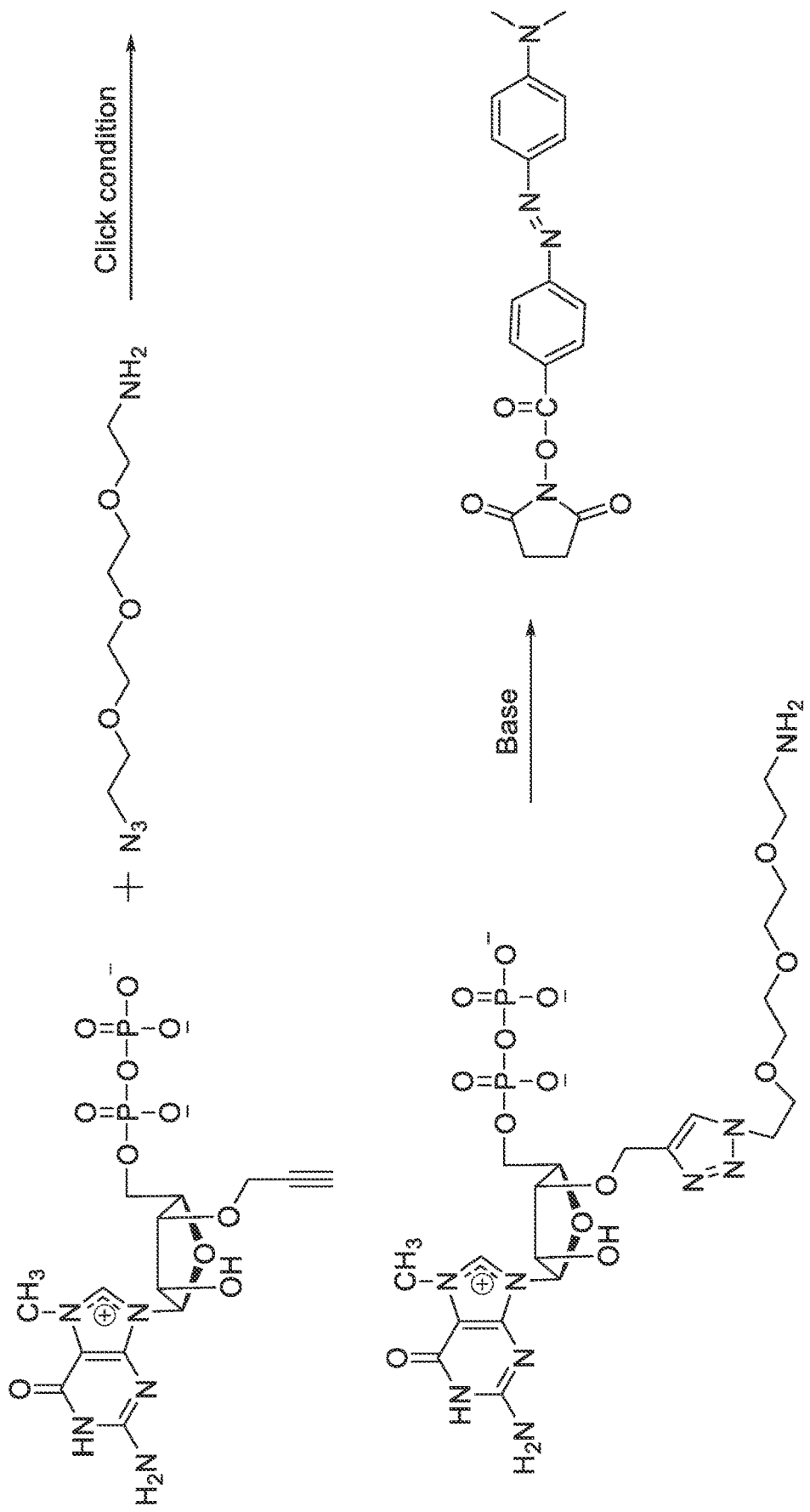
FIGS. 8A and 8B illustrate an exemplary synthetic scheme to make Imm$^7$GDP Containing Dye, which is used in the synthetic scheme for the trinucleotide cap analogs containing a dye of FIG. 7.
Figure 8B:
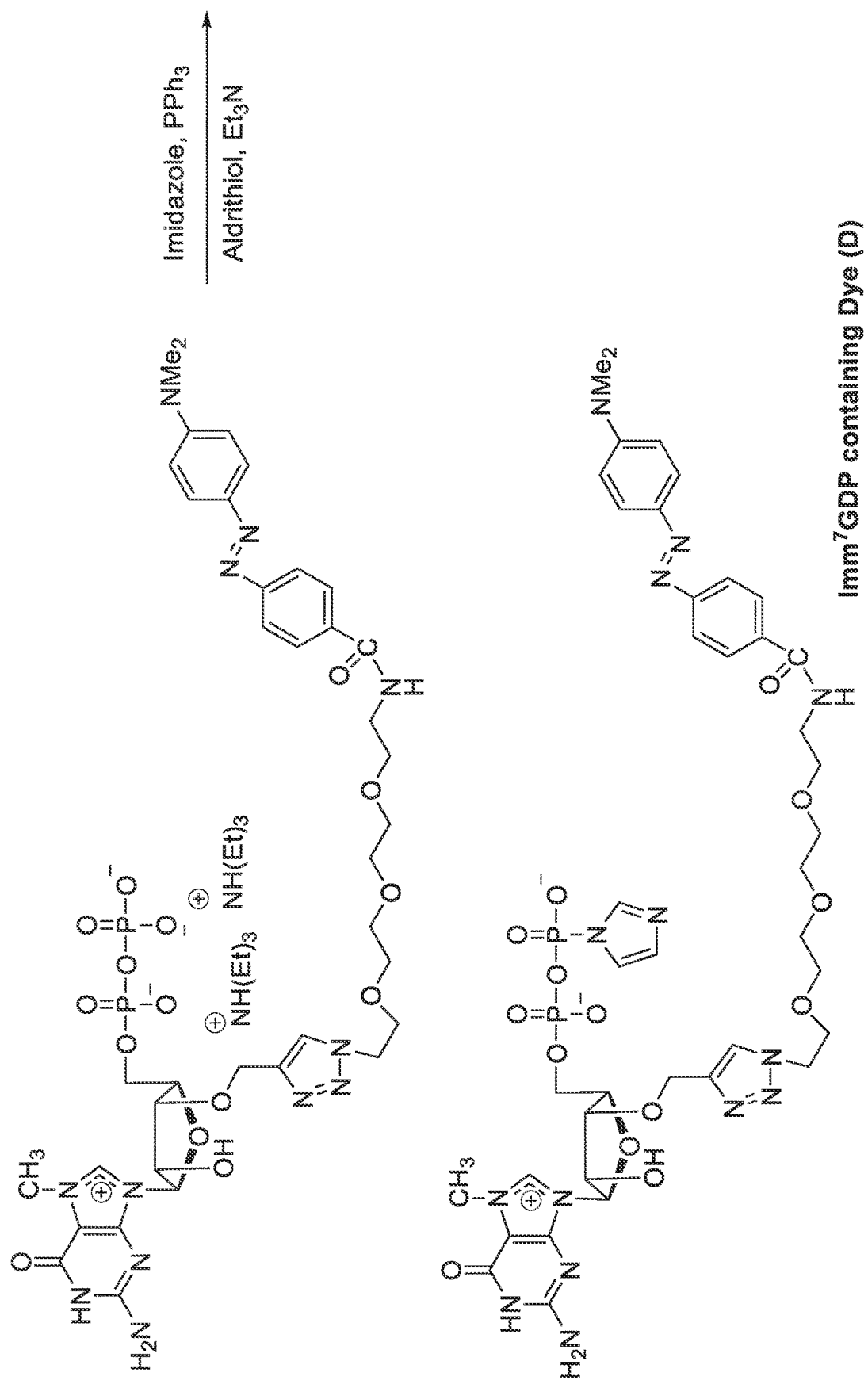

Table 1 provides a listing of sequences used herein.

TABLE 1

| SEQ ID No. | Sequence | Description |
|---|---|---|
| 1 | GYSTPPKKKRKVEDP | cell-penetrating peptide |
| 2 | GYSTPPKTRRRP | cell-penetrating peptide |
| 3 | GYSTPGRKKR | cell-penetrating peptide |
| 4 | GYSTPRRNRRRRW | cell-penetrating peptide |
| 5 | PDEVKRKKKPPTSYG | cell-penetrating peptide |
| 6 | PRRRTKPPTSYG | cell-penetrating peptide |
| 7 | RKKRGPTSYG | cell-penetrating peptide |
| 8 | WRRRRNRRPTSYG | cell-penetrating peptide |
| 9 | GYGPPKKKRKVEAPYKA | cell-penetrating peptide |

TABLE 1-continued

| SEQ ID No. | Sequence | Description |
|---|---|---|
| 10 | PAAKRVKLD | cell-penetrating peptide |
| 11 | RQRRNELKRSP | cell-penetrating peptide |
| 12 | KRPAATKKAGQAKKKK | cell-penetrating peptide |
| 13 | VRKKRKTEEESPLKDKDAKKSKQE | cell-penetrating peptide |
| 14 | RLRRDAGGRGGVYEHLGGAPRRRK | cell-penetrating peptide |
| 15 | KRKGDEVDGVDECAKKSKK | cell-penetrating peptide |
| 16 | NQSSNFGPMKGGNFGGRSSGPYGGGGQYFAKPRNQGGY | cell-penetrating peptide |
| 17 | GGKRTADGSEFESPKKARKVEAYPKAW | cell-penetrating peptide |
| 18 | GGKRTADGSEFESPKKKRAVEAYPKAW | cell-penetrating peptide |
| 19 | GGKRTADGSEFESPKKKAKVEAYPKAW | cell-penetrating peptide |
| 20 | GGKRTADGSEFESPKKKRKVEAPYKAWK | cell-penetrating peptide |
| 21 | GGKRTADGSEFESPKKKRKVEYKAWK | cell-penetrating peptide |
| 22 | GYGPAAKRVKLDEAYPKAWK | cell-penetrating peptide |
| 23 | GGKRTADGSEFEPAAKRVKLDEAYPKAWK | cell-penetrating peptide |
| 24 | GTGPKKKRKVGGGGYGPKKKRLVG | cell-penetrating peptide |
| 25 | KRPAATKKAGQAKKKKLEAYPKAWK | cell-penetrating peptide |
| 26 | ATKGTKRSYEQMETGE | cell-penetrating peptide |
| 27 | GKWERKPIRCAS | cell-penetrating peptide |
| 28 | GYGKRTADSQHSTPPKKKRKVEAPYKAWK | cell-penetrating peptide |
| 29 | KRTADSQHSTPPKKKRKVEAPYKAWK | cell-penetrating peptide |
| 30 | GYGPPKKKRKVEAPYKAWKWAKYPAMRRAHHRRRRASHRRRTTTGT | cell-penetrating peptide |
| 31 | GYGPPKKKRKVEAPYKAWKRGARRYSKMKRRRRVARRHRRRP | cell-penetrating peptide |
| 32 | FWGYGYGPPKKKRKVEAPYKAWK | cell-penetrating peptide |
| 33 | GKPSSDDEATADSQHSTPPKKKERKVED | cell-penetrating peptide cell-penetrating peptide |
| 34 | GKPTADDQHSTPPKKKRKVED | cell-penetrating peptide |
| 35 | GGKRTADGSEFESPKKARKVEAYPKAK | cell-penetrating peptide |
| 36 | EKIRLRPGRKKRYRLKHL | cell-penetrating peptide |
| 37 | PEGTRQARRNRRRRWRKR | cell-penetrating peptide |
| 38 | PEGTRQPRRNRRRRWRKR | cell-penetrating peptide |
| 39 | GVKRSYGAARGDDRRRPNVVAPYKAW | cell-penetrating peptide |
| 40 | KSVPNRTRTYIKLKRLRFKGAPYKAW | cell-penetrating peptide |
| 41 | EMRRRREEEGLQLRKQKREEQLFKRRN | cell-penetrating peptide |
| 42 | FEAALAEALAEALA | cell-penetrating peptide |
| 43 | Ac-LARLLPRLLARL-NHCH$_3$ | cell-penetrating peptide |
| 44 | GLLEELLELLEELWEELLEG | cell-penetrating peptide |
| 45 | GWEGLIEGIEGGWEGLIEG | cell-penetrating peptide |

TABLE 1-continued

| SEQ ID No. | Sequence | Description |
|---|---|---|
| 46 | GLFEALAEFIEGGWEGLIEG | cell-penetrating peptide |
| 47 | GLFEALLELLESLWELLLEA | cell-penetrating peptide |
| 48 | GGYCLEKWMIVASELKCFGNTA | cell-penetrating peptide |
| 49 | GGYCLTRWMLIEAELKCFGNTAV | cell-penetrating peptide |
| 50 | WEAALAEALAEALAEHLAEALAEALEALAA | cell-penetrating peptide |
| 51 | GLFGAIAGFIENGWEGMIDGWYG | cell-penetrating peptide |
| 52 | GIGAVLKVLTTGLPALISWIKRKRQQ | cell-penetrating peptide |
| 53 | GRKKRRQRRRPPQ | cell-penetrating peptide |
| 54 | RQIKIWFQNRRMKWKK | cell-penetrating peptide |
| 55 | GWTLNSAGYLLGKINLKALAALAKKIL | cell-penetrating peptide |
| 56 | WEAKLAKALAKALAKHLAKALAKALKACEA | cell-penetrating peptide |
| 57 | GLFKALLKLLKSLWKLLLKA | cell-penetrating peptide |
| 58 | GLFRALLRLLRSLWRLLLRA | cell-penetrating peptide |
| 59 | GLFEALLELLESLYELLLEA | cell-penetrating peptide |
| 60 | GLFEALEELWEA | cell-penetrating peptide |
| 61 | GLFLLEEWLE | cell-penetrating peptide |
| 62 | GLFLLEEWLEK | cell-penetrating peptide |
| 63 | GLFEALLELLESLWELLLEAK | cell-penetrating peptide |
| 64 | Suc-GLFKLLEEWLE | cell-penetrating peptide |
| 65 | Suc-GLFKLLEEWLEK | cell-penetrating peptide |
| 66 | GLFEAIAEFIEGGWEGLIEG | cell-penetrating peptide |
| 67 | GLFKAIAKFIKGGWKGLIKG | cell-penetrating peptide |
| 68 | IRFKKTKLIASIAMALC | cell-penetrating peptide |
| 69 | ALAGTHAGASLTFQVLDKV1EELGKVSRK | cell-penetrating peptide |
| 70 | GLFEAIEGFIENGWEGMIDGWYG | cell-penetrating peptide |
| 71 | GYICRRARGDNPDDRCT | cell-penetrating peptide |
| 72 | GLFEAIAEFIEGGWEGLIEGCA | cell-penetrating peptide |
| 73 | GLFHAIAHFIHGGWHGLIHGWWYG | cell-penetrating peptide |
| 74 | RRRQRRKKRGGDIMGEWGNEIFGAIAGFLG | cell-penetrating peptide |
| 75 | GLFEAIADFIENGWEGMIDGGG | cell-penetrating peptide |
| 76 | ALAGTIIAGASLTFQVLDKV1EELGKVSRKK | cell-penetrating peptide |
| 77 | IRFKKTKLIASIAMA | cell-penetrating peptide |
| 78 | GLWHLLLHLWRRLLRLLR | cell-penetrating peptide |
| 79 | KKIMLLLMTLLLVSLPLAQEQ | cell-penetrating peptide |
| 80 | GLFEALLELLESLWELLLEAWYG | cell-penetrating peptide |
| 81 | RLLRLLLRLWRRLLRLLR | cell-penetrating peptide |
| 82 | LLELELLELELLLELELLELELLLEL | cell-penetrating peptide |
| 83 | GLFEALLELLESLWELLLEARRRRRRRR | cell-penetrating peptide |
| 84 | GLFEALLELLESLWELLLEARRRRRR | cell-penetrating peptide |

TABLE 1-continued

| SEQ ID No. | Sequence | Description |
|---|---|---|
| 85 | GLFEALLELLESLWELLLEAKKKKKKKK | cell-penetrating peptide |
| 86 | GLFEALLELLESLWELLLEAKKKKKK | cell-penetrating peptide |
| 87 | GLFEALLELLESLWELLLEAKK | cell-penetrating peptide |
| 88 | GLFEALLELLESLWELLLEAKKK | cell-penetrating peptide |
| 89 | GLFEALLELLESLWELLLEAEE | cell-penetrating peptide |
| 90 | GLFEALLELLESLWELLLEAEEEE | cell-penetrating peptide |
| 91 | GLFEALLELLESLWELLLEAEEEEEE | cell-penetrating peptide |
| 92 | GLFEALLELLESLWELLL | cell-penetrating peptide |
| 93 | PLSSIFSRIGDPRGARRYAKMKRRRRRVARRHRRRP | cell-penetrating peptide |
| 94 | GPFHYFQFLFPPV | cell-penetrating peptide |
| 95 | GSSSWWQRWWPPW | cell-penetrating peptide |
| 96 | RRRQRRKKR | cell-penetrating peptide |
| 97 | KKKK | cell-penetrating peptide |
| 98 | KKKKKK | cell-penetrating peptide |
| 99 | KKKKKKKK | cell-penetrating peptide |
| 100 | KKKKKKKKKK | cell-penetrating peptide |
| 101 | KKKKKKKKKKKK | cell-penetrating peptide |
| 102 | KKKKKKKKKKKKKKK | cell-penetrating peptide |
| 103 | KKKKKKKKKKKKKKKKKK | cell-penetrating peptide |
| 104 | KKKKKKKKKKKKKKKKKKKKKKKK | cell-penetrating peptide |
| 105 | RRRR | cell-penetrating peptide |
| 106 | RRRRRR | cell-penetrating peptide |
| 107 | RRRRRRRR | cell-penetrating peptide |
| 108 | RRRRRRRRRR | cell-penetrating peptide |
| 109 | RRRRRRRRRRRR | cell-penetrating peptide |
| 110 | RRRRRRRRRRRRRRR | cell-penetrating peptide |
| 111 | RRRRRRRRRRRRRRRRRRR | cell-penetrating peptide |
| 112 | RRRRRRRRRRRRRRRRRRRRRRRR | cell-penetrating peptide |
| 113 | YKA | cell-penetrating peptide |
| 114 | KKKKKKKKWKGGGGACYGLPHLFCG | cell-penetrating peptide |
| 115 | YKAKKKKKKKKWK | cell-penetrating peptide |
| 116 | KTPKKAKKPKTPKKAKKP | cell-penetrating peptide |
| 117 | KKAKKPAATRKSSKNPKKPKTVKPKKVAK | cell-penetrating peptide |
| 118 | RGARRYSKMKRRRRRVARRHRRRP | cell-penetrating peptide |
| 119 | TRQARRNRRRRWRERQRGSGSG | cell-penetrating peptide |
| 120 | KRPRGRPKGSKKNWRRRKRRASRRSPRRR | cell-penetrating peptide |
| 121 | KRGRGRPRKQPPKEPSEVPTPKRPRGRPKGSKNK | cell-penetrating peptide |
| 122 | KEKYEKDIAAYRAKGKPAAKKGVVKAEKSKKKK | cell-penetrating peptide |

TABLE 1-continued

| SEQ ID No. | Sequence | Description |
|---|---|---|
| 123 | YKAKKKKKKKKKKWK | cell-penetrating peptide |
| 124 | KKKKKKKGGC | cell-penetrating peptide |
| 125 | YRARRRRRRRRWR | cell-penetrating peptide |
| 126 | YRARRRRRRRRRRWR | cell-penetrating peptide |
| 127 | KGDPKKPRGKMSSYAFFVQTCREEHKKKHPDASVNFSEFSKK | cell-penetrating peptide |
| 128 | KKQLKKQLKKQLKQWK | cell-penetrating peptide |
| 129 | KKSPKKSPKKSPKKSK | cell-penetrating peptide |
| 130 | KLSKLEKKSKLEK | cell-penetrating peptide |
| 131 | KLSKLEKKLSKLEKKSKLEK | cell-penetrating peptide |
| 132 | KSLKKSLKKSLKKSK | cell-penetrating peptide |
| 133 | KIRRRGKNKVAARTCRQRRTDR | cell-penetrating peptide |
| 134 | KIRRRGKNKVAAQNCRKRKLET | cell-penetrating peptide |
| 135 | KRRIRREKNKMAAAKCRNRRRELT | cell-penetrating peptide |
| 136 | KDRSNLLERHTR | cell-penetrating peptide |
| 137 | KRPAATKKAGQAKKKL | cell-penetrating peptide |
| 138 | RRRRRREEEE | cell-penetrating peptide |
| 139 | RRRRRREEEEE | cell-penetrating peptide |
| 140 | RRRRRREEEEEEE | cell-penetrating peptide |
| 141 | RRRRRRRREEEE | cell-penetrating peptide |
| 142 | RRRRRRRREEEEE | cell-penetrating peptide |
| 143 | RRRRRRRREEEEEEE | cell-penetrating peptide |
| 144 | RRRRRRRRRRRREEEE | cell-penetrating peptide |
| 145 | RRRRRRRRRRRREEEEEE | cell-penetrating peptide |
| 146 | RRRRRRRRRRRREEEEEEE | cell-penetrating peptide |
| 147 | KLSKLEKK | cell-penetrating peptide |
| 148 | SKLEK | cell-penetrating peptide |
| 149 | KLSKLEKKLSKLEKK | cell-penetrating peptide |
| 150 | PKKKRKVGGGRGDSP | cell-penetrating peptide |
| 151 | LPHKSMPCG | cell-penetrating peptide |
| 152 | GACLQHKSMPCG | cell-penetrating peptide |
| 153 | YGLPHLFCG | cell-penetrating peptide |
| 154 | SERSMNFCG | cell-penetrating peptide |
| 155 | DHYSLYEDLERGTDK | cell-penetrating peptide |
| 156 | ISLPRTSGAQRASTTR | cell-penetrating peptide |
| 157 | EKLQTKYGLPHKVEFCG | cell-penetrating peptide |
| 158 | TRISESQAKPGD | cell-penetrating peptide |
| 159 | LVFFDY | cell-penetrating peptide |
| 160 | WGGNGPTTFDCSGYTKYVFAK | cell-penetrating peptide |

TABLE 1-continued

| SEQ ID No. | Sequence | Description |
|---|---|---|
| 161 | INIGTTGWGDHYSLY | cell-penetrating peptide |
| 162 | YDNIHG | cell-penetrating peptide |
| 163 | AGWGKFLVGFGRV | cell-penetrating peptide |
| 164 | SIGYPLP | cell-penetrating peptide |
| 165 | TTHWGFTL | cell-penetrating peptide |
| 166 | HLQIQPYPQISG | cell-penetrating peptide |
| 167 | KLNIVSVNG | cell-penetrating peptide |
| 168 | RGH | cell-penetrating peptide |
| 169 | DNRIRLQAKAA | cell-penetrating peptide |
| 170 | KIKMVISWKG | cell-penetrating peptide |
| 171 | LPWYSYLYAVSA | cell-penetrating peptide |
| 172 | WNLPWYYSVSPT | cell-penetrating peptide |
| 173 | WNL | cell-penetrating peptide |
| 174 | PWYYSVSPT | cell-penetrating peptide |
| 175 | SSWESYKSGGGTRL | cell-penetrating peptide |
| 176 | RDWSSQHPGRCNGETHLK | cell-penetrating peptide |
| 177 | SLPTLTL | cell-penetrating peptide |
| 178 | VICTGGDYSFALPVGQWPVMT | cell-penetrating peptide |
| 179 | DKPSYQFGGHNSVDFEEDTLPKV | cell-penetrating peptide |
| 180 | RARRRKRASATQLYQTCKASGTCPPD | cell-penetrating peptide |
| 181 | SGDYSFALPVGQWPWMTG | cell-penetrating peptide |
| 182 | CTGGDYSFALPVGQWPW | cell-penetrating peptide |
| 183 | FYYDYDFFFDYWGQG | cell-penetrating peptide |
| 184 | HLRRLRRRLLREAEG | cell-penetrating peptide |
| 185 | DYYCAAWDDSLNGYSVF | cell-penetrating peptide |
| 186 | YYCLQSMEDPYTFGG | cell-penetrating peptide |
| 187 | YYCARSDGNYGYYYALDYDY | cell-penetrating peptide |
| 188 | AARSPSYYRYDY | cell-penetrating peptide |
| 189 | GPYYAMDYD | cell-penetrating peptide |
| 190 | YYCQQRSSYPYTEGGAYPKAWK | cell-penetrating peptide |
| 191 | YYCQRYDSDWSFGQGTKL | cell-penetrating peptide |
| 192 | YYCARSGYYAMDYWGQGT | cell-penetrating peptide |
| 193 | RVRRGACRGDCLG | cell-penetrating peptide |
| 194 | RVRRGACRYDCLG | cell-penetrating peptide |
| 195 | YYCAKGTHWGFWSGYFDYWGQGT | cell-penetrating peptide |
| 196 | GRENYHGCTTHWGFTLC | cell-penetrating peptide |
| 197 | VQATQSNQHTPRGGGSK | cell-penetrating peptide |
| 198 | DPRAPGS | cell-penetrating peptide |
| 199 | YYCQQRSSYPYTFGG | cell-penetrating peptide |

TABLE 1-continued

| SEQ ID No. | Sequence | Description |
|---|---|---|
| 200 | AARSPSYYRYDYGPYYAMDYD | cell-penetrating peptide |
| 201 | GPKLTGILISILSLFVES | cell-penetrating peptide |
| 202 | KYILRWRPKNS | cell-penetrating peptide |
| 203 | IKVAV | cell-penetrating peptide |
| 204 | WTPPRAQITGYRLTVGLTRR | cell-penetrating peptide |
| 205 | AASIKVAVSADR | cell-penetrating peptide |
| 206 | KLDAPT | cell-penetrating peptide |
| 207 | NRWHSIYITRFG | cell-penetrating peptide |
| 208 | PHSRN | cell-penetrating peptide |
| 209 | SSFHFDGSGYAM | cell-penetrating peptide |
| 210 | RGDS | cell-penetrating peptide |
| 211 | IAFQRN | cell-penetrating peptide |
| 212 | GRGDSP | cell-penetrating peptide |
| 213 | TWYKIAFQRRK | cell-penetrating peptide |
| 214 | EDGIHEL | cell-penetrating peptide |
| 215 | SLVRNRRVITIQ | cell-penetrating peptide |
| 216 | YRVRVTPKEKTGPMKE | cell-penetrating peptide |
| 217 | LQVQLSR | cell-penetrating peptide |
| 218 | SPPRRARVT | cell-penetrating peptide |
| 219 | RKRLQVQLSIRT | cell-penetrating peptide |
| 220 | ATETTITIS | cell-penetrating peptide |
| 221 | NAPFPKLSWTIQ | cell-penetrating peptide |
| 222 | VSPPRRARVTDATETTITISWRTKTETITGG | cell-penetrating peptide |
| 223 | WTIQTTVDRGLL | cell-penetrating peptide |
| 224 | KPDVRSYTITG | cell-penetrating peptide |
| 225 | DTINNGRDHMILI | cell-penetrating peptide |
| 226 | ANGQTPIQRYIK | cell-penetrating peptide |
| 227 | MILISIGKSQKRM | cell-penetrating peptide |
| 228 | PRARITGYIIKYEKPGSPPREVVPRPRPGV | cell-penetrating peptide |
| 229 | PPFLMLLKGSTR | cell-penetrating peptide |
| 230 | WQPPRARI | cell-penetrating peptide |
| 231 | NQRLASFSNAQQS | cell-penetrating peptide |
| 232 | WQPPRARITGYIIKYEKPG | cell-penetrating peptide |
| 233 | ISNVFVQRMSQSPEVLD | cell-penetrating peptide |
| 234 | YEKPGSPPREVVPRPRPGV | cell-penetrating peptide |
| 235 | KARSFNVNQLLQD | cell-penetrating peptide |
| 236 | KNNQKSEPLIGRKKT | cell-penetrating peptide |
| 237 | KNSFMALYLSKG | cell-penetrating peptide |

TABLE 1-continued

| SEQ ID No. | Sequence | Description |
| --- | --- | --- |
| 238 | EILDVPST | cell-penetrating peptide |
| 239 | KNSFMALYLSKGRLVFALG | cell-penetrating peptide |
| 240 | IDAPS | cell-penetrating peptide |
| 241 | RDSFVALYLSEGHVIFAGLG | cell-penetrating peptide |
| 242 | VVIDASTAIDAPSNL | cell-penetrating peptide |
| 243 | KPRLQFSLDIQT | cell-penetrating peptide |
| 244 | LDVPS | cell-penetrating peptide |
| 245 | DGQWHSVTVSIK | cell-penetrating peptide |
| 246 | REDV | cell-penetrating peptide |
| 247 | FVLYLGSKNAKK | cell-penetrating peptide |
| 248 | PHSRNRGDSP | cell-penetrating peptide |
| 249 | LAIKNDNLVYVY | cell-penetrating peptide |
| 250 | LWVTVRSQQRGLF | cell-penetrating peptide |
| 251 | AYFSIVKIERVG | cell-penetrating peptide |
| 252 | GTNNWWQSPSIQN | cell-penetrating peptide |
| 253 | DVISLYNFKHIY | cell-penetrating peptide |
| 254 | WVTVTLDLRQVFQ | cell-penetrating peptide |
| 255 | FFDGSSYAVVRD | cell-penetrating peptide |
| 256 | RQVFQVAYIIIKA | cell-penetrating peptide |
| 257 | LHVFYDFGFGFSNG | cell-penetrating peptide |
| 258 | LTRYKITPRRGPPT | cell-penetrating peptide |
| 259 | LKKAQINDAKYREISIIYHN | cell-penetrating peptide |
| 260 | LLEFTSARYIRL | cell-penetrating peptide |
| 261 | RAYFNGQSFIAS | cell-penetrating peptide |
| 262 | YIRLRLQRIRTL | cell-penetrating peptide |
| 263 | SRLRGKNPTKGK | cell-penetrating peptide |
| 264 | RRYYYSIKDISV | cell-penetrating peptide |
| 265 | LHKKGKNSSKPK | cell-penetrating peptide |
| 266 | SINNTAVNQRLT | cell-penetrating peptide |
| 267 | RLKTRSSHGMIF | cell-penetrating peptide |
| 268 | GGFLKYTVSYDI | cell-penetrating peptide |
| 269 | GEKSQFSIRLKT | cell-penetrating peptide |
| 270 | RDQLMTVLANVT | cell-penetrating peptide |
| 271 | TLFLAHGRLVFM | cell-penetrating peptide |
| 272 | ANVTHLLIRANY | cell-penetrating peptide |
| 273 | LVFMFNVGHKKL | cell-penetrating peptide |
| 274 | AGTFALRGDNPQG | cell-penetrating peptide |
| 275 | TLFLAHGRLVFMFNVGHKKL | cell-penetrating peptide |
| 276 | VLIKGGRARKHV | cell-penetrating peptide |

TABLE 1-continued

| SEQ ID No. | Sequence | Description |
|---|---|---|
| 277 | DFMTLFLAHGRLVFMGNVG | cell-penetrating peptide |
| 278 | LSNIDYLIKAS | cell-penetrating peptide |
| 279 | HKKLKIRSQEKY | cell-penetrating peptide |
| 280 | LQQSRIANISME | cell-penetrating peptide |
| 281 | GAAWKIKGPIYL | cell-penetrating peptide |
| 282 | NLLLLLVKANLK | cell-penetrating peptide |
| 283 | VIRDSNVVQLDV | cell-penetrating peptide |
| 284 | HRDELLLWARKI | cell-penetrating peptide |
| 285 | GLIYYVAHQNQM | cell-penetrating peptide |
| 286 | KRRARDLVHRAE | cell-penetrating peptide |
| 287 | DYATLQLQEGRLHFMFDLG | cell-penetrating peptide |
| 288 | SQFQESVDNITK | cell-penetrating peptide |
| 289 | KKGSYNNIVVHV | cell-penetrating peptide |
| 290 | PGGMREKGRKAR | cell-penetrating peptide |
| 291 | ADNLLFYLGSAK | cell-penetrating peptide |
| 292 | MEMQANLLLDRL | cell-penetrating peptide |
| 293 | GSAKFIDFLAIE | cell-penetrating peptide |
| 294 | LSEIKLLISAR | cell-penetrating peptide |
| 295 | KVSFLWWVGSGV | cell-penetrating peptide |
| 296 | RDFTKATNIRLRFLR | cell-penetrating peptide |
| 297 | SYWYRIEASRTG | cell-penetrating peptide |
| 298 | ISTVMFKFRTFS | cell-penetrating peptide |
| 299 | YFDGTGFAKAVG | cell-penetrating peptide |
| 300 | KQANISIVDIDSN | cell-penetrating peptide |
| 301 | NGQWHKVTAKKI | cell-penetrating peptide |
| 302 | FSTRNESGIILL | cell-penetrating peptide |
| 303 | AKKIKNRLELVV | cell-penetrating peptide |
| 304 | RRQTTQAYYAIF | cell-penetrating peptide |
| 305 | GFPGGLNQFGLTTN | cell-penetrating peptide |
| 306 | YAIFLNKGRLEV | cell-penetrating peptide |
| 307 | NQFGLTTNIRFRG | cell-penetrating peptide |
| 308 | KNRLTIELEVRT | cell-penetrating peptide |
| 309 | IRSLKLTKGTGKP | cell-penetrating peptide |
| 310 | GLLFYMARINHA | cell-penetrating peptide |
| 311 | AKALELRGVQPVS | cell-penetrating peptide |
| 312 | VQLRNGFPYFSY | cell-penetrating peptide |
| 313 | GQLFHVAYILIKF | cell-penetrating peptide |
| 314 | HKIKIVRVKQEG | cell-penetrating peptide |

TABLE 1-continued

| SEQ ID No. | Sequence | Description |
|---|---|---|
| 315 | NVLSLYNFKTTF | cell-penetrating peptide |
| 316 | DFGTVQLRNGFPFFSYDLG | cell-penetrating peptide |
| 317 | SQRIYQFAKLNYT | cell-penetrating peptide |
| 318 | NIRLRFLRTNTL | cell-penetrating peptide |
| 319 | EVNVTLDLGQVFH | cell-penetrating peptide |
| 320 | GKNTGDHFVLYM | cell-penetrating peptide |
| 321 | GQVFHVAYVLIKF | cell-penetrating peptide |
| 322 | VVSLYNFEQTFML | cell-penetrating peptide |
| 323 | HQQDLGTAGSCLRKFSTMFLF | cell-penetrating peptide |
| 324 | RFDQELRLVSYN | cell-penetrating peptide |
| 325 | HQQDLGTAGSCLRKFSTMFLFCNI | cell-penetrating peptide |
| 326 | RLVSYSGVLFFLK | cell-penetrating peptide |
| 327 | VAEIDGIEL | cell-penetrating peptide |
| 328 | NWRHISYITRFG | cell-penetrating peptide |
| 329 | GIIFFL | cell-penetrating peptide |
| 330 | KRLQVQLRSIRT | cell-penetrating peptide |
| 331 | ASKAIQVFLLGG | cell-penetrating peptide |
| 332 | TWYKIAFQRNRK | cell-penetrating peptide |
| 333 | VLVRVERATVFS | cell-penetrating peptide |
| 334 | QVFQVAYIIIKA | cell-penetrating peptide |
| 335 | TVFSVDQDNMLE | cell-penetrating peptide |
| 336 | GEFYFDLRLKGDK | cell-penetrating peptide |
| 337 | RLRGPQRVFDLH | cell-penetrating peptide |
| 338 | GTPGPQGIA | cell-penetrating peptide |
| 339 | FDLHQNMGSVN | cell-penetrating peptide |
| 340 | GQRDVV | cell-penetrating peptide |
| 341 | LRAHAVDVNG | cell-penetrating peptide |
| 342 | TAGSCLRKFSTM | cell-penetrating peptide |
| 343 | LFSHAVSSNG | cell-penetrating peptide |
| 344 | KGHRGF | cell-penetrating peptide |
| 345 | TAGSCLRKFSTMFLF | cell-penetrating peptide |
| 346 | TAGSCLRKFSTMFLFCNI | cell-penetrating peptide |
| 347 | DLGTAGSCLRKFSTM | cell-penetrating peptide |
| 348 | HQQDLGTAGSCLRKFSTM | cell-penetrating peptide |
| 349 | RNIAEIIKDI | cell-penetrating peptide |
| 350 | SIGFRGDGQTC | cell-penetrating peptide |
| 351 | LNRQELFPFG | cell-penetrating peptide |
| 352 | RIQNLLKITNLRIKFVK | cell-penetrating peptide |
| 353 | KKQRFRHRNRKGYRSQ | cell-penetrating peptide |

TABLE 1-continued

| SEQ ID No. | Sequence | Description |
|---|---|---|
| 354 | SINNTAVMQRLT | cell-penetrating peptide |
| 355 | FRHRNRKGY | cell-penetrating peptide |
| 356 | RYRVRVTPKEKTGPMKE | cell-penetrating peptide |
| 357 | SETTVKYIFRLHE | cell-penetrating peptide |
| 358 | GHRGPTGRPGKRGKQGQKGDS | cell-penetrating peptide |
| 359 | KAFDITYVRLKF | cell-penetrating peptide |
| 360 | GDLGRPGRKGRPGPP | cell-penetrating peptide |
| 361 | YIGSR | cell-penetrating peptide |
| 362 | RGEFYFDLRLKGDK | cell-penetrating peptide |
| 363 | LAGSCLARFSTM | cell-penetrating peptide |
| 364 | LALFLSNGHFVA | cell-penetrating peptide |
| 365 | ISRCQVCMKKRH | cell-penetrating peptide |
| 366 | PGRWHKVSVRWE | cell-penetrating peptide |
| 367 | TDIPPCPHGWISLWK | cell-penetrating peptide |
| 368 | VRWGMQQIQLVV | cell-penetrating peptide |
| 369 | TAIPSCPEGTVPLYS | cell-penetrating peptide |
| 370 | KMPYVSLELEMR | cell-penetrating peptide |
| 371 | GPAGKDGEAGAQG | cell-penetrating peptide |
| 372 | VLLQANDGAGEF | cell-penetrating peptide |
| 373 | GLPGER | cell-penetrating peptide |
| 374 | DGRWHRVAVIMG | cell-penetrating peptide |
| 375 | LAGSCLPVFSTL | cell-penetrating peptide |
| 376 | APVNVTASVQIQ | cell-penetrating peptide |
| 377 | TAGSCLRRFSTM | cell-penetrating peptide |
| 378 | KQGKALTQRHAK | cell-penetrating peptide |
| 379 | TAGSCLRKF | cell-penetrating peptide |
| 380 | RYVVLPR | cell-penetrating peptide |
| 381 | TAGSCL | cell-penetrating peptide |
| 382 | SPYTFIDSLVLMPY | cell-penetrating peptide |
| 383 | TAG | cell-penetrating peptide |
| 384 | PDSGR | cell-penetrating peptide |
| 385 | QQNLGSVNVSTG | cell-penetrating peptide |
| 386 | SRATAQKVSRRS | cell-penetrating peptide |
| 387 | DPGYIGSR | cell-penetrating peptide |
| 388 | GSLSSHLEFVGI | cell-penetrating peptide |
| 389 | VILQQSAADIAR | cell-penetrating peptide |
| 390 | RNRLHLSMLVRP | cell-penetrating peptide |
| 391 | KDISEKVAVYST | cell-penetrating peptide |

TABLE 1-continued

| SEQ ID No. | Sequence | Description |
|---|---|---|
| 392 | APMSGRSPSLVLK | cell-penetrating peptide |
| 393 | LGTIPG | cell-penetrating peptide |
| 394 | AFGVLALWGTRV | cell-penetrating peptide |
| 395 | TDIRVTLNRLNTF | cell-penetrating peptide |
| 396 | IENVVTTFAPNR | cell-penetrating peptide |
| 397 | AFSTLEGRPSAY | cell-penetrating peptide |
| 398 | LEAEFHFTHLIM | cell-penetrating peptide |
| 399 | TSAEAYNLLLRT | cell-penetrating peptide |
| 400 | HLIMTFKTFRPA | cell-penetrating peptide |
| 401 | LNRRYEQARNIS | cell-penetrating peptide |
| 402 | KTWGVYRYFAYD | cell-penetrating peptide |
| 403 | SLLSQLNNLLDQ | cell-penetrating peptide |
| 404 | TNLRIKFVKLHT | cell-penetrating peptide |
| 405 | RDIAEIIKDI | cell-penetrating peptide |
| 406 | KRLVTGQR | cell-penetrating peptide |
| 407 | SHAVSS | cell-penetrating peptide |
| 408 | GPGVVVVERQYI | cell-penetrating peptide |
| 409 | ADTPPV | cell-penetrating peptide |
| 410 | NEPKVLKSYYYAI | cell-penetrating peptide |
| 411 | LRAHAVDING | cell-penetrating peptide |
| 412 | YYAISDFAVGGR | cell-penetrating peptide |
| 413 | DSITKYFQMSLE | cell-penetrating peptide |
| 414 | LPFFNDRPWRRAT | cell-penetrating peptide |
| 415 | YTALIIATDN | cell-penetrating peptide |
| 416 | FDPELYRSTGHGGH | cell-penetrating peptide |
| 417 | VITVKDINDN | cell-penetrating peptide |
| 418 | TNAVGYSVYDIS | cell-penetrating peptide |
| 419 | GLDRESYPYY | cell-penetrating peptide |
| 420 | APVKFLGNQVLSY | cell-penetrating peptide |
| 421 | MKVSATDADD | cell-penetrating peptide |
| 422 | SFSFRVDRRDTR | cell-penetrating peptide |
| 423 | PQVTRGDVFTMP | cell-penetrating peptide |
| 424 | TWSKVGGHLRPGIVQSG | cell-penetrating peptide |
| 425 | KEAEREVTDLLR | cell-penetrating peptide |
| 426 | RGDV | cell-penetrating peptide |
| 427 | AAEPLKNIGILF | cell-penetrating peptide |
| 428 | FALWDAIIGEL | cell-penetrating peptide |
| 429 | VGVAPG | cell-penetrating peptide |
| 430 | LWPLLAVLAAVA | cell-penetrating peptide |

TABLE 1-continued

| SEQ ID No. | Sequence | Description |
|---|---|---|
| 431 | PGVGV | cell-penetrating peptide |
| 432 | VFDNFVLK | cell-penetrating peptide |
| 433 | TSIKIRGTYSER | cell-penetrating peptide |
| 434 | TTSWSQCSKS | cell-penetrating peptide |
| 435 | DPETGV | cell-penetrating peptide |
| 436 | KRSR | cell-penetrating peptide |
| 437 | QGADTPPVGV | cell-penetrating peptide |
| 438 | SVVYGLR | cell-penetrating peptide |
| 439 | PLDREAIAKY | cell-penetrating peptide |
| 440 | DGRGDSVAYG | cell-penetrating peptide |
| 441 | HAVDI | cell-penetrating peptide |
| 442 | LALERKDHSG | cell-penetrating peptide |
| 443 | DQNDN | cell-penetrating peptide |
| 444 | YSMKKTTMKIIPFNRLTIG | cell-penetrating peptide |
| 445 | QDPELPDKNM | cell-penetrating peptide |
| 446 | RGDF | cell-penetrating peptide |
| 447 | LVVQAADLQG | cell-penetrating peptide |
| 448 | GVYYQGGTYSKAS | cell-penetrating peptide |
| 449 | NDDGGQFVVT | cell-penetrating peptide |
| 450 | TAGSCLRKFSCL | cell-penetrating peptide |
| 451 | YILHVAVTN | cell-penetrating peptide |
| 452 | CNYYSNSYSFWLASLNPER | cell-penetrating peptide |
| 453 | TYRIWRDTAN | cell-penetrating peptide |
| 454 | TGLSCLQRFTTM | cell-penetrating peptide |
| 455 | GFTCECSIGFRGDGQTCYGIVFWSEV | cell-penetrating peptide |
| 456 | HHLGGAKQAGDV | cell-penetrating peptide |
| 457 | SCLPGFSGDGRACRDVDECGH | cell-penetrating peptide |
| 458 | MAPRPSLAKKQRFRHRNRKGYRSQRGHSRG | cell-penetrating peptide |
| 459 | KKQKFRHRNRKGYRSQ | cell-penetrating peptide |
| 460 | KKQKFKHRNRKGYRS | cell-penetrating peptide |
| 461 | KKQKFRRRNRKGYRSH | cell-penetrating peptide |
| 462 | TAIPPCPHGWISLWK | cell-penetrating peptide |
| 463 | KKQKSRHRSRKRYRS | cell-penetrating peptide |
| 464 | KKQKSRRRSRKGYRS | cell-penetrating peptide |
| 465 | ISRCTVC | cell-penetrating peptide |
| 466 | ISRCQVCMKRRH | cell-penetrating peptide |
| 467 | VSRCTVC | cell-penetrating peptide |
| 468 | TDIPPCPQGWISLWK | cell-penetrating peptide |

TABLE 1-continued

| SEQ ID No. | Sequence | Description |
|---|---|---|
| 469 | TVKAGELEKIISRCQVMKKRH | cell-penetrating peptide |
| 470 | TDIPSCPHGWISLWK | cell-penetrating peptide |
| 471 | TDIPPCPAGWISLWK | cell-penetrating peptide |
| 472 | TEIPPCPQGWISLWK | cell-penetrating peptide |
| 473 | TDVPPCPQGWISLWK | cell-penetrating peptide |
| 474 | RLVSYNGILFFLK | cell-penetrating peptide |
| 475 | RLVSYSGVIFFLK | cell-penetrating peptide |
| 476 | RLVSYNGILFFL | cell-penetrating peptide |
| 477 | RLVSYSGIIFFLK | cell-penetrating peptide |
| 478 | RFEQELRLVSYSGVLFFLKQ | cell-penetrating peptide |
| 479 | RLVSYNGIIFFLK | cell-penetrating peptide |
| 480 | DPAFKIEDPYSPRIQNLLKITNLRIKFVKL | cell-penetrating peptide |
| 481 | TKRFEQELRLVSYSGVLFFL | cell-penetrating peptide |
| 482 | GGRLKYSVAF | cell-penetrating peptide |
| 483 | GGFLRYTVSYDI | cell-penetrating peptide |
| 484 | GGFLKYTVSYDV | cell-penetrating peptide |
| 485 | LGNKLTAFGGFLKYTVSYDIPV | cell-penetrating peptide |
| 486 | GGYLKYTVSYDI | cell-penetrating peptide |
| 487 | GEIFFDMRLKGDK | cell-penetrating peptide |
| 488 | GEIYFDLRLKGDK | cell-penetrating peptide |
| 489 | GEIYLDMRLKGDK | cell-penetrating peptide |
| 490 | IGQPGAKGEPGEFYFDLRLKGDKGDPGFPG | cell-penetrating peptide |
| 491 | GEVFFDMRLKGDK | cell-penetrating peptide |
| 492 | LAGSCLPIFSTL | cell-penetrating peptide |
| 493 | AHNQDLGLAGSCLARFSTMPFLYCNPGDIC | cell-penetrating peptide |
| 494 | QEKAHNQDLGLAGSCLPVFSTLPFAYCNIH | cell-penetrating peptide |
| 495 | LAGSCLPVFSTM | cell-penetrating peptide |
| 496 | GNKRAHGQDLGTAGSCLRRFSTMPFMFCNI | cell-penetrating peptide |
| 497 | RAHGQDLGTAGSCLRRFSTMP | cell-penetrating peptide |
| 498 | RKRLQVQLNIRT | cell-penetrating peptide |
| 499 | HLVLPLQQSDVRKRLQVQLSIRTFASSGLI | cell-penetrating peptide |
| 500 | RKRLSVQLRIRT | cell-penetrating peptide |
| 501 | DLGTAGSCLRRFSTM | cell-penetrating peptide |
| 502 | RNIAEIIKDI | cell-penetrating peptide |
| 503 | TAGSCLRKFSTMRRRRRRRRRR | cell-penetrating peptide |
| 504 | FTLTGLLGTLVTMGLLT | cell-penetrating peptide |
| 505 | APYKAWK | cell-penetrating peptide |
| 506 | STSKTNRGDDSNWSKRVTNNKPS | cell-penetrating peptide |
| 507 | STSKRKRGDDSNWSKRVTKKKPS | cell-penetrating peptide |

TABLE 1-continued

| SEQ ID No. | Sequence | Description |
|---|---|---|
| 508 | STSKRKRGDDSNWSKRVSKKKPS | cell-penetrating peptide |
| 509 | STSKRKRGDDANWSKRVTKKKPS | cell-penetrating peptide |
| 510 | PLAGSKRKRADEVAWSKRGTKKKPER | cell-penetrating peptide |
| 511 | PLAGSKRKRADEVAWSKRGTKKKPERTSAARAGPSRRIR | cell-penetrating peptide |
| 512 | STSKRKRGDDANWSKRTTKKKPSS | cell-penetrating peptide |
| 513 | STSKRKRGDDANWSKRTTKKKPSSAGLKRAGSKADRPSL | cell-penetrating peptide |
| 514 | PTTAGKRKRSDDAAWSKRARPKAGRT | cell-penetrating peptide |
| 515 | PTTAGKRKRSDDAAWSKRARPKAGRTSAARPGTSVRRIR | cell-penetrating peptide |
| 516 | SSSLGKRKRSDEGAWSKGKSKKKAMR | cell-penetrating peptide |
| 517 | SSSLGKRKRSDEGAWSKGKSKKKAMRGSSSRRPGPVRGP | cell-penetrating peptide |
| 518 | PTTAGKRKRTDDAAWSKRARPKAGR | cell-penetrating peptide |
| 519 | PTTAGKRKRTDDAAWSKRARPKAGRTSAARPGTAVRRVR | cell-penetrating peptide |
| 520 | PATAGKRKRSDDAAWSKRARPKAGRTSAAR | cell-penetrating peptide |
| 521 | PATAGKRKRSDDAAWSKRARPKAGRTSAARPGTSVRRIR | cell-penetrating peptide |
| 522 | SSSLGKRKRSNGGDWSKRSAKKKPA | cell-penetrating peptide |
| 523 | SSSLGKRKRSNGGDWSKRSAKKKPAGTPSRRAGPGRGPR | cell-penetrating peptide |
| 524 | SSSLGKRKRSDEGAWSKGKSKKKAMR | cell-penetrating peptide |
| 525 | SSSLGKRKRSDEGAWSKGKSKKKAMRGSSSRRPGPVRGP | cell-penetrating peptide |
| 526 | STSKRKRGDDANWNKRPTKKKPSS | cell-penetrating peptide |
| 527 | STSKRKRGDDANWNKRPTKKKPSSAGLKKAGSKAERPSL | cell-penetrating peptide |
| 528 | SGALKRKRSDEVAWSRRRPVKKPV | cell-penetrating peptide |
| 529 | SGALKRKRSDEVAWSRRRPVKKPVRRAPPPRAGPSVRRG | cell-penetrating peptide |
| 530 | SGALKRKRSDEVAWSRRKPAKKPAR | cell-penetrating peptide |
| 531 | SGALKRKRSDEVAWSRRKPAKKPARQPPPPRAGPSVRRG | cell-penetrating peptide |
| 532 | AGALKRKRSDEVAWSRRKPAKKPAR | cell-penetrating peptide |
| 533 | AGALKRKRSDEVAWSRRKPAKKPARAPPPRAGPSVRRGL | cell-penetrating peptide |
| 534 | STSKRKRGDDSNWSKRVTKKKPSSAGLKRAGSKADRPSLQIQTLQHAGTTMITVPSGGVCDLINTYARGSDEGNRHTSETLTYKIAIDYHFVADAAACRYSNTGTGVMWLVYDTTPGGQAPTPQTIFSYPDTLKAWPATWKVSRELCHRFVVKRRWLFNMETDGRIGSDIPPSNASWKPCKRNIYFHKFTSGLGVRTQWKNVTDGGVGAIQRGALYMVIAPGNGLTFTAHGQTRLYFKSVGNQ | cell-penetrating peptide |
| 535 | DPQNALYYQPRVPTAAPTSGGVPWSRVGEVAILSFVALICFYLLYLWVLRDLILVLKARQGRSTEELIFGGQAVDRSNPIPNIPAPPSQGNPGPFVPGTG | cell-penetrating peptide |

TABLE 1-continued

| SEQ ID No. | Sequence | Description |
| --- | --- | --- |
| 536 | GSQLVPPPSAFNYIESQRDEFQLSHDLTEIVLQFPS TASQITARLSRSCMKIDHCVIEYRQQVPINASGTVI VEIHDKRMTDNESLQASWTFPIRCNIDLHYFSSSF FSLKDPIPWKLYYRVSDSNVHQMTHFAKFKGKL KLSSAKHSVDIPFRAPTVKILAKQFSEKDIDFWHV GYGKWERRLVKSASSSRFGLRGPIEINPGESWAT KSAIVTPNRNADLDIEEELLPYRELNRLGTNILDPG ESASIVGIQRSQSNITMSMSQLNELVRSTVHECIKT SCIPSTPKSLS | cell-penetrating peptide |
| 537 | RTGVKRSYGAARGDDRRRPNVV | cell-penetrating peptide |
| 538 | SYVKTVPNRTRTYIKLRVR | cell-penetrating peptide |
| 539 | MYSTSNRRGRSQTQRGSHVRRTGVKRSYGAARG DDRRRPNVVSKTQVEPRMTIQRVQENQFGPEFVL SQNSALSTFVTYPSYVKTVPNRTRTYIKLKRVRFK GTLKIERGQGDTIMDGPSSNIEGVFSMVIVVDRKP HVSQSGRLHTFDELFGARIHCHGNLSVVPALKDR YYIRHVTKRVVSLEKDTLLIDLHGTTQLSNKRYN CWASFSDLERDCNGVYGNITKNALLVYYCWLSD AQSKASTYVSFELDYLG | cell-penetrating peptide |
| 540 | RRRRRRRRRRRRVDYGKWERKPIRCASMSR | cell-penetrating peptide |
| 541 | RRRRRRRRRRRRGKWERKPIRCAS | cell-penetrating peptide |
| 542 | KKKKKKKKKKKKKKKGKWERKPIRCAS | cell-penetrating peptide |
| 543 | RRRRRRRRRRRRVDFSHVDYGKWERKPIRCASM SRLGLRG | cell-penetrating peptide |
| 544 | GVKRSYGAARGDDRRRPNVVAPYKAWRRRRRR RRRRRR | cell-penetrating peptide |
| 545 | KSVPNRTRTYIKLRLRFKGAPYKAWRRRRRRRR RRRR | cell-penetrating peptide |
| 546 | RTGVKRSYGAARGDDRRRPNVVRRRRRRRRRR R | cell-penetrating peptide |
| 547 | SYVKTVPNRTRTYIKGGGGRRRRRRRRRRRR | cell-penetrating peptide |
| 548 | VDIPFRAPTIKILSKQFTEDDIDFWHVGYGKWERK LVRPASLSGRRGLRR | cell-penetrating peptide |
| 549 | IDFWHVGYGKWERKLVRPASLSGRRGLRR | cell-penetrating peptide |
| 550 | IDFWSVEKGETRRRLLNPTPHAHSPRPIAHR | cell-penetrating peptide |
| 551 | IDFSHVGYGKWERKMIRSASISRLGLHN | cell-penetrating peptide |
| 552 | VDFSHVGYGKWERKLIRSASTVKYGLPS | cell-penetrating peptide |
| 553 | IDFSHVDYGKVERKLVKCESSSRLGLHS | cell-penetrating peptide |
| 554 | IDFWSVGRKAQQRKLVQGPSLIGSRSMRY | cell-penetrating peptide |
| 555 | IDFWSVGSKPQTRRLVDGSRLIGHSSRSLRV | cell-penetrating peptide |
| 556 | IDFWSVERGETRRRLLNPTPSAGSNRALSKR | cell-penetrating peptide |
| 557 | VDFWSVGKPKPIRRLIQNDPGTDYDTGPKYR | cell-penetrating peptide |
| 558 | VDFWSVEKPKPIRRLLNPGPNQGPYPNTGHR | cell-penetrating peptide |
| 559 | VDFSHVDYGKWERKLIRSASTSRYGLRS | cell-penetrating peptide |
| 560 | VDFSHVDYGKWERKTLRSRSLSRIGLTG | cell-penetrating peptide |
| 561 | IDFWHVGYGKWERRLVKSASSSRFGIRG | cell-penetrating peptide |
| 562 | VDFFHVDYGRWERKHIRCASMSRVGLRG | cell-penetrating peptide |
| 563 | GTFQHVDYGKWERKPIRCQSMSRVGYRR | cell-penetrating peptide |

TABLE 1-continued

| SEQ ID No. | Sequence | Description |
|---|---|---|
| 564 | VGYGKWERKLVRPASLS | cell-penetrating peptide |
| 565 | VEKGETRRRLLNPTPHA | cell-penetrating peptide |
| 566 | VGYGKWERKLIRSASTV | cell-penetrating peptide |
| 567 | VEKPKPIRRLLNPGPNQ | cell-penetrating peptide |
| 568 | VDYGKWERKLIRSASTS | cell-penetrating peptide |
| 569 | VDYGKWERKTLRSRSLS | cell-penetrating peptide |
| 570 | VGYGKWERRLVKSASSS | cell-penetrating peptide |
| 571 | VDYGRWERKHIRCASMS | cell-penetrating peptide |
| 572 | VERPKPIRRLLTPTPGC | cell-penetrating peptide |
| 573 | PFRAPTIKILSKQFTEDDIDFWHVGYGKWERKLVRPASLSGRRGLRR | cell-penetrating peptide |
| 574 | PFRAPTVKILSKQFTDKDIDFSHVGYGKWERKMIRSASISRLGL | cell-penetrating peptide |
| 575 | DIAFRAPTVKILSKQFTDRDVDFSHVGYGKWERKLIRSASTVKYGL | cell-penetrating peptide |
| 576 | DIRFKPPTINILSKDYTADCVDFWSVEKPKPIRRLLNPGPNQGPYPNTG | cell-penetrating peptide |
| 577 | DIPFRAPTVKIHSKQFSHRDVDFSHVDYGKWERKTLRSRSLSRIGL | cell-penetrating peptide |
| 578 | DIPFRAPTVKILAKQFSEKDIDFWHVGYGKWERRLVKSASSSRFGI | cell-penetrating peptide |
| 579 | DIPFRAPTVKILSKQFTDKDVDFFHVDYGRWERKHIRCASMSRVGL | cell-penetrating peptide |
| 580 | DIKYKPPTIKILSKDYTADCVDFWSVERPKPIRRLLTPTPGCG | cell-penetrating peptide |
| 581 | ARTKQTARKSTGGKAPRKQLATKAARKSAPATGGVKKPHRYRPGTVA | cell-penetrating peptide |
| 582 | SGRGKGGKGLGKGGAKRHRKVLRDNIQGITKPAI | cell-penetrating peptide |
| 583 | GRKKRRQRRR | cell-penetrating peptide |

DETAILED DESCRIPTION

The present disclosure relates, in part, to trinucleotide cap analogs, compositions comprising trinucleotide cap analogs, and methods of use thereof, for example, for use in transcription, for use in intracellular stability, for use in detection, and isolation of capped RNA, and for use of the resultant isolated RNA in translation both in vitro and in vivo. Trinucleotide cap analogs as disclosed herein can have the advantage of being improved substrates for T7-RNA or other RNA polymerases, and can lead to a better in vitro transcription yield, improved intracellular molecular stability of 5' capped mRNAs, improved translational efficiency as compared to other anti-reverse cap analog (ARCA) substrates, and improved transfection into specific cell lines.

In addition to the caps themselves, the present disclosure relates to compositions and methods for producing capped mRNA molecules. Such compositions and methods include those where caps are designed to match initiation site nucleotide sequences and formulations (e.g., in vitro transcription formulations) are designed to facilitate efficient mRNA (e.g., capped mRNA) production. Such efficient mRNA production includes compositions and methods for the production of mRNA molecules where a high percentage of the mRNA molecules are capped mRNA (e.g., from about 75% to about 99%, from about 80% to about 99%, from about 85% to about 99%, from about 90% to about 99%, from about 95% to about 99%, from about 80% to about 96%, from about 85% to about 96%, from about 90% to about 96%, etc. of the total number of mRNA molecules produced) and where mRNA is produced in high yield (i.e., 3 milligrams of RNA per 1 milliliter of reaction mixture).

RNA yield (e.g., mRNA yield) may be determined by comparison of the amount of RNA produced to the amount of one or more components of the reaction mixture used to produce the RNA. One formula that may be used is the amount of RNA produced for a fixed amount of a single reaction mixture component for a specific volume of reaction mixture. By way of example, a 20 µl reaction mixture with a CTP concentration of 7.5 mM is used for in vitro transcription, then RNA yields of over 80 µg. A second example is where a 20 µl reaction mixture with a cap concentration of 10 mM is used, with an RNA yield of 120 µg.

Composition and methods set out herein allow for the production of RNA in amount greater than 40 μg/20 μl (e.g., from about 40 μg to about 200 μg, from about 40 μg to about 160 μg, from about 40 μg to about 120 μg, from about 80 μg to about 200 μg, from about 80 μg to about 200 μg, from about 80 μg to about 180 μg, from about 80 μg to about 160 μg, from about 80 μg to about 120 μg, from about 100 μg to about 150 μg, etc.).

RNA yield may also be expressed as the amount of RNA produced as a function of reaction mixture volume. For example, 100 μg of RNA produced in 20 μl is 5 mg of RNA produced in 1 milliliter of reaction mixture. When corrected for volume, composition and methods set out herein allow for the production of RNA in amount greater than or equal to 2 mg/ml (e.g., from about 2 mg/ml to about 20 mg/ml, from about 2 mg/ml to about 16 mg/ml, from about 2 mg/ml to about 10 mg/ml, from about 2 mg/ml to about 7, mg/ml, from about 4 mg/ml to about 20 mg/ml, from about 4 mg/ml to about 20 mg/ml, from about 5 mg/ml to about 20 mg/ml, from about 6 mg/ml to about 20 mg/ml, from about 4 mg/ml to about 20 mg/ml, from about 7 mg/ml to about 20 mg/ml, from about 4 mg/ml to about 16 mg/ml, from about 4 mg/ml to about 18 mg/ml, from about 4 mg/ml to about 14 mg/ml, from about 6 mg/ml to about 16 mg/ml, from about 7 mg/ml to about 19 mg/ml, etc.).

In one aspect is a trinucleotide cap analog of Formula (I):

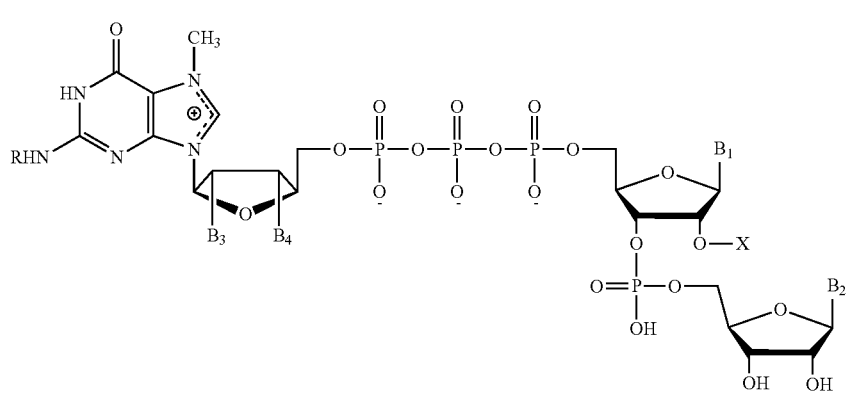

wherein $B_3$ is chosen from —OH, halogen, dyes, —OR$^1$, wherein R$^1$ is chosen from propargyl, tert-butyldimethylsilyl, and a methylene bridge with the 4'C;

$B_4$ is chosen from —OH, dyes, and —OR$^2$, wherein R$^2$ is chosen from propargyl and tert-butyldimethylsilyl;

or R$^1$ joins with R$^2$ such that $B_3$ and $B_4$ form-2',3'-O-isopropylidine;

on the condition that $B_3$ and $B_4$ cannot both be —OH

X is chosen from —H and —CH$_3$;

$B_1$ and $B_2$ are each independently chosen from adenine, guanine, cytosine, and uracil;

R is chosen from H, a linker-bound cell-penetrating peptide, a linker-bound cell-penetrating peptide covalently linked to a dye, and a linker-bound dye.

In some embodiments, R is chosen from a linker-bound cell-penetrating peptide chosen from any of SEQ ID NO:1-583, wherein the linker bound to the cell penetrating peptides can be chosen from those commercially available, such as biotin, 3' maleimidobenzoic acid N-hydroxysuccinimide ester, or

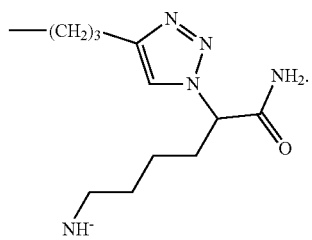

In some embodiments, R is

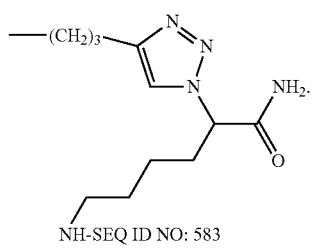

NH-SEQ ID NO: 583

In some embodiments, R is chosen from a linker-bound cell-penetrating peptide covalently linked to a dye, wherein the cell penetrating peptide is chosen from any of SEQ ID NO:1-583. In some embodiments, R is a linker-bound dye.

In some embodiments, each dye is independently chosen from azobenzene dyes, naphthalene containing dyes, cyanine dyes, rhodamine dyes, coumarin, and pyrene dyes. In some embodiments, each dye is independently chosen from:

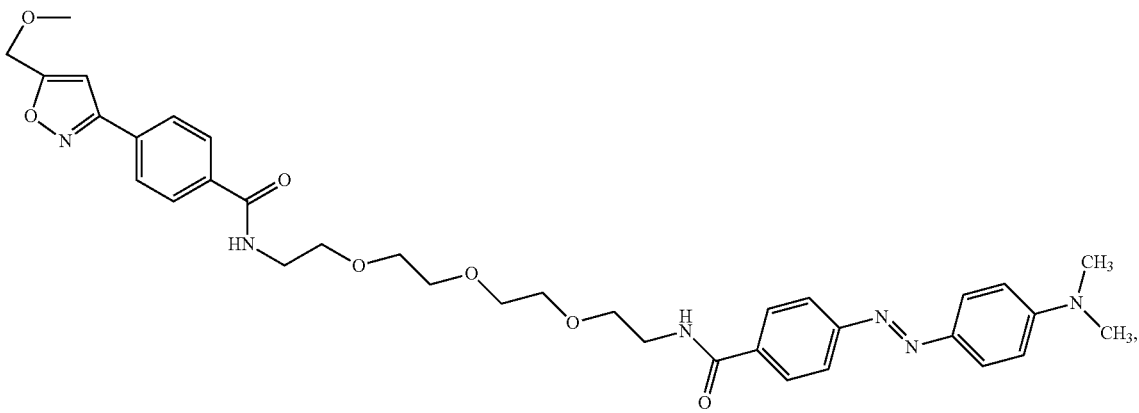

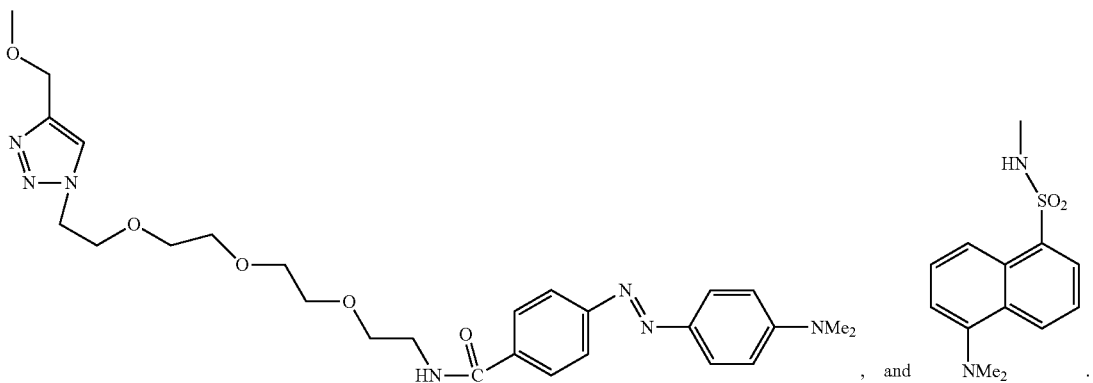

In some embodiments, $B_3$ is —$OR^1$ and $B_4$ is —$OR^2$ wherein $R^1$ joins with $R^2$ such that $B_3$ and $B_4$ form-2',3'-O-isopropylidene; X is —$CH_3$; and R is H. In some embodiments, $B_3$ is —$OR^1$ and $B_4$ is —$OR^2$ wherein $R^1$ joins with $R^2$ such that $B_3$ and $B_4$ form-2',3'-O-isopropylidene; and R is chosen from

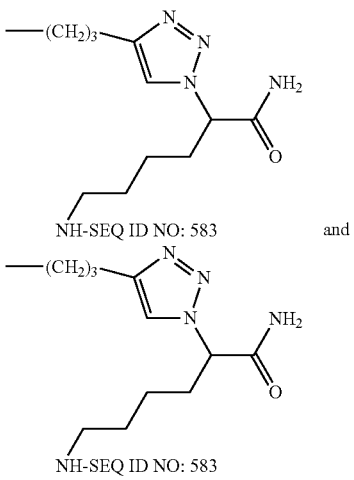

covalently linked to a dye. In some embodiments, $B_3$ is chosen from —$OR^1$ wherein $R^1$ is chosen from propargyl and tert-butyldimethylsilyl; $B_4$ is —OH; and R is H. In some embodiments, $B_3$ is chosen from —$OR^1$ wherein $R^1$ is chosen from propargyl and tert-butyldimethylsilyl; $B_4$ is —OH; and R is chosen from

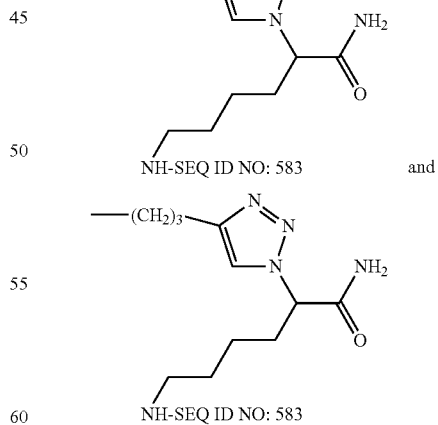

covalently linked to a dye. In some embodiments, each dye is independently chosen from azobenzene dyes, naphthalene containing dyes, cyanine dyes, rhodamine dyes, coumarin, and pyrene dyes. In some embodiments, each dye is independently chosen from

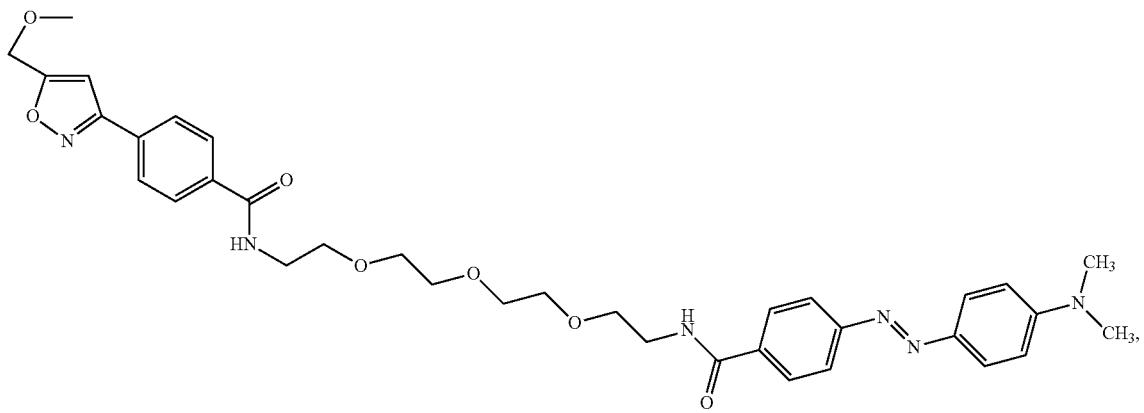
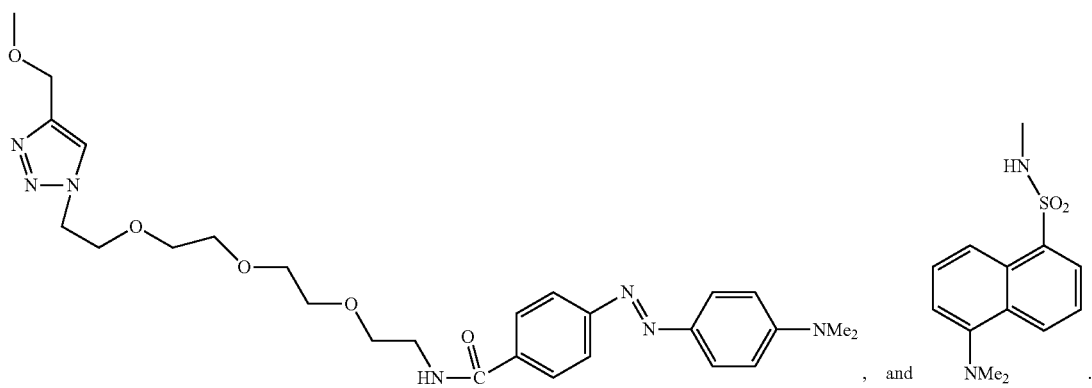
In some embodiments, $B_3$ is a dye; $B_4$ is —OH; and R is H. In some embodiments, $B_3$ is a dye; $B_4$ is —OH; and R is chosen from
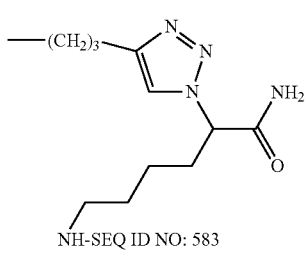
and
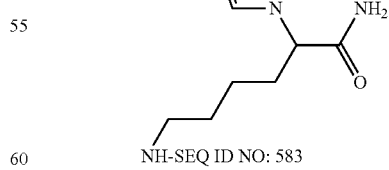
covalently linked to a dye. In some embodiments, each dye is independently chosen from azobenzene dyes, naphthalene containing dyes, cyanine dyes, rhodamine dyes, coumarin, and pyrene dyes. In some embodiments, each dye is independently chosen from

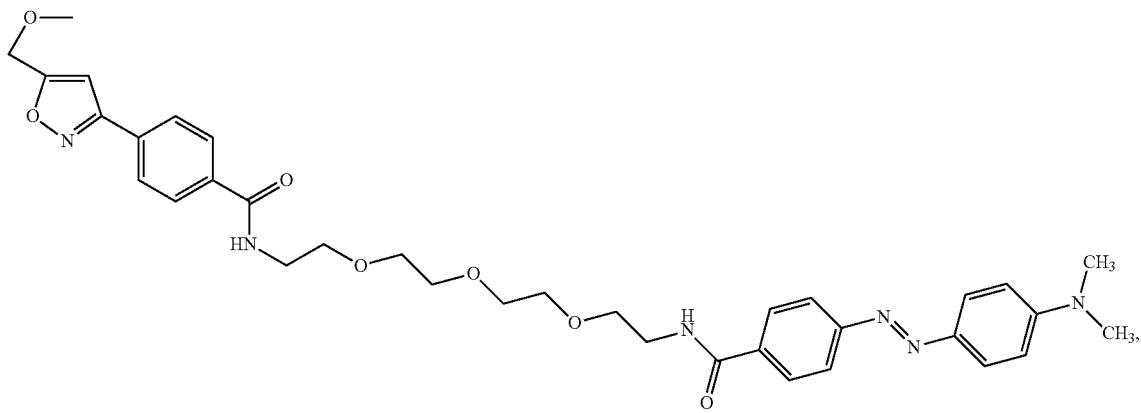

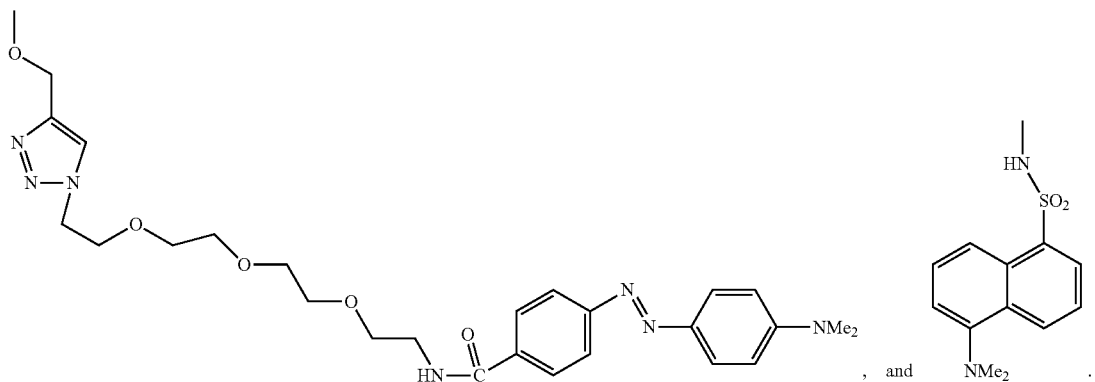

In some embodiments, $B_3$ is —OH; $B_4$ is chosen from —OR² wherein R² is chosen from propargyl and tert-butyldimethylsilyl; and R is H. In some embodiments, $B_3$ is —OH; $B_4$ is chosen from —OR² wherein R² is chosen from propargyl and tert-butyldimethylsilyl; and R is chosen from

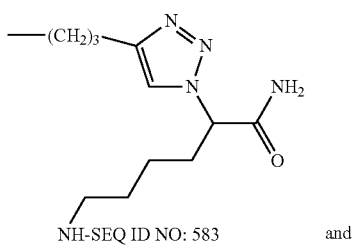

and

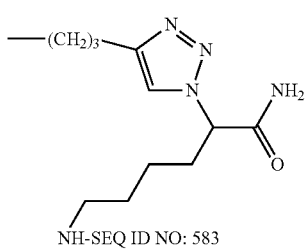

covalently linked to a dye. In some embodiments, $B_3$ is —OH; $B_4$ is a dye; R is H; and X=—CH₃. In some embodiments, $B_3$ is —OH; $B_4$ is a dye; and R is chosen from

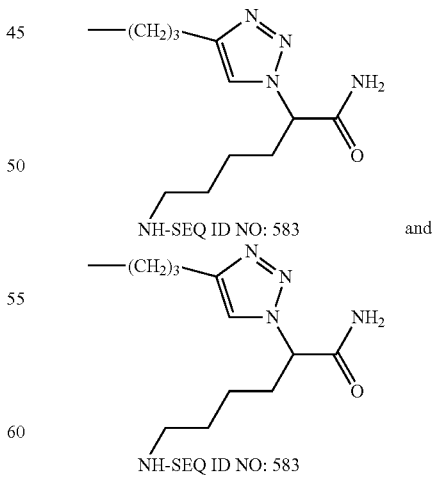

covalently linked to a dye. In some embodiments, each dye is independently chosen from azobenzene dyes, naphthalene containing dyes, cyanine dyes, rhodamine dyes, coumarin, and pyrene dyes. In some embodiments, each dye is independently chosen from

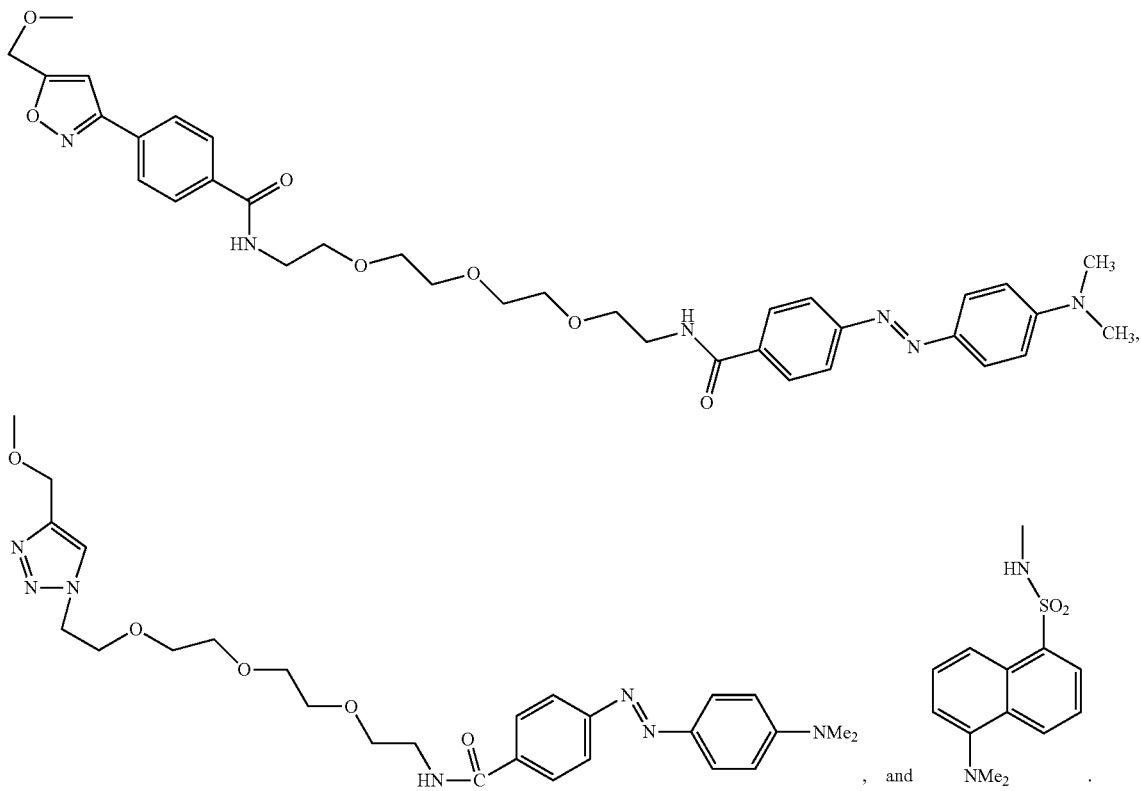 [SMILES: COCc1cc(-c2ccc(C(=O)NCCOCCOCCOCCNC(=O)c3ccc(/N=N/c4ccc(N(C)C)cc4)cc3)cc2)no1 ; COCc1cn(CCOCCOCCOCCNC(=O)c2ccc(/N=N/c3ccc(N(C)C)cc3)cc2)nn1 ; CNS(=O)(=O)c1cccc2c(N(C)C)cccc12]

In some embodiments of the trinucleotide cap analog of Formula (I), $B_3$ is —$OR^1$, and $R^1$ forms a methylene bridge with the 4'C such that the trinucleotide cap analog is Formula (I) is the locked trinucleotide cap analog of Formula (II):

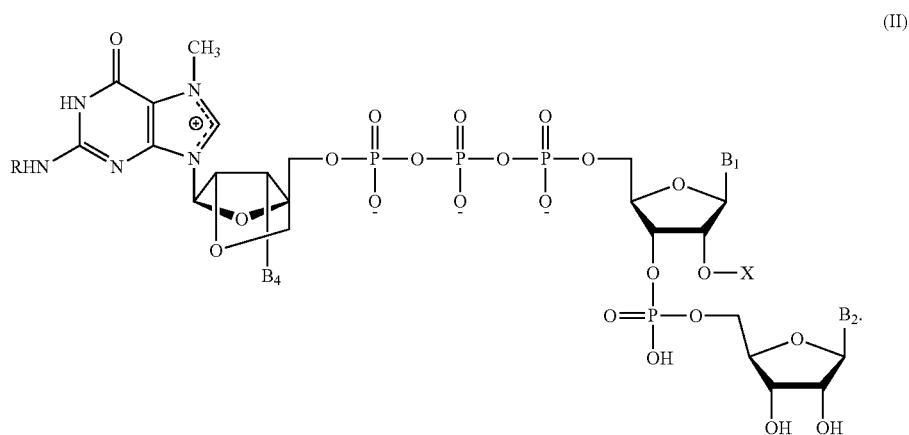

(II)

In some embodiments, R is chosen from a linker-bound cell-penetrating peptide, wherein the cell-penetrating peptide is chosen from any of SEQ ID NO: 1-583. In some embodiments, R is chosen from a linker-bound cell-penetrating peptide covalently linked to a dye, wherein the cell penetrating peptide is chosen from any of SEQ ID NO:1-583. In some embodiments, $B_4$ is —OH and R is H. In some embodiments, $B_4$ is —OH; and R is chosen from

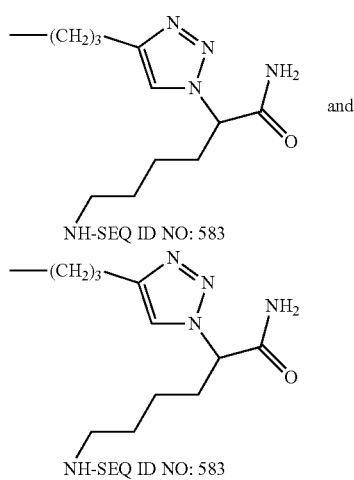

covalently linked to a dye. In some embodiments, $B_4$ is a dye; and R is H. In some embodiments, each dye is independently chosen from azobenzene dyes, naphthalene containing dyes, cyanine dyes, rhodamine dyes, coumarin, and pyrene dyes. In some embodiments, each dye is independently chosen from at least one cationic lipid, optionally one or more neutral lipids, and optionally one or more conjugated lipid that prevents aggregation (e.g., PEG lipids, and/or polyglycol lipids) and optionally one or more cell penetrating peptides, or any combination thereof.

Another aspect of the present disclosure is a composition comprising RNA having a trinucleotide cap analog of Formula (I), or any of the embodiments thereof disclosed herein, covalently bonded thereto. In some embodiments, the composition further comprises at least one RNA delivery agent. In some embodiments, the at least one RNA delivery agent comprises at least one cationic lipid. In some embodiments, the at least one RNA delivery agent further comprises at least one neutral lipid. In some embodiments, the at least one RNA delivery agent is chosen from cell penetrating peptides.

In some embodiments, the at least one cationic lipid is chosen from:

2,3-dioleyloxy-N-[2(sperminecarboxamido) ethyl]-N,N-dimethyl-1-propanaminium trifluoroacetate (DOSPA), 1,3-dioleoyloxy-2-(6-carboxy-spermyl) propylamide (DOSPER), dioctadecylamido-glycylspermine (DOGS), tetramethyltetrapalmitylspermine (TMTPS), tetramethyltetrapalmitoylspermin (TMTOS), tetramethlytetralauryl spermine (TMTLS), tetramethyltetramyristyl spermine (TMTMS), tetramethyldioleylspermine TMDOS), N-1-dim-

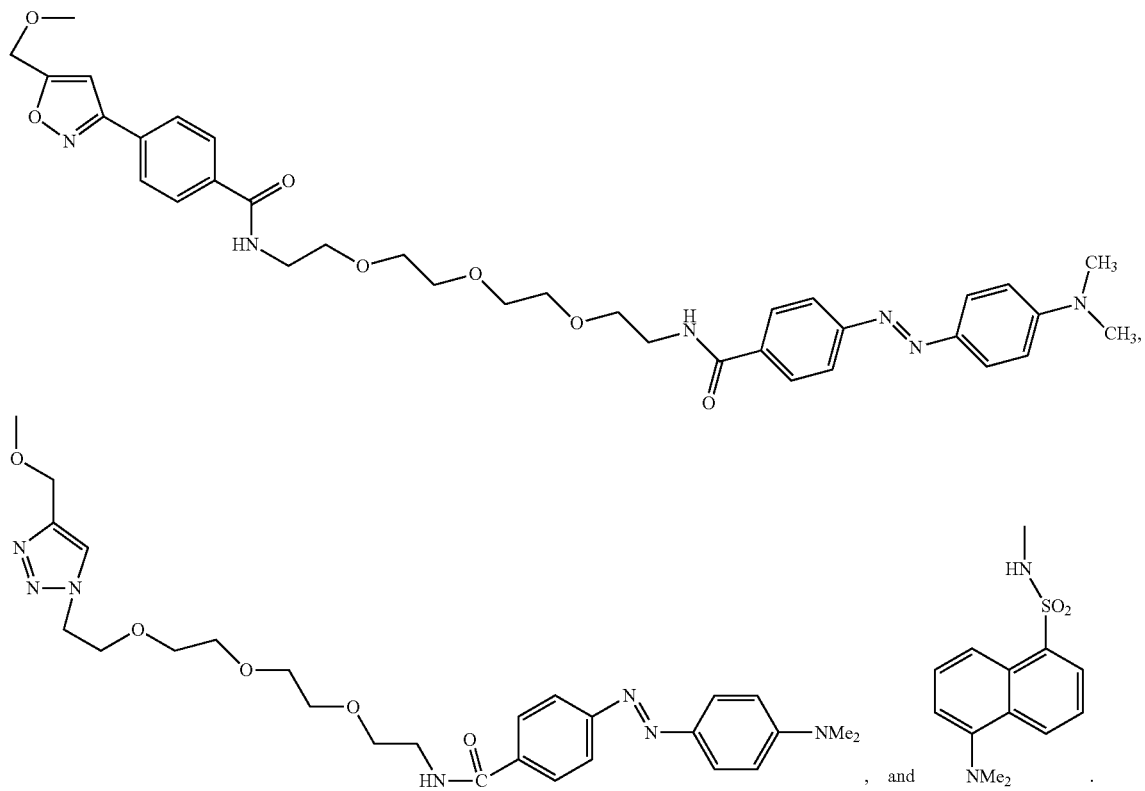 [SMILES: COCc1cc(-c2ccc(C(=O)NCCOCCOCCOCCNC(=O)c3ccc(/N=N/c4ccc(N(C)C)cc4)cc3)cc2)no1 ; COCc1cn(CCOCCOCCOCCNC(=O)c2ccc(/N=N/c3ccc(N(C)C)cc3)cc2)nn1 ; CNS(=O)(=O)c1cccc2c(N(C)C)cccc12]

Another aspect of the present disclosure is a composition comprising a trinucleotide cap analog of Formula (I) or any of the embodiments thereof disclosed herein.

Another aspect of the present disclosure is a method of making a lipid nanoparticle, comprising combining a composition comprising a trinucleotide cap analog of Formula (I) or any of the embodiments thereof disclosed herein with ethyl-N-1-(2,3-diaoleoyloxypropyl)-2-hydroxypropane-1,3-diamine, N-1-dimethyl-N-1-(2,3-diamyristyloxypropyl)-2-hydroxypropane-1,3-diamine, N-1-dimethyl-N-1-(2,3-diapalmityloxypropyl)-2-hydroxypropane-1,3-diamine, N-1-dimethyl-N-1-(2,3-diaoleoyloxypropyl)-2-(3-amino-2-hydroxypropyloxy)propane-1,3-diamine, N-1-dimethyl-N-1-(2,3-diamyristyloxypropyl)-2-(3-amino-2-hydroxypropyloxy)propane-1,3-diamine, N-1-dimethyl-N-1-(2,3-diapalmityloxypropyl)-2-(3-amino-2-hydroxypropyloxy)propane-1,3-diamine, L-spermine-5-carboxyl-3-(DL-1,2-dipalmitoyl-dimethylaminopropyl-β-hydroxyethylamine, 3,5-(N,N-di-lysyl)-diaminobenzoyl-glycyl-3-(DL-1,2-dipalmitoyl-dimethylaminopropyl-p-hydroxyethylamine), L-Lysine-bis(O,O'-oleoyl-p-hydroxyethyl)amide dihydrochloride, L-Lysine-bis-(O,O'-palmitoyl-p-hydroxyethyl)amide dihydrochloride, 1,4-bis[(3-(3-aminopropyl)-alkylamino)-2-hydroxypropyl)piperazine, L-Lysine-bis-(O,O'-myristoyl-β-hydroxyethyl)amide dihydrochloride, L-Ornithine-bis-(O,O'-myristoyl-p-hydroxyethyl)amide dihydrochloride, L-Ornithine-bis-(O,O'-oleoyl-p-hydroxyethyl)amide dihydrochloride, 1,4-bis[(3-(3-aminopropyl)-oleylamino)-2-hydroxypropyl]piperazine, L-Ornithine-bis-(O,O'-palmitoyl-p-hydroxyethyl)amide dihydrochloride, 1,4,-bis[(3-amino-2-hydroxypropyl)-oleylamino]-butane-2,3-diol, 1,4,-bis[(3-amino-2-hydroxypropyl)-palmitylamino]-butane-2,3-diol, 1,4,-bis[(3-amino-2-hydroxypropyl)-myristylamino]-butane-2,3-diol, 1,4-bis[(3-oleylamino)propyl]piperazine, L-Arginine-bis-(O,O'-oleoyl-p-hydroxyethyl)amide dihydrochloride, bis[(3-(3-aminopropyl)-myristylamino)2-hydroxypropyl]piperazine, L-Arginine-bis-(O,O'-palmitoyl-β-hydroxyethyl)amide dihydrochloride, L-Serine-bis-(O,O'-oleoyl-β-hydroxyethyl)amide dihydrochloride, 1,4-bis[(3-(3-aminopropyl)-palmitylamino)-2-hydroxypropyl]piperazine, Glycine-bis-(O,O'-palmitoyl-p-hydroxyethyl)amide dihydrochloride, Sarcosine-bis-(O,O'-palmitoyl-p-hydroxyethyl)amide dihydrochloride, L-Histidine-bis-(O,O'-palmitoyl-p-hydroxyethyl)amide dihydrochloride, cholesteryl-30-carboxyl-amidoethylenetrimethylammonium iodide, 1,4-bis[(3-myristylamino)propyl]piperazine, 1-dimethylamino-3-trimethylammonio-DL-2-propyl-cholesteryl carboxylate iodide, cholesteryl-30-carboxyamidoethyleneamine, cholesteryl-30-oxysuccinamidoethylenetrimethylammonium iodide, 1-dimethylamino-3-trimethylammonio-DL-2-propyl-cholesteryl-30-oxysuccinate iodide, 2-[(2-trimethylammonio)-ethylmethylamino]ethyl-cholesteryl-30-oxysuccinate iodide, 30[N—(N',N'-dimethylaminoethane)carbamoyl]cholesterol, and 30-[N-(polyethyleneimine)-carbamoyl]cholesterol, 1,4-bis[(3-palmitylamino)propyl]piperazine, L-Ornithylglycyl-N-(1-heptadecyloctadecyl)glycinamide, $N^2,N^5$-Bis(3-aminopropyl)-L-ornithylglycyl-N-(1-heptadecyloctadecyl)glycinamide, 1,4-bis[(3-(3-amino-2-hydroxypropyl)-alkylamino)-2-hydroxypropyl piperazine $N^2$—[$N^2,N^5$-Bis(3-aminopropyl)-L-ornithyl]-N,N-dioctadecyl-L-glutamine, $N^2$—[$N^2,N^5$-Bis(aminopropyl)-L-ornithyl]-N—N-dioctadecyl-L-α-glutamine, 1,4-bis[(3-(3-amino-2-hydroxypropyl)-oleylamino)2-hydroxypropyl]piperazine, $N^2$—[$N^2,N^5$-Bis(aminopropyl)-L-ornithyl]-N—N-dioctadecyl-L-α-asparagine, $N^2$—[$N^2$—[$N^2,N^5$-Bis[(1,1-dimethylethoxy)carbonyl]-$N^2,N^5$-bis[3-[(1,1-dimethylethoxy)carbonyl]aminopropyl]-L-ornithyl-N—N-dioctadecyl-L-glutaminyl]-L-glutamic acid, $N^2$—[$N^2,N^5$-Bis(3-aminopropyl)-L-ornithyl]-N,N-diolyl-L-glutamine, $N^2$—[$N^2,N^5$-Bis(aminopropyl)-L-ornithyl]-N—N-dioleyl-L-α-glutamine, 4-bis[(3-(3-amino-2-hydroxypropyl)-myristylamino)-2-hydroxypropyl]piperazine, $N^2$—[$N^2,N^5$-Bis(aminopropyl)-L-ornithyl]-N—N-dioleyl-L-α-asparagine, N—[$N^2$—$N^5$-Bis[(1,1-dimethylethoxy)carbonyl]-$N^2,N^5$-bis[3-[(1,1-dimethylethoxy)carbonyl]aminopropyl]-L-ornithyl-N—N-dioleyl-L-glutaminyl]-L-glutamic acid, 1,4-bis[(3-(3-aminopropyl)-oleylamino)propyl]piperazine, $N^2$—[$N^2,N^5$-Bis(3-aminopropyl)-L-ornithyl]-N,N-dipalmityl-L-glutamine, $N^2$—[$N^2,N^5$-Bis(aminopropyl)-L-ornithyl]-N— dipalmityl-L-α-glutamine, $N^2$—[$N^2,N^5$-Bis(aminopropyl)-L-ornithyl]-N—N-dipalmityl-L-α-asparagine, N—[$N^2$—[$N^2,N^5$-Bis[(1,1-dimethylethoxy)carbonyl]-$N^2,N^5$-bis[3-[(1,1-dimethylethoxy)carbonyl]aminopropyl]-L-ornithyl-N—N-dipalmityl-L-glutaminyl]-L-glutamic acid, $N^2$—[$N^2,N^5$-Bis(3-aminopropyl)-L-ornithyl]-N,N-dimyristyl-L-glutamine, $N^2$—[$N^2,N^5$-Bis(aminopropyl)-L-ornithyl]-N—N-dimyristyl-L-α-glutamine, $N^2$—[$N^2,N^5$-Bis(aminopropyl)-L-ornithyl]-N—N-dimyristyl-L-α-asparagine, 1,4-bis[(3-(3-amino-2-hydroxypropyl)-palmitylamino)-2-hydroxypropyl]piperazine, N—[$N^2$—[$N^2,N^5$-Bis[(1,1-dimethylethoxy)carbonyl]-$N^2,N^5$-bis[3-[(1,1-dimethylethoxy)carbonyl]aminopropyl]-L-ornithyl-N—N-dimyristyl-L-glutaminyl]-L-glutamic acid, 1,4-bis[(3-(3-aminopropyl)-myristylamino)propyl]piperazine, $N^2$—[$N^2,N^5$-Bis(3-aminopropyl)-L-ornithyl]-N,N-dilaureyl-L-glutamine, $N^2$-8 $N^2,N^5$-Bis(aminopropyl)-L-ornithyl]-N—N-dilaureyl-L-α-glutamine, $N^2$—[$N^2,N^5$-Bis(aminopropyl)-L-ornithyl]-N—N-dilaureyl-L-α-asparagine, N—[$N^2$—[$N^2,N^5$-Bis[(1,1-dimethylethoxy)carbonyl]-$N^2,N^5$-bis[3-[(1,1-dimethylethoxy)carbonyl]aminopropyl]-L-ornithyl-N-dilaureyl-L-glutaminyl]-L-glutamic acid, 3-[N',N"-bis(2-tertbutyloxycarbonylaminoethyl)guanidino]-N,N-dioctadec-9-enylpropionamide, 3-[N',N"-bis(2-tertbutyloxycarbonylaminoethyl)guanidino]-N,N-dipalmitylpropionamide, 3-[N',N"-bis(2-tertbutyloxycarbonylaminoethyl)guanidino]-N,N-dimyristylpropionamide, 1,4-bis[(3-(3-aminopropyl)-palmitylamino)propyl]piperazine, 1,4-bis[(3-(3-amino-2-hydroxypropyl)-oleylamino)propyl]piperazine, N,N-(2-hydroxy-3-aminopropyl)-N-2-hydroxypropyl-3-N,N-diolylaminopropane, N,N-(2-hydroxy-3-aminopropyl)-N-2-hydroxypropyl-3-N,N-dipalmitylaminopropane, N,N-(2-hydroxy-3-aminopropyl)-N-2-hydroxypropyl-3-N,N-dimyristylaminopropane, 1,4-bis[(3-(3-amino-2-hydroxypropyl)-myristylamino)propyl]piperazine, [(3-aminopropyl)-bis-(2-tetradecyloxyethyl)]methyl ammonium bromide, [(3-aminopropyl)-bis-(2-oleyloxyethyl)]methyl ammonium bromide, [(3-aminopropyl)-bis-(2-palmityloxyethyl)]methyl ammonium bromide, Oleoyl-2-hydroxy-3-N,N-dimethyamino propane, 2-didecanoyl-1-N,N-dimethylaminopropane, palmitoyl-2-hydroxy-3-N,N-dimethyamino propane, 1,2-dipalmitoyl-1-N,N-dimethylaminopropane, myristoyl-2-hydroxy-3-N,N-dimethyamino propane, 1,2-dimyristoyl-1-N,N-dimethylaminopropane, (3-Amino-propyl)→4-(3-aminopropylamino)-4-tetradecylcarbamoyl-butylcarbamic acid cholestryl ester, (3-Amino-propyl)→4-(3-amino-propylamino-4-carbamoylbutylcarbamic acid cholestryl ester, (3-Amino-propyl)→4-(3-amino-propylamino)-4-(2-dimethylamino-ethylcarbamoyl)-butylcarbamic acid cholestryl ester, Spermine-5-carboxyglycine (N'-stearyl-N'-oleyl) amide tetratrifluoroacetic acid salt, Spermine-5-carboxyglycine (N'-stearyl-N'-elaidyl) amide tetratrifluoroacetic acid salt, Agmatinyl carboxycholesterol acetic acid salt, Spermine-5-carboxy-β-alanine cholesteryl ester tetratrifluoroacetic acid salt, 2,6-Diaminohexanoeyl β-alanine cholesteryl ester bistrifluoroacetic acid salt, 2,4-Diaminobutyroyl β-alanine cholesteryl ester bistrifluoroacetic acid salt, N,N-Bis (3-aminopropyl)-3-aminopropionyl β-alanine cholesteryl ester tristrifluoroacetic acid salt, [N,N-Bis(2-hydroxyethyl)-2-aminoethyl]aminocarboxy cholesteryl ester, Stearyl carnitine ester, Palmityl carnitine ester, Myristyl carnitine ester, Stearyl stearoyl carnitine ester chloride salt, L-Stearyl Stearoyl Carnitine Ester, Stearyl oleoyl carnitine ester chloride, Palmityl palmitoyl carnitine ester chloride, Myristyl myristoyl carnitine ester chloride, L-Myristyl myristoyl carnitine ester chloride, 1,4-bis[(3-(3-amino-2-hydroxypropyl)-palmitylamino)propyl]piperazine, N-(3-aminopropyl)-N,N'-bis-(dodecyloxyethyl)-piperazinium bromide, N-(3-aminopropyl)-N,N'-bis-(oleyloxyethyl)-piperazinium bromide, N-(3-aminopropyl)-N,N'-bis-(palmityloxyethyl)-piperazinium bromide, N-(3-aminopropyl)-N,N'-bis-(myristyloxyethyl)-piperazinium bromide, N-(3-aminopropyl)-N'-methyl-N,N'-(bis-2-dodecyloxyethyl)-piperazinium bromide, N-(3-aminopropyl)-N'-methyl-N,N'-(bis-2-oleyloxyethyl)-piperazinium bromide, N-(3-aminopropyl)-N'-methyl-N,N'-(bis-2-palmityloxyethyl)-piperazinium bromide, N-(3-aminopropyl)-N'-methyl-N,N'-(bis-2-myristyloxyethyl)-piperazinium bromide, Phospholipids useful in the compositions and methods may be selected from the non-limiting group consisting of 1,2-distearoyl-sn-glycero-3-phosphocholine (DSPC), 1,2-dioleoyl-sn-glycero-3-phosphoethanolamine (DOPE), 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), dipalmitoylphosphatidylglycerol (DPPG), palmitoyloleoylphosphatidylethanolamine (POPE), distearoyl-phosphatidyl-ethanolamine (DSPE), dipalmitoyl phosphatidyl ethanolamine (DPPE), dimyristoylphosphoethanolamine (DMPE), 1-stearoyl-2-oleoyl-phosphatidylethanolamine (SOPE), 1-stearoyl-2-oleoyl-phosphatidylcholine (SOPC), sphingomyelin, phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine (LPE),

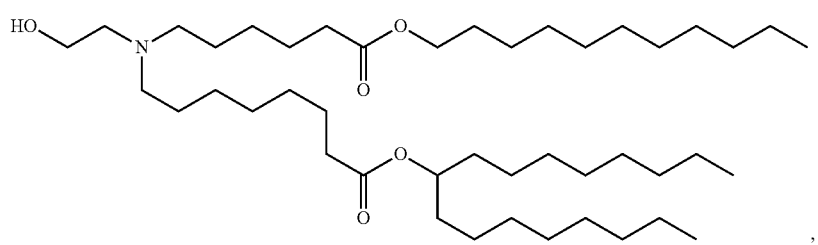

Compound 1

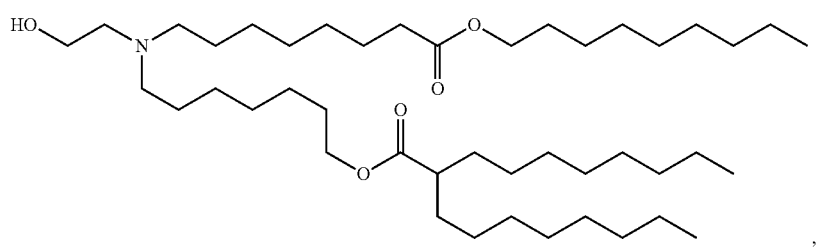

Compound 2

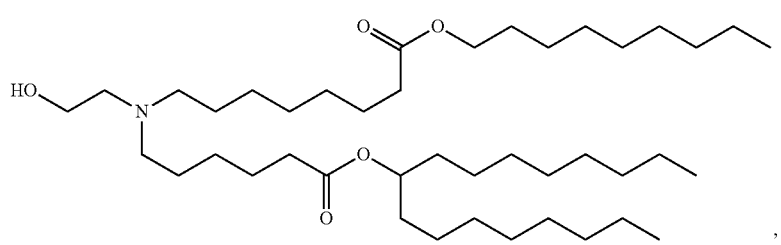

Compound 3

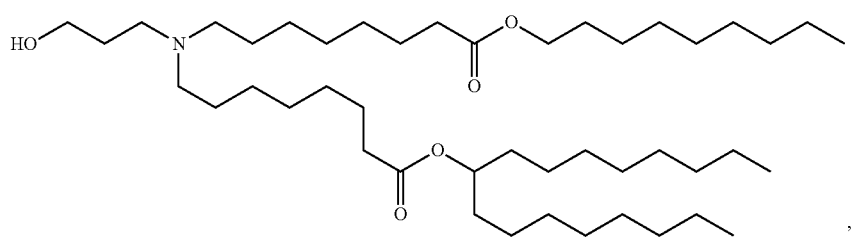

Compound 4

-continued
Compound 5
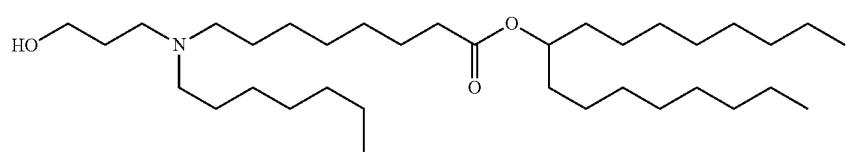
Compound 6
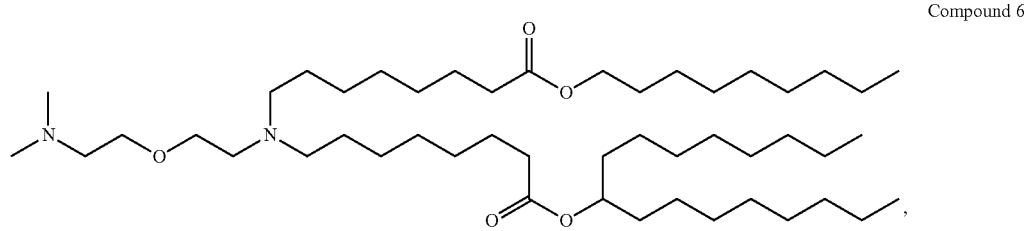
Compound 7
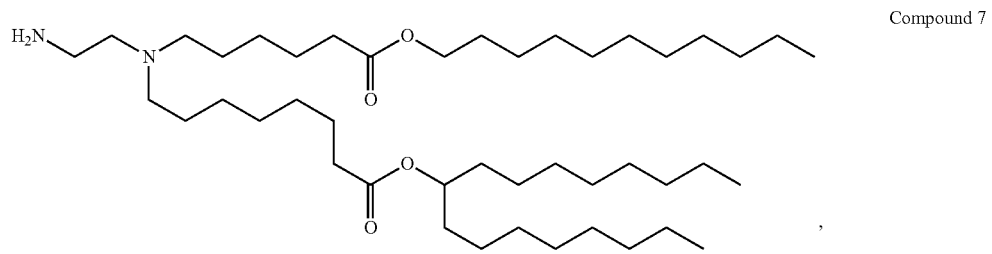
Compound 8
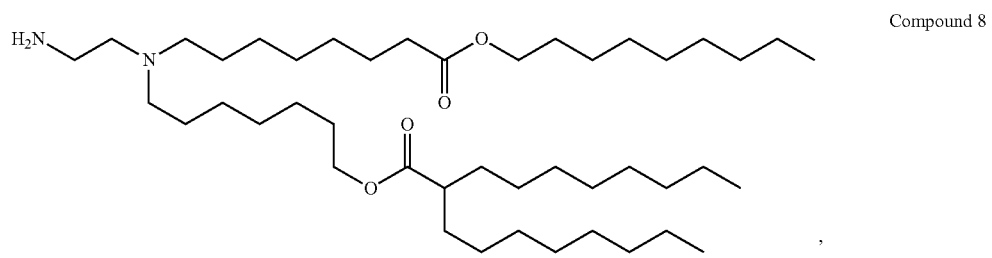
Compound 9
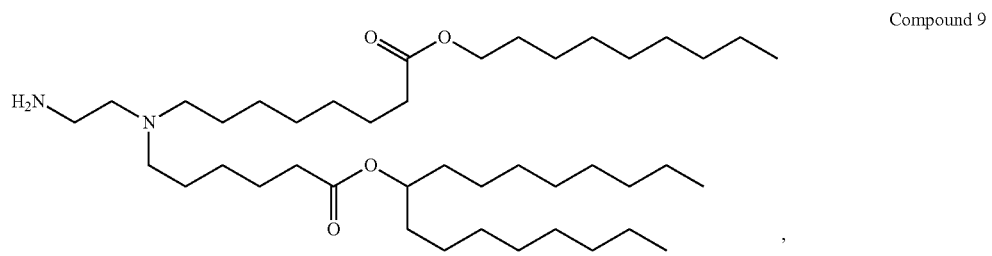
Compound 10
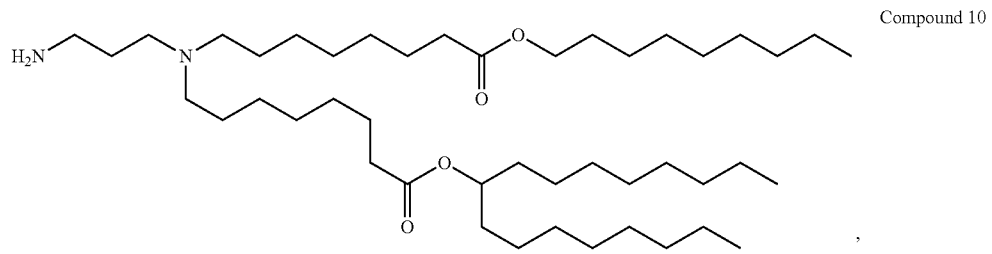
Compound 11
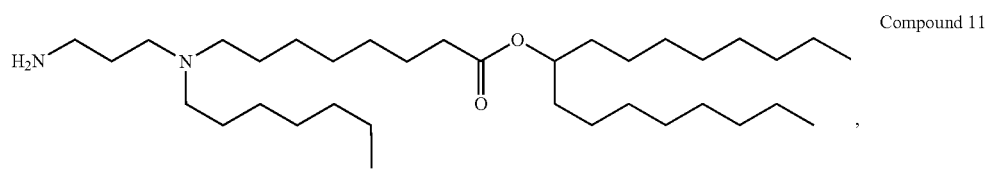

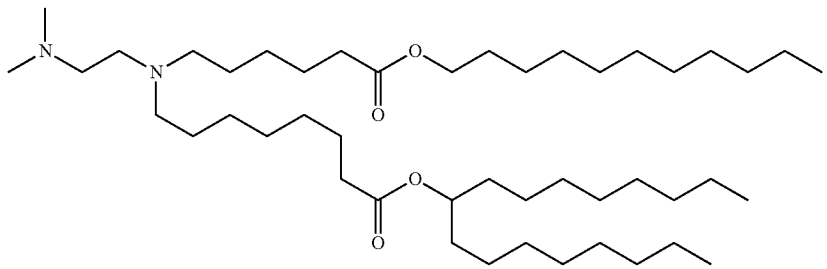

Compound 12

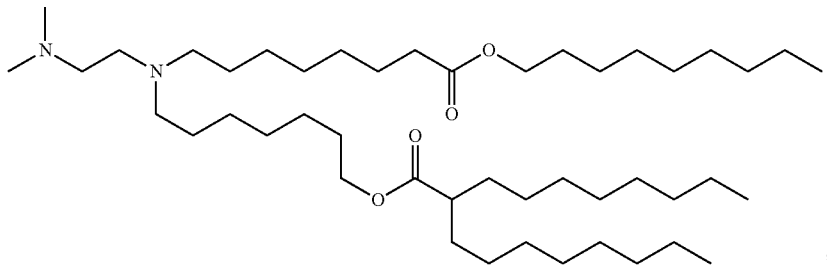

Compound 13

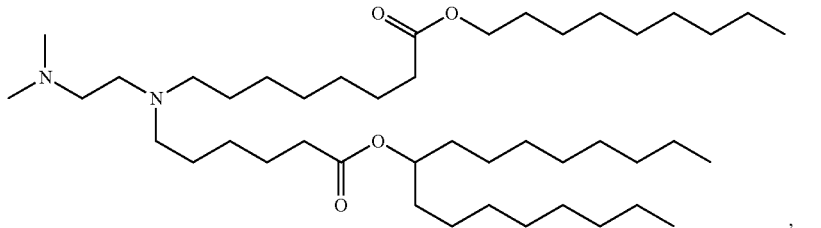

Compound 14

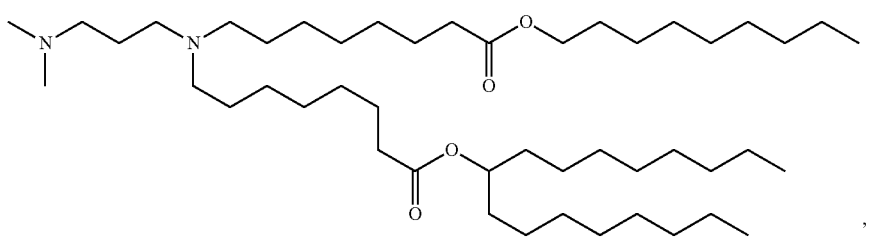

Compound 15, and

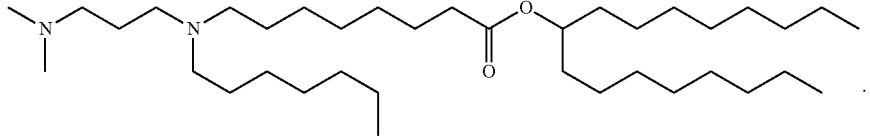

Compound 16.

In some embodiments, the at least one neutral lipid is chosen from: cholesterol, dioleoylphosphatidylethanolamine (DOPE), dioleoylphosphatidylcholine (DOPC), and diphytanoylphosphatidylethanolamine (DDhPE).

In some embodiments, the compositions disclosed herein further comprise a pharmaceutically acceptable carrier.

Another aspect of the present disclosure is a kit comprising a trinucleotide cap analog of Formula (I), as well as any components of compositions set out herein (e.g., one or more RNAse inhibitor, etc.); nucleotide triphosphate molecules; and an RNA polymerase.

Another aspect of the present disclosure is a method of producing trinucleotide capped RNA comprising contacting a nucleic acid substrate with an RNA polymerase and a trinucleotide cap analog of Formula (I) or any of the embodiments thereof disclosed herein, in the presence of nucleotide triphosphates under conditions and for a time sufficient to produce a trinucleotide capped RNA.

Further aspects of the present disclosure include a method comprising contacting a cell with the trinucleotide cap analog comprising a trinucleotide cap analog of Formula (I) or any of the embodiments thereof disclosed herein. In some embodiments, the method is for increasing intracellular stability of an RNA, comprising incorporating a trinucleotide cap analog according to Formula (I) or any of the embodiments thereof disclosed herein into the RNA. In some embodiments, the method is for introducing an RNA into a cell, comprising contacting the cell. In some embodiments, the method is for RNA translation inhibition in a cell.

For the purposes of interpreting this specification, the following definitions will apply and whenever appropriate, terms used in the singular will also include the plural and vice versa. In the event that any definition set forth below conflicts with the usage of that word in any other document, the definition set forth below shall always control for purposes of interpreting this specification and its associated claims unless a contrary meaning is clearly intended (for example in interpreting the document where the term is originally used). The use of "or" herein means "and/or" unless stated otherwise or where the use of "and/or" is clearly inappropriate. The use of "a" herein means "one or more" unless stated otherwise or where the use of "one or more" is clearly inappropriate. The use of "comprise," "comprises," "comprising," "include," "includes," and "including" are interchangeable and not intended to be limiting.

As used herein, the term "moiety" and "group" are used interchangeably to refer to a portion of a molecule, typically having a particular functional or structural feature, e.g., a linking group (a portion of a molecule connecting two other portions of the molecule), or an ethyl moiety (a portion of a molecule with a structure closely related to ethane).

As used herein, "Me" is equivalent to "$CH_3$;" "$OCH_3$" or "OMe" denotes an oxygen atom bound to a methyl group; "CHO" denotes a carbon atom, C, bonded to a hydrogen atom, H, and double-bonded to an oxygen atom, O, (O=CH—); and "Et" denotes "$C_2H_5$".

As used herein, the names of bases: adenine, guanine, cytosine, and uracil are interchangeable with their capitalized initials: "A," "G," "C," and "U," respectively.

As used herein, the term "cap" refers to a non-extendible di-nucleotide (also referred to herein as a "dimer") that facilitates translation or localization, and/or prevents degradation of an RNA transcript when incorporated at the 5' end of an RNA transcript, typically having an m7GpppG or m7GpppA structure. Caps generally consist in nature of the modified base 7-methylguanosine joined in the opposite orientation, 5' to 5' rather than 5' to 3', to the rest of the molecule via three phosphate groups, i.e., PI-guanosine-5'-yl P3-7-methylguanosine-5'-yl triphosphate ($m^7$G5'ppp5'G).

As used herein, the term "cap analog" refers to a structural derivative of an RNA cap that may differ by as little as a single element. Cap analogs may be trinucleotides (also referred to herein as a "trimer"), as well as pentamers and longer multimers (e.g., nucleic acid multimers that are five, six, seven, eight or nine nucleotides in length).

As used herein, the term "capped oligonucleotides" or "capped primers" refer to a transcriptional initiating primer containing a Cap 0, Cap 1, Cap 2 or 2,2,7-trimethylguanosine (TMG)-Cap structure on 5'-end of the primer. The capped primers will generally have an unmodified or open 3'-OH group and it may be extended by RNA polymerase through the incorporation of an NTP onto the 3'-end of the primer. Such oligonucleotides will generally be able to initiate in vitro transcription under the control of a promoter in a transcription system. The term "capped oligonucleotides" or "capped primers" include caps such as those set out herein that can be used to generate capped RNA molecules by transcription (see, e.g., the cap analog generated in the workflow set out in FIG. 9). Also used herein, "initiating primer" or "initiating oligonucleotide primer" refers to an oligonucleotide, carrying a terminal 3'-OH group that can act as a substrate for RNA polymerase in initiation of RNA synthesis (e.g., template directed RNA synthesis). By way of example, naturally occurring caps that may be added to RNA molecules by transcription are cap primers. Thus, cap primers may include naturally occurring caps or cap analogs, such as caps or cap analogs set out herein.

The term "nucleotide", as referred to herein, includes naturally-occurring nucleotides, synthetic nucleotides and modified nucleotides, unless indicated otherwise.

Figure 9:
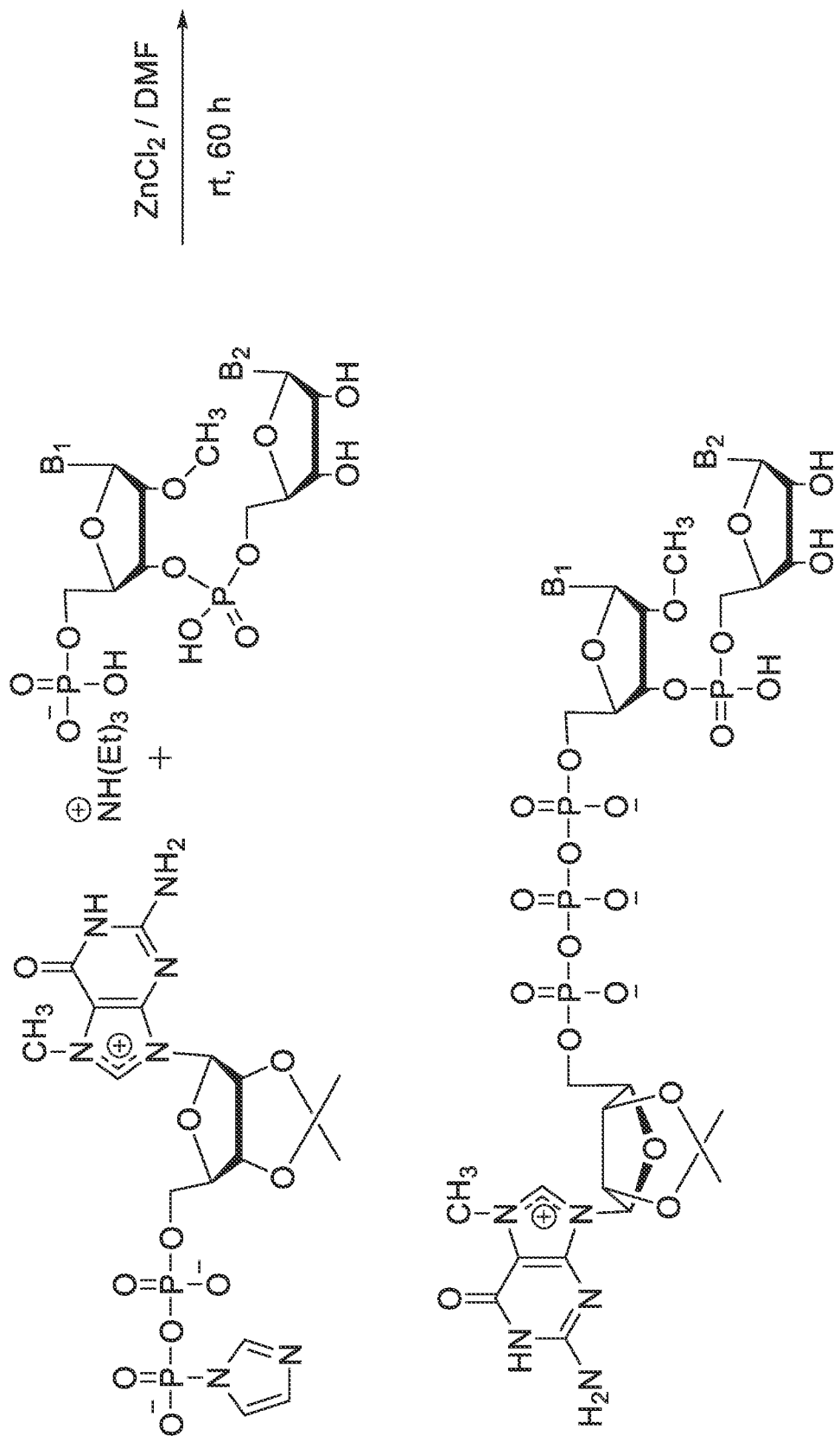
FIG. 9 illustrates an exemplary synthetic scheme to make trinucleotide cap analogs containing isopropylidene moieties as described herein. $B_1$=G, A, U, or C; $B_2$=G, A, U, or C
Figure 10:
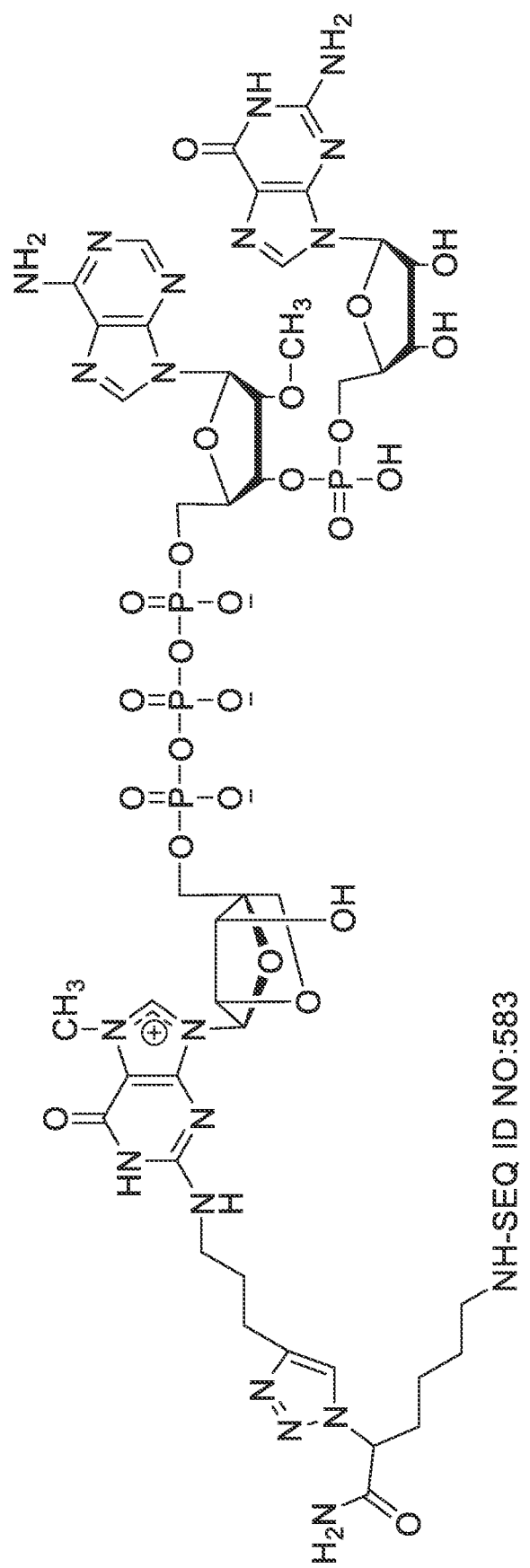
FIG. 10 illustrates an exemplary chemical structure of a trinucleotide cap analog containing linker-bound cell-penetrating peptide as disclosed herein.

The term "trinucleotide cap analog" refers to a cap or cap analog that comprises three nucleotides. By way of example, the cap analog generated in the workflow set out in FIG. 9 is a trinucleotide cap analog where the first nucleotide (on the left) is separated from the other two nucleotides (on the right) by three phosphate groups. At least one of the two nucleotides on the right will generally be designed to hybridize to the initiation site and act to primer transcription driven by RNA polymerase. Caps and cap analogs set out and used herein may be longer than three nucleotides. For example, there may be more than two nucleotides analogous to those on the right hand side of FIG. 9. In particular, caps and cap analogs may contain anywhere from four to twenty in which three to nineteen (e.g., from about three to about sixteen, from about three to about twelve, from about four to about sixteen, from about four to about ten, from about five to about ten, etc.) of these nucleotide may be capable of hybridizing to an initiation site and act to primer transcription driven by RNA polymerase.

As used herein, the term "promoter" refers to a nucleic acid region that is recognized by RNA polymerase and capable of acting as an initiation template for operably linked nucleic acid region, resulting in transcription of part of all of the operably linked nucleic acid region. Promoters may be of eukaryotic, prokaryotic, viral, or organelle origin. Further, promoters can be natural occurring, modified naturally occurring, or synthetic (e.g., fusions of two naturally occurring promoters or promoters designed from consensus sequences of naturally occurring promoters). One category of promoters is the "T7 like" promoters, such as those set out in FIG. 16.

Figure 16:
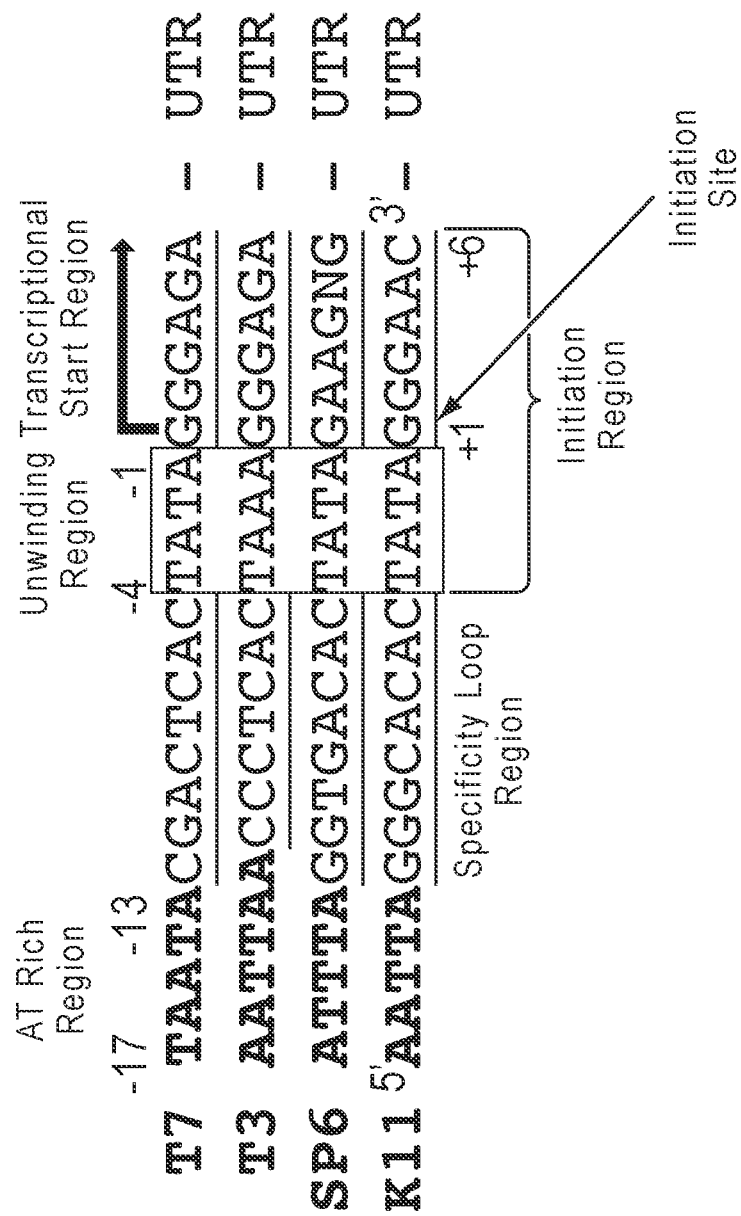
FIG. 16 is a schematic representation of non-template strands of four exemplary wildtype bacteriophage promoters. These promoters are each 23 base pairs in length. Further, each promoter contains an AT rich region, a polymerase specificity loop region, an unwinding region (positions −4 to −1), and an initiation region (positions +1 to +6). The "N" at position +5 of the SP6 promoter may be any nucleotide but, in many instances, will be a G or an A. From top to bottom SEQ ID NO: 591, SEQ ID NO: 592, SEQ ID NO: 593, and SEQ ID NO: 594. "UTR" refers to DNA that forms untranslated regions of transcribe mRNA molecules.
Figure 17:
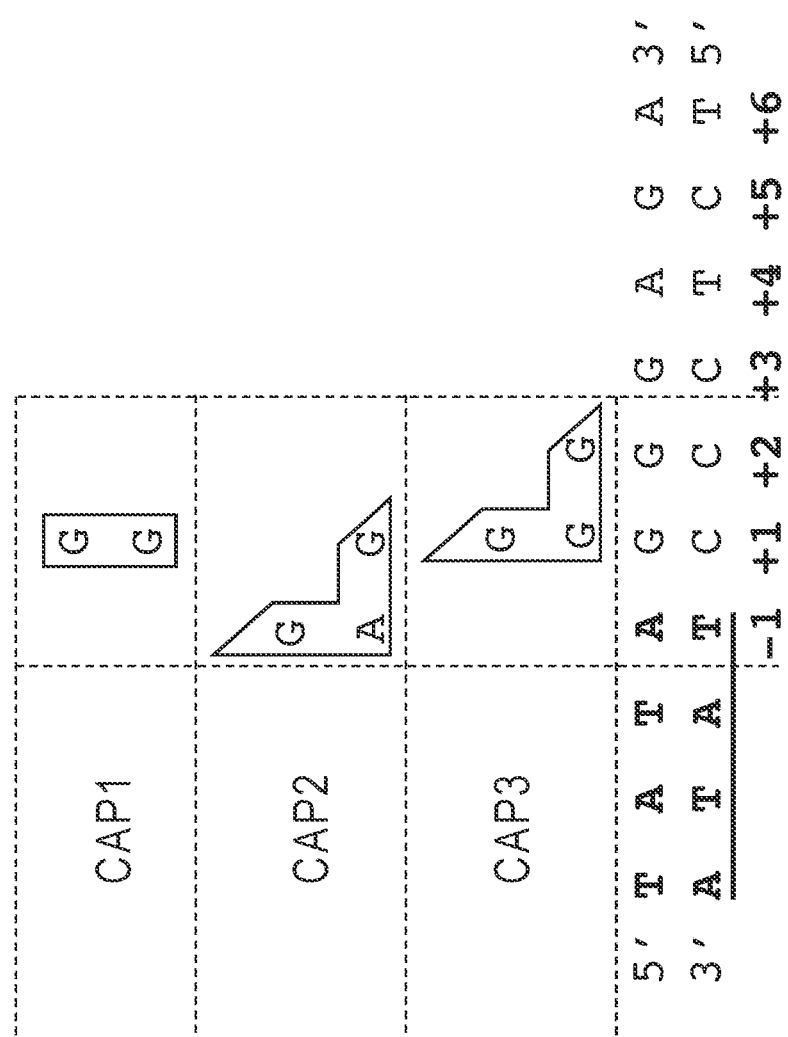
FIG. 17 is a schematic representation of three different mRNA caps binding to a transcriptional initiation site. CAP1 is a dinucleotide cap in which both bases are guanine. CAP2 is a trinucleotide cap in which two bases are guanine with an intervening adenine base. CAP3 is a trinucleotide cap in which all three bases are guanine. The first base in all three instances (guanine) is shown above another base because this first base does not directly interact with the promoter. The lower portion of this figure shows the non-template (5' to 3') and template strands (3' to 5') of a portion of the promoter where four bases of an unwinding region (shown underlined) meet a transcriptional initiation site. CAP1, CAP2 and CAP3 are positioned in the figure in the location to which they are complementary to the template strand of the initiation region (+1, −1 to +1, and +1 to +2, respectively, for each cap).

In many instances, promoters will be double stranded nucleic acid composed of a template strand and a non-template strand. FIG. 16 shows non-template strands of four different promoters and FIG. 17 shows both template and non-template strands of a portion of a bacteriophage promoter.

In some instances, promoters will be single stranded nucleic acid composed of a template strand or a nontemplate strand. Examples of such promoters are promoters of RNA and DNA single stranded viruses (e.g., Alphaviruses, Hantaviruses, and Flaviviruses).

Promoters are typically located immediately adjacent to (or partially overlapping with) the nucleic acid to be transcribed. Nucleotide positions in the promoter are generally designated relative to the transcriptional start site, normally referred to as position +1 (see FIG. 16) in wild-type systems. At least one base of the initiating oligonucleotide primer (e.g., mRNA cap or cap analog) is complementary to the template strand of the initiation site of promoter sequence which is used for initiation of transcription (e.g., position +1, −1 and +1, or +1 and +2 as set out in FIG. 16).

As herein, the term "initiation complex" refers to the association of primer and the template strand of a nucleic acid molecule, under conditions in which allow for the initiation of transcription of an RNA molecule by an RNA polymerase. In many instances, the primer will be a cap analog (e.g., a mRNA cap analog provided herein). Exemplary cap analog RNA initiation complex structures are set out schematically in FIG. 17.

As herein, the term "initiation site" refers to the base or bases on the template strand of a promoter where capped primers bind for the initiation of RNA transcription. In many instances, initiation sites will be identified by the nucleotide sequence of the non-template strand (see, e.g., FIG. 16). Numerical values herein for both initiation sites and surrounding nucleic acid are in reference to native initiation sites (see, e.g., FIG. 16). Thus, using FIG. 17 for reference, naturally occurring transcriptional initiation based upon T7 promoters with a GG capped primer (CAP3) is believed to normally begin at position +1. Thus, hybridization of a AG capped primer (CAP2) at position −1 and +1 of FIG. 17 means that the capped primer hybridizes to one base of the 'TATA box" and the +1 position, the naturally occurring initiation site. In such an instance, transcriptional initiation begins at the −1 position. Further, when the capped primer hybridizes to positions −1 and +1, then the initiation site is located at positions −1 and +1.

As used herein the term "in vitro transcription and translation (IVTT)" refers the generation of messenger RNA (mRNA) molecules and the production of proteins from these mRNA molecules. Typically, IVTT will employ cellular extracts that contain transcription and translation "machinery" (e.g., ribosomes, tRNA synthetases, charged and uncharged tRNA molecules, RNA polymerases, etc.). These are cellular components capable of performing transcription and translation reactions. Together with transcription components that include T7 RNA polymerase and nucleotides, IVTT can be employed transcribe and translate genes that are supplied in the form of a purified DNA molecule. Cellular components used in IVTT reactions may obtained for essentially any cell type and may be supplemented with various reagents (e.g., buffers, amino acids, tRNA molecules, etc.).

IVTT reactions are composed of two sub-components: (1) "in vitro transcription" (IVTr, or IVT) and (2) "in vitro translation" (IVTl). These processes may occur in a single reaction mixture or may be performed in separate reaction mixtures.

As used herein, the term "cationic lipid" refers to a lipid that which under physiological conditions possess at least one positive charge.

The term "ARCA" or anti-reverse cap analog refers to a modified cap analog in which either the 3'-OH group or the 2'-OH group of the m⁷G is modified. This modification forces RNA polymerases to initiate transcription with the remaining —OH group in the G residue of the cap and thus synthesize RNA transcripts capped exclusively in the correct orientation. Therefore, use of the cap analog provided herein allows for synthesis of capped RNAs that are 100% functional in contrast to transcription reactions using traditional cap analogs where only half of the cap analog is incorporated in the correct orientation. Capped mRNAs provided herein are used for protein synthesis in reticulocyte lysates, wheat germ lysates, and other in vitro systems, or can be, for example, microinjected, electroporated, or transfected into cells or organisms for in vivo studies. They can also be used in RNA splicing and stability studies.

As used herein, the term "cell-penetrating peptide" refers to a modified peptide or other entity that aides in cellular uptake of an RNA, e.g., by facilitating transfer of a cargo molecule from the membrane to the cytoplasm and nucleus. Non-limiting examples of suitable cell penetrating peptides useful in the embodiments disclosed herein include the peptides listed in Table 2, and the peptides listed in Table 2 optionally covalently linked to a dye:

TABLE 2

| SEQ ID No. | Sequence |
|---|---|
| 1 | GYSTPPKKKRKVEDP |
| 2 | GYSTPPKTRRRP |
| 3 | GYSTPGRKKR |
| 4 | GYSTPRRNRRRRW |
| 5 | PDEVKRKKKPPTSYG |
| 6 | PRRRTKPPTSYG |
| 7 | RKKRGPTSYG |
| 8 | WRRRRNRRPTSYG |
| 9 | GYGPPKKKRKVEAPYKA |
| 10 | PAAKRVKLD |
| 11 | RQRRNELKRSP |
| 12 | KRPAATKKAGQAKKKK |
| 13 | VRKKRKTEEESPLKDKDAKKSKQE |
| 14 | RLRRDAGGRGGVYEHLGGAPRRRK |
| 15 | KRKGDEVDGVDECAKKSKK |
| 16 | NQSSNFGPMKGGNFGGRSSGPYGGGGQYFAKPRNQGGY |
| 17 | GGKRTADGSEFESPKKARKVEAYPKAW |
| 18 | GGKRTADGSEFESPKKKRAVEAYPKAW |
| 19 | GGKRTADGSEFESPKKKAKVEAYPKAW |
| 20 | GGKRTADGSEFESPKKKRKVEAPYKAWK |
| 21 | GGKRTADGSEFESPKKKRKVEYKAWK |
| 22 | GYGPAAKRVKLDEAYPKAWK |
| 23 | GGKRTADGSEFEPAAKRVKLDEAYPKAWK |
| 24 | GTGPKKKRKVGGGGYGPKKKRLVG |
| 25 | KRPAATKKAGQAKKKKLEAYPKAWK |
| 26 | ATKGTKRSYEQMETGE |
| 27 | GKWERKPIRCAS |
| 28 | GYGKRTADSQHSTPPKKKRKVEAPYKAWK |
| 29 | KRTADSQHSTPPKKKRKVEAPYKAWK |
| 30 | GYGPPKKKRKVEAPYKAWKWAKYPAMRRAHHRRRRASHRRRTTTGT |
| 31 | GYGPPKKKRKVEAPYKAWKRGARRYSKMKRRRRRVARRHRRRP |
| 32 | FWGYGYGPPKKKRKVEAPYKAWK |
| 33 | GKPSSDDEATADSQHSTPPKKKERKVED |
| 34 | GKPTADDQHSTPPKKKRKVED |
| 35 | GGKRTADGSEFESPKKARKVEAYPKAK |
| 36 | EKIRLRPGRKKRYRLKHL |
| 37 | PEGTRQARRNRRRRWRKR |
| 38 | PEGTRQPRRNRRRRWRKR |

TABLE 2-continued

| SEQ ID No. | Sequence |
|---|---|
| 39 | GVKRSYGAARGDDRRRPNVVAPYKAW |
| 40 | KSVPNRTRTYIKLKRLRFKGAPYKAW |
| 41 | EMRRRREEEGLQLRKQKREEQLFKRRN |
| 42 | FEAALAEALAEALA |
| 43 | Ac-LARLLPRLLARL-NHCH$_3$ |
| 44 | GLLEELLELLEELWEELLEG |
| 45 | GWEGLIEGIEGGWEGLIEG |
| 46 | GLFEALAEFIEGGWEGLIEG |
| 47 | GLFEALLELLESLWELLLEA |
| 48 | GGYCLEKWMIVASELKCFGNTA |
| 49 | GGYCLTRWMLIEAELKCFGNTAV |
| 50 | WEAALAEALAEALAEHLAEALAEALEALAA |
| 51 | GLFGAIAGFIENGWEGMIDGWYG |
| 52 | GIGAVLKVLTTGLPALISWIKRKRQQ |
| 53 | GRKKRRQRRRPPQ |
| 54 | RQIKIWFQNRRMKWKK |
| 55 | GWTLNSAGYLLGKINLKALAALAKKIL |
| 56 | WEAKLAKALAKALAKHLAKALAKALKACEA |
| 57 | GLFKALLKLLKSLWKLLLKA |
| 58 | GLFRALLRLLRSLWRLLLRA |
| 59 | GLFEALLELLESLYELLLEA |
| 60 | GLFEALEELWEA |
| 61 | GLFLLEEWLE |
| 62 | GLFLLEEWLEK |
| 63 | GLFEALLELLESLWELLLEAK |
| 64 | Suc-GLFKLLEEWLE |
| 65 | Suc-GLFKLLEEWLEK |
| 66 | GLFEAIAEFIEGGWEGLIEG |
| 67 | GLFKAIAKFIKGGWKGLIKG |
| 68 | IRFKKTKLIASIAMALC |
| 69 | ALAGTIIAGASLTFQVLDKV1EELGKVSRK |
| 70 | GLFEAIEGFIENGWEGMIDGWYG |
| 71 | GYICRRARGDNPDDRCT |
| 72 | GLFEAIAEFIEGGWEGLIEGCA |
| 73 | GLFHAIAHFIHGGWHGLIHGWWYG |
| 74 | RRRQRRKKRGGDIMGEWGNEIFGAIAGFLG |
| 75 | GLFEAIADFIENGWEGMIDGGG |
| 76 | ALAGTIIAGASLTFQVLDKV1EELGKVSRKK |
| 77 | IRFKKTKLIASIAMA |
| 78 | GLWHLLLHLWRRLLRLLR |
| 79 | KKIMLLLMTLLLVSLPLAQEQ |
| 80 | GLFEALLELLESLWELLLEAWYG |
| 81 | RLLRLLLRLWRRLLRLLR |
| 82 | LLELELLELELLLELELLELELLLEL |
| 83 | GLFEALLELLESLWELLLEARRRRRRRR |
| 84 | GLFEALLELLESLWELLLEARRRRRR |
| 85 | GLFEALLELLESLWELLLEAKKKKKKKK |
| 86 | GLFEALLELLESLWELLLEAKKKKKK |
| 87 | GLFEALLELLESLWELLLEAKK |
| 88 | GLFEALLELLESLWELLLEAKKKK |
| 89 | GLFEALLELLESLWELLLEAEE |
| 90 | GLFEALLELLESLWELLLEAEEEE |
| 91 | GLFEALLELLESLWELLLEAEEEEEE |
| 92 | GLFEALLELLESLWELLL |
| 93 | PLSSIFSRIGDPRGARRYAKMKRRRRRVARRHRRRP |
| 94 | GPFHYFQFLFPPV |
| 95 | GSSSWWQRWWPPW |
| 96 | RRRQRRKKR |
| 97 | KKKK |
| 98 | KKKKKK |
| 99 | KKKKKKKK |
| 100 | KKKKKKKKKK |
| 101 | KKKKKKKKKKKK |
| 102 | KKKKKKKKKKKKKK |
| 103 | KKKKKKKKKKKKKKKKKK |
| 104 | KKKKKKKKKKKKKKKKKKKKKK |
| 105 | RRRR |
| 106 | RRRRRR |
| 107 | RRRRRRRR |
| 108 | RRRRRRRRRR |
| 109 | RRRRRRRRRRRR |
| 110 | RRRRRRRRRRRRRR |
| 111 | RRRRRRRRRRRRRRRRRR |
| 112 | RRRRRRRRRRRRRRRRRRRRRR |
| 113 | YKA |
| 114 | KKKKKKKKWKGGGGACYGLPHLFCG |

TABLE 2-continued

| SEQ ID No. | Sequence |
|---|---|
| 115 | YKAKKKKKKKWK |
| 116 | KTPKKAKKPKTPKKAKKP |
| 117 | KKAKKPAATRKSSKNPKKPKTVKPKKVAK |
| 118 | RGARRYSKMKRRRRRVARRHRRRP |
| 119 | TRQARRNRRRRWRERQRGSGSG |
| 120 | KRPRGRPKGSKKNWRRRKRRASRRSPRRR |
| 121 | KRGRGRPRKQPPKEPSEVPTPKRPRGRPKGSKNK |
| 122 | KEKYEKDIAAYRAKGKPAAKKGVVKAEKSKKKK |
| 123 | YKAKKKKKKKKKWK |
| 124 | KKKKKKKGGC |
| 125 | YRARRRRRRRWR |
| 126 | YRARRRRRRRRRWR |
| 127 | KGDPKKPRGKMSSYAFFVQTCREEHKKKHPDASVNFSEFSKK |
| 128 | KKQLKKQLKKQLKQWK |
| 129 | KKSPKKSPKKSPKKSK |
| 130 | KLSKLEKKSKLEK |
| 131 | KLSKLEKKLSKLEKKSKLEK |
| 132 | KSLKKSLKKSLKKSK |
| 133 | KIRRRGKNKVAARTCRQRRTDR |
| 134 | KIRRRGKNKVAAQNCRKRKLET |
| 135 | KRRIRREKNKMAAAKCRNRRRELT |
| 136 | KDRSNLLERHTR |
| 137 | KRPAATKKAGQAKKKL |
| 138 | RRRRREEEE |
| 139 | RRRRRREEEEE |
| 140 | RRRRRREEEEEEE |
| 141 | RRRRRRREEEE |
| 142 | RRRRRRREEEEEE |
| 143 | RRRRRRREEEEEEEE |
| 144 | RRRRRRRRRREEEE |
| 145 | RRRRRRRRRREEEEEE |
| 146 | RRRRRRRRRREEEEEEE |
| 147 | KLSKLEKK |
| 148 | SKLEK |
| 149 | KLSKLEKKLSKLEKK |
| 150 | PKKKRKVGGGRGDSP |
| 151 | LPHKSMPCG |
| 152 | GACLQHKSMPCG |
| 153 | YGLPHLFCG |
| 154 | SERSMNFCG |
| 155 | DHYSLYEDLERGTDK |
| 156 | ISLPRTSGAQRASTTR |
| 157 | EKLQTKYGLPHKVEFCG |
| 158 | TRISESQAKPGD |
| 159 | LVFFDY |
| 160 | WGGNGPTTFDCSGYTKYVFAK |
| 161 | INIGTTGWGDHYSLY |
| 162 | YDNIHG |
| 163 | AGWGKFLVGFGRV |
| 164 | SIGYPLP |
| 165 | TTHWGFTL |
| 166 | HLQIQPYPQISG |
| 167 | KLNIVSVNG |
| 168 | RGH |
| 169 | DNRIRLQAKAA |
| 170 | KIKMVISWKG |
| 171 | LPWYSYLYAVSA |
| 172 | WNLPWYYSVSPT |
| 173 | WNL |
| 174 | PWYYSVSPT |
| 175 | SSWESYKSGGGTRL |
| 176 | RDWSSQHPGRCNGETHLK |
| 177 | SLPTLTL |
| 178 | VICTGGDYSFALPVGQWPVMT |
| 179 | DKPSYQFGGHNSVDFEEDTLPKV |
| 180 | RARRRKRASATQLYQTCKASGTCPPD |
| 181 | SGDYSFALPVGQWPWMTG |
| 182 | CTGGDYSFALPVGQWPW |
| 183 | FYYDYDFFFDYWGQG |
| 184 | HLRRLRRRLLREAEG |
| 185 | DYYCAAWDDSLNGYSVF |
| 186 | YYCLQSMEDPYTFGG |
| 187 | YYCARSDGNYGYYYALDYDY |
| 188 | AARSPSYYRYDY |
| 189 | GPYYAMDYD |
| 190 | YYCQQRSSYPYTEGGAYPKAWK |

TABLE 2-continued

| SEQ ID No. | Sequence |
|---|---|
| 191 | YYCQRYDSDWSFGQGTKL |
| 192 | YYCARSGYYAMDYWGQGT |
| 193 | RVRRGACRGDCLG |
| 194 | RVRRGACRYDCLG |
| 195 | YYCAKGTHWGFWSGYFDYWGQGT |
| 196 | GRENYHGCTTHWGFTLC |
| 197 | VQATQSNQHTPRGGGSK |
| 198 | DPRAPGS |
| 199 | YYCQQRSSYPYTFGG |
| 200 | AARSPSYYRYDYGPYYAMDYD |
| 201 | GPKLTGILISILSLFVES |
| 202 | KYILRWRPKNS |
| 203 | IKVAV |
| 204 | WTPPRAQITGYRLTVGLTRR |
| 205 | AASIKVAVSADR |
| 206 | KLDAPT |
| 207 | NRWHSIYITRFG |
| 208 | PHSRN |
| 209 | SSFHFDGSGYAM |
| 210 | RGDS |
| 211 | IAFQRN |
| 212 | GRGDSP |
| 213 | TWYKIAFQRRK |
| 214 | EDGIHEL |
| 215 | SLVRNRRVITIQ |
| 216 | YRVRVTPKEKTGPMKE |
| 217 | LQVQLSR |
| 218 | SPPRRARVT |
| 219 | RKRLQVQLSIRT |
| 220 | ATETTITIS |
| 221 | NAPFPKLSWTIQ |
| 222 | VSPPRRARVTDATETTITISWRTKTETITGG |
| 223 | WTIQTTVDRGLL |
| 224 | KPDVRSYTITG |
| 225 | DTINNGRDHMILI |
| 226 | ANGQTPIQRYIK |
| 227 | MILISIGKSQKRM |
| 228 | PRARITGYIIKYEKPGSPPREVVPRPRPGV |

TABLE 2-continued

| SEQ ID No. | Sequence |
|---|---|
| 229 | PPFLMLLKGSTR |
| 230 | WQPPRARI |
| 231 | NQRLASFSNAQQS |
| 232 | WQPPRARITGYIIKYEKPG |
| 233 | ISNVFVQRMSQSPEVLD |
| 234 | YEKPGSPPREVVPRPRPGV |
| 235 | KARSFNVNQLLQD |
| 236 | KNNQKSEPLIGRKKT |
| 237 | KNSFMALYLSKG |
| 238 | EILDVPST |
| 239 | KNSFMALYLSKGRLVFALG |
| 240 | IDAPS |
| 241 | RDSFVALYLSEGHVIFAGLG |
| 242 | VVIDASTAIDAPSNL |
| 243 | KPRLQFSLDIQT |
| 244 | LDVPS |
| 245 | DGQWHSVTVSIK |
| 246 | REDV |
| 247 | FVLYLGSKNAKK |
| 248 | PHSRNRGDSP |
| 249 | LAIKNDNLVYVY |
| 250 | LWVTVRSQQRGLF |
| 251 | AYFSIVKIERVG |
| 252 | GTNNWWQSPSIQN |
| 253 | DVISLYNFKHIY |
| 254 | WVTVTLDLRQVFQ |
| 255 | FFDGSSYAVVRD |
| 256 | RQVFQVAYIIIKA |
| 257 | LHVFYDFGFGFSNG |
| 258 | LTRYKITPRRGPPT |
| 259 | LKKAQINDAKYREISIIYHN |
| 260 | LLEFTSARYIRL |
| 261 | RAYFNGQSFIAS |
| 262 | YIRLRLQRIRTL |
| 263 | SRLRGKNPTKGK |
| 264 | RRYYYSIKDISV |
| 265 | LHKKGKNSSKPK |
| 266 | SINNTAVNQRLT |

TABLE 2-continued

| SEQ ID No. | Sequence |
|---|---|
| 267 | RLKTRSSHGMIF |
| 268 | GGFLKYTVSYDI |
| 269 | GEKSQFSIRLKT |
| 270 | RDQLMTVLANVT |
| 271 | TLFLAHGRLVFM |
| 272 | ANVTHLLIRANY |
| 273 | LVFMFNVGHKKL |
| 274 | AGTFALRGDNPQG |
| 275 | TLFLAHGRLVFMFNVGHKKL |
| 276 | VLIKGGRARKHV |
| 277 | DFMTLFLAHGRLVFMGNVG |
| 278 | LSNIDYLIKAS |
| 279 | HKKLKIRSQEKY |
| 280 | LQQSRIANISME |
| 281 | GAAWKIKGPIYL |
| 282 | NLLLLLVKANLK |
| 283 | VIRDSNVVQLDV |
| 284 | HRDELLLWARKI |
| 285 | GLIYYVAHQNQM |
| 286 | KRRARDLVHRAE |
| 287 | DYATLQLQEGRLHFMFDLG |
| 288 | SQFQESVDNITK |
| 289 | KKGSYNNIVVHV |
| 290 | PGGMREKGRKAR |
| 291 | ADNLLFYLGSAK |
| 292 | MEMQANLLLDRL |
| 293 | GSAKFIDFLAIE |
| 294 | LSEIKLLISAR |
| 295 | KVSFLWWVGSGV |
| 296 | RDFTKATNIRLRFLR |
| 297 | SYWYRIEASRTG |
| 298 | ISTVMFKFRTFS |
| 299 | YFDGTGFAKAVG |
| 300 | KQANISIVDIDSN |
| 301 | NGQWHKVTAKKI |
| 302 | FSTRNESGIILL |
| 303 | AKKIKNRLELVV |
| 304 | RRQTTQAYYAIF |
| 305 | GFPGGLNQFGLTTN |
| 306 | YAIFLNKGRLEV |
| 307 | NQFGLTTNIRFRG |
| 308 | KNRLTIELEVRT |
| 309 | IRSLKLTKGTGKP |
| 310 | GLLFYMARINHA |
| 311 | AKALELRGVQPVS |
| 312 | VQLRNGFPYFSY |
| 313 | GQLFHVAYILIKF |
| 314 | HKIKIVRVKQEG |
| 315 | NVLSLYNFKTTF |
| 316 | DFGTVQLRNGFPFFSYDLG |
| 317 | SQRIYQFAKLNYT |
| 318 | NIRLRFLRTNTL |
| 319 | EVNVTLDLGQVFH |
| 320 | GKNTGDHFVLYM |
| 321 | GQVFHVAYVLIKF |
| 322 | VVSLYNFEQTFML |
| 323 | HQQDLGTAGSCLRKFSTMFLF |
| 324 | RFDQELRLVSYN |
| 325 | HQQDLGTAGSCLRKFSTMFLFCNI |
| 326 | RLVSYSGVLFFLK |
| 327 | VAEIDGIEL |
| 328 | NWRHISYITRFG |
| 329 | GIIFFL |
| 330 | KRLQVQLRSIRT |
| 331 | ASKAIQVFLLGG |
| 332 | TWYKIAFQRNRK |
| 333 | VLVRVERATVFS |
| 334 | QVFQVAYIIIKA |
| 335 | TVFSVDQDNMLE |
| 336 | GEFYFDLRLKGDK |
| 337 | RLRGPQRVFDLH |
| 338 | GTPGPQGIA |
| 339 | FDLHQNMGSVN |
| 340 | GQRDVV |
| 341 | LRAHAVDVNG |
| 342 | TAGSCLRKFSTM |

TABLE 2-continued

| SEQ ID No. | Sequence |
|---|---|
| 343 | LFSHAVSSNG |
| 344 | KGHRGF |
| 345 | TAGSCLRKFSTMFLF |
| 346 | TAGSCLRKFSTMFLFCNI |
| 347 | DLGTAGSCLRKFSTM |
| 348 | HQQDLGTAGSCLRKFSTM |
| 349 | RNIAEIIKDI |
| 350 | SIGFRGDGQTC |
| 351 | LNRQELFPFG |
| 352 | RIQNLLKITNLRIKFVK |
| 353 | KKQRFRHRNRKGYRSQ |
| 354 | SINNTAVMQRLT |
| 355 | FRHRNRKGY |
| 356 | RYRVRVTPKEKTGPMKE |
| 357 | SETTVKYIFRLHE |
| 358 | GHRGPTGRPGKRGKQGQKGDS |
| 359 | KAFDITYVRLKF |
| 360 | GDLGRPGRKGRPGPP |
| 361 | YIGSR |
| 362 | RGEFYFDLRLKGDK |
| 363 | LAGSCLARFSTM |
| 364 | LALFLSNGHFVA |
| 365 | ISRCQVCMKKRH |
| 366 | PGRWHKVSVRWE |
| 367 | TDIPPCPHGWISLWK |
| 368 | VRWGMQQIQLVV |
| 369 | TAIPSCPEGTVPLYS |
| 370 | KMPYVSLELEMR |
| 371 | GPAGKDGEAGAQG |
| 372 | VLLQANDGAGEF |
| 373 | GLPGER |
| 374 | DGRWHRVAVIMG |
| 375 | LAGSCLPVFSTL |
| 376 | APVNVTASVQIQ |
| 377 | TAGSCLRRFSTM |
| 378 | KQGKALTQRHAK |
| 379 | TAGSCLRKF |
| 380 | RYVVLPR |
| 381 | TAGSCL |
| 382 | SPYTFIDSLVLMPY |
| 383 | TAG |
| 384 | PDSGR |
| 385 | QQNLGSVNVSTG |
| 386 | SRATAQKVSRRS |
| 387 | DPGYIGSR |
| 388 | GSLSSHLEFVGI |
| 389 | VILQQSAADIAR |
| 390 | RNRLHLSMLVRP |
| 391 | KDISEKVAVYST |
| 392 | APMSGRSPSLVLK |
| 393 | LGTIPG |
| 394 | AFGVLALWGTRV |
| 395 | TDIRVTLNRLNTF |
| 396 | IENVVTTFAPNR |
| 397 | AFSTLEGRPSAY |
| 398 | LEAEFHFTHLIM |
| 399 | TSAEAYNLLLRT |
| 400 | HLIMTFKTFRPA |
| 401 | LNRRYEQARNIS |
| 402 | KTWGVYRYFAYD |
| 403 | SLLSQLNNLLDQ |
| 404 | TNLRIKFVKLHT |
| 405 | RDIAEIIKDI |
| 406 | KRLVTGQR |
| 407 | SHAVSS |
| 408 | GPGVVVERQYI |
| 409 | ADTPPV |
| 410 | NEPKVLKSYYYAI |
| 411 | LRAHAVDING |
| 412 | YYAISDFAVGGR |
| 413 | DSITKYFQMSLE |
| 414 | LPFFNDRPWRRAT |
| 415 | YTALIIATDN |
| 416 | FDPELYRSTGHGGH |
| 417 | VITVKDINDN |
| 418 | TNAVGYSVYDIS |

TABLE 2-continued

| SEQ ID No. | Sequence |
|---|---|
| 419 | GLDRESYPYY |
| 420 | APVKFLGNQVLSY |
| 421 | MKVSATDADD |
| 422 | SFSFRVDRRDTR |
| 423 | PQVTRGDVFTMP |
| 424 | TWSKVGGHLRPGIVQSG |
| 425 | KEAEREVTDLLR |
| 426 | RGDV |
| 427 | AAEPLKNIGILF |
| 428 | FALWDAIIGEL |
| 429 | VGVAPG |
| 430 | LWPLLAVLAAVA |
| 431 | PGVGV |
| 432 | VFDNFVLK |
| 433 | TSIKIRGTYSER |
| 434 | TTSWSQCSKS |
| 435 | DPETGV |
| 436 | KRSR |
| 437 | QGADTPPVGV |
| 438 | SVVYGLR |
| 439 | PLDREAIAKY |
| 440 | DGRGDSVAYG |
| 441 | HAVDI |
| 442 | LALERKDHSG |
| 443 | DQNDN |
| 444 | YSMKKTTMKIIPFNRLTIG |
| 445 | QDPELPDKNM |
| 446 | RGDF |
| 447 | LVVQAADLQG |
| 448 | GVYYQGGTYSKAS |
| 449 | NDDGGQFVVT |
| 450 | TAGSCLRKFSCL |
| 451 | YILHVAVTN |
| 452 | CNYYSNSYSFWLASLNPER |
| 453 | TYRIWRDTAN |
| 454 | TGLSCLQRFTTM |
| 455 | GFTCECSIGFRGDGQTCYGIVFWSEV |
| 456 | HHLGGAKQAGDV |
| 457 | SCLPGFSGDGRACRDVDECGH |
| 458 | MAPRPSLAKKQRFRHRNRKGYRSQRGHSRG |
| 459 | KKQKFRHRNRKGYRSQ |
| 460 | KKQKFKHRNRKGYRS |
| 461 | KKQKFRRRNRKGYRSH |
| 462 | TAIPPCPHGWISLWK |
| 463 | KKQKSRHRSRKRYRS |
| 464 | KKQKSRRRSRKGYRS |
| 465 | ISRCTVC |
| 466 | ISRCQVCMKRRH |
| 467 | VSRCTVC |
| 468 | TDIPPCPQGWISLWK |
| 469 | TVKAGELEKIISRCQVMKKRH |
| 470 | TDIPSCPHGWISLWK |
| 471 | TDIPPCPAGWISLWK |
| 472 | TEIPPCPQGWISLWK |
| 473 | TDVPPCPQGWISLWK |
| 474 | RLVSYNGILFFLK |
| 475 | RLVSYSGVIFFLK |
| 476 | RLVSYNGILFFL |
| 477 | RLVSYSGIIFFLK |
| 478 | RFEQELRLVSYSGVLFFLKQ |
| 479 | RLVSYNGIIFFLK |
| 480 | DPAFKIEDPYSPRIQNLLKITNLRIKFVKL |
| 481 | TKRFEQELRLVSYSGVLFFL |
| 482 | GGRLKYSVAF |
| 483 | GGFLRYTVSYDI |
| 484 | GGFLKYTVSYDV |
| 485 | LGNKLTAFGGFLKYTVSYDIPV |
| 486 | GGYLKYTVSYDI |
| 487 | GEIFFDMRLKGDK |
| 488 | GEIYFDLRLKGDK |
| 489 | GEIYLDMRLKGDK |
| 490 | IGQPGAKGEPGEFYFDLRLKGDKGDPGFPG |
| 491 | GEVFFDMRLKGDK |
| 492 | LAGSCLPIFSTL |
| 493 | AHNQDLGLAGSCLARFSTMPFLYCNPGDIC |
| 494 | QEKAHNQDLGLAGSCLPVFSTLPFAYCNIH |

TABLE 2-continued

| SEQ ID No. | Sequence |
|---|---|
| 495 | LAGSCLPVFSTM |
| 496 | GNKRAHGQDLGTAGSCLRRFSTMPFMFCNI |
| 497 | RAHGQDLGTAGSCLRRFSTMP |
| 498 | RKRLQVQLNIRT |
| 499 | HLVLPLQQSDVRKRLQVQLSIRTFASSGLI |
| 500 | RKRLSVQLRIRT |
| 501 | DLGTAGSCLRRFSTM |
| 502 | RNIAEIIKDI |
| 503 | TAGSCLRKFSTMRRRRRRRRRRR |
| 504 | FTLTGLLGTLVTMGLLT |
| 505 | APYKAWK |
| 506 | STSKTNRGDDSNWSKRVTNNKPS |
| 507 | STSKRKRGDDSNWSKRVTKKKPS |
| 508 | STSKRKRGDDSNWSKRVSKKKPS |
| 509 | STSKRKRGDDANWSKRVTKKKPS |
| 510 | PLAGSKRKRADEVAWSKRGTKKKPER |
| 511 | PLAGSKRKRADEVAWSKRGTKKKPERTSAARAGPSRRIR |
| 512 | STSKRKRGDDANWSKRTTKKKPSS |
| 513 | STSKRKRGDDANWSKRTTKKKPSSAGLKRAGSKADRPSL |
| 514 | PTTAGKRKRSDDAAWSKRARPKAGRT |
| 515 | PTTAGKRKRSDDAAWSKRARPKAGRTSAARPGTSVRRIR |
| 516 | SSSLGKRKRSDEGAWSKGKSKKKAMR |
| 517 | SSSLGKRKRSDEGAWSKGKSKKKAMRGSSSRRPGPVRGP |
| 518 | PTTAGKRKRTDDAAWSKRARPKAGR |
| 519 | PTTAGKRKRTDDAAWSKRARPKAGRTSAARPGTAVRRVR |
| 520 | PATAGKRKRSDDAAWSKRARPKAGRTSAAR |
| 521 | PATAGKRKRSDDAAWSKRARPKAGRTSAARPGTSVRRIR |
| 522 | SSSLGKRKRSNGGDWSKRSAKKKPA |
| 523 | SSSLGKRKRSNGGDWSKRSAKKKPAGTPSRRAGPGRGPR |
| 524 | SSSLGKRKRSDEGAWSKGKSKKKAMR |
| 525 | SSSLGKRKRSDEGAWSKGKSKKKAMRGSSSRRPGPVRGP |
| 526 | STSKRKRGDDANWNKRPTKKKPSS |
| 527 | STSKRKRGDDANWNKRPTKKKPSSAGLKKAGSKAERPSL |
| 528 | SGALKRKRSDEVAWSRRRPVKKPV |
| 529 | SGALKRKRSDEVAWSRRRPVKKPVRRAPPPRAGPSVRRG |
| 530 | SGALKRKRSDEVAWSRRKPAKKPAR |
| 531 | SGALKRKRSDEVAWSRRKPAKKPARQPPPRAGPSVRRG |
| 532 | AGALKRKRSDEVAWSRRKPAKKPAR |
| 533 | AGALKRKRSDEVAWSRRKPAKKPARAPPPRAGPSVRRGL |
| 534 | STSKRKRGDDSNWSKRVTKKKPSSAGLKRAGSKADRPSLQIQT LQHAGTTMITVPSGGVCDLINTYARGSDEGNRHTSETLTYKIAI DYHFVADAAACRYSNTGTGVMWLVYDTTPGGQAPTPQTIFSYP DTLKAWPATWKVSRELCHRFVVKRRWLFNMETDGRIGSDIPPS NASWKPCKRNIYFHKFTSGLGVRTQWKNVTDGGVGAIQRGAL YMVIAPGNGLTFTAHGQTRLYFKSVGNQ |
| 535 | DPQNALYYQPRVPTAAPTSGGVPWSRVGEVAILSFVALICFYLL YLWVLRDLILVLKARQGRSTEELIFGGQAVDRSNPIPNIPAPPS QGNPGPFVPGTG |
| 536 | GSQLVPPPSAFNYIESQRDEFQLSHDLTEIVLQFPSTASQITAR LSRSCMKIDHCVIEYRQQVPINASGTVIVEIHDKRMTDNESLQA SWTFPIRCNIDLHYFSSSFFSLKDPIPWKLYYRVSDSNVHQMTH FAKFKGKLKLSSAKHSVDIPFRAPTVKILAKQFSEKDIDFWHVG YGKWERRLVKSASSSRFGLRGPIEINPGESWATKSAIVTPNRNA DLDIEEELLPYRELNRLGTNILDPGESASIVGIQRSQSNITMSM SQLNELVRSTVHECIKTSCIPSTPKSLS |
| 537 | RTGVKRSYGAARGDDRRRPNVV |
| 538 | SYVKTVPNRTRTYIKLRVR |
| 539 | MYSTSNRRGRSQTQRGSHVRRTGVKRSYGAARGDDRRRPNVV SKTQVEPRMTIQRVQENQFGPEFVLSQNSALSTFVTYPSYVKTV PNRTRTYIKLKRVRFKGTLKIERGQGDTIMDGPSSNIEGVFSMV IVVDRKPHVSQSGRLHTFDELFGARIHCGNLSVVPALKDRYYI RHVTKRVVSLEKDTLLIDLHGTTQLSNKRYNCWASFSDLERDCN GVYGNITKNALLVYYCWLSDAQSKASTYVSFELDYLG |
| 540 | RRRRRRRRRRRRVDYGKWERKPIRCASMSR |
| 541 | RRRRRRRRRRRRGKWERKPIRCAS |
| 542 | KKKKKKKKKKKKKKKGKWERKPIRCAS |
| 543 | RRRRRRRRRRRRVDFSHVDYGKWERKPIRCASMSRLGLRG |
| 544 | GVKRSYGAARGDDRRRPNVVAPYKAWRRRRRRRRRRRR |
| 545 | KSVPNRTRTYIKLKRLRFKGAPYKAWRRRRRRRRRRRR |
| 546 | RTGVKRSYGAARGDDRRRPNVVRRRRRRRRRRRR |
| 547 | SYVKTVPNRTRTYIKGGGGRRRRRRRRRRRR |
| 548 | VDIPFRAPTIKILSKQFTEDDIDFWHVGYGKWERKLVRPASLSG RRGLRR |
| 549 | IDFWHVGYGKWERKLVRPASLSGRRGLRR |
| 550 | IDFWSVEKGETRRRLLNPTPHAHSPRPIAHR |
| 551 | IDFSHVGYGKWERKMIRSASISRLGLHN |
| 552 | VDFSHVGYGKWERKLIRSASTVKYGLPS |
| 553 | IDFSHVDYGKVERKLVKCESSSRLGLHS |
| 554 | IDFWSVGRKAQQRKLVQGPSLIGSRSMRY |
| 555 | IDFWSVGSKPQTRRLVDGSRLIGHSSRSLRV |
| 556 | IDFWSVERGETRRRLLNPTPSAGSNRALSKR |
| 557 | VDFWSVGKPKPIRRLIQNDPGTDYDTGPKYR |
| 558 | VDFWSVEKPKPIRRLLNPGPNQGPYPNTGHR |
| 559 | VDFSHVDYGKWERKLIRSASTSRYGLRS |
| 560 | VDFSHVDYGKWERKTLRSRSLSRIGLTG |

TABLE 2-continued

| SEQ ID No. | Sequence |
|---|---|
| 561 | IDFWHVGYGKWERRLVKSASSSRFGIRG |
| 562 | VDFFHVDYGRWERKHIRCASMSRVGLRG |
| 563 | GTFQHVDYGKWERKPIRCQSMSRVGYRR |
| 564 | VGYGKWERKLVRPASLS |
| 565 | VEKGETRRRLLNPTPHA |
| 566 | VGYGKWERKLIRSASTV |
| 567 | VEKPKPIRRLLNPGPNQ |
| 568 | VDYGKWERKLIRSASTS |
| 569 | VDYGKWERKTLRSRSLS |
| 570 | VGYGKWERRLVKSASSS |
| 571 | VDYGRWERKHIRCASMS |
| 572 | VERPKPIRRLLTPTPGC |
| 573 | PFRAPTIKILSKQFTEDDIDFWHVGYGKWERKLVRPASLSGRRGLRR |
| 574 | PFRAPTVKILSKQFTDKDIDFSHVGYGKWERKMIRSASISRLGL |
| 575 | DIAFRAPTVKILSKQFTDRDVDFSHVGYGKWERKLIRSASTVKYGL |
| 576 | DIRFKPPTINILSKDYTADCVDFWSVEKPKPIRRLLNPGPNQGPYPNTG |
| 577 | DIPFRAPTVKIHSKQFSHRDVDFSHVDYGKWERKTLRSRSLSRIGL |
| 578 | DIPFRAPTVKILAKQFSEKDIDFWHVGYGKWERRLVKSASSSRFGI |
| 579 | DIPFRAPTVKILSKQFTDKDVDFFHVDYGRWERKHIRCASMSRVGL |
| 580 | DIKYKPPTIKILSKDYTADCVDFWSVERPKPIRRLLTPTPGCG |
| 581 | ARTKQTARKSTGGKAPRKQLATKAARKSAPATGGVKKPHRYRPGTVA |
| 582 | SGRGKGGKGLGKGGAKRHRKVLRDNIQGITKPAI |
| 583 | GRKKRRQRRR |

As used herein, the term "linker-bound cell-penetrating peptide" refers to a modified peptide or other entity that aides in cellular uptake of an RNA, e.g., by facilitating transfer of a cargo molecule from the membrane to the cytoplasm and nucleus, which is bound to a linking moiety that allows the cell-penetrating peptide to conjugate or attach to the trinucleotide cap analogs described herein. One skilled in the art would understand the linker bound to the cell-penetrating peptide can be chosen from those commercially available, such as biotin, 3' maleimidobenzoic acid N-hydroxysuccinimide ester, and

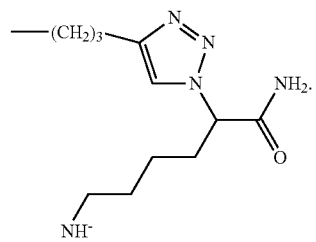

In some embodiments the cell penetrating peptides disclosed herein may be covalently attached to the RNA caps disclosed herein. By way of example, in some embodiments, the cell penetrating peptide may be incorporated into a fluorescent label that is attached to the RNA cap disclosed herein. In some embodiments, cell penetrating peptides are not covalently linked to the RNA caps disclosed herein. For example, in some embodiments, provided are compositions that comprise an RNA molecule with a CAP as described herein, in combination with one or more cell penetrating peptides.

As used herein, the terms "click" or "click chemistry," as used herein, refer to the Huisgen cycloaddition or the 1,3-dipolar cycloaddition between an azide and an alkyne to form a 1,2,4-triazole.

As used herein, the term "enzymatically incorporatable" means that a nucleotide is capable of being enzymatically incorporated onto the terminus, e.g., 3' terminus, of a polynucleotide chain, or internally through nick-translation of a polynucleotide chain, through action of a template-dependent or template-independent polymerase enzyme. A nucleotide-5'-triphosphate is an example of an enzymatically incorporatable nucleotide.

As used herein, the term "enzymatically extendable" or "3' extendable" means a nucleotide or polynucleotide that is capable of being appended to a nucleotide or polynucleotide by enzyme action. A polynucleotide containing a 3' hydroxyl group is an example of an enzymatically extendable polynucleotide.

As used herein, the term "halogen" refers to nonmetal elements of Group 7A of the Periodic Table of the Elements comprising fluorine, F, chlorine, Cl, bromine, Br, iodine, I, and astatine, At. Halogens are monovalent, readily form negative ions and occur as compounds or ions.

As used herein, the terms "intracellular molecular stability" and "intracellular stability" refers to the ability of RNA to exist in a cell without degradation leading to loss of function. Thus, increasing intracellular stability refers to an increase of the duration that an RNA exists in a cell. By way of non-limiting example, uncapped RNA can exist in a cell an average of 4 to 6 hours, whereas a capped RNA can exist an average of 10 to 48 hours depending on the cap.

As used herein, the term "locked nucleic acid" (LNA) refers to a bridge between the 2'O and 4'C methylene bicyclonucleotide monomers.

As used herein, the term "nucleobase" refers to a nitrogen containing heterocyclic moiety nucleobase. Non-limiting examples of suitable nucleobases include: adenine, cytosine, guanine, thymine, uracil, 5-propynyl-uracil, 2-thio-5-propynyl-uracil, 5-methylcytosine, pseudoisocytosine, 2-thiouracil, 2-thiothymine, 2-aminopurine, N9-(2-amino-6-chloropurine), N9-(2,6-diaminopurine), hypoxanthine, N9-(7-deaza-guanine), N9-(7-deaza-8-aza-guanine) and N8-(8-aza-7-deazaadenine).

As used herein, the term "nucleoside" refers to a compound consisting of a nucleobase linked to the C-1' carbon of a ribose sugar or analog thereof. The ribose or analog may be substituted or unsubstituted. Substituted ribose sugars include, but are not limited to, those riboses in which one or more of the carbon atoms, preferably the 3'-carbon atom, is substituted with one or more of the same or different substituents such as —R, —OR, —NRR or halogen (e.g., fluoro, chloro, bromo, or iodo), where each R group is independently H, $C_1$-$C_6$ alkyl or $C_3$-$C_{14}$ aryl. Particularly, riboses are ribose, 2'-deoxyribose, 2',3'-dideoxyribose, 3'-haloribose (such as 3'-fluororibose or 3'-chlororibose) and 3'-alkylribose. Typically, when the nucleobase is A or G, the ribose sugar is attached to the $N^9$-position of the nucleobase. When the nucleobase is C, T or U, the pentose sugar is attached to the $N^1$-position of the nucleobase (Kornberg and Baker, *DNA Replication*, $2^{nd}$ Ed., Freeman, San Francisco, Calif., (1992)). Examples of ribose analogs include arabinose, 2'-O-methyl ribose, and locked nucleoside analogs (e.g., WO 99/14226), for example, although many other analogs are also known in the art.

As used herein, the term "nucleotide" refers to a phosphate ester of a nucleoside as a monomer unit or within a polynucleotide.

As used herein, the term "nucleotide triphosphate" refers to a nucleotide with a triphosphate ester group at the 5' position.

As used herein, nucleosides and/or nucleotides of the present teachings can comprise "natural sugars" (i.e., -ribose, 2'-deoxyribose, and the like) or sugar analogs.

The term "reporter moiety" and "reporter" are interchangeable and refer to a moiety that is detectable. In some embodiments, the reporter is specifically bound by an affinity moiety. In some embodiments, the interaction of the reporter moiety and the affinity moiety provides for the isolation of 1,4-triazole-derivatized RNA that is attached to the reporter moiety. Examples include, but are not limited to biotin or iminobiotin and avidin or streptavidin. A sub-class of reporter moiety is an "epitope tag," which refers to a tag that is recognized and specifically bound by an antibody or an antigen-binding fragment thereof. Other reporters include, but are not limited to tags (with affinity partner), epitope tags (with antibody), and enzyme substrate (with enzyme). The reporter moiety can allow for attachment to a solid support for purification of the capped RNA. The reporter can be, for example, a dye, biotin, or a peptide. Examples of biotin molecules that can comprise the reporter moiety include $C_5$-$C_{20}$ O-biotin, SS-biotin, XX-biotin ((6-((6-((biotinoyl)amino)hexanoyl)amino)hexanoic acid succinimidyl ester), and NHS esters. For use in certain methods herein, the reporter includes an azide group to allow use in "click" technology.

As used herein, the term "sugar analog" refers to analogs of the sugar ribose. Exemplary ribose sugar analogs include, but are not limited to, substituted or unsubstituted furanoses having more or fewer than 5 ring atoms, e.g., erythroses and hexoses and substituted or unsubstituted 3-6 carbon acyclic sugars. Typical substituted furanoses and acyclic sugars are those in which one or more of the carbon atoms are substituted with one or more of the same or different —R, —OR, —NRR or halogen groups, where each R is independently —H, $(C_1$-$C_6)$ alkyl or $(C_1$-$C_{14})$ aryl. Examples of substituted furanoses having 5 ring atoms include but are not limited to 2'-deoxyribose, 2'-$(C_1$-$C_6)$alkylribose, 2'-$(C_1$-$C_6)$ alkoxyribose, 2'-$(C_5$-$C_{14})$aryloxyribose, 2',3'-dideoxyribose, 2',3'-didehydroribose, 2'-deoxy-3'-haloribose, 2'-deoxy-3'-fluororibose, 2'-deoxy-3'-chlororibose, 2'-deoxy-3'-aminoribose, 2'-deoxy-3'-$(C_1$-$C_6)$alkylribose, 2'-deoxy-3'-$(C_1$-$C_6)$ alkoxyribose, 2'-deoxy-3'-$(C_5$-$C_{14})$aryloxyribose, 3'-$(C_1$-$C_6)$ alkylribose-5'-triphosphate, 2'-deoxy-3-'-$(C_1$-$C_6)$ alkylribose-5'-triphosphate, 2'-deoxy-3'-$(C_1$-$C_6)$ alkoxyribose-5'-triphosphate, 2'-deoxy-3'-$(C_5$-$C_{14})$ aryloxyribose-5'-triphosphate, 2'-deoxy-3'-haloribose-5'-triphosphate, 2'-deoxy-3'-aminoribose-5'-triphosphate, 2',3'-dideoxyribose-5'-triphosphate or 2',3'-didehydroribose-5'-triphosphate. Further sugar analogs also include so called locked nucleic acids (LNAs) having the structure

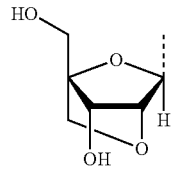

and those described in Wengel et al., WO 99/14226.

As used herein, the terms "polynucleotide", "oligonucleotide" and "nucleic acid' are used interchangeably and refer to single stranded and double stranded polymers of nucleotide monomers, including ribonucleotides (RNA) and 2'-deoxyribonucleotides (DNA) linked by internucleotide phosphodiester bond linkages. A polynucleotide may be composed entirely of deoxyribonucleotides, entirely of ribonucleotides or chimeric mixtures thereof.

As used herein, the term "terminator" means an enzymatically incorporatable nucleotide which prevents subsequent incorporation of nucleotides to the resulting polynucleotide chain and thereby halts polymerase-mediated extension. Typical terminators lack a 3'-hydroxyl substituent and include 2',3'-dideoxyribose, 2',3'-didehydroribose, and 2',3'-dideoxy-3'-haloribose, e.g. 3'-deoxy-3'-fluoro-ribose or 2',3'-dideoxy-3'-fluororibose, for example. Alternatively, a ribofuranose analog can be used, such as 2',3'-dideoxy-β-D-ribofuranosyl, β-D-arabinofuranosyl, 3'-deoxy-β-D-arabinofuranosyl, 3'-amino-2',3'-dideoxy-β-D-ribofuranosyl, and 2',3'-dideoxy-3'-fluoro-β-D-ribofuranosyl (see, for example, Chidgeavadze et al., *Nucleic Acids Res.*, 12:1671-1686 (1984), and Chidgeavadze et al., *FEB. Lett.*, 183:275-278 (1985)). Nucleotide terminators also include reversible nucleotide terminators (Metzker et al., *Nucleic Acids Res.*, 22(20):4259 (1994)).

As used herein, the term "TBDMS" refers to tert-butyldimethylsilyl.

As used herein the term "RNA delivery agent refers to one or more compounds (e.g., lipids, peptides and the like), that facilitate uptake of RNA molecules, such as the capped RNA molecules described herein, by a cell (in vitro or in vivo). Non-limiting examples of RNA delivery agents include cationic lipids and cell-penetrating peptides, optionally in combination with one or more neutral lipids, one or more PEG lipids, or any combination thereof.

Exemplary cationic lipids useful in the embodiments disclosed herein include, but are not limited to, 2,3-dioleyloxy-N-[2(sperminecarboxamido) ethyl]-N,N-dimethyl-1-propanaminium trifluoroacetate (DOSPA), 1,3-dioleoyloxy-2-(6-carboxy-spermyl) propylamide (DOSPER), dioctadecylamido-glycylspermine (DOGS), tetramethyltetrapalmitylspermine (TMTPS), tetramethyltetrapalmitoylspermin (TMTOS), tetramethyltetralauryl spermine (TMTLS), tetramethyltetramyristyl spermine (TMTMS), tetramethyldioleylspermine (TMDOS), N-1-dimethyl-N-1-(2,3-diaoleoyloxypropyl)-2-hydroxypropane-1,3-diamine, N-1-dimethyl-N-1-(2,3-diamyristyloxypropyl)-2-hydroxypropane-1,3-diamine, N-1-dimethyl-N-1-(2,3-diapalmityloxypropyl)-2-hydroxypropane-1,3-diamine, N-1-dimethyl-N-1-(2,3-diaoleoyloxypropyl)-2-(3-amino-2-hydroxypropyloxy)propane-1,3-diamine, N-1-dimethyl-N-1-(2,3-diamyristyloxypropyl)-2-(3-amino-2-hydroxypropyloxy)propane-1,3-diamine, N-1-dimethyl-N-1-(2,3-diapalmityloxypropyl)-2-(3-amino-2-hydroxypropyloxy)propane-1,3-diamine, L-spermine-5-carboxyl-3-(DL-1,2-dipalmitoyl-dimethylaminopropyl-β-hydroxyethylamine, 3,5-(N,N-di-lysyl)-diaminobenzoyl-glycyl-3-(DL-1,2-dipalmitoyl-dimethylaminopropyl-p-hydroxyethylamine), L-Lysine-bis(O,O'-oleoyl-p-hydroxyethyl)amide dihydrochloride, L-Lysine-bis-(O,O'-palmitoyl-p-hydroxyethyl)amide dihydrochloride, 1,4-bis[(3-(3-aminopropyl)-alkylamino)-2-hydroxypropyl]piperazine, L-Lysine-bis-(O,O'-myristoyl-β-hydroxyethyl)amide dihydrochloride, L-Ornithine-bis-(O,O'-myristoyl-p-hydroxyethyl)amide dihydrochloride, L-Ornithine-bis-(O,O'-oleoyl-p-hydroxyethyl)amide dihydrochloride, 1,4-bis[(3-(3-aminopropyl)-oleylamino)-2-hydroxypropyl]piperazine, L-Ornithine-bis-(O,O'-palmitoyl-p-hydroxyethyl)amide dihydrochloride, 1,4,-bis[(3-amino-2-hydroxypropyl)-oleylamino]-butane-2,3-diol, 1,4,-bis[(3-amino-2-hydroxypropyl)-palmitylamino]-butane-2,3-diol, 1,4,-bis[(3-amino-2-hydroxypropyl)-myristylamino]-butane-2,3-diol, 1,4-bis[(3-oleylamino)propyl]piperazine, L-Arginine-bis-(O,O'-oleoyl-p-hydroxyethyl)amide dihydrochloride, bis[(3-(3-aminopropyl)-myristylamino)2-hydroxypropyl]piperazine, L-Arginine-bis-(O,O'-palmitoyl-p-hydroxyethyl)amide dihydrochloride, L-Serine-bis-(O,O'-oleoyl-β-hydroxyethyl)amide dihydrochloride, 1,4-bis[(3-(3-aminopropyl)-palmitylamino)-2-hydroxypropyl]piperazine, Glycine-bis-(O,O'-palmitoyl-p-hydroxyethyl)amide dihydrochloride, Sarcosine-bis-(O,O'-palmitoyl-p-hydroxyethyl)amide dihydrochloride, L-Histidine-bis-(O,O'-palmitoyl-p-hydroxyethyl)amide dihydrochloride, cholesteryl-3ß-carboxyl-amidoethylenetrimethylammonium iodide, 1,4-bis[(3-myristylamino)propyl]piperazine, 1-dimethylamino-3-trimethylammonio-DL-2-propyl-cholesteryl carboxylate iodide, cholesteryl-3ß-carboxyamidoethyleneamine, cholesteryl-3ß-oxysuccinamidoethylenetrimethylammonium iodide, 1-dimethylamino-3-trimethylammonio-DL-2-propyl-cholesteryl-3ß-oxysuccinate iodide, 2-[(2-trimethylammonio)-ethylmethylamino]ethyl-cholesteryl-3ß-oxysuccinate iodide, 3ß[N—(N',N'-dimethylaminoethane)carbamoyl]cholesterol, and 3ß-[N-(polyethyleneimine)-carbamoyl]cholesterol, 1,4-bis[(3-palmitylamino)propyl]piperazine, L-Ornithylglycyl-N-(1-heptadecyloctadecyl)glycinamide, N²,N⁵-Bis(3-aminopropyl)-L-ornithylglycyl-N-(1-heptadecyloctadecyl)glycinamide, 1,4-bis[(3-(3-amino-2-hydroxypropyl)-alkylamino)-2-hydroxypropyl]piperazine N²—[N²,N⁵-Bis(3-aminopropyl)-L-ornithyl]-N,N-dioctadecyl-L-glutamine, N²—[N²,N⁵-Bis(aminopropyl)-L-ornithyl]-N—N-dioctadecyl-L-α-glutamine, 1,4-bis[(3-(3-amino-2-hydroxypropyl)-oleylamino)2-hydroxypropyl]piperazine, N²—[N²,N⁵-Bis(aminopropyl)-L-ornithyl]-N—N-dioctadecyl-L-α-asparagine, N—[N²—[N²,N⁵-Bis[(1,1-dimethylethoxy)carbonyl]-N²,N⁵-bis[3-[(1,1-dimethylethoxy)carbonyl]aminopropyl]-L-ornithyl-N—N-dioctadecyl-L-glutaminyl]-L-glutamic acid, N²—[N²,N⁵-Bis(3-aminopropyl)-L-ornithyl]-N,N-diolyl-L-glutamine, N²—[N²,N⁵-Bis(aminopropyl)-L-ornithyl]-N—N-dioleyl-L-α-glutamine, 4-bis[(3-(3-amino-2-hydroxypropyl)-myristylamino)-2-hydroxypropyl]piperazine, N²—[N²,N⁵-Bis(aminopropyl)-L-ornithyl]-N—N-dioleyl-L-α-asparagine, N—[N²—N⁵-Bis[(1,1-dimethylethoxy)carbonyl]-N²,N⁵-bis[3-[(1,1-dimethylethoxy)carbonyl]aminopropyl]-L-ornithyl-N—N-dioleyl-L-glutaminyl]-L-glutamic acid, 1,4-bis[(3-(3-aminopropyl)-oleylamino)propyl]piperazine, N²—[N²,N⁵-Bis(3-aminopropyl)-L-ornithyl]-N,N-dipalmityl-L-glutamine, N²—[N²,N⁵-Bis(aminopropyl)-L-ornithyl]-N-dipalmityl-L-α-glutamine, N²—[N²,N⁵-Bis(aminopropyl)-L-ornithyl]-N—N-dipalmityl-L-α-asparagine, N—[N²—[N²,N⁵-Bis[(1,1-dimethylethoxy)carbonyl]-N²,N⁵-bis[3-[(1,1-dimethylethoxy)carbonyl]aminopropyl]-L-ornithyl-N—N-dipalmityl-L-glutaminyl]-L-glutamic acid, N²—[N²,N⁵-Bis(3-aminopropyl)-L-ornithyl]-N,N-dimyristyl-L-glutamine, N²—[N²,N⁵-Bis(aminopropyl)-L-ornithyl]-N—N-dimyristyl-L-α-glutamine, N²—[N²,N⁵-Bis(aminopropyl)-L-ornithyl]-N—N-dimyristyl-L-α-asparagine, 1,4-bis[(3-(3-amino-2-hydroxypropyl)-palmitylamino)-2-hydroxypropyl]piperazine, N—[N²—[N²,N⁵-Bis[(1,1-dimethylethoxy)carbonyl]-N²,N⁵-bis[3-[(1,1-dimethylethoxy)carbonyl]aminopropyl]-L-ornithyl-N—N-dimyristyl-L-glutaminyl]-L-glutamic acid, 1,4-bis[(3-(3-aminopropyl)-myristylamino)propyl]piperazine, N²—[N²,N⁵-Bis(3-aminopropyl)-L-ornithyl]-N,N-dilaureyl-L-glutamine, N²-8 N²,N⁵-Bis(aminopropyl)-L-ornithyl]-N—N-dilaureyl-L-α-glutamine, N²—[N²,N⁵-Bis(aminopropyl)-L-ornithyl]-N—N-dilaureyl-L-α-asparagine, N—[N²—[N²,N⁵-Bis[(1,1-dimethylethoxy)carbonyl]-N²,N⁵-bis[3-[(1,1-dimethylethoxy)carbonyl]aminopropyl]-L-ornithyl-N-dilaureyl-L-glutaminyl]-L-glutamic acid, 3-[N',N"-bis(2-tertbutyloxycarbonylaminoethyl)guanidino]-N,N-dioctadec-9-enylpropionamide, 3-[N',N"-bis(2-tertbutyloxycarbonylaminoethyl)guanidino]-N,N-dipalmitylpropionamide, 3-[N',N"-bis(2-tertbutyloxycarbonylaminoethyl)guanidino]-N,N-dimyristylpropionamide, 1,4-bis[(3-(3-aminopropyl)-palmitylamino)propyl]piperazine, 1,4-bis[(3-(3-amino-2-hydroxypropyl)-oleylamino)propyl]piperazine, N,N-(2-hydroxy-3-aminopropyl)-N-2-hydroxypropyl-3-N,N-diolylaminopropane, N,N-(2-hydroxy-3-aminopropyl)-N-2-hydroxypropyl-3-N,N-dipalmitylaminopropane, N,N-(2-hydroxy-3-aminopropyl)-N-2-hydroxypropyl-3-N,N-dimyristylaminopropane, 1,4-bis[(3-(3-amino-2-hydroxypropyl)-myristylamino)propyl]piperazine, [(3-aminopropyl)-bis-(2-tetradecyloxyethyl)]methyl ammonium bromide, [(3-aminopropyl)-bis-(2-oleyloxyethyl)]methyl ammonium bromide, [(3-aminopropyl)-bis-(2-palmityloxyethyl)]methyl ammonium bromide, Oleoyl-2-hydroxy-3-N,N-dimethyamino propane, 2-didecanoyl-1-N,N-dimethylaminopropane, palmitoyl-2-hydroxy-3-N,N-dimethyamino propane, 1,2-dipalmitoyl-1-N,N-dimethylaminopropane, myristoyl-2-hydroxy-3-N,N-dimethyamino propane, 1,2-dimyristoyl-1-N,N-dimethylaminopropane, (3-Amino-propyl)→4-(3-aminopropylamino)-4-tetradecylcarbamoyl-butylcarbamic acid cholstryl ester, (3-Amino-propyl)→4-(3-amino-propylamino-4-carbamoylbutylcarbamic acid cholstryl ester, (3-Amino-propyl)→4-(3-amino-propylamino)-4-(2-dimethylamino-ethylcarbamoyl)-butylcarbamic acid cholstryl ester, Spermine-5-carboxyglycine (N'-stearyl-N'oleyl) amide tetratrifluoroacetic acid salt, Spermine-5-carboxyglycine (N'-stearyl-N'-elaidyl) amide tetratrifluoroacetic acid salt, Agmatinyl carboxycholesterol acetic acid salt, Spermine-5-carboxy-β-alanine cholesteryl ester tetratrifluoroacetic acid salt, 2,6-Diaminohexanoeyl β-alanine cholesteryl ester bistrifluoroacetic acid salt, 2,4-Diaminobutyroyl β-alanine cholesteryl ester bistrifluoroacetic acid salt, N,N-Bis (3-aminopropyl)-3-aminopropionyl β-alanine cholesteryl ester tristrifluoroacetic acid salt, [N,N-Bis(2-hydroxyethyl)-

2-aminoethyl]aminocarboxy cholesteryl ester, Stearyl carnitine ester, Palmityl carnitine ester, Myristyl carnitine ester, Stearyl stearoyl carnitine ester chloride salt, L-Stearyl Stearoyl Carnitine Ester, Stearyl oleoyl carnitine ester chloride, Palmityl palmitoyl carnitine ester chloride, Myristyl myristoyl carnitine ester chloride, L-Myristyl myristoyl carnitine ester chloride, 1,4-bis[(3-(3-amino-2-hydroxypropyl)-palmitylamino)propyl]piperazine, N-(3-aminopropyl)-N,N'-bis-(dodecyloxyethyl)-piperazinium bromide, N-(3-aminopropyl)-N,N'-bis-(oleyloxyethyl)-piperazinium bromide, N-(3-aminopropyl)-N,N'-bis-(palmityloxyethyl)-piperazinium bromide, N-(3-aminopropyl)-N,N'-bis-(myristyloxyethyl)-piperazinium bromide, N-(3-aminopropyl)-N'-methyl-N,N'-(bis-2-dodecyloxyethyl)-piperazinium bromide, N-(3-aminopropyl)-N'-methyl-N,N'-(bis-2-oleyloxyethyl)-piperazinium bromide, N-(3-aminopropyl)-N'-methyl-N,N'-(bis-2-palmityloxyethyl)-piperazinium bromide, N-(3-aminopropyl)-N'-methyl-N,N'-(bis-2-myristyloxyethyl)-piperazinium bromide, Phospholipids useful in the compositions and methods may be selected from the non-limiting group consisting of 1,2-distearoyl-sn-glycero-3-phosphocholine (DSPC), 1,2-dioleoyl-sn-glycero-3-phosphoethanolamine (DOPE), 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), dipalmitoylphosphatidylglycerol (DPPG), palmitoyloleoylphosphatidylethanolamine (POPE), distearoyl-phosphatidyl-ethanolamine (DSPE), dipalmitoyl phosphatidyl ethanolamine (DPPE), dimyristoylphosphoethanolamine (DMPE), 1-stearoyl-2-oleoyl-phosphatidyethanolamine (SOPE), 1-stearoyl-2-oleoyl-phosphatidylcholine (SOPC), sphingomyelin, phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine (LPE),

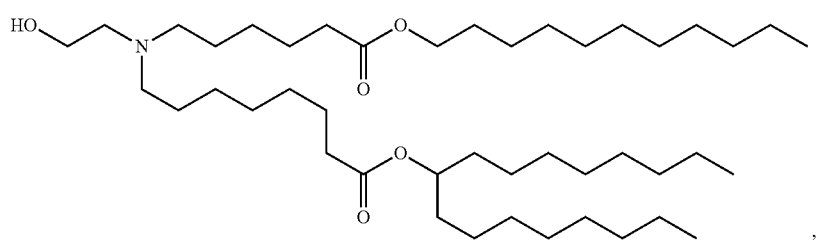

Compound 1

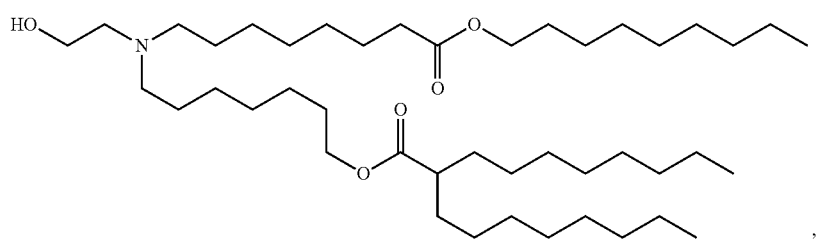

Compound 2

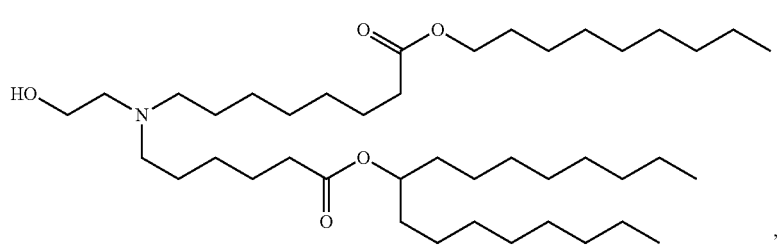

Compound 3

-continued
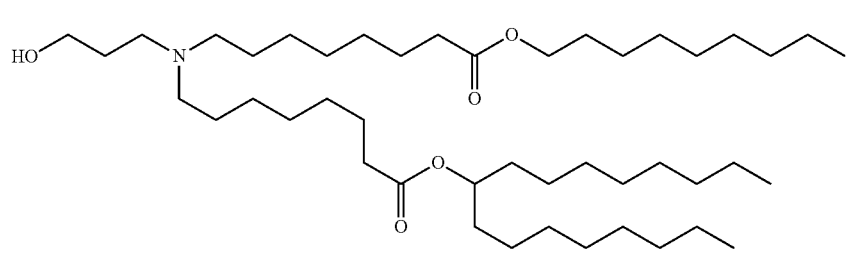
Compound 4
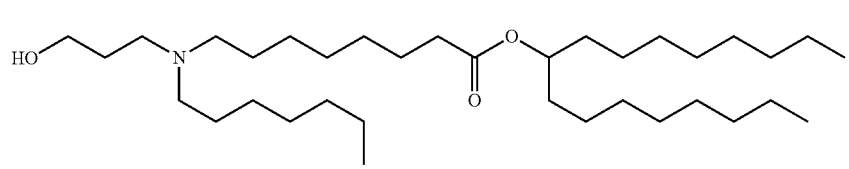
Compound 5
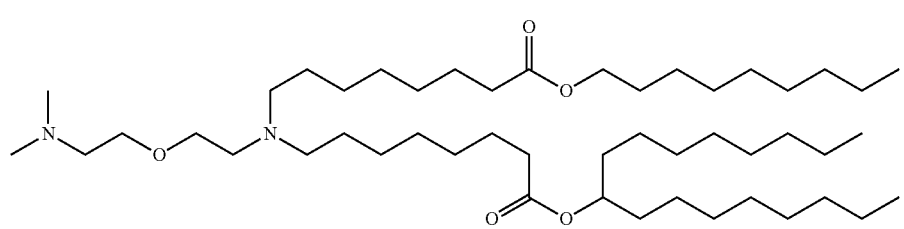
Compound 6
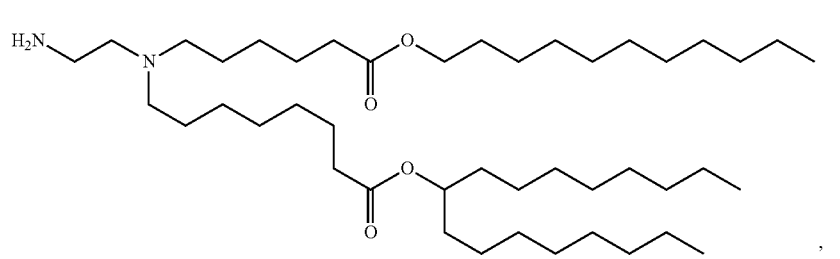
Compound 7
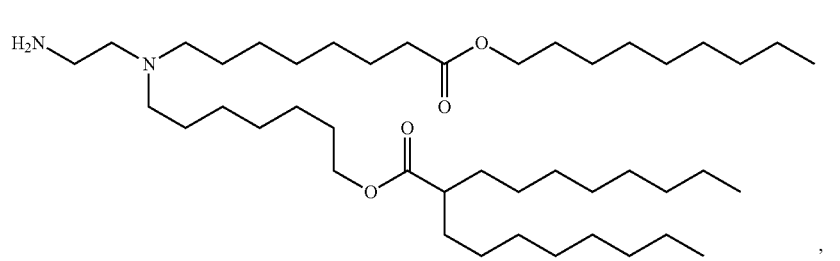
Compound 8
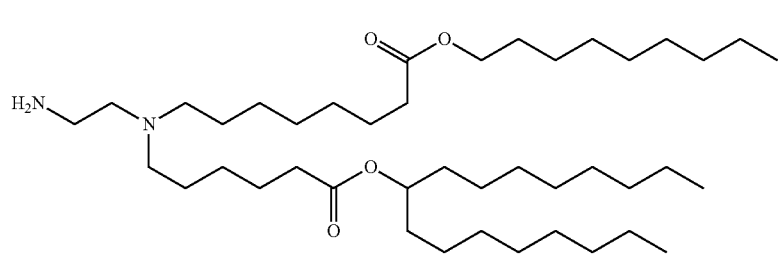
Compound 9
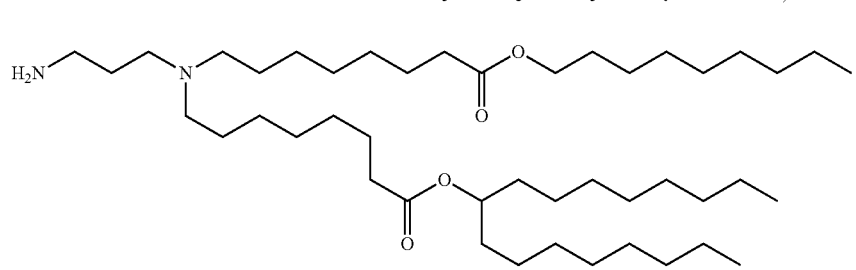
Compound 10

Compound 11
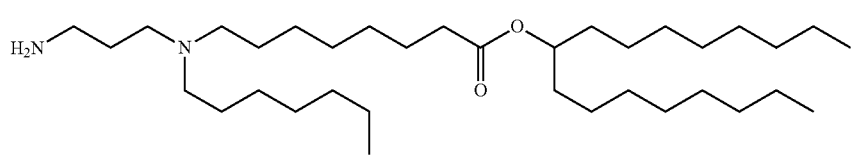,

Compound 12
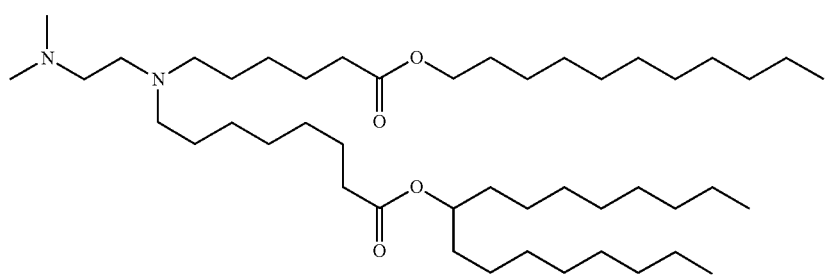,

Compound 13
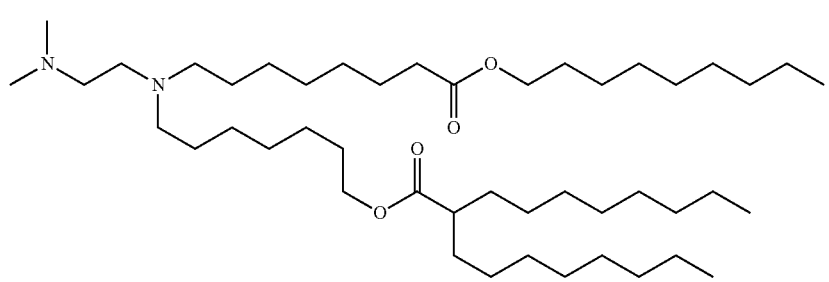,

Compound 14
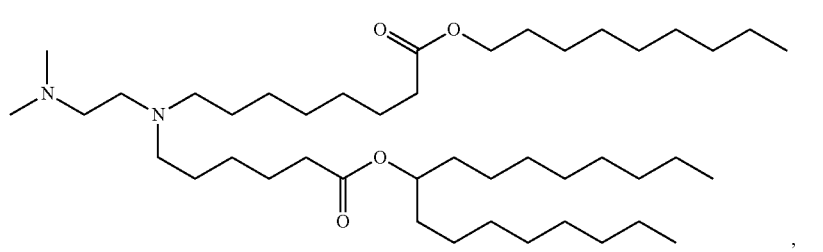,

Compound 15
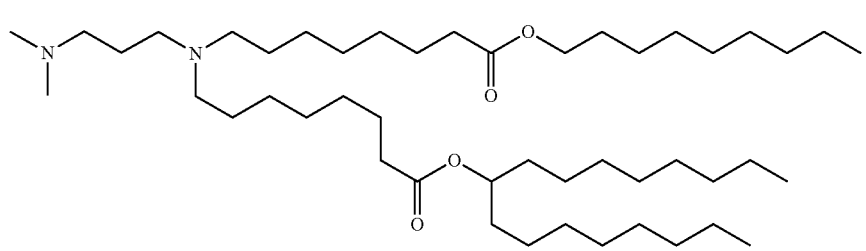, and

Compound 16
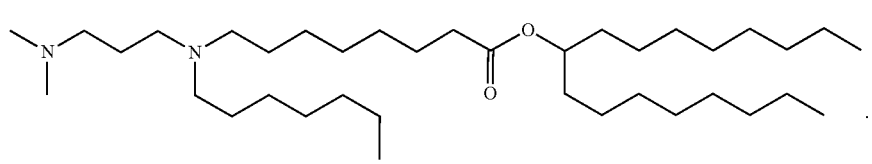.

In some embodiments, an RNA delivery agent as described herein can include one or more neutral, or uncharged lipids. Neutral lipids useful in the embodiments described herein include, for example cholesterol, dioleoylphosphatidylethanolamine (DOPE), Dioleoylphosphatidylcholine (DOPC), and diphytanoylphosphatidylethanolamine (DDhPE) fecosterol, sitosterol, ergosterol, campesterol, stigmasterol, brassicasterol, tomatidine, tomatine, ursolic acid, alpha-tocopherol, or combinations thereof.

RNA delivery agent as described herein can include one or more agents that inhibit aggregation of lipid/RNA particles. An exemplary agent that inhibits aggregation of lipid/RNA particles includes PEG lipids, or PEGylated lipids, or polyglyceral lipids, e.g., as described in Fiedl, et al. (2020) Nanomedicine 15(19), 1829-1841.

RNA delivery agent as described herein can include one or more PEG lipids. As used herein, a "PEG lipid" or "PEGylated lipid" refers to a lipid comprising a polyethylene glycol component. A PEG lipid may be selected from the non-limiting group consisting of PEG-modified phosphatidylethanolamines, PEG-modified phosphatidic acids, PEG-modified ceramides (PEG-CER), PEG-modified dialkylamines, PEG-modified diacylglycerols (PEG-DEG), PEG-modified dialkylglycerols, and mixtures thereof. For example, a PEG lipid may be PEG-c-DOMG, PEG-DMG, PEG-DLPE, PEG-DMPE, PEG-DPPC, or a PEG-DSPE lipid.

The RNA can be transfected into a cell to be translated intracellularly. Methods of transfection are known to those of skill in the art and include microinjection, electroporation, transfection, chemical treatments and the like. In some aspects, the RNA compositions provided herein are delivered to cells in vitro. In some aspects, the RNA compositions provided herein can be used for ex vivo delivery of mRNA to cells. In other aspects, the RNA compositions provided herein can be used for in vivo delivery of mRNA to cells, e.g., in the context of mRNA vaccines or the like. Cells for use in in vivo translation include any patient cell for which it is desired to express a protein of interest. Non-limiting examples of cells useful in the embodiments disclosed herein include immune cells (e.g., T cells, B cells, NK cells, dendritic cells, macrophages, etc.), liver cells, lung cells, pancreatic cells, bone marrow cells, tissue culture cells, germ cells, stem cells such as induced pluripotent stem cells (iPSCs), human embryonic stem cells (hESCs), mesenchymal stem cells (MSCs), adipose-derived stem cells (ADSCs), and the like.

Dyes that are suitable for use are known to those skilled in the art and include, but are not limited to coumarin, cyanine, benzofuran, a quinoline, a quinazolinone, an indole, a benzazole, a borapolyazaindacene and xanthenes including fluorescein, rhodamine and rhodol as well as other dyes described in RICHARD P. HAUGLAND, MOLECULAR PROBES HANDBOOK OF FLUORESCENT PROBES AND RESEARCH CHEMICALS (11$^{th}$ edition, January 2010.

Fluorescent dyes used herein include, without limitation; a pyrene (including any of the corresponding derivative compounds disclosed in U.S. Pat. Nos. 5,132,432 and 8,039, 642), an anthracene, a naphthalene, an acridine, a stilbene, an indole or benzindole, an oxazole or benzoxazole, a thiazole or benzothiazole, a 4-amino-7-nitrobenz-2-oxa-1, 3-diazole (NBD), a cyanine (including any corresponding compounds in U.S. Pat. Nos. 6,977,305; 6,974,873; 6,664, 047; 4,981,977; 5,268,486; 5,569,587; 5,569,766; 5,486, 616; 5,627,027; 5,808,044; 5,877,310; 6,002,003; 6,004, 536; 6,008,373; 6,043,025; 6,127,134; 6,130,094; 6,133, 445, 7,446,202; 7,598,390; 7,776,529; PCT International Publication Nos. WO 02/26891, WO 97/40104, WO 99/51702, WO 01/21624, WO 2018/085449; and European Patent Application Publication No. 1 065 250 A1), a benzocyanine (including any corresponding compounds in U.S. Pat. Nos. 9,249,307; 9,751,868; 10,000,467; 10,053,447; 10,125,120; 10,351,551; 10,526,317; and US2017/0158858); a carbostyryl, a porphyrin, a salicylate, an anthranilate, an azulene, a perylene, a pyridine, a quinoline, a borapolyazaindacene (including any corresponding compounds disclosed in U.S. Pat. Nos. 4,774,339; 5,187,288; 5,248,782; 5,274,113; and 5,433,896), a xanthene (including any corresponding compounds disclosed in U.S. Pat. Nos. 6,162,931; 6,130,101; 6,229,055; 6,339,392; 5,451,343 and 6,716,979), an oxazine (including any corresponding compounds disclosed in U.S. Pat. No. 4,714,763) or a benzoxazine, a carbazine (including any corresponding compounds disclosed in U.S. Pat. No. 4,810,636), a phenalenone, a coumarin (including an corresponding compounds disclosed in U.S. Pat. Nos. 5,696,157; 5,459,276; 5,501,980 and 5,830,912), a benzofuran (including an corresponding compounds disclosed in U.S. Pat. Nos. 4,603, 209 and 4,849,362) and benzphenalenone (including any corresponding compounds disclosed in U.S. Pat. No. 4,812, 409) and derivatives thereof. As used herein, oxazines include resorufins (including any corresponding compounds disclosed in U.S. Pat. No. 5,242,805), aminooxazinones, diaminooxazines, and their benzo-substituted analogs.

When the dye is a xanthene, the dye is optionally a fluorescein, a rhodol (including any corresponding compounds disclosed in U.S. Pat. Nos. 5,227,487 and 5,442, 045), or a rhodamine (including any corresponding compounds in U.S. Pat. Nos. 5,798,276; 5,846,737; 6,562,632; 7,256,292; 7,985,602; 8,729,267; 9,040,674; 9,315,859; 9,745,336; 9,783,560; 9,790,544; 10,131,936).

Typically the fluorescent dye contains one or more aromatic or heteroaromatic rings, that are optionally substituted one or more times by a variety of substituents, including without limitation, halogen, nitro, cyano, alkyl, perfluoroalkyl, alkoxy, alkenyl, alkynyl, cycloalkyl, arylalkyl, acyl, aryl or heteroaryl ring system, benzo, or other substituents typically present on fluorescent dyes known in the art.

Caps/Cap Analogs and Promoters

Provided herein are compositions and methods in which (1) RNA caps and cap analogs and (2) promoters function to result in the production of capped RNA, such as messenger RNA (mRNA). In some instances, these compositions and methods relate to mRNA caps or cap analogs that interact with specific promoters (e.g., modified naturally occurring promoters) in manner that allows for the production of capped RNA.

In some instances, compositions and methods provided herein will be designed interact in a manner that result in the high yield production of mRNA with high capping efficiency. As used herein, high yield production of mRNA refers to 3 mg/ml (60 μg/20 μl) or higher of RNA. As used herein, RNA capping efficiency refers to the percentage of RNA present in a composition that contains caps. By way of example, if an uncapped population of RNA molecules is subjected to a process by which caps or cap analogs are added to these molecules, capping efficiency would be determined by the percentage of RNA molecules in the resulting composition containing caps. Similarly, when capped mRNA is formed by transcription, capping efficiency would also be determined the percentage of RNA molecule in the resulting composition containing caps. High capping efficiency refer to the production of RNA population where the percentage of the capped RNA molecules (e.g., target RNA molecules) compared to uncapped RNA molecules (e.g., target RNA molecules) is greater than or equal to 70% (e.g., from about 75% to about 99%, from about 80% to about 99%, from about 85% to about 99%, from about 90% to about 99%, from about 95% to about 99%, from about 75% to about 95%, from about 75% to about 90%, from about 80% to about 95%, from about 85% to about 95%, from about 75% to about 100%, from about 80% to about 100%, from about 90% to about 100%, from about 95% to about 100%, etc.). The term "target RNA molecules" refers to RNA molecules which are the desired subject of capping processes. By way of example, if a coupled transcription/translation system is used, then ribosomal RNA molecules present for translation would not be considered to "target RNA molecules". Said another way, capping efficiency relates to the RNA molecule that are intended for capping (e.g., RNA molecules coding for specific proteins) and does not include other RNA molecules in a reaction mixture.

Figure 15:
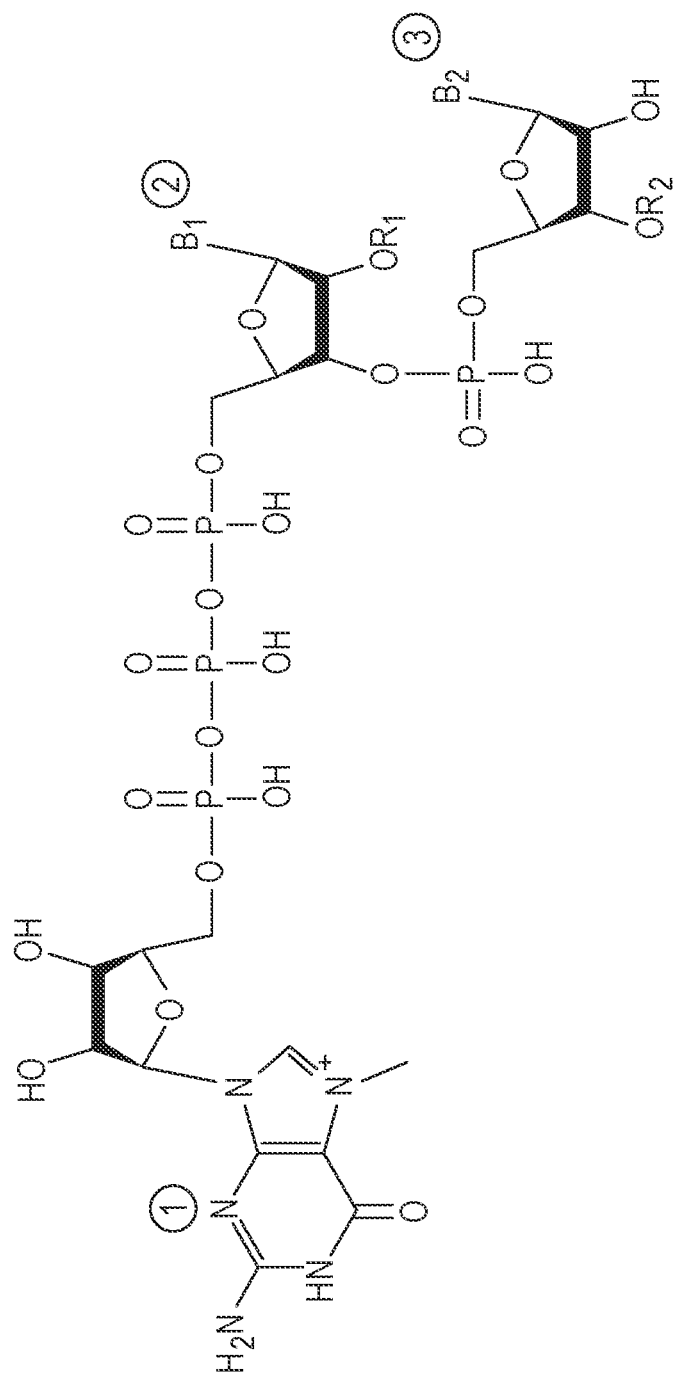
FIG. 15 shows the general structure of an exemplary 7-methylguanosine trinucleotide cap structure, including Cap 0 ($R_1$=H) and Cap 1 ($R_1$=CH$_3$) types. $B_1$ and $B_2$ are bases that may be the same or different. $R_2$ represents one or more additional nucleosides linked by an intervening phosphate.

FIG. 15 shows the structure of an exemplary 7-methylguanosine trinucleotide cap analog, that in many instances set out here may function as a capped primer. This cap analog schematic indicates where the bases can be located at $B_1$ and $B_2$. The three bases of this cap analog are labeled with the numbers 1, 2 and 3 in circles. Of course, any number of cap analog variations may be present in compositions and used in methods set out herein.

Caps and cap analogs may vary substantially in terms of nucleotide sequences. Using the cap analog structure set out in FIG. 15 for purposes of illustration, the first bases, labeled with circled number 1, will generally be G. The other two bases, labeled with circled numbers 2 and 3, will generally be complementary to one or more bases at initiations sites of nucleic acid molecules in reaction mixture for which transcription is desired. Further, the initiation site may vary from the positions marked off as such in FIG. 16.

Figure 19:
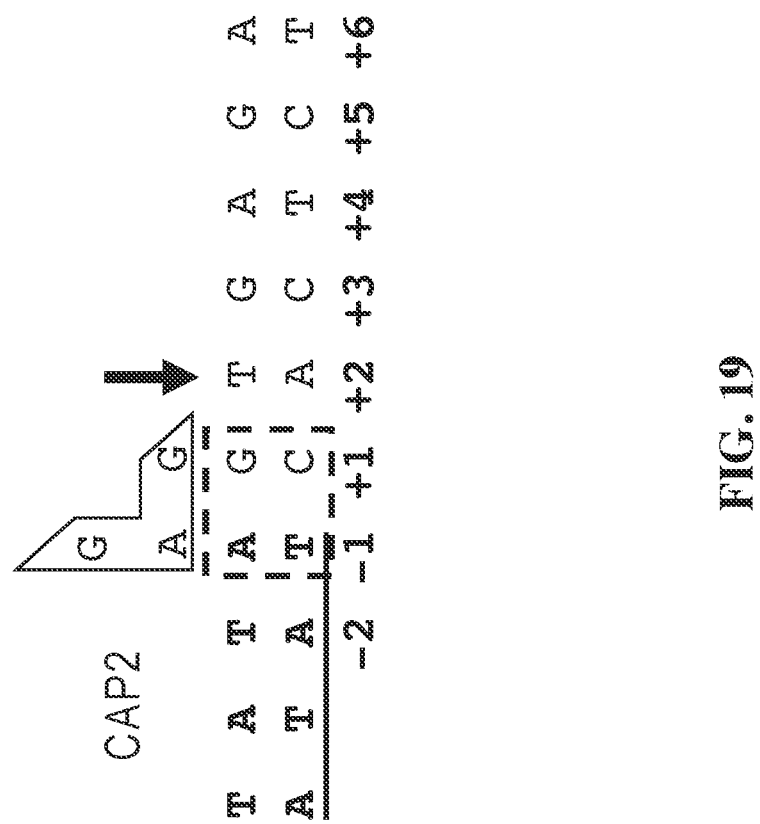
FIG. 19 is also a schematic representation that is similar to that of FIG. 17. This figure shows CAP2 associated with the −1 to +1 positions of an initiation region (see dashed line box). Further, the base pair at position +2 of the of the non-template strand is thymine (see downward arrow) with adenine being present in the template strand (not shown).

The nucleotide sequence of one exemplary capped primer is shown in FIG. 19 as GAG. This AG portion of this capped primer (cap analog positions 2 and 3) are complementary to positions −1 and +1 of the initiation region of the template strand shown. In this instance, positions −1 and +1 of the initiation regions are referred to herein as the initiation site. Exemplary capped primer nucleotide sequences and initiation sites they are complementary to are set out in Table 3.

TABLE 3

Exemplary Cap/Initiation Site Specifications

| No. | Capped Primer Sequence | Capped Primer Type | Initiation Site | Promoter Positions (FIG. 16) | |
|---|---|---|---|---|---|
| 1 | GAG | Trimer | TC | −1 to +1 | +2 to +3 |
| 2 | GAU | Trimer | TA | −1 to +1 | +2 to +3 |
| 3 | GAGG | Tetramer | TCC | −1 to +2 | +2 to +4 |
| 4 | GAGGG | Pentamer | TCCC | −1 to +3 | +2 to +5 |
| 5 | GAGGGU | Hexamer | TCCCA | −1 to +4 | +2 to +6 |
| 6 | GGG | Trimer | CC | +1 to +2 | +2 to +3 |
| 7 | GGGG | Tetramer | CCC | +1 to +3 | +2 to +5 |
| 8 | GAA | Trimer | TT | −1 to +1 | +2 to +3 |
| 9 | GGA | Trimer | CT | −1 to +1 | +2 to +3 |

RNA caps and cap analogs that may be contained in compositions and used in methods set out herein include those set out herein and specifically include commercially available trimer caps and cap analogs, such as those sold by TriLink Biotechnologies (San Diego, CA) (e.g., CLEANCAP® Reagent GG, cat. no. N-7133; CLEANCAP® Reagent AU, cat. no. N-7114; CLEANCAP® Reagent GG (3' OMe), cat. no. N-7433; CLEANCAP® Reagent AG (3' OMe), cat. no. N-7413; and CLEANCAP® Reagent AG, cat. no. N-7113).

As shown in Table 3, capped primers containing more than three nucleotides may be used in the practice of subject matter set out herein. Such caps and cap analogs may contain from about three to about twenty bases (e.g., from about three to about nineteen, from about three to about eighteen, from about three to about fifteen, from about three to about twelve, from about three to about ten, from about three to about eight, from about three to about six, from about three to about four, from about four to about ten, from about four to about eight, etc.). Further, such caps and cap analogs may have sequence complementarity to the template strand of a promoter initiation site.

FIG. 16 shows a comparison of four bacteriophage promoters of T7, T3, SP6 and K11 phages. Each of the bacteriophage promoters shown in FIG. 16 are 19 nucleotides in length and include a ten nucleotide initiation region at positions −4 to +6. Nucleotides +1 to +6 are referred to herein as the transcription start region, with initiation typically beginning at position +1. In bacteriophage promoters, the +1 position is conserved as a G and positions +2 to +5 are conserved as purines (A and G). Thus, pyrimidines (T and C) are typically not found at these positions. Further, FIG. 16 shows only purine bases present from positions −1 to +5. Also the only promoter shown to contain a purine (i.e., C) at position +6 is the K11 promoter.

Promoter positions −5 to −12 interact with a T7 RNA polymerase structural domain located near the carboxyl terminus of the protein. The AT rich region (positions −17 to −13) is believed to interact with a T7 RNAP structural domain located near the amino terminus of the protein.

FIG. 17 shows three different caps designed to have sequence complementarity at or near the transcriptional initiation region. CAP1 is a dinucleotide cap with sequence complementarity to the +1 position of the transcriptional initiation region. CAP2 is a trinucleotide cap with sequence complementarity to the −1 and +1 positions of the transcriptional initiation region. CAP3 is a trinucleotide cap with sequence complementarity to the +1 and +2 positions of the transcriptional initiation region.

Ishikawa et al., "Preparation of eukaryotic mRNA having differently methylated adenosine at the 5'-terminus and the effect of the methyl group in translation", *Nucleic Acids Symposium Series No.* 53, pages 129130 Oxford University Press (2009), performed a study using several different mRNA cap similar to CAP2 shown in FIG. 17 and showed that these caps could initiate transcription on template with 2'-deoxycytidine residues at template positions +1 and +2 ("CC" template; Nucleic Acids Symposium Series No. 53: 129 (2009)). The authors state, "The different result from the case of using $^{m7}$G5'pppG may be caused from base pairing between additional adenosine (N1) in $^{m7}$G5'pppN1pG and 2'-deoxythymidine in T7 promoter at −1 position."

Figure 18:
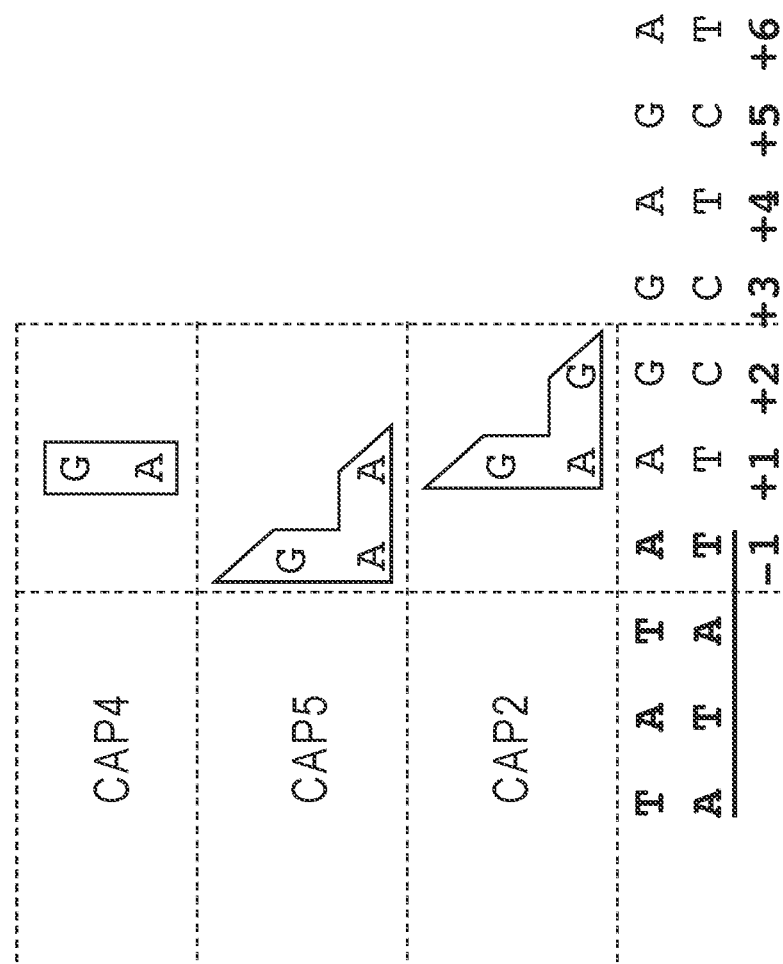
FIG. 18 is a schematic representation similar to that of FIG. 17 with the following differences. CAP4 is a dinucleotide cap in which the first bases is guanine and the second base is adenine. CAP5 is a trinucleotide cap in which the first base is guanine the following two bases are adenine. CAP2 is the same as set out in FIG. 17. Further, the base at position +1 of the non-template strand is adenine instead of guanine.

FIG. 18 is similar to FIG. 17 but the base pairs at +1 position of the initiation region have been changed from G/C to A/T. Also, the CAP4, CAP5 and CAP2 are positioned above their cognate complementary hybridization initiation sequences.

FIG. 19 is similar to FIGS. 17 and 18 but it shows only a single mRNA cap, CAP2, and above its cognate complementary hybridization initiation sequence at positions −1 and +1. Further, the initiation region is structured so that neither of the two bases of the cap that hybridized to the initiation region are complementary to the immediate flanking bases at positions −2 and +2.

A number of promoters and modified promoters may be present in compositions and used in methods provided herein. Using the schematic of FIG. 16 for reference, promoters present in compositions and used in methods provided herein may be wild-type promoters or maybe be modified in some manner. Such modifications include (1) 5' and 3' truncations and/or (2) internal substitutions and/or deletions.

When transcriptional initiation at the −1 or +1 position is desired, promoters may be designed to facilitate such initiation. For example, when a trinucleotide capped primer is used for initiation at the −1 position, then promoters having the following non-template strand nucleotide sequences may be used: TATY$_1$ Y$_2$Z. In this context, Y$_1$ is at the −1 position, Y$_2$ is at the +1 position, and Z is at position +2, which is "adjacent" to +1 end of the initiation site. By "adjacent" is meant that a base is located as the first base before and/or after the initiation site. Further, when a trinucleotide capped primer is used for initiation at the +1 position, then promoters having the following non-template nucleotide sequences may be used: TATA $Y_1Y_2Z$. In these instances, $Y_1$ and $Y_2$ are the same base as the second and third bases of the trinucleotide capped primer. Thus, the template strand would contain bases at positions corresponding to $Y_1$ and $Y_2$ that are complementary to the bases of the trinucleotide capped primer. Further, Z is transcriptional blocking nucleotide, the base of which may independently be A, T or C, as well as a chemically modified nucleotide.

By way of illustration, when a GAG primer is used for initiation at the −1 position, then suitable promoters include those comprising the following nucleotide sequences: (1) 5'-TATA GA-3', (2) 5'-TATA GT-3', and (3) 5'-TATA GC-3'.

When transcriptional initiation at the +2 position is desired, promoters may also be designed to facilitate such initiation. For example, when a trinucleotide capped primer is used for initiation, then promoters having the following non-template strand nucleotide sequences may be used: TATA $X_1Y_1Y_2X_2$, where $Y_1$ and $Y_2$ (located at positions +2 and +3) are the same as the second and third bases of the trinucleotide capped primer. Further, $X_1$ and $X_2$ are transcriptional blocking nucleotides (located at positions +1 and +4), the bases of which may independently be A, T or C, or chemically modified nucleotides. In this context, $Y_1$ is at the +2 position, $Y_2$ is at the +3 position, and $X_1$ and $X_2$ at positions +1 and +4 are said to be "adjacent" to each end of the +2/+3 initiation site. Further, in some instances, $X_1$ may be a transcriptional blocking nucleotide and $X_2$ is not a transcriptional blocking nucleotide By way of illustration, when a GAG primer is used for transcriptional initiation at the +2 position, then suitable promoters include those comprising the following nucleotide sequences: (1) 5'-TATA TAGA-3', (2) 5'-TATA TAGT-3', (3) 5'-TATA TAGC-3', (4) 5'-TATA AAGA-3', (5) 5'-TATA AAGT-3', (6) 5'-TATA CAGC-3', and (7) 5'-TATA CAGA-3'.

Provided herein are compositions, as well as methods for using such compositions, for the production of RNA in which transcriptional initiation occurs at a position other than the natural +1 transcriptional initiation position. As examples, initiation may occur at the −2/−1, −1/+1, +2/+3, −1/+1/+2, −1/+1/+2/+3, or +2/+3/+4 positions. In many instances, the bases A, T or C may be located at one or both positions adjacent to one or both termini of initiation sites. Further, other transcriptional initiation blocking nucleotides may be located at the same positions.

Also, provided herein are compositions, as well as methods for using such compositions, comprising multimeric capped primers comprising three of more nucleotides (e.g., from about three to about ten, from about three to about eight, from about three to about seven, from about three to about five, from about three to about four, from about four to about eight, etc., nucleotides) and promoters comprising transcriptional initiation sites in which the template strand is complementary to bases of the capped primers. In many instances, the capped primers will be designed to hybridize to transcriptional initiation sites located in positions other than at, or in addition to, the +1/+2 positions. In many additional instances, the bases A, T, or C will be located at one or both position adjacent to initiation sites (e.g., at position +1 and +4, when a +2/+3 initiation site is used). Further provided herein are compositions, as well as methods for using such compositions, comprising trimeric caps and promoters comprising +1/+2 transcriptional initiation sites where the base at position +3 is A, T or C.

Further provided herein are compositions, as well as methods for using such compositions, for transcriptional initiation using multimeric capped primers greater than three nucleotides in length. An exemplary tetrameric capped primers primer has the nucleotide sequence GAGG. When this capped primer is used to initiate transcription at the +1/+2+3 position, the promoter used for transcriptional initiation may comprise one of the following nucleotide sequences: (1) 5'-TATA AGGA-3', (2) 5'-TATA AGGT-3', (3) 5'-TATA AGGC-3', (4) 5'-TATA GAGGT-3', (5) 5'-TATA GAGGA-3', and (6) 5'-TATA GAGGC-3'.

In some aspects, provided herein are promoters that contain a transcriptional initiation site, flanked by transcriptional initiation blocking nucleotides. "Transcriptional initiation blocking nucleotide" are nucleotides that are not preferred for transcriptional initiation at the position they are located in. By way of example, with respect to T7 RNA polymerase promoters, the base thymine in the non-template strand may be used to increase capping efficiency when placed at position +2, proceeded by the sequence AG, and when a GAG capped primer is used for RNA capping. In this instance, thymidine at position +2 would be a transcriptional initiation blocking nucleotide.

Transcriptional initiation blocking nucleotides may be any nucleotide that is disfavored for transcriptional initiation while not significantly effecting transcriptional initiation at the desired initiation site. Transcriptional initiation blocking nucleotides function in conjunction with the promoter, capped primer, and reaction conditions being used. In some instances, transcriptional initiation blocking nucleotides may be deoxythymidine, thymidine, cytidine, adenosine, guanosine, and/or uridine. Transcriptional initiation blocking nucleotides may also be chemically modified. Further, such chemical modifications may be of the bases, the sugars, the phosphate linkages, or a combination of these.

The use of transcriptional initiation blocking nucleotides may increase capping efficiency by at least 20% (e.g., from about 20% to about 200%, from about 20% to about 180%, from about 20% to about 150%, from about 20% to about 120%, from about 20% to about 100%, from about 20% to about 80%, from about 20% to about 60%, from about 20% to about 40%, from about 30% to about 100%, from about 40% to about 90%, from about 50% to about 150%, from about 30% to about 60%, etc.). One exemplary assay for measuring increased capping efficiency is by comparing the capping efficiency under two different conditions. Under these exemplary conditions a GAG capped primer is used to produce capped mRNA with two different promoters. The non-template strand of one promoter comprises the nucleotide sequence TATA AGG and the other promoter comprises the nucleotide sequence TATA AGT, the difference being the presence of T at the +2 position.

Transcriptional initiation blocking nucleotides may be used in a number of different ways. Along these lines, the position and number of transcriptional initiation blocking nucleotides may vary. For example, more than one (e.g., one, two, three, etc.) transcriptional initiation blocking nucleotide may be adjacent to one or both termini of transcriptional initiation sites. One exemplary promoter sequence is as follows: 5'-TATA TAGTT-3', where AG is the initiation site. In this instance, one transcriptional initiation blocking nucleotide is adjacent to the 5' end of the initiation site and two transcriptional initiation blocking nucleotides are adjacent to the 3' end of the initiation site.

Transcription Reaction Mixtures

Variables in addition of caps and cap analogs to RNA molecules and promoters that can affect capped mRNA yield and capping efficiency include the composition of reaction mixtures used in the RNA production process (e.g., mRNA production process).

Some prior methods for generating capped mRNA through the use of capped primers use reagent mixtures in which the amount GTP present is lower amount than the amount of cap and the other three NTPs. This is so because if high concentrations of GTP are used with dimeric caps that initiate transcription at the +1 position with a G, then the GTP competes efficiently with the dimeric caps for initiation from the +1 nucleotides at NTP concentrations closer to the Kd (2 mM), producing large proportion of RNA that starts with pppG. While decreasing the GTP concentration results in a higher capping efficiency, it also results in lower capped mRNA yields. Provided herein are compositions and methods for the production of capped RNA molecules with both high yields and high capping efficiency.

Some aspects provided herein relate to IVT reaction mixtures that contribute to the production of mRNA populations in which a high percentage of the RNA molecules present are capped (high capping efficiency). In some aspects, IVT reaction mixtures and methods set out herein may be designed to result in high yield production of RNA. In additional aspects, IVT reaction mixtures and methods set out herein may be designed to result in both high capping efficiency and high yield production of RNA.

Reaction mixtures that may be employed to result in both high capping efficiency and high yield production of RNA may comprise chemically modified RNA components designed, for example, to enhance the production of mRNA and/or to stabilize RNA present in the reaction mixture and/or increase translation or reduced immunogenicity.

IVT reaction mixtures will generally contain the following components: (1) One or more RNA polymerase, (2) one or more cap (e.g., one or more capping primer), (3) all four standard nucleotide triphosphates (i.e., GTP, ATP, CTP, and UTP), and (4) one or more nucleic acid template (e.g., one or more DNA templates, one or more RNA templates, a combination of one or more DNA templates and one or more RNA templates, etc.).

IVT reaction mixtures used in methods set out herein may also contain one or more of the following components: (1) One or more buffer (e.g., phosphate, histidine, citrate, maleate, tartrate, acetate, tris-(hydroxymethyl)-aminomethane (tris), and bicarbonate, etc.), (2) one or more divalent metal ion (e.g., $Ca^{2+}$, $Mg^{2+}$, $Mn^{2+}$, $Co^{2+}$, $Ni^{2+}$, etc.), (3) one or more chemically modified nucleotide triphosphate (e.g., pseudouridine (ψ) triphosphate, 1-nethylpseudouridine ($m^1\psi$) triphosphate, 5-methoxyuridine ($mo^5U$) triphosphate, 5-methylcytidine ($m^5C$) triphosphate, α-thio-guanosine triphosphate, α-thio-adenosine triphosphate, etc.), (4) one or more polyamine (e.g., spermidine, spermine, tris(2-aminoethyl)amine, diethylenetriamine, etc.), (5) one or more reducing agent (e.g., DTT (2,3 dihydroxybutane-1,4-dithiol/, also referred to as "dithiothreitol"), DTE (2,3 dihydroxybutane-1,4-dithiol), thioglycolate, cysteine, sulfites, bisulfites, sulfides, bisulfides, TCEP (tris(2-carboxyethyl) phosphine), 2-mercaptoethanol, etc.), (6) one or more nonionic detergent (e.g., octylphenoxypolyethoxyethanol (nonidet P-40); polyoxyethylene glycol sorbitan alkyl esters, such as Polysorbate 20 or Polysorbate 80; block copolymers of polyethylene glycol and polypropylene glycol (Poloxamers), such as Poloxamer 407; polyethoxylated tallow amine (POEA) salt; nonoxynols, such as Nonoxynol-9; Triton X-100; Tween 80, etc.), (7) one or more crowding agents (e.g., polyethylene glycol, dextran and ficoll, etc.) and/or (8) one or more RNAse inhibitors (e.g., one or more vanadyl ribonucleoside complex (VRC), one or more nucleotide analog, SUPERASE-IN™ (Thermo Fisher Scientific, cat. no. AM2696), RNASEOUT™ (Thermo Fisher Scientific, cat. no. 10777019), inorganic pyrophosphatase (e.g., Thermo Fisher Scientific, cat. no. EF0221), etc.).

The concentrations of nucleoside triphosphates and cap analog present in an IVT reaction mixture may vary. In some embodiments, NTPs and cap analog are present in the reaction at equimolar concentrations. In some embodiments, the molar ratio of cap analog (e.g., trinucleotide cap) to nucleoside triphosphates in the reaction is greater than 1:1. For example, the molar ratio of cap analog to any one nucleoside triphosphate (e.g., ATP) in the reaction may be from about 1.1:1 to about 25:1, from about 2:1 to about 25:1, from about 3:1 to about 25:1, from about 5:1 to about 25:1, from about 1.1:1 to about 15:1, from about 2:1 to about 15:1, from about 4:1 to about 15:1, from about 6:1 to about 15:1, from about 8:1 to about 15:1, from about 1.1:1 to about 10:1, from about 2:1 to about 10:1, from about 3:1 to about 10:1, from about 4:1 to about 10:1, or from about 2:1 to about 6:1. In many instances, the molar ratio of cap analog to any one nucleoside triphosphate (e.g., ATP) in the reaction may be from about 1:1 to about 10:1 (e.g., from about 1.5:1 to about 8:1, from about 2:1 to about 8:1, from about 2:1 to about 6:1, from about 2:1 to about 5:1, from about 1.5:1 to about 5:1, from about 2:1 to about 4:1, etc.).

In some embodiments, the molar ratio of cap analog (e.g., trinucleotide cap) to any one nucleoside triphosphate in the reaction is less than 1:1. For example, the molar ratio of cap analog (e.g., trinucleotide cap) to nucleoside triphosphates in the reaction may be from about 1:1.1 to about 1:25, from about 1:2 to about 1:25, from about 1:4 to about 1:25, from about 1:5 to about 1:25, from about 1:1.1 to about 1:10, from about 1:2 to about 1:10, from about 1:4 to about 1:10, from about 1:2 to about 1:6, or from about 1:3 to about 1:6.

The concentrations of individual NTPs (e.g., the "standard" NTPs (ATP, UTP, CTP, GTP)) present in an IVT reaction may also vary. Further, such variances may be due to factors such as cap nucleotide sequences, the initiation site sequence, and/or the presence of "non-standard" NTPs (e.g., pseudouridine (ψ) triphosphate, 1-methylpseudouridine (m1ψ) triphosphate, 5-methoxyuridine (mo5U) triphosphate, etc.).

For purposes of illustration, when a dimer cap is used in an IVT reaction, then the concentration of the NTP capable of hybridizing at position +1 of the initiation site may be lower than the other NTPs in the reaction mixture. Thus, compositions and methods are provided herein where three standard NTPs are present in equimolar amount and one standard NTP is present in a lower amount. Using the promoter sequence in FIG. 17 for specific illustration, where the base at position +1 of the template strand is C. Thus, in some such instances, IVT reaction mixtures will contain equimolar amounts of ATP, UTP, and CTP but a lower amount of GTP. Further, the ratio of the three other NTPs to GTP may be from about 1:0.1 to about 1:0.95 (e.g., from about 1:0.1 to about 1:0.9, from about 1:0.2 to about 1:0.9, from about 1:0.25 to about 1:0.9, from about 1:0.3 to about 1:0.9, from about 1:0.4 to about 1:0.9, from about 1:0.2 to about 1:0.7, from about 1:0.25 to about 1:0.6, from about 1:0.15 to about 1:0.6, etc.). Further, if, for example, the dimer cap has the nucleotide sequence G-A, then the amount of ATP present in a transcription reaction mixture may be lower than for the other three NTPs.

In some instances, GTP, CTP and UTP may be used in excess of ATP in transcription reaction mixtures. As a non-limiting example, an IVT reaction may include 7.5 millimolar GTP, 75 millimolar CTP, 7.5 millimolar UTP, and 3.75 millimolar ATP. The same IVT reaction mixture may include 3.75 millimolar cap analog (e.g., trimer cap). In some instances, the molar ratio of G:C:U:A:cap may be 1:1:1:0.5:0.5, 1:1:0.5:1:0.5, 1:0.5:1:1:0.5, 0.5:1:1:1:0.5, 0.9:0.9:1:1:0.5, 0.9:0.9:1:0.5:0.5. In some instances, the ratio of one or both of the NTPs that form three hydrogen bond with their cognate bases (GTP and CTP) may be in lower ratios compared to the NTPS that form two hydrogen bonds (ATP and UTP). Further, the ratio ATP/UTP to CTP/UTP present in IVT reaction mixtures may be from 1.5 to 1 to 1.1 to 1.

RNA Molecules with Chemical Modifications

In some instances, it may be desirable to generate RNA molecules comprising one or more chemical modifications. In this context a chemical modification refers to a chemical alteration not normally found in RNA generated in IVT systems containing the four standard NTPs. Thus, chemical modifications include the well over 100 naturally occurring RNA chemical modifications, such as N 6-methyladenosine (m6A), pseudouridine, 3-methylcytidine (m3C), and 2'-O-methyl modifications.

Examples of naturally-occurring nucleotides used for the production of RNA, e.g., in an IVT reaction, as provided herein include adenosine triphosphate (ATP), guanosine triphosphate (GTP), cytidine triphosphate (CTP), uridine triphosphate (UTP), and 5-methyluridine triphosphate ($m^5$UTP). In some embodiments, adenosine diphosphate (ADP), guanosine diphosphate (GDP), cytidine diphosphate (CDP), and/or uridine diphosphate (UDP) are used. One method for generation RNA molecules (e.g., mRNA molecules) containing chemical modifications is by the inclusion of chemically modified nucleosides or other components in IVT reaction mixtures.

Examples of nucleotide analogs include that can be used in IVT reactions using the compositions described herein include, but are not limited to, antiviral nucleotide analogs, phosphate analogs (soluble or immobilized hydrolyzable or non-hydrolyzable), dinucleotide, trinucleotide, tetranucleotide. e.g., a cap analog, or a precursor/substrate for enzymatic capping (vaccinia or ligase), a nucleotide labeled with a functional group to facilitate ligation/conjugation of cap or 5' moiety (IRES), a nucleotide labeled with a 5' $PO_4$ to facilitate ligation of cap or 5' moiety, or a nucleotide labeled with a functional group/protecting group that can be chemically or enzymatically cleaved. Examples of antiviral nucleotide/nucleoside analogs include, but are not limited to, Ganciclovir, Entecavir, Telbivudine, Vidarabine and Cidofovir.

Modified nucleotides may include modified nucleobases. For example, a RNA transcript (e.g., mRNA transcript) of the present disclosure may include a modified nucleobase selected from pseudouridine (ψ), 1-methylpseudouridine ($m^1$ψ), 1-ethylpseudouridine, 2-thiouridine, 4'-thiouridine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudo uridine, 4-thio-1-methyl-pseudouridine, 4-thio-pseudouridine, 5-aza-uridine, dihydropseudouridine, 5-methyluridine, 5-methoxyuridine ($mo^5$U) and 2'-O-methyl uridine. In some embodiments, a RNA transcript (e.g., mRNA transcript) includes a combination of at least two (e.g., 2, 3, 4 or more) of the foregoing modified nucleobases.

The nucleoside triphosphates (NTPs) as provided herein may comprise unmodified or modified ATP, modified or unmodified UTP, modified or unmodified GTP, and/or modified or unmodified CTP. In some embodiments, NTPs of an IVT reaction comprise unmodified ATP. In some embodiments, NTPs of an IVT reaction comprise modified ATP. In some embodiments, NTPs of an IVT reaction comprise unmodified UTP. In some embodiments, NTPs of an IVT reaction comprise modified UTP. In some embodiments, NTPs of an IVT reaction comprise unmodified GTP. In some embodiments, NTPs of an IVT reaction comprise modified GTP. In some embodiments, NTPs of an IVT reaction comprise unmodified CTP. In some embodiments, NTPs of an IVT reaction comprise modified CTP.

In some embodiments, a RNA transcript (e.g., mRNA transcript) includes a modified nucleobase selected from pseudouridine (ψ), 1-methylpseudouridine ($m^1$ψ), 5-methoxyuridine ($mo^5$U), 5-methylcytidine ($m^5$C), a-thio-guanosine and a-thio-adenosine. In some embodiments, a RNA transcript (e.g., mRNA transcript) includes a combination of at least two (e.g., 2, 3, 4 or more) of modified nucleobases, such as modified nucleobases set out herein.

In some embodiments, an RNA transcript (e.g., mRNA transcript) includes pseudouridine (ψ). In some embodiments, an RNA transcript (e.g., mRNA transcript) includes 1-methylpseudouridine ($m^1$ψ). In some embodiments, an RNA transcript (e.g., mRNA transcript) includes 5-methoxyuridine ($mo^5$U). In some embodiments, an RNA transcript (e.g., mRNA transcript) includes 5-methylcytidine ($m^5$C). In some embodiments, a RNA transcript (e.g., mRNA transcript) includes a-thio-guanosine. In some embodiments, a RNA transcript (e.g., mRNA transcript) includes a-thio-adenosine.

In some embodiments, the polynucleotide (e.g., RNA polynucleotide, such as mRNA polynucleotide) is uniformly modified (e.g. fully modified, modified throughout the entire sequence) for a particular modification. For example, a polynucleotide can be uniformly modified with 1-methylpseudouridine ($m^1$ψ), meaning that all uridine residues in the mRNA sequence are replaced with 1-methylpseudouridine ($m^1$ψ). Similarly, a polynucleotide can be uniformly modified for any type of nucleoside residue present in the sequence by replacement with a modified residue such as any of those set forth above. Alternatively, the polynucleotide (e.g., RNA polynucleotide, such as mRNA polynucleotide) may not be uniformly modified (e.g., partially modified, part of the sequence is modified).

Capped RNA Preparations

Without wishing to be bound by a particular theory, the use of capped RNA (e.g., capped mRNA molecules) preparations where with a high ratio of capped/uncapped RNA may result in increased expression compared to preparations with a lower capped/uncapped RNA ratio. Thus, in many instances, it will be desirable to separate capped RNA (e.g., capped mRNA molecules) from uncapped RNA (e.g., uncapped mRNA molecules) prior to introduction of the capped RNA molecules into cells. Such separation may occur by any number methods, including purification of capped RNA (e.g., capped mRNA molecules) by methods such as high performance liquid chromatography (HPLC) or electrophoresis and/or selective degradation of uncapped RNA molecules.

Methods and compositions described herein provide for methods of generating RNAs incorporating cap analogs as described herein. The efficiency of mRNA produced in IVT reactions using the cap analogs as described herein can be at least 40%, at least 50%, at least 60%, at least 70%, at least 80%, at least 90%, at least 95% or more, or any value in between, of the yield of mRNA produced in an IVT reaction under identical conditions, except for the inclusion of a cap analog as described herein.

The methods and compositions provided herein provide for method of generating RNAs wherein at least 50%, at least 60%, at least 70%, at least 80%, at least 90%, at least 95% or more, or any value in between, of the total mRNA produced in an IVT is capped with the cap analogs described herein. In other words, the capping efficiency is at least 50%, 55%, 60%, 65%, 70%, 75%, 80%, 85%, 90%, 91%, 92%, 93%, 94%, 95%, or more (e.g., from about 50% to about 99%, from about 60% to about 99%, from about 70% to about 99%, from about 80% to about 99%, from about 85% to about 99%, from about 85% to about 95%, from about 90% to about 96%, etc.).

Methods provided herein for making RNA preparations incorporating the caps provided herein can advantageously include the step of degrading RNA that is not capped, thereby purifying or enriching the capped RNA species. Removal of uncapped RNA can be accomplished by any means known to those skilled in the art, including but not limited to enzymatic digestion. For example, RNA preparations can be treated with RNA 5' polyphosphatases, which removes pyrophosphate from 5' triphosphorylated RNA, leaving a monophosphate 5' end. The preparation can subsequently be treated with a 5'→3' exoribonucleases, which requires a 5' monophosphate RNA as a substrate. One category of such enzymes are the XRN 5'→3' exoribonucleases (see Nagarajan et al., "*XRN 5'→3' exoribonucleases: Structure, mechanisms and functions*", Biochim Biophys Acta., 1829:590-603. (2013)). Thus, treatment with these two enzymes will selectively degrade uncapped RNAs, leaving capped RNAs intact.

Methods set out herein include those where RNA molecules (e.g., mRNA molecules) that are not capped are preferentially degraded over capped RNA molecules (e.g., capped mRNA molecules), as well as compositions used to perform such methods. Such methods may be performed with or without treatment of RNA present in the reaction mixture prior to preferential degradation of uncapped RNA. When reaction mixtures are treated to prepare a subpopulation of RNA molecules (e.g., uncapped RNA molecules) for degradation this preparation may occur before or at the same time as degradation of RNA with a 5'→3' exoribonuclease. Thus, both preparation of RNA molecules for degradation by a 5'→3' exoribonuclease and degradation of the RNA molecules may occur in the same reaction mixture at different times or at the same time. In some instances, the 5' termini of RNA molecule for which degradation is desired may need to be modified so that a 5'→3' exoribonucleases will act upon the termini. One example of this is when an XRN1 exoribonuclease is used to degrade uncapped RNA molecules.

XRN1 is a progressive XRN1 exoribonuclease that degrades termini of RNA molecules that contain a single 5' phosphate group. One commercially available XRN1 exoribonuclease is available from New England Biolabs (cat. no. M0338S). In instances where some or all of the RNA molecules present that one seeks to degrade contain more than one 5' phosphate group, it will normally be desirable to reduce the number of phosphate groups down to one. A number of methods of methods may be used to remove 5' phosphate groups from RNA, including methods that employ phosphatases for enzymatic removal of these groups. One category of such enzymes are the RNA 5' polyphosphatases (e.g., Lucigen, cat. no. RP8092H).

Methods set out herein include those where the amount of capped RNA is increased over uncapped RNA by at least 50% (e.g., by at least from about 50% to about 500%, from about 100% to about 500%, from about 150% to about 500%, from about 200% to about 500%, from about 250% to about 500%, from about 300% to about 500%, from about 50% to about 1,000%, from about 150% to about 1,000%, from about 300% to about 1,000%, from about 400% to about 1,000%, etc.). The following is an example of how percent increase may be calculated. Assume that there are 100 mg of capped RNA and 50 mg of uncapped RNA in a sample. If the amount of uncapped RNA is decreased to 25 mg, then the total amount of uncapped RNA is decreased by half. Further, the ratio of capped RNA to uncapped RNA would go from 2:1 to 4:1 and the amount of capped RNA would increase over uncapped RNA by 21%.

Compositions comprising trinucleotide capped RNA as described herein can be used for in vitro transcription, in vitro translation, and in vivo translation, for example. Current biotechnology efforts for in vitro, in situ, and in vivo protein production will also benefit from these methods and compositions. Further, compositions provided herein are useful for therapeutic purposes. For example, the present technology may be useful for generating vaccines against infectious diseases or cancers, protein replacement therapies, and the like. The skilled artisan will readily appreciate that the capping technology and the compositions described herein can be used generally in mRNA vaccines. For example, the RNA caps described herein can be incorporated into RNA sequences useful in vaccines, including but not limited to sequences described in US20180318409A1, US20190351040, US20180271970, US20190054112, US20190336595, US20180311336, US20180303929, WO2017/070601, WO2019/202035, WO2020/002525, WO2019/193183, WO2019/115635, WO2019/038332, WO2019/008001, WO2018/167320, WO2018/115527, WO2018/115525, WO2018/115507, WO2018/104538, WO2018/104540.

Alkyne-derivitized capped RNA can be used to produce non-infectious particles of a virus containing an RNA encoding immunogen. These non-replicating viral particles can be injected into humans where they can enter host cells. Once in the host cell, the viral particles dissociate and the mRNA encoding the immunogen is translated into protein. These proteins can induce an immune response.

RNA-based vaccines may be used to vaccinate against infectious agents such as viruses, e.g., corona viruses (such as MERS, SARS-CoV and SARS-CoV-2), human immunodeficiency virus (HIV), feline immunodeficiency virus, human papilloma virus type 16, tumors, lassa virus, Ebola virus, Marburg virus, anthrax toxin from *Bacillus* anthraces, and botulinum toxin. Accordingly, non-limiting examples of viruses for which an RNA vaccine could be used for include: Adeno-associated virus, Aichi virus, Australian bat lyssavirus, BK polyomavirus, Banna virus, Barmah forest virus, Bunyamwera virus, Bunyavirus La Crosse, Bunyavirus snowshoe hare, Cercopithecine herpesvirus, Chandipura virus, Chikungunya virus, Cosavirus A, Cowpox virus, Coxsackievirus, Crimean-Congo hemorrhagic fever virus, Dengue virus, Dhori virus, Dugbe virus, Duvenhage virus, Eastern equine encephalitis virus, Ebolaviurs, Echovirus, Encephalomycarditis virus, Epstein-Barr virus, European bat lyssavirus, GB virus C/Hepatitis G virus, Hantaan virus, Hendra virus, Hepatitis A virus, Hepatitis B virus, Hepatitis C virus, Hepatitis E virus Human herpesvirus 1, s, Hepatitis delta virus, Horsepox virus, Human adenovirus, Human astrovirus, Human coronavirus, Human cytomegalovirus, Human herpesvirus 1, Human herpesvirus 2, Human herpesvirus 6, Human herpesvirus 7, Human herpesvirus 8, Human immunodeficiency virus, Human papilloma virus 1, Human papilloma virus 2, Human papilloma virus 16, 18, Human parainfluenza, Human parovirus B19, Human respiratory syncytial virus, Human rhinovirus, Human SARS coronavirus, Human spumaretrovirus, Human T-lymphotropic virus, Human toroviurs, Influenza A virus, Influenza B virus, Influenza C virus, Isfahan virus, JC polyomavirus, Japanese encephalitis virus, Junin arenavirus, KI polyomavirus, Kunjin virus, Lagos bat virus, Lake Victoria Marburgvirus, Langat virus, Lassa virus, Lordsdale virus, Louping ill virus, Lymphocytic choriomeningitis virus, Machupo virus, Mayaro virus, MERS coronavirus, Measles virus, Mengo encephalomyocarditis virus, Merkel cell polymavirus, Mokola virus, Molluscum contagiosum virus, Monkeypox virus, Mumps virus, Murray valley encephalitis virus, New York virus, Nipah virus, Norwalk virus, O'nyong-nyong virus, Orf virus, Oropouche virus, Pichinde virus, Poliovirus, Punta toro phlebovirus, Puumala virus, Rabies virus, Rift valley fever virus, Rosavirus A, Ross river virus, Rotavirus A, Rotavirus B, Rotavirus C, Rubella virus Sagiyama virus, Salivirus A, Sandfly fever Sicilian virus, Sapporo virus, SARS coronavirus 2, Semliki forest virus, Seoul virus, Simian foam virus, Simian virus 5, Sindbis virus, Southampton virus, St. louis encephalitis virus, Tick-borne Powassan virus, Torque teno virus, Toscana virus, Uukuniemi virus, Vaccinia virus, Varicella-zoster virus, Variola virus, Venezuelan equine encephalitis virus, Vesicular stomatitis virus, Western equine encephalitis virus, WU polyomavirus, West Nile virus, Yaba monkey tumor virus, Yaba-like disease virus, Yellow fever virus, Zika virus.

These vaccine strategies can require large quantities of capped RNA. The present methods facilitate such synthesis and subsequent purification of capped RNA so as to make these vaccines commercially feasible. As well, strategies to increase the percentage of full-length capped RNA in a transcription reaction leading to a more homogenous product will be preferred in the vaccine industry as highly pure components are usually required for human use. In addition, researchers prefer to use products that are as pure as possible to minimize the number of variables in an experiment. As well, the purer the product, the more potent it is.

An additional embodiment relates to the administration of a composition which generally comprises an active ingredient (e.g., trinucleotide capped RNA) formulated with a pharmaceutically acceptable excipient. Excipients may include, for example, sugars, starches, celluloses, gums, and proteins. Various formulations are commonly known and are thoroughly discussed in the latest edition of Remington's Pharmaceutical Sciences (Maack Publishing, Easton Pa.). Such compositions may include novel cap analogs, antibodies to novel cap analogs, and mimetics, agonists, antagonists, or inhibitors of novel cap analogs.

In various embodiments, the compositions described herein, such as pharmaceutical compositions, may be administered by any number of routes including, but not limited to, oral, intravenous, intramuscular, intra-arterial, intramedullary, intrathecal, intraventricular, pulmonary, transdermal, subcutaneous, intraperitoneal, intranasal, enteral, topical, sublingual, or rectal means.

Embodiments of the present disclosure can be further understood in light of the following examples, which should not be construed as limiting the scope of the present disclosure in any way.

Those having ordinary skill in the art will understand that many modifications, alternatives, and equivalents are possible. All such modifications, alternatives, and equivalents are intended to be encompassed herein.

EXAMPLES

The following examples provide methods of producing trinucleotide cap analogs.

Reagents: Reagents and solvents are used as such without further purification, unless otherwise stated, 3'-O-propargyl guanosine was purchased from Chemgenes, USA, $^1$H NMR and $^{31}$P NMR spectra were recorded in $D_2O$ on a Burker 400 MHz instrument. ESI mass spectra were recorded on an Applied Biosystems/Sciex API 150 model. HPLC was run on a waters 2996 (Waters Corporation) using anion exchange column. Ion exchange chromatography was performed in an AKTA purifier (Amersham Biosciences, GE Healthcare) using a DEAE Sepharose column. The gel shift assay is performed by using a pTri β actin template and the IVT reaction uses linearized AmbLuc poly(A) DNA template and a MEGASCRIPT kit (Thermo Fisher Scientific). Radiation in the gel bands of interest is quantified by a phosphorimager (GE Healthcare). Purifications of the RNA from these transcription reactions are done by using the MEGACLEAR Kit (Life Technologies Corporation) as per manufacturer's protocol. Luminometer (POLARstar OPTIMA. BMG Labtech) in 96-well plates is used for the luciferase assay readings as per manufacturer's protocol.

Example 1: Intermediate Synthetic Schemes

Exemplary synthetic routes to obtain the intermediates used in the trinucleotide synthesis are set forth below Intermediate Scheme A: Synthesis of Imm$^7$(LNA)GDP (8)

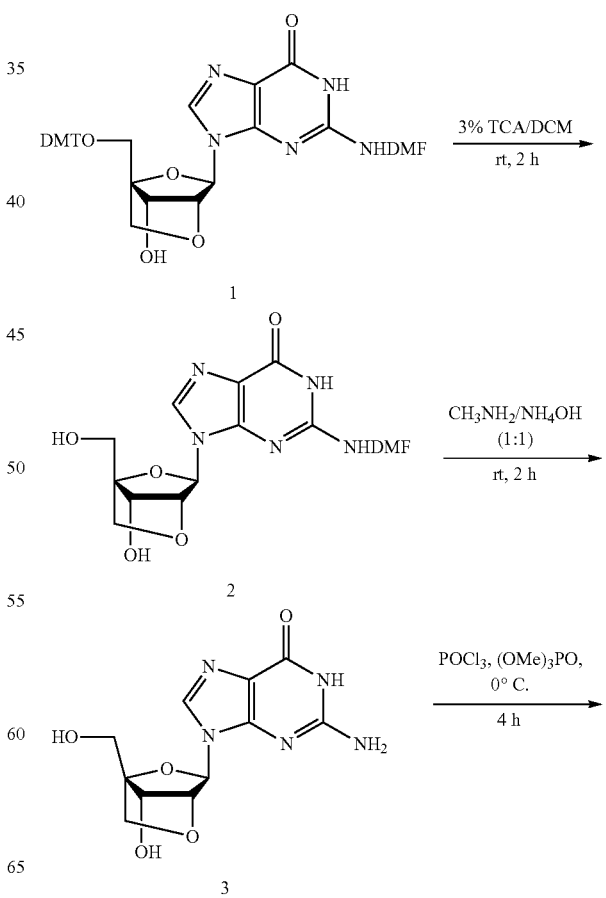

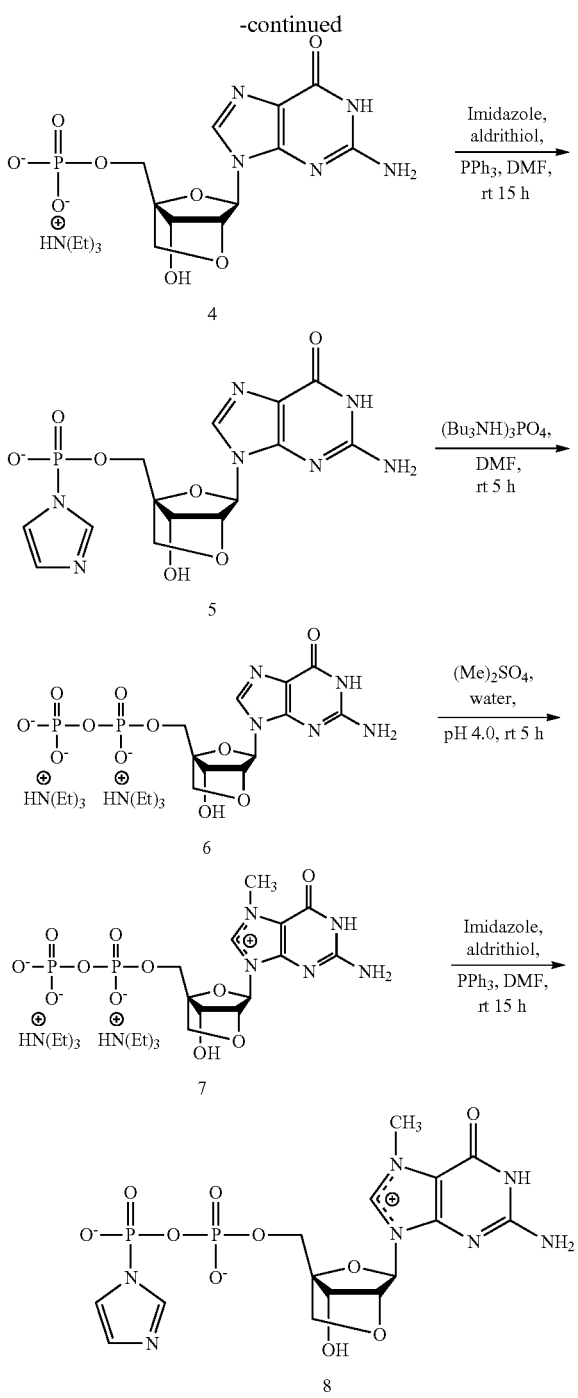

Intermediate Example 1: Synthesis of DMF-Protected LNA Guanosine (2)

To a stirred solution of 50 mL 3% trichloroacetic acid in dichloromethane, 5'-DMT-N-DMF LNA guanosine 1 (5.00 g, 7.48 mmol) was added and the reaction mixture was stirred for 2 h at room temperature. The reaction mixture was evaporated to dryness under rotary evaporator. To the resulting orange solid, 50 mL diethyl ether was added and allowed to stir at room temperature for 30 min. The resulting mixture was filtered and dried under vacuum to get a white colored solid 2 (Yield: 2.67 g, 95%). This crude material was used for next step without further purification.

Intermediate Example 2: Synthesis of LNA Guanosine (3)

To a stirred solution of 40 mL 1:1 mixture of aqueous 40% methyl amine and 28% ammonium hydroxide, DMF-protected LNA guanosine 2 (2.67 g, 7.04 mmol) was added and the reaction mixture was stirred at room temperature for 2 h. After 2 h, the reaction mixture was evaporated under rotavapor to get a white colored solid 3 (Yield, 1.98 g, 95%). This crude material was used for next step without further purification.

Intermediate Example 3: Synthesis of LNA-GMP (4)

To a stirred solution of POCl$_3$ (1.69 g, 11.19 mmol) and (MeO)$_3$P (15.0 mL) at 0° C. under argon atmosphere, LNA guanosine 6 (1.10 g, 3.72 mmol) was added and the reaction mixture was stirred for 4 h at 0° C. After 4 h, 50.0 mL water was added to the reaction mixture. The resulting reaction mixture was washed with ethyl acetate (2×50 mL) to remove phosphorylating agent. The collected aqueous solution was adjusted to pH 1.5 and allowed to stir at 4° C. for 15 h. After 15 h, the aqueous solution was adjusted to pH 5.5 and loaded on a DEAE Sepharose column. The desired product was eluted using a linear gradient of 0-1M TEAB (triethyl ammonium bicarbonate, pH 7.5) and the fractions containing the product were pooled, evaporated and dried in vacuum desiccator over phosphorous pentoxide to give a fine white powder 4 (Yield: 1.43 g, 78%). Data for 4. $^1$H NMR (D$_2$O, 400 MHz) δ 8.01 (s, 1H), 5.91 (s, 1H), 4.63 (s, 1H), 4.58 (s, 1H), 4.16 (m, 3H), 4.03 (d, J=8.4 Hz, 1H), 3.20 (q, J=7.6 Hz, 6H), 1.28 (t, J=7.2 Hz, 9H); $^{31}$P NMR (D$_2$O, 162 MHz) δ −5.40 (s, 1P); MS (m/z): 374 [M-H]$^-$.

Intermediate Example 4: Synthesis of ImLNA-GMP (5)

To a stirred solution of LNA-GMP TEA salt 4 (1.35 g, 2.84 mmol) in 20 mL dry DMF, imidazole (0.97 g, 14.24 mmol), triphenyl phosphine (1.50 g, 5.70 mmol), aldrithiol (1.25 g, 5.70 mmol) and triethylamine (0.29 g, 2.84 mmol) were added. The reaction mixture was stirred under argon atmosphere at room temperature for 15 h. To a solution of sodium perchlorate (2 g) in 100 mL acetone in a centrifuge tube at 0° C., the above reaction mixture was added slowly for 5 minutes. The resulting mixture was centrifuged, and the supernatant liquid was removed. The solid was ground with a new portion of acetone (100 mL), cooled, and centrifuged again. This process was repeated for two more times, and the resulting solid was dried in a vacuum desiccator over P$_2$O$_5$ to give a white powder 5 (Yield: 1.05 g, 83%). MS (m/z): 424 [M-H]$^-$.

Intermediate Example 5: Synthesis of LNA-GDP (6)

To a stirred solution of ImLNA-GMP 5 (1.00 g, 2.23 mmol) and zinc chloride (0.61 g, 4.46 mmol) in 10.0 mL dry DMF, 15 mL of 1M tris(tributylammonium) phosphate in DMF was added under argon atmosphere. The reaction mixture was stirred at room temperature for 5 h. After 5 h, the reaction mixture was diluted with 50.0 mL of water. The resulting reaction mixture was washed with ethyl acetate (2×50 mL) to remove phosphorylating agent. The collected aqueous solution was adjusted to pH 5.5 and loaded on a DEAE Sepharose column. The desired product was eluted using a linear gradient of 0-1M TEAB and the fractions containing the product were pooled, evaporated and dried in vacuum desiccator over phosphorous pentoxide to give a fine white powder 6 (Yield 1.10 g, 75%). Data for 6. $^1$H NMR (D$_2$O, 400 MHz) δ 8.00 (s, 1H), 5.95 (s, 1H), 4.63 (s, 2H), 4.37 (m, 2H), 4.14 (d, J=8.4 Hz, 1H), 4.04 (d, J=8.4 Hz, 1H), 3.20 (q, J=7.2 Hz, 12H), 1.28 (t, J=7.6 Hz, 18H); $^{31}$P NMR (D$_2$O, 162 MHz) δ −8.94 (d, J=20.9 Hz, 1P), 9.99 (d, J=21.3 Hz, 1P); MS (m/z): 454 [M-H]$^-$.

Intermediate Example 6: Synthesis of m$^{7(LNA)}$GDP (7)

To a stirred solution of LNA-GDP 6 (1.00 g, 1.52 mmol) in 20.0 mL of water, acetic acid was added slowly to adjust the pH of the solution to 4.0. To this mixture, dimethyl sulfate (2.0 mL) was added drop wise over a period of 30 min. and the reaction mixture was allowed to stir at room temperature for 5 h. As the methylation proceeds, the pH drops down to around 2.0 and the pH was readjusted back to 4.0 using 1M NaOH solution. After 5 h, the reaction mixture was extracted with ethyl acetate (3×50 mL) to remove unreacted excess dimethyl sulfate. The collected aqueous solution was adjusted to pH 5.5 and loaded on a DEAE Sephadex column. The desired product was eluted using a linear gradient of 0-1M TEAB and the fractions containing the product were pooled, evaporated and dried in vacuum desiccator over phosphorous pentoxide to give a fine white powder 7 (Yield 0.70 g, 68%). Data for 7. $^1$H NMR (D$_2$O, 400 MHz) δ 6.05 (s, 1H), 4.73 (s, 1H), 4.55 (s, 1H), 4.42 (m, 1H), 4.32 (m, 1H), 4.13 (s, 3H), 4.11 (d, J=6.0 Hz, 1H), 4.00 (d, J=8.8 Hz, 1H), 3.20 (q, J=7.2 Hz, 12H), 1.28 (t, J=7.2 Hz, 18H); $^{31}$P NMR (D$_2$O, 162 MHz) δ −6.18 (d, J=23.0 Hz, 1P), −9.56 (d, J=22.8 Hz, 1P); MS (m/z): 468 [M-H]$^-$.

Intermediate Example 7: Synthesis of Imm$^{7(LNA)}$GDP (8)

To a stirred solution of m$^{7(LNA)}$GDP TEA salt 7 (0.65 g, 0.96 mmol) in 15 mL dry DMF, imidazole (0.33 g, 4.84 mmol), triphenyl phosphine (0.51 g, 1.93 mmol), aldrithiol (0.43 g, 1.93 mmol) and triethylamine (0.10 g, 0.96 mmol) were added. The reaction mixture was stirred under argon atmosphere at room temperature for 15 h. To a solution of sodium perchlorate (2 g) in 100 mL acetone in a centrifuge tube at 0° C., the above reaction mixture was added slowly for 5 minutes. The resulting mixture was centrifuged, and the supernatant liquid was removed. The solid was ground with a new portion of acetone (100 mL), cooled, and centrifuged again. This process was repeated for two more times, and the resulting solid was dried in a vacuum desiccator over P$_2$O$_5$ to give a white powder 8 (Yield: 0.42 g, 80%). MS (m/z): 517 [M-H]$^-$.

Intermediate Scheme B: Synthesis of Dinucleotide pAmpG (13)

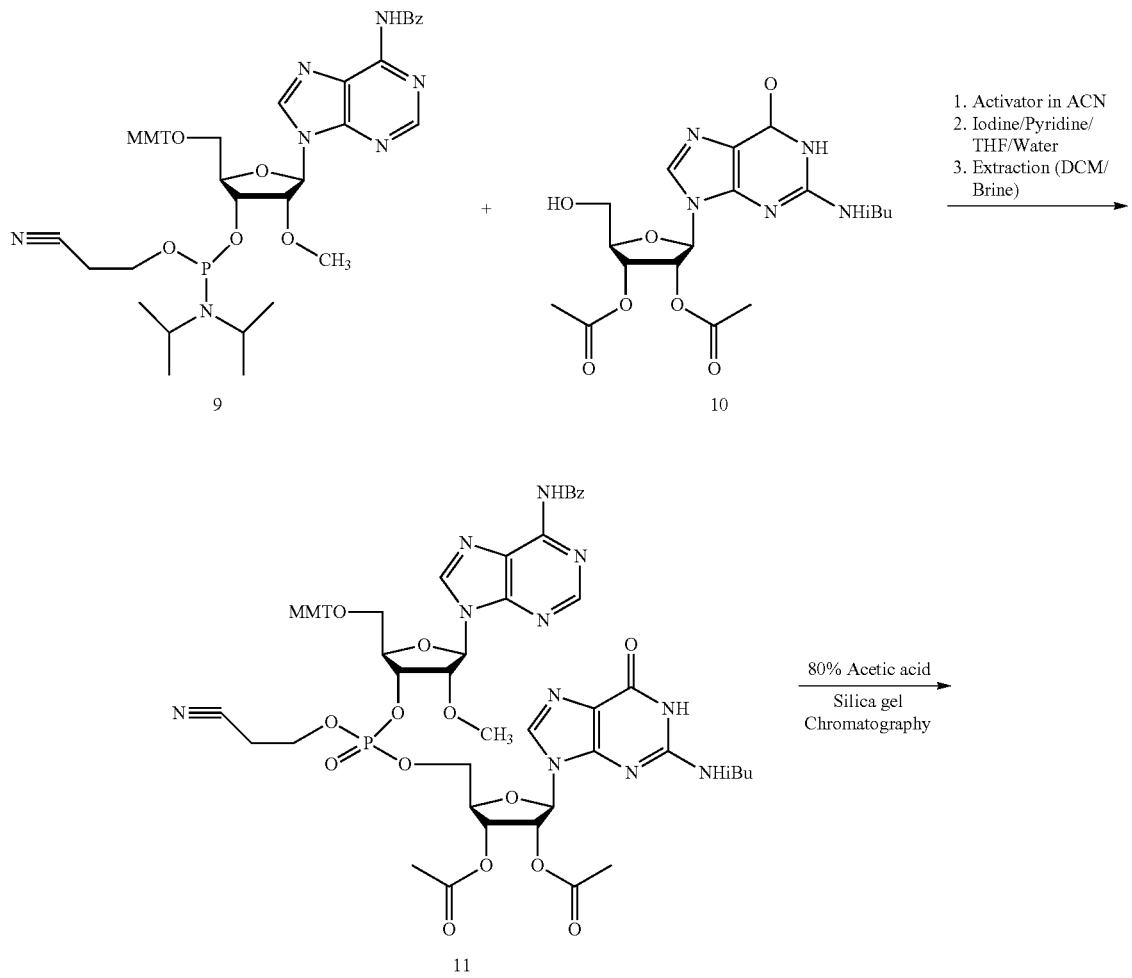

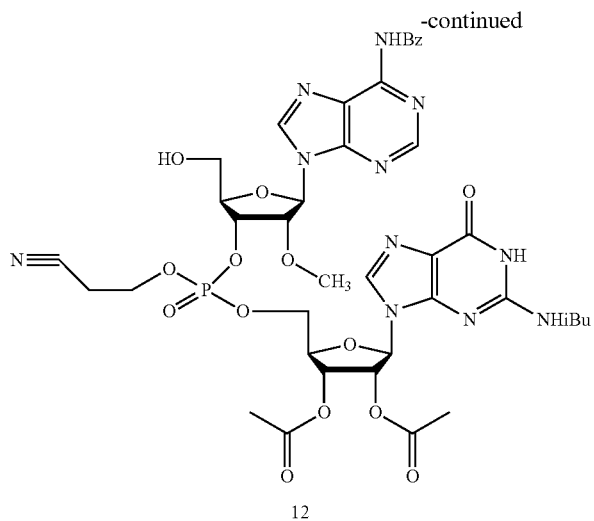

1. Phosphitylating reagent and activator in ACN
2. Iodine/Pyridine/THF/Water
3. Extraction (DCM/Brine)
4. Ammonia deprotection
5. Anion exchange and reverse phase chromatography

12

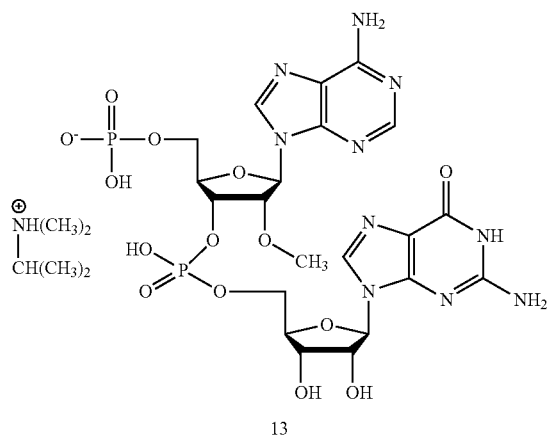

13

Intermediate Example 8: Synthesis of Dinucleotide pAmpG (13)

In a typical reaction, MMT-2'-O-Methyl Adenosine (n-bz) CED phosphoramidite 9 (2.0 mmol) and 2',3'-Diacetyl Guanosine (n-ibu) 10 (2.0 mmol) are reacted in 20 mL of acetonitrile containing 4.5 molar equivalents of activator (tetrazole in acetonitrile). After 2 hours of stirring at room temperature the intermediate product is oxidized from the P(III) to P(V) state with Iodine/Pyridine/THF/Water and extracted with dichloromethane (400 mL) and brine (400 mL). The resulting organic layer is dried with sodium sulfate and is evaporated to solid form intermediate 11.

To remove the 5'-MMT group, intermediate 11 is dissolved in 20 mL of 80% acetic acid and resulting reaction mixture is stirred at room temperature for about 2 to 3 hours. After reaction is completed, the mixture is evaporated and co-evaporated with methanol (6×60 mL) to remove acetic acid. The crude 5'-OH dimer 12 is isolated and purified by silica gel chromatography using 5% methanol in dichloromethane as an eluent.

The 5'-OH dimer 12 (2.0 mmol) is phosphitylated with four equivalents of bis-cyanoethyl-N, N-diisopropyl-phosphoramidite and four equivalents of activator (tetrazole in 20 mL acetonitrile). After 45 minutes of stirring at room temperature the 5'-phosphitylated dimer is oxidized from the P(III) to P(V) state with Iodine/Pyridine/THF/Water and extracted with dichloromethane (300 mL) and brine (300 mL). The organic layer is evaporated to an oily residue, co-evaporated with methanol (2×60 mL), and dissolved in 25 mL of methanol and concentrated ammonia (25 mL) was added. The resulting mixture was kept at room temperature for over 48 hours until deprotection of the pAmpG dimer 13 is complete. The mixture is evaporated and co-evaporated with methanol and resulting dimer is characterized by LC/MS (MS (m/z): 705 [M-H]$^-$) and used for further conjugation to synthesize trinucleotide cap analog.

Example 2: Synthesis of LNA Trinucleotide Cap Analog (14)

The General Trinucleotide Scheme below illustrates the combination of the intermediates from Intermediate Scheme (A) and Intermediate Scheme (B) to arrive at an exemplary trinucleotide cap analog described herein. In this illustration, the trinucleotide analog of the present disclosure (14) is a locked cap analog.

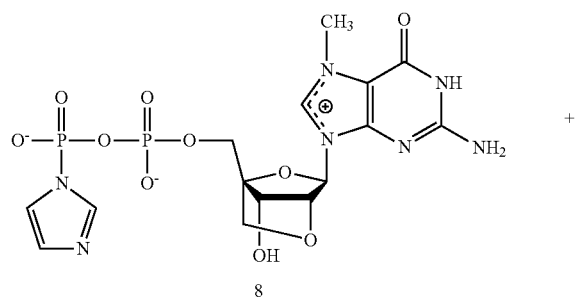

8

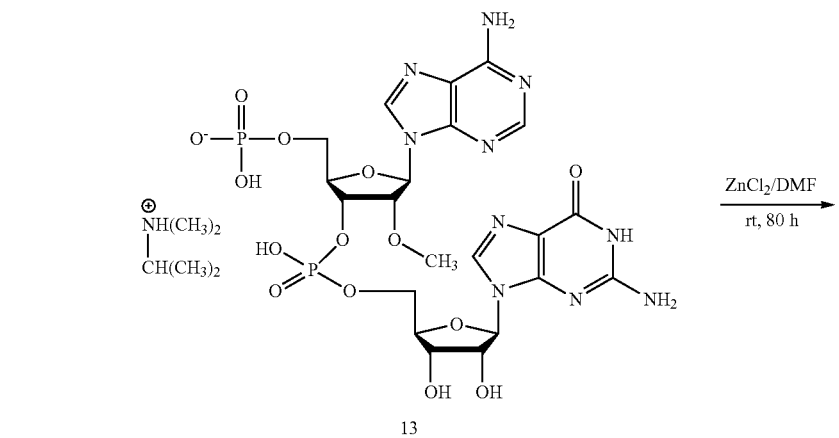

13

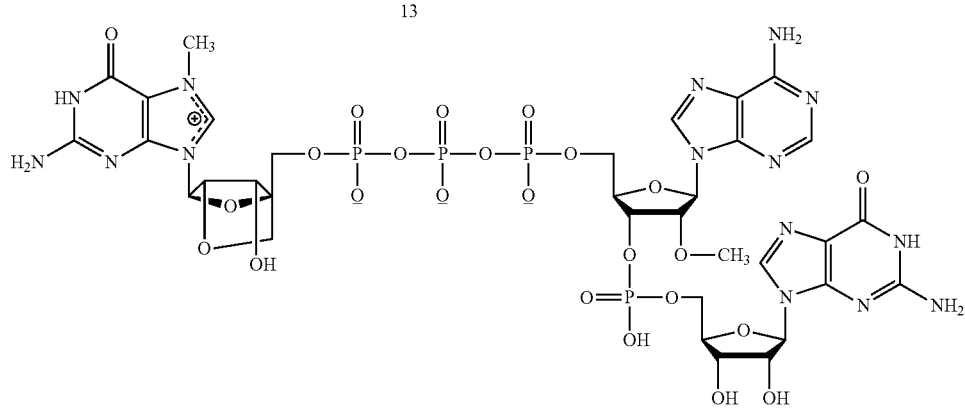

14

Trinucleotide Cap Analog Example 1—Synthesis of LNA Trinucleotide Cap Analog (14)

To a stirred solution of Imm[7(LNA)]GDP 8 (0.10 g, 0.18 mmol) and pAmpG N,N-dimethyl isopropyl ammonium salt 13 (0.14 g, 0.18 mmol) in 10.0 mL dry DMF, zinc chloride (0.15 g, 1.10 mmol) was added under argon atmosphere and the reaction mixture was stirred at room temperature for 80 h. The reaction mixture was added to a solution of EDTA disodium (0.55 g, 1.48 mmol) in 100.0 mL of water at 0° C. The resulting aqueous solution was adjusted to pH 5.5 and loaded on a DEAE Sephadex column. The desired product was eluted using a linear gradient of 0-1M TEAB and the fractions containing the product were pooled, evaporated and concentrated to 10.0 mL TEA salt of 14. The TEA salt of the product was dissolved in water (5 mL) and then poured into a solution of sodium perchlorate (2.0 g) in acetone (50 mL). The resulting mixture was centrifuged, and the supernatant liquid was discarded. The solid obtained was washed with acetone (2×50 mL) and dried in vacuum to give a sodium salt of LNA trinucleotide cap Analog 14. (Yield: 0.12 g, 55%) Data for 14. $^1$H NMR (D$_2$O, 400 MHz) δ 8.39 (s, 1H), 7.94 (s, 1H), 7.84 (s, 1H), 6.01 (d, J=6.0 Hz, 1H), 5.87 (d, J=6.0 Hz, 1H), 5.55 (s, 1H), 4.83 (m, 1H), 4.43 (m, 4H), 4.31 (m, 2H), 4.23 (m, 4H), 4.10 (m, 3H), 3.99 (m, 1H), 3.93 (m, 1H), 3.91 (s, 3H), 3.29 (s, 3H); $^{31}$P NMR (D$_2$O, 162 MHz) δ −0.92 (s, 1P), −11.11 (d, J=19.4 Hz, 1P), −10.42 (d, J=17.8 Hz, 1P), −22.91 (t, J=17.8 Hz, 1P); MS (MALDI, m/z): 1156 [M-H]$^-$.

Example 3: In Vitro Transcription with LNA Trinucleotide CAP Analog

Figure 11:
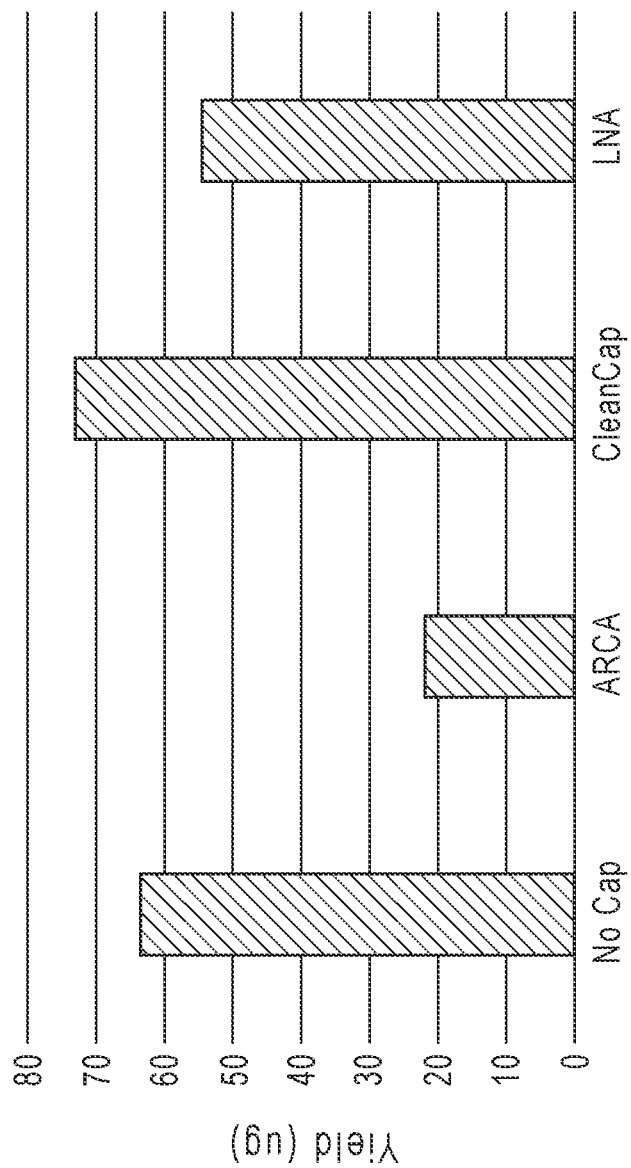
FIG. 11 is a bar graph showing the mRNA yield of IVT reactions performed in the presence of different mRNA CAP analogs, as indicated and as described in Example 3.
Figure 12:
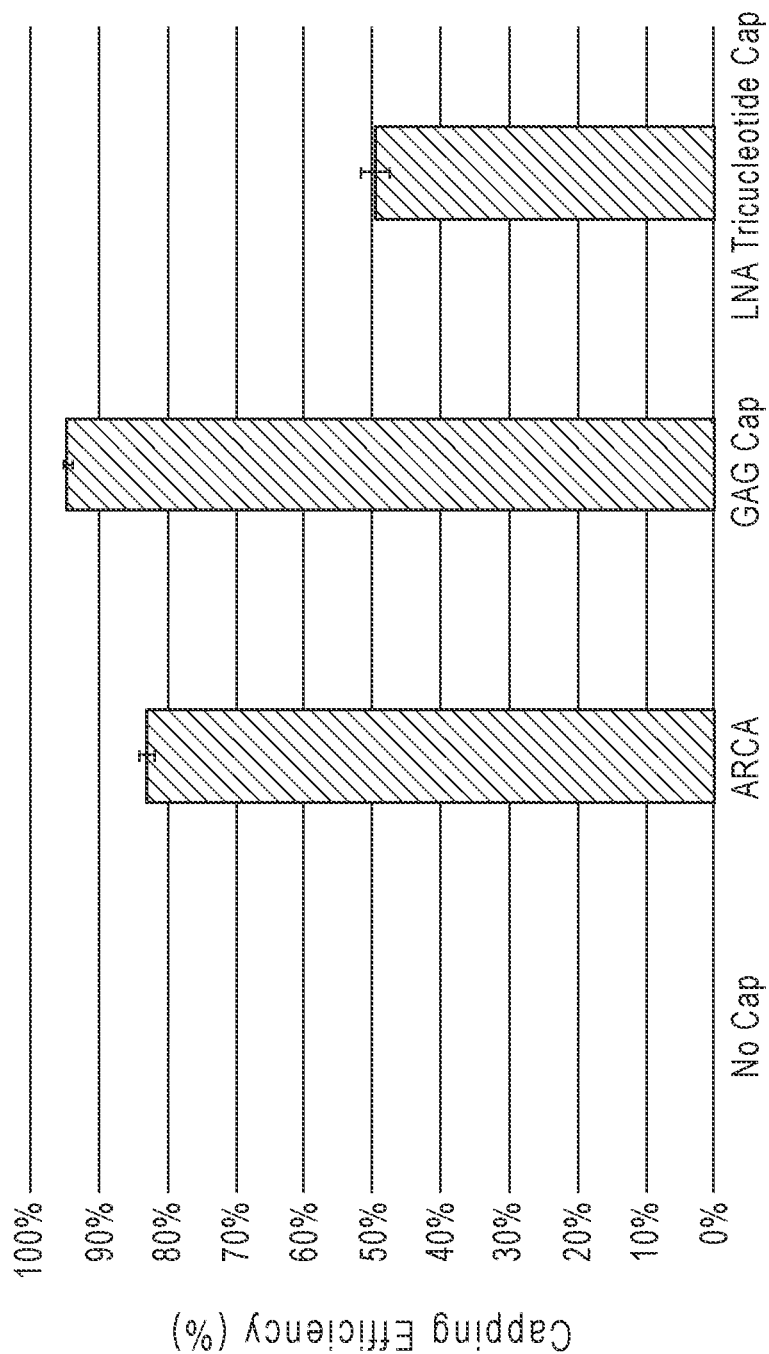
FIG. 12 is a bar graph showing the mRNA capping efficiency of mRNAs capped with ARCA, GAG cap, or LNA-modified GAG cap.

The following example demonstrates that the synthetic CAPs described herein can be incorporated into mRNA in vitro. Briefly, linearized DNA including the coding sequence for GFP under control of a T7 promoter was used in an in vitro transcription reaction using the buffer and enzymes from the mMessage mMachine™ T7 Kit (Thermo Fisher Scientific, cat. no. AM1344), and a NTP/cap mixture. The NTP/cap mixture contained a mixture of NTPs and either no cap, ARCA cap analog (Thermo Fisher Scientific, cat. no. AM8045), GAG Cap analog) (CLEANCAP™ AG, Trilink Biotechnologies, cat. no. N-7113), or Compound (14) as described herein. Reactions with ARCA or no cap were performed using a DNA template containing the wild-type T7 promoter which contains a GGG start. A DNA template containing a modified T7 promoter containing an AGG start was used for reactions with GAG Cap cap analog or LNA-modified GAG Cap cap (Compound 14). In all reactions except for those with ARCA, the concentration of each NTP and cap was 5 mM. The reactions with ARCA contained the following cap/NTP concentrations: 6 mM ARCA, 1.5 mM GTP, and 7.5 mM ATP, CTP, and UTP each. Reactions were processed according to the manufacturer's instructions. Each reaction generated full-length RNA transcripts that are approximately 1000 nucleotides, including ~120 nt poly(A) tail. RNA transcripts were purified using the MEGACLEAR™ RNA purification kit (Thermo Fisher Scientific, cat. no. AM1908) according to the manufacturer's instructions, and RNA yield was quantified by measuring absorbance at 260 nm in a NANODROP™ 2000C spectrometer (Thermo Fisher Scientific, cat. no. ND-2000C). As shown in FIG. 11, the RNA yield in the reactions containing the LNA Cap analog was superior to the ARCA cap reaction.

Example 4: Capping Efficiency with LNA Cap Analogs

The capping efficiency of LNA cap analogs was compared to no cap control, ARCA cap analogs, and CLEANCAP™ cap analogs. Briefly, in vitro transcription reactions were performed as described Example 3. In order to be able to resolve uncapped vs. capped mRNAs, e.g., on a Bioanalyzer, 1-2 μg RNA sample from the in vitro transcription reaction was treated with a DNAzyme oligonucleotide to trim the RNAs to 30 nucleotides long from 5' end (no cap), 31 nucleotides long (ARCA, GAG-cap (GpppAG)), LNA Cap Analog (LNA-modified GAG cap) in a reaction containing 5 μl of 200 mM Tris-HCl, pH 7.5, 1 μl of 10 μM DNAzyme oligonucleotide TTGAGGTTGCTAGTGAAGGCTAGC-TACAACGAACAGTTGTGTCAGAAGC (SEQ ID NO: 584) and water to a total volume of 16 μl. The mixture was preheated at 85° C. for 30 seconds, and equilibrated at 37° C. for 5 minutes. 4 μl of 50 mM MgCl$_2$ was added to the mixture, which was allowed to incubate at 37° C. for one hour. To stop the reaction, 2 μl TURBO™ DNAse (Thermo Fisher Scientific, cat. no. AM2238) was added and incubated at 37° C. for 30 minutes. 1-2 μl of the reaction was loaded onto a Bioanalyzer chip (Agilent, San Jose, CA) using the small RNA Analysis kit (Agilent, Cat. No. 5067-1548), according to the manufacturer's protocol. Uncapped mRNA molecules were 1 base shorter than mRNA species that were successfully capped with ARCA or LNA-cap analogs, respectively. The capping efficiency was calculated as amount capped mRNA/total mRNA, by measuring the area under the peaks corresponding to capped or uncapped species As shown in FIG. 13 the capping efficiency of the LNA cap analog is lower than the ARCA cap analog and the GAG cap analog.

Example 5: Transfection Efficiency and Expression Efficiency of mRNA Capped with LNA Cap Analogs The transfection efficiency and expression efficiency of LNA cap analogs was compared to uncapped mRNA, ARCA cap analogs, and GAG cap (CLEANCAP™) cap analogs. The JAWSII murine immortalized dendritic cell line were used for the analysis. Transfections were done with "crude" mRNA or "HPLC Purified mRNA." For "crude" mRNA, transcripts were used directly after purification using the MEGACLEAR™ RNA purification kit as described in Example 3. For "HPLC Purified" mRNA, uncapped mRNA was removed by mixing 10 ug mRNA with 20 units of RNA 5' Polyphosphatase (Lucigen, cat. RP8092H), which dephosphorylates uncapped, but not capped mRNAs leaving monophosphate 5' ends, and incubating for an hour at 37° C. RNA transcripts were purified using GeneJET RNA Cleanup and Concentration Micro Kit™ (Thermo Fisher Scientific, cat. no. K0842) according to the manufacturer's instructions. This purified mRNA was added to 2 units of XrnI (New England Biolabs, cat. M0338S, a processive 5'→3' exoribonuclease, that requires a 5' monophosphate as a substrate, and incubated at 37° C. for an hour. The mRNA transcripts were purified using GeneJET RNA Cleanup and Concentration Micro Kit™ (Thermo Fisher Scientific, cat. no. K0842) according to the manufacturer's instructions. Removal of uncapped transcripts was confirmed by performing the capping assay as described in Example 4. Double stranded RNA (dsRNA) was removed from the above treated samples using an Agilent Technologies Series 1260 Infinity HPLC equipped with a Clarity® 5 μm Oligo-RP 150×4.6 mm column set to 65° C. A linear gradient of buffer B (0.1 M triethylammonium acetate pH 7.0 and 25% acetonitrile) from 38% to 70% in buffer A (0.1 M triethylammonium acetate pH 7.0) over 10 min at 1 ml/min was applied. RNA was recovered from collected fractions using the GeneJET RNA Cleanup and Concentration Micro kit. Concentration of the recovered mRNA was determined by Nanodrop, and depletion of dsRNA was confirmed by performing a dot blot with the anti-dsRNA J2 antibody. The quality of the transcripts was also checked using the Bioanalyzer with the RNA Nano 6000 kit.

Crude and HPLC purified mRNAs were then used to transfect JAWS II cells. The cells were cultured according to protocols outlined by American Tissue Cell Collection (ATCC) organization. 50,000 cells were seeded onto a 96 well plate so that cells are 70-90% confluent the next day (day of transfection). Cells were transfected using LIPO-FECTAMINE™ MESSSENGERMAX™ transfection reagent (Thermo Fisher, Cat. LMRNA001). 25 ng crude or HPLC purified mRNA mixed with 0.3 μL MESSENGER-MAX™ transfection reagent per manufacturer's protocols, and the mix was added to the cells and incubated at 37 C. 24 hours after transfection, media containing suspension cells was removed and added to a clean plate, and the adherent cells were detached with 50 μL TRYPLE™ Express Enzyme (Thermo Fisher Cat. No. 12604013) according to the manufacturer's protocol. The detached cells were transferred to the plate containing the suspension cells. This cell mixture was run through an ATTUNE NxT™ flow cytometer (Thermo Fisher Cat. No. A29004), and the GFP fluorescence for 10,000 cells were measured for each sample. Cells were gated on live single cells based on forward and side scattering. The gating for GFP was determined by using cells with no GFP. Transfection efficiency was measured by determining the percentage of cells in the GFP-positive gate, and GFP expression was quantified by taking the median fluorescence intensity (MFI) for each sample in the GFP-positive gate. Data were analyzed using FLOWJO™ software.

Figure 13:
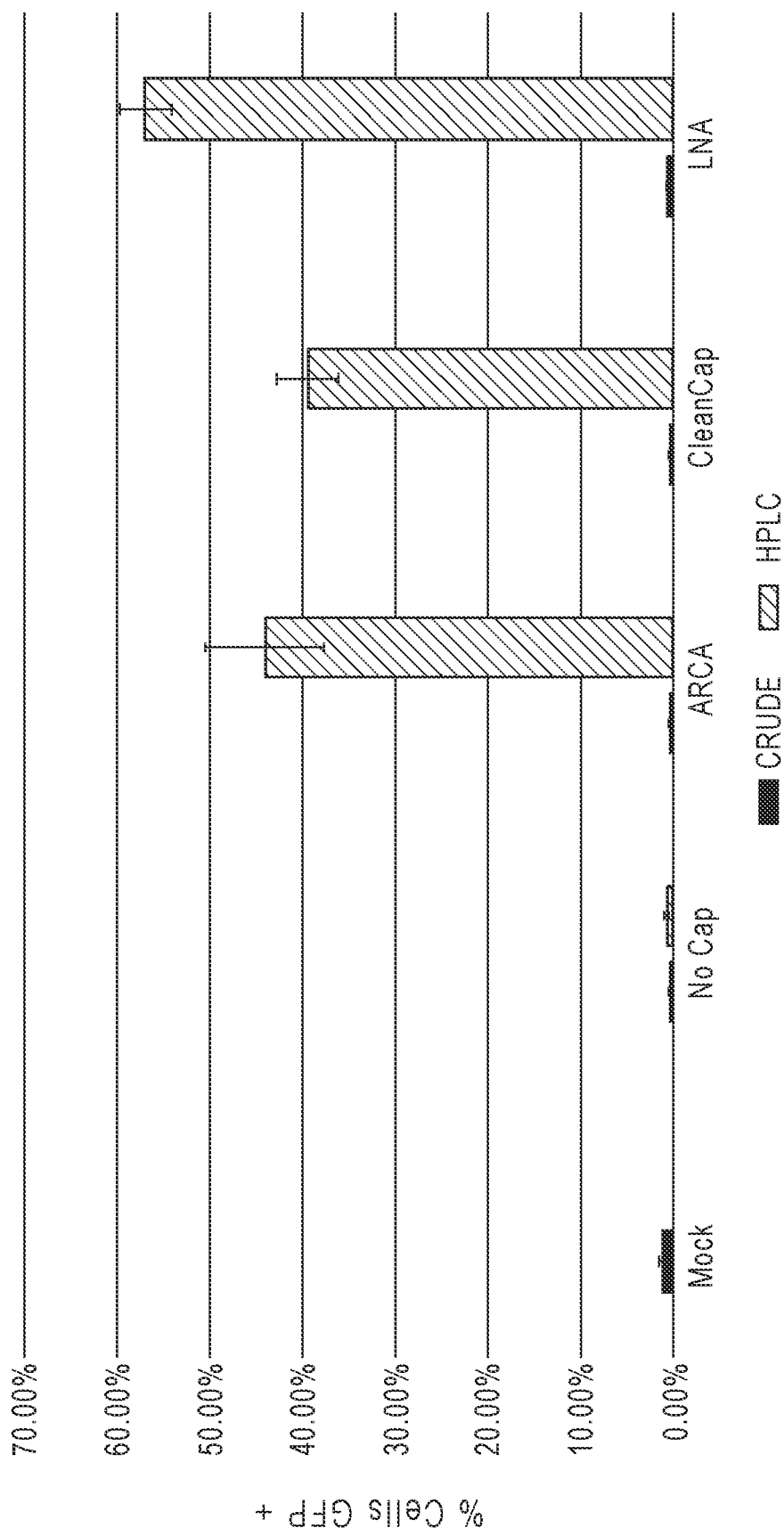
FIG. 13 is a bar graph showing the % cells that are GFP positive, when transfected with crude or HPLC purified mRNA's having no cap, ARCA, GAG cap, or LNA-modified GAG cap as described in Example 4.
Figure 14:
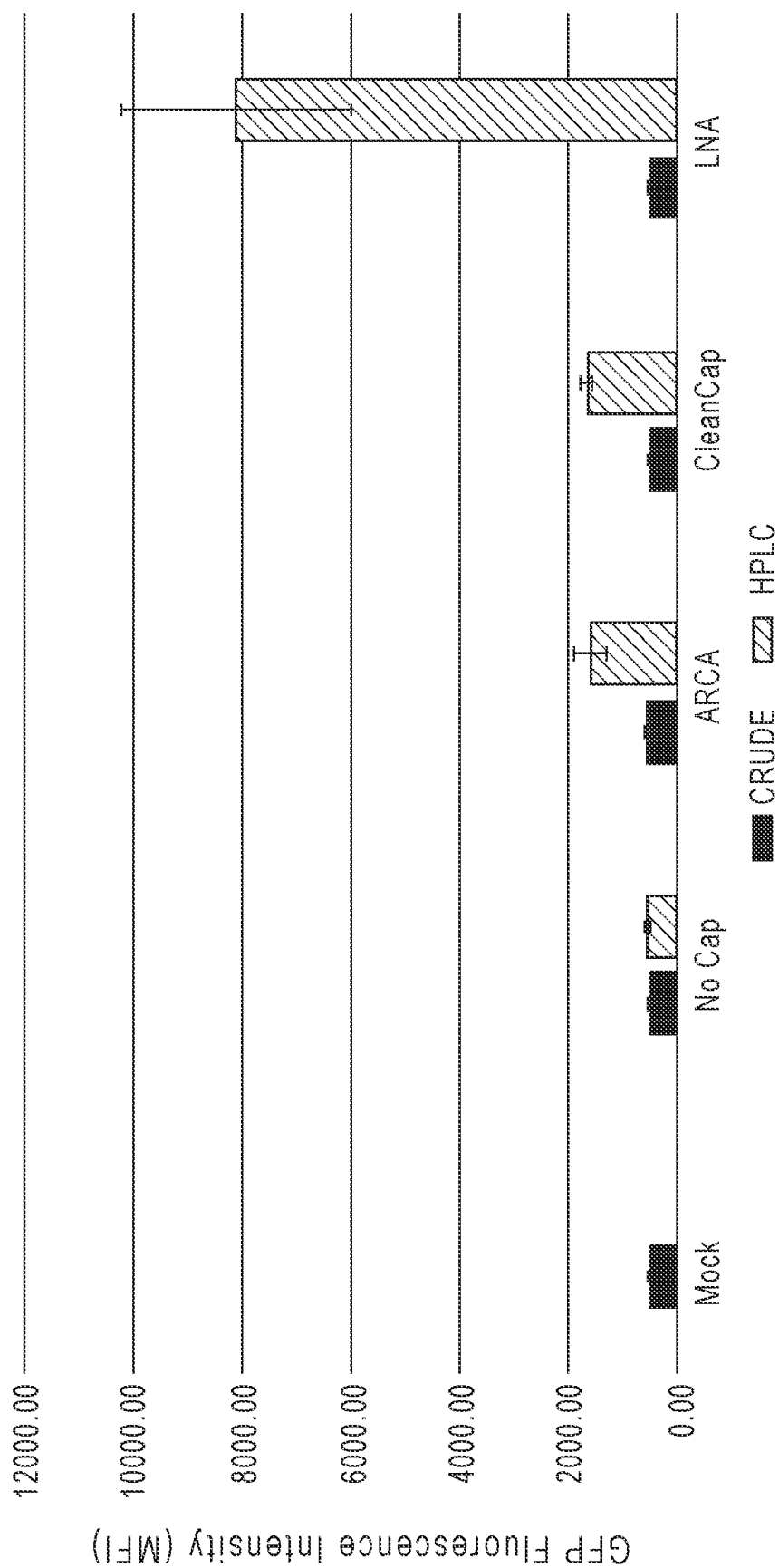
FIG. 14 is a bar graph showing the median fluorescence intensity (MFI), of cells transfected with "crude" or "HPLC purified" mRNA preparations capped with no cap, ARCA cap analog, GAG cap analog, or LNA-modified GAG cap analog, as described in Example 4.

As shown in FIG. 13, mRNA transcripts capped with the LNA cap analog showed significantly higher transfection efficiency, when compared to uncapped mRNA, mRNA capped with ARCA cap analog, and mRNA capped with GAG-cap (CLEANCAP™ AG) cap analog. Furthermore, FIG. 14 shows that the expression efficiency of mRNA capped with the LNA cap analog was more than 4 fold greater than compared to uncapped mRNA transcripts, mRNA transcripts capped with the ARCA cap analog, and mRNA transcripts capped with GAG-cap (CLEANCAP™ AG) cap analog.

Example 6

Creation of In Vitro Transcription Templates

The various in vitro transcription (IVT) templates were created by PCR with a DNA plasmid containing the wild-type (WT) T7 promoter, 5'-UTR, eGFP, and 3'-UTR sequences using the PLATINUM™ SUPERFI™ II Green PCR Master Mix (Thermo Fisher Scientific, cat. no. 12369010). Modified T7 promoters were added by site-directed mutagenesis via the forward primer (Table 4). The PCR products were purified using the PURELINK™ PCR Purification kit (Thermo Fisher Scientific, cat. no. K310001) and diluted to 100 ng/µL in water.

In Vitro Transcription Reaction

Twenty microliter (20 µL) IVT reactions were performed with 500 ng DNA template, 10 µL 2×NTP/cap mix (described below), 2 µL 10× T7 Reaction Buffer, and 2 µL T7 Enzyme Mix. The reaction buffer and enzyme mix were from the mMESSAGE mMACHINE™ T7 Ultra kit (Thermo Fisher Scientific, cat. no. AMB13455). Reaction mixtures were incubated at 37° C. for 2 hours to synthesize the RNA transcripts. At the end of the reaction, 1 µL TURBO™ DNase (Thermo Fisher Scientific, cat. no. AM2239) was added and incubated at 37° C. for 15 minutes to degrade the DNA template. The RNA transcripts were purified by the MEGACLEAR™ Transcription Clean-Up kit (Thermo Fisher Scientific, cat. no. AM1908). A NANODROP™ spectrophotometer (Thermo Fisher Scientific, cat. no. ND-2000C) was used to measure the concentration of the purified RNA samples.

The 2×NTP/cap mixture was prepared depending on the cap used. The ARCA mixture, which has a 4:1 ARCA:GTP ratio, consisted of 3 mM GTP, 15 mM ATP/CTP/UTP each, and 12 mM ARCA. The CLEANCAP® mixture contained 10 mM GTP/ATP/CTP/UTP each and 10 mM CLEANCAP® (TriLink Biotechnologies, cat. nos. N-7113). For the testing of the different CLEANCAP®:NTP ratios, the CLEANCAP® concentration was changed with respect to the NTP concentration (e.g., 4:1 CLEANCAP®:NTP ratio means that the 2×NTP/cap mixture contained 10 mM GTP/ATP/CTP/UTP each and 40 mM CLEANCAP®). The no cap reactions used a 2×NTP mixture containing 10 mM of each NTP.

Capping Efficiency Assay

A 10-23 DNAzyme was designed to cut the RNA transcripts 30 nucleotides from the expected transcription start site (Cairns et al., "Optimisation of the 10-23 DNAzyme-substrate pairing interactions enhanced RNA cleavage activity at purine-cytosine target sites", Nucleic Acids Res. 31(11):2883-2889 (2003)). The DNAzyme reaction was performed in a 20 µl reaction containing 1-2 µg RNA and 0.5 µM DNAzyme in 50 mM Tris-HCl pH 7.5. The reaction mixture was preheated at 85° C. for 30 seconds and equilibrate at 37° C. for 5 minutes and added magnesium chloride to 10 mM so that the total volume was 20 µl. The reaction mixture was incubated at 37° C. for 1 hour and stopped by adding 2 µL TURBO DNase and incubating at 37° C. for 30 minutes.

The DNAzyme reaction mixture was prepared for gel analysis by mixing with 2× NOVEX™ TBE-Urea sample buffer (Thermo Fisher Scientific, cat. no. LC6876) and heating at 70° C. for 2 minutes. The sample was loaded onto a NovEx™ 15% TBE-Urea gel (Thermo Fisher Scientific, cat. no. EC68855BOX) and ran at 15 V, 15 mA for 1 hour and 40 minutes or until the bromophenol blue dye migrated to the bottom of the gel. The gel was removed from the cassette, washed in water, and stained with SYBR™ Gold Nucleic Acid Gel Stain (Thermo Fisher Scientific, cat. no. S11494) for 5-10 minutes. Following a brief wash in water, the gel was visualized over an UV light and an image was captured using an iBRIGHT™ system (Thermo Fisher Scientific). Capping efficiency was determined using ALPHAVIEW™ software (ProteinSimple) to measure band intensities of the fast and slow migrating transcripts (capped transcripts are longer than uncapped transcripts; therefore uncapped migrates faster).

Results

Figure 20:
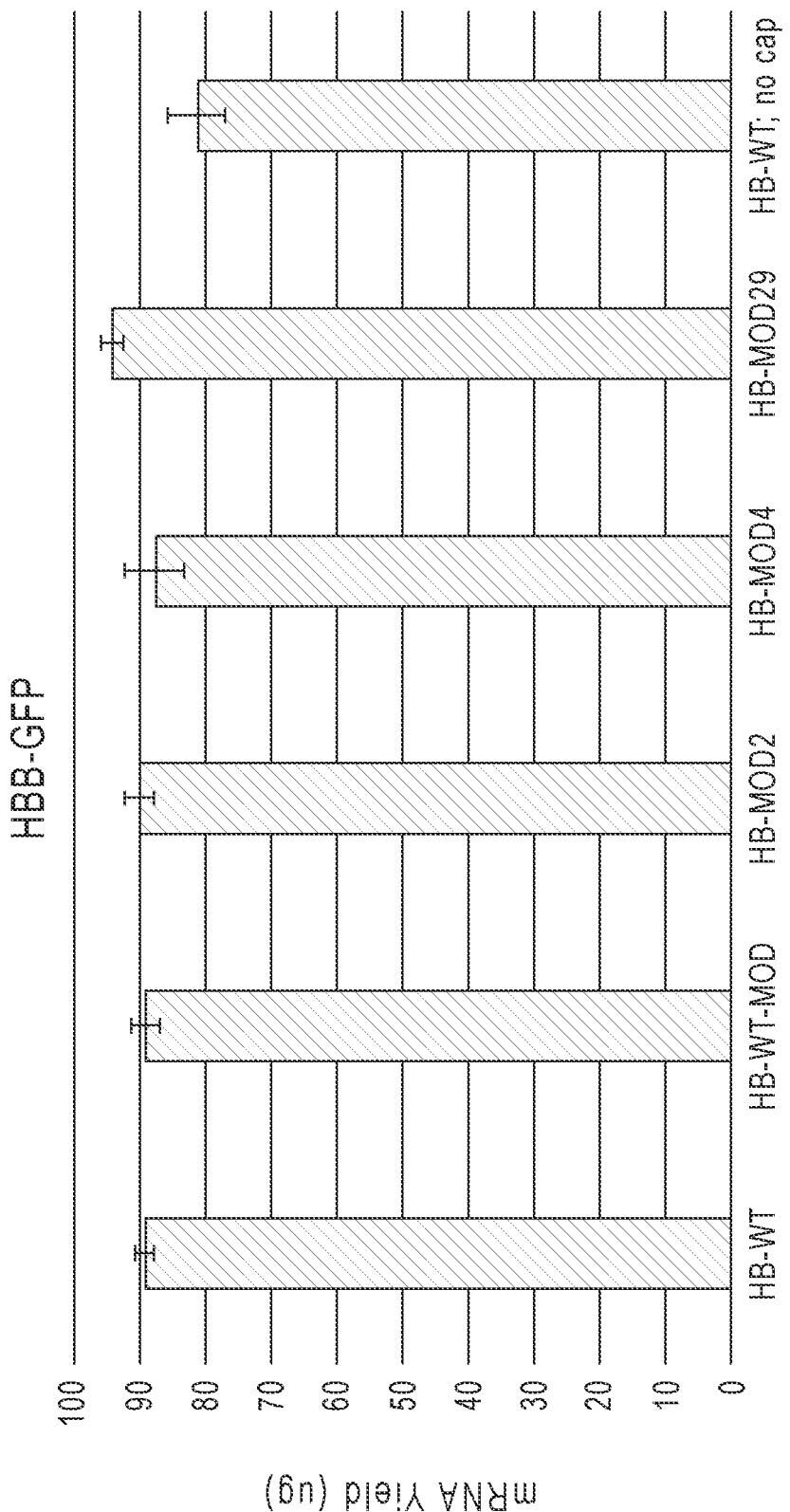
FIG. 20 shows RNA yield generated with different promoter sequences and position −1 initiation for HB-WT, HB-MOD2, HB-MOD4, and HB-MOD29. An AGG cap and a +1 initiation site were used for WT-MOD. The template for HB-WT was designed for +1 initiation but no cap was in the reaction mixture. The data used to generate this figure is set out Table 5. HB-GFP refers to a template composed of human beta globin 5' and 3' untranslated regions (UTRs).

Results from a number of experiments are set out in FIG. 20 and in Tables 6 through 8.

TABLE 4

Forward Primers used for Template Generation

| ID | Sequence | SEQ ID NO: |
|---|---|---|
| HB-WT | AGTAATACGACTCACTATAGGGAGA ACATTTGCTTCTGACACAAC | 585 |
| HB-WT-MOD | AGTAATACGACTCACTATAAGGAGA ACATTTGCTTCTGACACAAC | 586 |
| HB-MOD2 | AGTAATACGACTCACTATAGTGAGA ACATTTGCTTCTGACACAAC | 587 |
| HB-MOD4 | AGTAATACGACTCACTATAGCGAGA ACATTTGCTTCTGACACAAC | 588 |
| HB-MOD29 | AGTAATACGACTCACTATAGAGAGA ACATTTGCTTCTGACACAAC | 589 |

Reverse primer for all PCR reactions:
GCCCTCTAGATCAACCACTTTGGCCCTCT
(SEQ ID NO: 590)

Table 4 lists the PCR forward and reverse primers used to create GFP templates with different promoter modifications

TABLE 5

Promoter Modifications and Designations

| No. | Promoter Designation | Sequence |
|---|---|---|
| 1 | Wild Type | TATA GGG |
| 2 | Wild Type Mod | TATA AGG |
| 3 | MOD2 | TATA GTG |

TABLE 5-continued

Promoter Modifications and Designations

| No. | Promoter Designation | Sequence |
|---|---|---|
| 4 | MOD4 | TATA GCG |
| 5 | MOD26 | TATG GTG |
| 6 | MOD27 | TATA TTG |
| 7 | MOD28 | TATT GTG |
| 8 | MOD29 | TATA GAG |

Table 5 lists modified promoters and their sequences. The base after the space in the sequence is the natural +1 position.

TABLE 6 mRNA Yield and Capping Efficiency Using −1/+1 Initiation Site and 1:1 NTP to Trinucleotide GAG Cap Ratio (FIG. 20)

| Template | Avg (ug) | St Dev | Avg % capped | St dev |
|---|---|---|---|---|
| HB-WT | 89.15 | 1.48 | 53.765 | 2.74 |
| HB-WT-MOD | 89 | 2.12 | 91.415 | 0.90 |
| HB-MOD2 | 89.95 | 2.05 | 82.3 | 2.28 |
| HB-MOD4 | 87.65 | 4.45 | 73.75 | 0.11 |
| HB-MOD29 | 94.15 | 1.63 | 77.5 | 1.20 |
| HB-WT; no cap | 81.25 | 4.31 | 0 | 0 |
| HB-WT Template, ARCA Cap (data to right) | | | 71.93 | 0.38 |

Table 6 lists the IVT yields and capping efficiencies for various modified promoters when using a 1:1 NTP to cap ratio. The −1 start promoters, HB-MOD2, HB-MOD4, and HB-MOD29, give high yields and high capping efficiencies.

TABLE 7

IVT yield of using HB-MOD2 promoter with Different Trinucleotide GAG Cap:NTP Ratios

| Promoter | Yield (ug) | | | | | | | | |
|---|---|---|---|---|---|---|---|---|---|
| Cap:NTP ratio | Mix 1 6:1 | Mix 2 4:1 | Mix 3 2:1 | Mix 4 1.5:1 | Mix 5 1.1:1 | Mix 6 1:1 | Mix 7 0.8:1 | Mix 8 0.5:1 | Mix 9 No cap |
| HB-WT | 52.9 | 83 | 86.4 | 84.5 | 86.8 | 91.7 | 85.1 | 86.4 | 82.8 |
| HB-MOD2 | 28.8 | 44.6 | 89.8 | 70.2 | 92.5 | 97.7 | 89.9 | 85.4 | 80.5 |

TABLE 8

IVT capping efficiency of HB-MOD2 promoter with Different Trinucleotide GAG Cap:NTP Ratios

| Promoter | Capping Efficiency (%) | | | | | | | | |
|---|---|---|---|---|---|---|---|---|---|
| Cap:NTP ratio | Mix 1 6:1 | Mix 2 4:1 | Mix 3 2:1 | Mix 4 1.5:1 | Mix 5 1.1:1 | Mix 6 1:1 | Mix 7 0.8:1 | Mix 8 0.5:1 | Mix 9 No cap |
| HB-WT | 85.89 | 83.14 | 65.75 | 58.53 | 51.99 | 53.11 | 51.83 | 41.56 | 1 |
| HB-MOD2 | 94.43 | 95.78 | 90.7 | 85.89 | 80.99 | 83.55 | 77.86 | 69.89 | 0 |

The cap:NTP ratio with the modified promoters influences IVT yield and capping efficiency as shown in Tables 7 and 8, respectively.

All of the following documents are individually incorporated by reference here in their entirety: US Patent Publication 2018/0318409A1; US Patent Publication 2019/0351040; US Patent Publication 2018/0271970; US Patent Publication 2019/0054112; US Patent Publication 2019/0336595; US Patent Publication 2018/0311336; US Patent Publication 2018/0303929; PCT Publication WO 2002/26891; PCT Publication WO 1997/40104; PCT Publication WO 1999/51702; PCT Publication WO 2001/21624; PCT Publication WO 1999/14226; PCT Publication WO 2018/085449; PCT Publication WO 2017/070601; PCT Publication WO 2019/202035; PCT Publication WO 2020/002525; PCT Publication WO 2019/193183; PCT Publication WO 2019/115635; PCT Publication WO 2019/038332; PCT Publication WO 2019/008001; PCT Publication WO 2018/167320; PCT Publication WO 2018/115527; PCT Publication WO 2018/115525; WO 2018/115507; PCT Publication WO 2018/104538; PCT Publication WO 2018/104540; U.S. Pat. Nos. 5,132,432; 8,039,642; 5,227,487; 5,442,045; 4,603,209; 4,849,362; 5,696,157; 5,459,276; 5,501,980; 5,830,912; 5,798,276; 5,846,737; 6,562,632; 7,256,292; 7,985,602; 8,729,267; 9,040,674; 9,315,859; 9,745,336; 9,783,560; 9,790,544; 10,131,936; 6,977,305; 6,974,873; 6,664,047; 4,774,339; 4,810,636; 4,714,763; 5,187,288; 5,248,782; 5,274,113; 5,433,896; 4,981,977; 5,268,486; 5,569,587; 5,569,766; 5,486,616; 5,627,027; 5,808,044; 5,877,310; 6,002,003; 6,004,536; 6,008,373; 6,043,025; 6,162,931; 6,130,101; 6,229,055; 6,339,392; 5,451,343; 6,716,979; 6,127,134; 6,130,094; 6,133,445; 7,446,202; 7,598,390; 7,776,529; 9,249,307; 9,751,868; 10,000,467; 10,053,447; 10,125,120; 10,351,551; 10,526,317; and RICHARD P. HAUGLAND, MOLECULAR PROBES HANDBOOK OF FLUORESCENT PROBES AND RESEARCH CHEMICALS (11th edition, January 2010).

What is claimed is:

1. A trinucleotide cap analog of Formula (I)

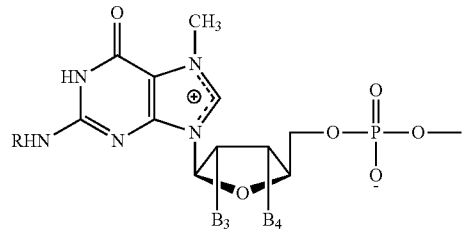

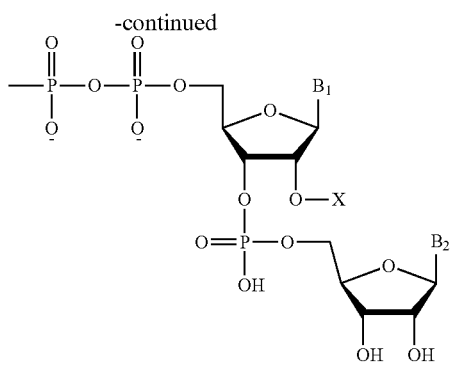

wherein
$B_3$ is chosen from —OH, halogen, dyes, —OR$^1$,
wherein R$^1$ is chosen from propargyl, tert-butyldimethylsilyl, and a methylene bridge with the 4'C;
$B_4$ is chosen from —OH, dyes, and —OR$^2$, wherein R$^2$ is chosen from propargyl and tert-butyldimethylsilyl;
or R$^1$ joins with R$^2$ such that $B_3$ and $B_4$ form -2',3'-O-isopropylidine;
on the condition that $B_3$ and $B_4$ cannot both be —OH
X is chosen from —H and —CH$_3$;
$B_1$ and $B_2$ are each independently chosen from adenine, guanine, cytosine, and uracil;
R is chosen from H, a linker-bound cell-penetrating peptide, a linker-bound cell-penetrating peptide covalently linked to a dye, and a linker-bound dye,
wherein the cell-penetrating peptide is selected from the group consisting of SEQ ID NOs: 1-10.

2. A composition comprising RNA having a trinucleotide cap analog of claim 1, covalently bonded thereto.

3. The composition of claim 2, further comprising at least one RNA delivery agent.

4. The composition of claim 3, wherein the at least one RNA delivery agent comprises at least one cationic lipid.

5. A kit comprising:
a trinucleotide cap analog claim 1;
nucleotide triphosphate molecules; and
an RNA polymerase.

6. The trinucleotide cap analog of claim 1, wherein $B_3$ is —OR$^1$, and R$^1$ forms a methylene bridge with the 4'C such that the trinucleotide cap analog is of Formula (II):

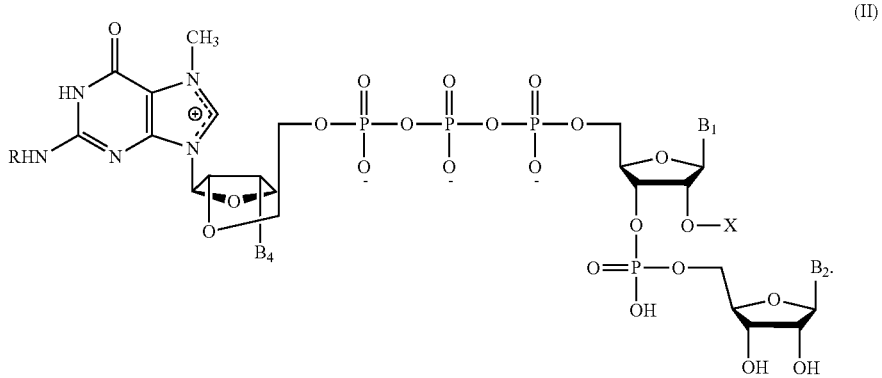

7. The trinucleotide cap analog of claim 1, wherein each dye is independently chosen from azobenzene dyes, naphthalene containing dyes, cyanine dyes, rhodamine dyes, coumarin, and pyrene dyes.

8. The trinucleotide cap analog of claim 1, wherein
$B_3$ is —OR$^1$ and $B_4$ is —OR$^2$ wherein R$^1$ joins with R$^2$ such that $B_3$ and $B_4$ form -2',3'-O-isopropylidene;
X is —CH$_3$; and
R is H.

9. The trinucleotide cap analog of claim 1, wherein
$B_3$ is chosen from —OR$^1$ wherein R$^1$ is chosen from propargyl and tert-butyldimethylsilyl;
$B_4$ is —OH; and
R is H.

10. The composition of claim 4, wherein the at least one RNA delivery agent comprises at least one cationic lipid and at least one neutral lipid.

11. The composition of claim 10, wherein the at least one neutral lipid is a phospholipid.

12. The composition of claim 10, wherein the at least one neutral lipid is a sterol.

13. The composition of claim 2, wherein the RNA comprises one or more modified nucleotides.

14. The composition of claim 13, wherein the one or more modified nucleotides is selected from the group consisting of pseudouridine (ψ) triphosphate, 1methylpseudouridine (m$^1$ψ) triphosphate, 5-methoxyuridine (mo$^5$U) triphosphate, 5-methylcytidine (m$^5$C) triphosphate, α-thio-guanosine triphosphate, α-thio-adenosine triphosphate, and any combination thereof.

15. The trinucleotide cap analog of claim 1, wherein $B_4$ is propargyl.

16. The trinucleotide cap analog of claim 15, having the structure
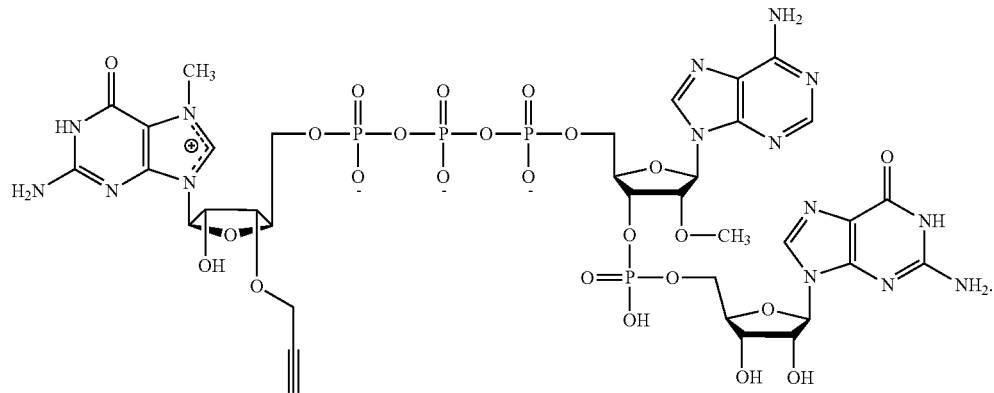
* * * * *